United States Patent
Hayama et al.

(10) Patent No.: US 10,784,446 B2
(45) Date of Patent: Sep. 22, 2020

(54) COMPOUND, ORGANIC ELECTROLUMINESCENCE ELEMENT MATERIAL, ORGANIC ELECTROLUMINESCENCE ELEMENT AND ELECTRONIC DEVICE

(71) Applicant: IDEMITSU KOSAN CO., LTD., Tokyo (JP)

(72) Inventors: Tomoharu Hayama, Sodegaura (JP); Tetsuya Masuda, Sodegaura (JP); Masahiro Kawamura, Sodegaura (JP); Hirokatsu Ito, Sodegaura (JP); Tasuku Haketa, Sodegaura (JP); Yumiko Mizuki, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 241 days.

(21) Appl. No.: 15/329,442

(22) PCT Filed: Nov. 27, 2015

(86) PCT No.: PCT/JP2015/083494
§ 371 (c)(1),
(2) Date: Jan. 26, 2017

(87) PCT Pub. No.: WO2016/084962
PCT Pub. Date: Jun. 2, 2016

(65) Prior Publication Data
US 2017/0213983 A1  Jul. 27, 2017

(30) Foreign Application Priority Data

Nov. 28, 2014 (JP) ................. 2014-241825

(51) Int. Cl.
| | | |
|---|---|---|
| *H01L 51/00* | (2006.01) | |
| *C07D 405/14* | (2006.01) | |
| *C07D 409/14* | (2006.01) | |
| *C09K 11/06* | (2006.01) | |
| *H01L 51/50* | (2006.01) | |

(52) U.S. Cl.
CPC ........ *H01L 51/0067* (2013.01); *C07D 405/14* (2013.01); *C07D 409/14* (2013.01); *C09K 11/06* (2013.01); *H01L 51/0052* (2013.01); *H01L 51/0054* (2013.01); *H01L 51/0058* (2013.01); *H01L 51/0059* (2013.01); *H01L 51/0061* (2013.01); *H01L 51/0072* (2013.01); *H01L 51/0073* (2013.01); *H01L 51/0074* (2013.01); *H01L 51/0077* (2013.01); *H01L 51/50* (2013.01); *C09K 2211/1007* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/5012* (2013.01); *H01L 51/5076* (2013.01)

(58) Field of Classification Search
CPC .... C07D 405/14; C07D 409/14; C09K 11/06; C09K 2211/1007; C09K 2211/1029; C09K 2211/1044; C09K 2211/1059; C09K 2211/1088; C09K 2211/1092; H01L 51/0052; H01L 51/0054; H01L 51/0058; H01L 51/0059; H01L 51/0061; H01L 51/0067; H01L 51/0072; H01L 51/0073; H01L 51/0074; H01L 51/0077; H01L 51/50; H01L 51/5012; H01L 51/5076
See application file for complete search history.

(56) References Cited

U.S. PATENT DOCUMENTS

| | | |
|---|---|---|
| 2004/0086745 A1 | 5/2004 | Iwakuma et al. |
| 2005/0158578 A1 | 7/2005 | Iwakuma et al. |
| 2006/0041126 A1 | 2/2006 | Schafer et al. |
| 2006/0141284 A1 | 6/2006 | Tomita et al. |

(Continued)

FOREIGN PATENT DOCUMENTS

| | | |
|---|---|---|
| CN | 102503938 A | 6/2012 |
| JP | 2003-045662 A | 2/2003 |

(Continued)

OTHER PUBLICATIONS

Translation of International Search Report on Patentability dated May 30, 2017 in PCT/JP2015/083494.
International Search Report issued on International Patent Application No. PCT/JP2015/083494 dated Jan. 26, 2016.
JP Office Action issued in the corresponding Japanese Patent Application Ser. No. 2016-561970, dated Jul. 30, 2019.

*Primary Examiner* — Dawn L Garrett
(74) *Attorney, Agent, or Firm* — Foley & Lardner LLP

(57) ABSTRACT

A compound is represented by a formula (100) below, where $X_1$, $X_2$ and $X_3$ are each independently a nitrogen atom or a carbon atom bonded with $R_2$, Y is an oxygen atom, a sulfur atom and the like, $R_1$, $R_2$, $R_{11}$, $R_{21}$ and $R_{22}$ are each a hydrogen atom or a substituent, $L_1$ is a single bond or a linking group, and $L_2$ is a linking group.

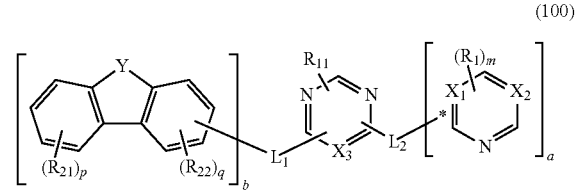

40 Claims, 1 Drawing Sheet

(56) References Cited

U.S. PATENT DOCUMENTS

| | | |
|---|---|---|
| 2006/0180806 A1 | 8/2006 | Arakane et al. |
| 2007/0051944 A1 | 3/2007 | Vestweber et al. |
| 2007/0069638 A1 | 3/2007 | Matsuura et al. |
| 2007/0159083 A1 | 7/2007 | Matsuura et al. |
| 2007/0190355 A1 | 8/2007 | Ikeda et al. |
| 2007/0224448 A1 | 9/2007 | Ikeda et al. |
| 2008/0145699 A1 | 6/2008 | Yabe et al. |
| 2009/0236973 A1 | 9/2009 | Yabe et al. |
| 2009/0243473 A1 | 10/2009 | Iwakuma et al. |
| 2010/0039026 A1 | 2/2010 | Yang et al. |
| 2010/0327738 A1 | 12/2010 | Toba et al. |
| 2011/0156014 A1 | 6/2011 | Kim et al. |
| 2011/0248257 A1 | 10/2011 | Kim et al. |
| 2011/0291081 A1 | 12/2011 | Inoue et al. |
| 2012/0104941 A1 | 5/2012 | Jung et al. |
| 2012/0119197 A1 | 5/2012 | Nishimura et al. |
| 2012/0126221 A1 | 5/2012 | Kitamura et al. |
| 2012/0126690 A1 | 5/2012 | Ise et al. |
| 2012/0126691 A1 | 5/2012 | Ise et al. |
| 2012/0126692 A1 | 5/2012 | Ise et al. |
| 2012/0211735 A1 | 8/2012 | Imada et al. |
| 2012/0238105 A1 | 9/2012 | Anemian et al. |
| 2012/0273771 A1 | 11/2012 | Jung et al. |
| 2013/0099214 A1 | 4/2013 | Kim et al. |
| 2013/0200357 A1 | 8/2013 | Ludemann et al. |
| 2013/0207540 A1 | 8/2013 | Itai et al. |
| 2013/0256646 A1 | 10/2013 | Fennimore et al. |
| 2013/0306962 A1 | 11/2013 | Yamamoto et al. |
| 2014/0001456 A1 | 1/2014 | Mizutani et al. |
| 2014/0077191 A1 * | 3/2014 | Mizutani ............... C07D 471/04 257/40 |
| 2014/0159023 A1 | 6/2014 | Matsumoto et al. |
| 2014/0272398 A1 | 9/2014 | Hakii et al. |
| 2014/0299865 A1 | 10/2014 | Nishimura et al. |
| 2014/0312338 A1 | 10/2014 | Mizutani et al. |
| 2015/0041785 A1 | 2/2015 | Sannomiya et al. |
| 2015/0236264 A1 * | 8/2015 | Kim ................... H01L 51/0054 257/40 |
| 2015/0340620 A1 | 11/2015 | Park et al. |
| 2016/0028021 A1 * | 1/2016 | Zeng ................... H01L 51/0067 257/40 |
| 2016/0093808 A1 * | 3/2016 | Adamovich ........ H01L 51/0052 257/40 |
| 2016/0197289 A1 | 7/2016 | Sado et al. |
| 2016/0329502 A1 * | 11/2016 | Dyatkin ............. H01L 51/0067 |
| 2017/0141329 A1 | 5/2017 | Koenen et al. |
| 2017/0317291 A1 | 11/2017 | Hayashi et al. |

FOREIGN PATENT DOCUMENTS

| | | |
|---|---|---|
| JP | 2004-171808 A | 6/2004 |
| JP | 2005-213188 A | 8/2005 |
| JP | 2005-276801 A | 10/2005 |
| JP | 2008-205488 A | 9/2008 |
| JP | 2008-252094 A | 10/2008 |
| JP | 2009-114370 A | 5/2009 |
| JP | 2010-141353 A | 6/2010 |
| JP | 2010-185047 A | 8/2010 |
| JP | 4741028 B1 | 8/2011 |
| JP | 2012-097006 A | 5/2012 |
| JP | 2012-142613 A | 7/2012 |
| JP | 2014-017389 A | 1/2014 |
| JP | 2014-123687 A | 7/2014 |
| JP | 2015-134743 A | 7/2015 |
| JP | 2016-019002 A | 2/2016 |
| JP | 2017-522291 A | 8/2017 |
| KR | 10-2014-0094408 A | 7/2014 |
| WO | WO-2006/013739 A1 | 2/2006 |
| WO | WO-2013/077352 A1 | 5/2013 |
| WO | WO-2013/100538 A1 | 7/2013 |
| WO | WO-2013/100540 A1 | 7/2013 |
| WO | WO-2013/137001 A1 | 9/2013 |
| WO | WO-2013/175746 A1 | 11/2013 |
| WO | WO-2013/175747 A1 | 11/2013 |
| WO | WO 2013/191177 A1 * | 12/2013 |
| WO | WO-2014/097711 A1 | 6/2014 |
| WO | WO-2014/122933 A1 | 8/2014 |
| WO | WO-2014/123369 A1 | 8/2014 |
| WO | WO-2014/166584 A1 | 10/2014 |
| WO | WO-2014/166585 A1 | 10/2014 |
| WO | WO-2014/166586 A1 | 10/2014 |
| WO | WO-2014/208755 A1 | 12/2014 |
| WO | WO-2015/182872 A1 | 12/2015 |
| WO | WO-2016/000803 A1 | 1/2016 |
| WO | WO-2016/076384 A1 | 5/2016 |

* cited by examiner

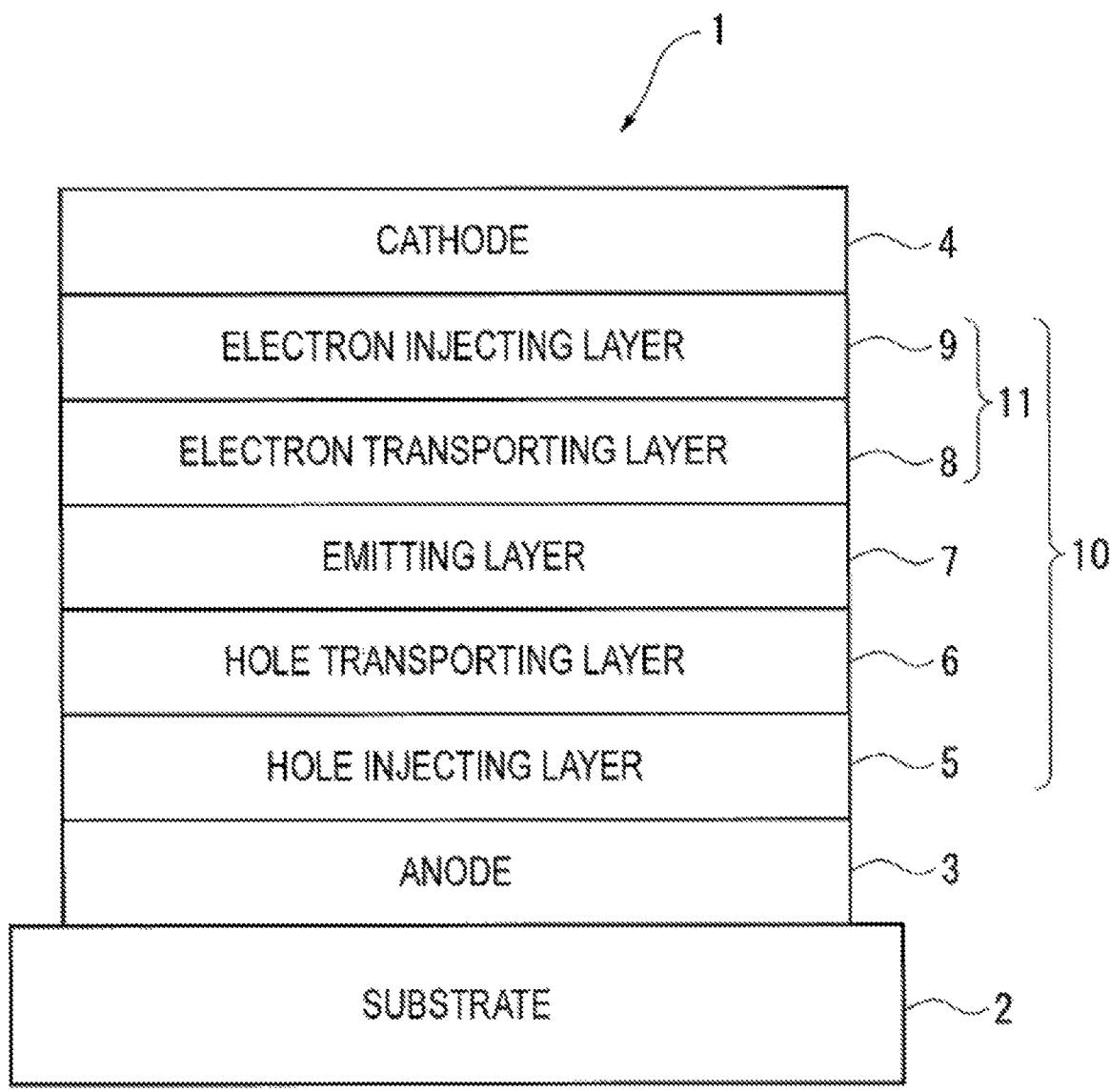

COMPOUND, ORGANIC ELECTROLUMINESCENCE ELEMENT MATERIAL, ORGANIC ELECTROLUMINESCENCE ELEMENT AND ELECTRONIC DEVICE

CROSS-REFERENCE TO RELATED APPLICATIONS

The present application is a U.S. national stage application claiming the benefit of International Patent Application No. PCT/JP2015/083494, filed Nov. 27, 2015, which claims the benefit of priority to Japanese Patent Application No. 2014-241825, filed Nov. 28, 2014, the entireties of which are hereby incorporated by reference.

TECHNICAL FIELD

The present invention relates to a compound, an organic-electroluminescence-device material, an organic electroluminescence device and an electronic device.

BACKGROUND ART

An organic electroluminescence device (hereinafter, occasionally abbreviated as organic EL device) using an organic substance is highly expected to be used as an inexpensive solid-emitting full-color display device having a large area and has been variously developed. A typical organic EL device includes an emitting layer and a pair of opposing electrodes between which the emitting layer is interposed. When an electric field is applied on both of the electrodes, electrons are injected from the cathode while holes are injected from the anode. Further, the electrons are recombined with the holes in the emitting layer to generate an excited state. When the excited state is returned to a ground state, energy is emitted as light.

A typical organic EL device exhibits a higher drive voltage, lower luminescence intensity and lower luminous efficiency than those of an inorganic light-emitting diode. Though the compound used for forming the organic layer has been improved and device performance has been gradually improved in recent organic EL devices, further improvement in the device performance has been desired.

For instance, Patent Literature 1 discloses that an organic EL device that includes an electron transporting zone containing a compound including a predetermined nitrogen-containing six-membered ring and oxygen-containing fused ring in a molecule emits at a high efficiency and is driven at a lower drive voltage.

CITATION LIST

Patent Literature

Patent Literature 1: International Publication WO 2013/077352

SUMMARY OF THE INVENTION

Problems to be Solved by the Invention

Enhancement of lifetime has also been demanded for further improvement in the performance of organic EL devices.

An object of the invention is to provide an organic electroluminescence device that is capable of keeping an appropriate drive voltage and of emitting for a long lifetime, a compound used for the organic electroluminescence device, an organic-electroluminescence-device material containing the compound, and an electronic device.

Means for Solving the Problems

According to an aspect of the invention, a compound represented by a formula (100) below is provided.

[Formula 1]

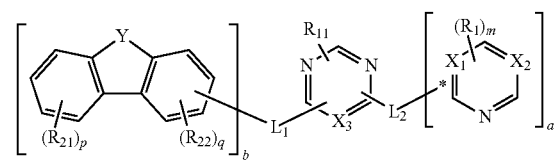

(100)

In the above formula (100):

$X_1$, $X_2$ and $X_3$ are each independently a nitrogen atom, or a carbon atom ($CR_2$) bonded with $R_2$;

Y is an oxygen atom, a sulfur atom, or a silicon atom ($SiR_{31}R_{32}$) bonded with $R_{31}$ and $R_{32}$;

$R_1$ and $R_2$ are each independently selected from the group consisting of: a hydrogen atom; a substituted or unsubstituted alkyl group having 1 to 30 carbon atoms; a substituted or unsubstituted alkenyl group having 2 to 30 carbon atoms; a substituted or unsubstituted alkynyl group having 2 to 30 carbon atoms; a substituted or unsubstituted aryl group having 6 to 30 ring carbon atoms; a substituted or unsubstituted alkoxy group having 1 to 30 carbon atoms; a substituted or unsubstituted aryloxy group having 6 to 30 ring carbon atoms; a substituted or unsubstituted alkylthio group having 1 to 30 carbon atoms; a substituted or unsubstituted arylthio group having 6 to 30 ring carbon atoms; a substituted or unsubstituted silyl group; a cyano group; and a halogen atom;

$R_{11}$, $R_{21}$, $R_{22}$, $R_{31}$ and $R_{32}$ are each independently selected from the group consisting of: a hydrogen atom; a substituted or unsubstituted alkyl group having 1 to 30 carbon atoms; a substituted or unsubstituted alkenyl group having 2 to 30 carbon atoms; a substituted or unsubstituted alkynyl group having 2 to 30 carbon atoms; a substituted or unsubstituted aryl group having 6 to 30 ring carbon atoms; a substituted or unsubstituted heterocyclic group having 5 to 30 ring atoms; a substituted or unsubstituted alkoxy group having 1 to 30 carbon atoms; a substituted or unsubstituted aryloxy group having 6 to 30 ring carbon atoms; a substituted or unsubstituted alkylthio group having 1 to 30 carbon atoms; a substituted or unsubstituted arylthio group having 6 to 30 ring carbon atoms; a substituted or unsubstituted silyl group; a cyano group; and a halogen atom;

$L_1$ is a single bond or a linking group selected from the group consisting of: a substituted or unsubstituted aromatic hydrocarbon group having 6 to 30 ring carbon atoms; a substituted or unsubstituted heterocyclic group having 5 to 30 ring atoms; a substituted or unsubstituted linear or branched hydrocarbon group having a carbon-carbon double bond and 2 to 30 carbon atoms; and a substituted or unsubstituted linear or branched hydrocarbon group having a carbon-carbon triple bond and 2 to 30 carbon atoms;

$L_2$ is a linking group selected from the group consisting of: a substituted or unsubstituted aromatic hydrocarbon group having 6 to 30 ring atoms;

m is an integer of 2 or more, a plurality of $R_1$ being the same or different;

a plurality of $R_2$ are the same or different;

$R_1$ and $R_2$ are optionally bonded to form a ring structure;

p is an integer ranging from 0 to 4, a plurality of $R_{21}$ being the same or different when p is an integer in a range from 2 to 4;

the plurality of $R_{21}$ are optionally bonded to each other to form a ring structure;

q is an integer ranging from 0 to 3, a plurality of $R_{22}$ being the same or different when q is 2 or 3;

the plurality of $R_{22}$ are optionally bonded to each other to form a ring structure;

a is an integer ranging from 1 to 5, a plurality of first moieties in the parentheses parenthesized by a being the same or different when the plurality of first moieties are bonded to $L_2$;

* represents a bonding site with $L_2$ of the first moiety in the parentheses parenthesized by a; and b is an integer ranging from 1 to 5, a plurality of second moieties in the parentheses parenthesized by a being the same or different when the plurality of second moieties are bonded to $L_1$.

According to another aspect of the invention, an organic-electroluminescence-device material including the compound according to the above aspect of the invention is provided.

According to still another aspect of the invention, an organic electroluminescence device including an anode, a cathode and one or more organic layers including an emitting layer is provided, at least one of the organic layers containing the compound according to the above aspect of the invention.

According to further aspect of the invention, an organic electroluminescence device including an anode, a cathode and an organic layer including an emitting layer and an electron transporting zone is provided, in which the emitting layer is provided between the anode and the cathode, the electron transporting zone is provided between the emitting layer and the cathode and the electron transporting zone contains the compound according to the above aspect of the invention.

According to still further aspect of the invention, an electronic device including the organic electroluminescence device according to the above aspect of the invention is provided.

According to the above aspects of the invention, an organic electroluminescence device that is capable of keeping an appropriate drive voltage and of emitting for a long lifetime, a compound used for the organic electroluminescence device, an organic-electroluminescence-device material including the compound, and an electronic device can be provided.

BRIEF DESCRIPTION OF DRAWING

The FIGURE schematically shows an exemplary arrangement of an organic EL device according to an exemplary embodiment.

DESCRIPTION OF EMBODIMENTS

Compound

A compound according to an exemplary embodiment includes a first moiety represented by a formula (10c) below, a second moiety represented by a formula (1a) below and a third moiety represented by a formula (1b) below in a molecule. The first moiety is bonded to the third moiety through a linking group. The second moiety is directly bonded to the third moiety or, alternatively, bonded to the third moiety through a linking group. The compound according to the exemplary embodiment may include a plurality of the first moieties, the plurality of first moieties being mutually the same or different. The compound according to the exemplary embodiment may include a plurality of the second moieties, the plurality of second moieties being mutually the same or different.

[Formula 2]

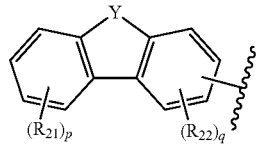

(1a)

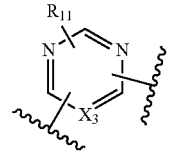

(1b)

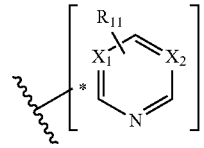

(10c)

(In the above formulae (1a), (1b) and (10c), $X_1$, $X_2$ and $X_3$ are mutually independently a nitrogen atom or a carbon atom ($CR_2$) bonded with $R_2$, Y is an oxygen atom, a sulfur atom or a silicon atom ($SiR_{31}R_{32}$) bonded with $R_{31}$ and $R_{32}$, $R_1$ and $R_2$ are each independently selected from the group consisting of a hydrogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted or unsubstituted silyl group, a cyano group and a halogen atom, $R_{11}$, $R_{21}$, $R_{22}$, $R_{31}$ and $R_{32}$ are each independently selected from the group consisting of a hydrogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted or unsubstituted silyl group, a cyano group and a halogen atom, $L_1$ is a single bond or a linking group, the linking group of $L_1$ is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted linear or branched hydrocarbon group having a carbon-carbon double bond and 2 to 30 carbon atoms and a substituted or unsubstituted linear or branched hydrocarbon group having a carbon-carbon triple bond and 2 to 30 carbon atoms, $L_2$ is a linking group selected from the group consisting of a substituted or unsubstituted aromatic hydrocarbon group having 6 to 30 ring carbon atoms, m is an integer of 2 or more, the plurality of $R_1$ may be the same or different, the plurality of $R_2$ may be the same or different, $R_1$ and $R_2$ may be bonded with each other to form a ring structure, p is an integer ranging from 0 to 4, a plurality of $R_{21}$ may be the same or different when p is an integer ranging from 2 to 4, the plurality of $R_{21}$ may be mutually bonded to form a ring structure, q is an integer ranging from 0 to 3, a plurality of $R_{22}$ may be the same or different when q is 2 or 3, the plurality of $R_{22}$ may be bonded to each other to form a ring structure, a is an integer ranging from 1 to 5, a plurality of first moieties may be the same or different when the plurality of first moieties in the parentheses parenthesized by a are bonded to $L_2$,*represents a bonding site of the first moiety in the parentheses parenthesized by a with $L_2$, b is an integer ranging from 1 to 5, and a plurality of second moieties may be the same or different when the plurality of second moieties in the parentheses parenthesized by b are bonded to $L_1$).

In the first moiety represented by the above formula (10c), it is preferable that $L_2$ is bonded to a six-membered ring including $X_1$, $X_2$ and N in the first moiety in the parentheses parenthesized by a. In the above arrangement, the first moiety is represented by a formula (1c) below and the compound according to the exemplary embodiment includes the first moiety represented by the formula (1c) below, the second moiety represented by the formula (1a) below and the third moiety represented by the formula (1b) below in a molecule. The first moiety is bonded to the third moiety through a linking group. The second moiety is directly bonded to the third moiety or, alternatively, bonded to the third moiety through a linking group. The compound according to the exemplary embodiment may include a plurality of first moieties, the plurality of first moieties being mutually the same or different. The compound according to the exemplary embodiment may include a plurality of second moieties, the plurality of second moieties being mutually the same or different.

[Formula 3]

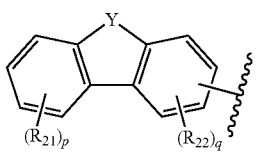

(1a)

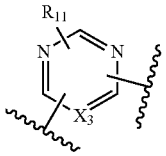

(1b)

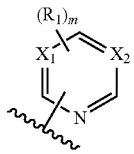

(1c)

(In the above formulae (1a), (1b) and (1c), $X_1$, $X_2$ and $X_3$ are mutually independently a nitrogen atom or a carbon atom ($CR_2$) bonded with $R_2$, Y is an oxygen atom, a sulfur atom or a silicon atom ($SiR_{31}R_{32}$) bonded with $R_{31}$ and $R_{32}$, $R_1$ and $R_2$ are each independently selected from the group consisting of a hydrogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted or unsubstituted silyl group, a cyano group and a halogen atom, $R_{11}$, $R_{21}$, $R_{22}$, $R_{31}$ and $R_{32}$ are each independently selected from the group consisting of a hydrogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted or unsubstituted silyl group, a cyano group and a halogen atom, m is an integer of 2 or more, the plurality of $R_1$ may be the same or different when m is 2, the plurality of $R_2$ may be the same or different, $R_1$ and $R_2$ may be bonded with each other to form a ring structure, p is an integer ranging from 0 to 4, a plurality of $R_{21}$ may be the same or different when p is an integer ranging from 2 to 4, the plurality of $R_{21}$ may be mutually bonded to form a ring structure, q is an integer ranging from 0 to 3, a plurality of $R_{22}$ may be the same or different when q is 2 or 3, and the plurality of $R_{22}$ may be bonded with each other to form a ring structure).

In the compound according to the exemplary embodiment, it is preferable that $R_1$ and $R_2$ are bonded to form a ring structure. In the above arrangement, it is preferable that $L_2$ in the first moiety represented by the above formula (10c) is bonded to a six-membered ring including $X_1$, $X_2$ and N in the first moiety in the parentheses parenthesized by a or, alternatively, it is preferable that $L_2$ is bonded with the ring structure formed by the bonded $R_1$ and $R_2$. The ring structure formed by the bonded $R_1$ and $R_2$ is preferably a five-membered ring or a six-membered ring, more preferably a six-membered ring.

In the compound according to the exemplary embodiment, it is also preferable that $R_1$ and $R_2$ are not bonded.

The compound of the exemplary embodiment is preferably represented by a formula (100) below.

[Formula 4]

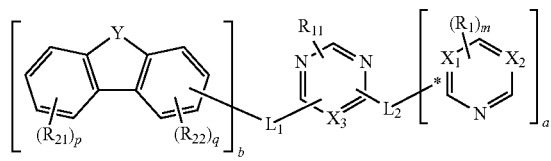

(100)

(In the above formula (100), $X_1$, $X_2$ and $X_3$ are mutually independently a nitrogen atom or a carbon atom ($CR_2$) bonded with $R_2$, Y is an oxygen atom, a sulfur atom or a silicon atom ($SiR_{31}R_{32}$) bonded with $R_{31}$ and $R_{32}$, $R_1$ and $R_2$ are each independently selected from the group consisting of a hydrogen atom, a substituted or unsubstituted alkyl group having 100 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted or unsubstituted silyl group, a cyano group and a halogen atom, $R_{11}$, $R_{21}$, $R_{22}$, $R_{31}$ and $R_{32}$ are each independently selected from the group consisting of a hydrogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted or unsubstituted silyl group, a cyano group and a halogen atom, $L_1$ is a single bond or a linking group, the linking group of $L_1$ is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted linear or branched hydrocarbon group having a carbon-carbon double bond and 2 to 30 carbon atoms and a substituted or unsubstituted linear or branched hydrocarbon group having a carbon-carbon triple bond and 2 to 30 carbon atoms, $L_2$ is a linking group selected from the group consisting of a substituted or unsubstituted aromatic hydrocarbon group having 6 to 30 ring carbon atoms, m is an integer of 2 or more, the plurality of $R_1$ may be the same or different, the plurality of $R_2$ may be the same or different, $R_1$ and $R_2$ may be bonded with each other to form a ring structure, p is an integer ranging from 0 to 4, a plurality of $R_{21}$ may be the same or different when p is an integer ranging from 2 to 4, the plurality of $R_{21}$ may be mutually bonded to form a ring structure, q is an integer ranging from 0 to 3, a plurality of $R_{22}$ may be the same or different when q is 2 or 3, a is an integer ranging from 1 to 5, the plurality of first moieties may be the same or different when the plurality of first moieties in the parentheses parenthesized by a are bonded to $L_2$, *represents a bonding site of the first moiety in the parentheses parenthesized by a with $L_2$, b is an integer ranging from 1 to 5, and a plurality of second moieties may be the same or different when the plurality of second moieties in the parentheses parenthesized by b are bonded to $L_1$).

The compound of the exemplary embodiment is preferably represented by a formula (1) below.

[Formula 5]

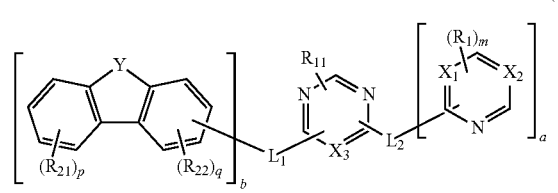

(1)

(In the above formula (1):

$X_1$, $X_2$ and $X_3$ are each independently a nitrogen atom, or a carbon atom ($CR_2$) bonded with $R_2$, Y is an oxygen atom, a sulfur atom, or a silicon atom ($SiR_{31}R_{32}$) bonded with $R_{31}$ and $R_{32}$, $R_1$ and $R_2$ are each independently selected from the group consisting of: a hydrogen atom, a substituted or unsubstituted alkyl group having 1 to 30 carbon atoms; a substituted or unsubstituted alkenyl group having 2 to 30 carbon atoms; a substituted or unsubstituted alkynyl group having 2 to 30 carbon atoms; a substituted or unsubstituted aryl group having 6 to 30 ring carbon atoms; a substituted or unsubstituted alkoxy group having 1 to 30 carbon atoms; a substituted or unsubstituted aryloxy group having 6 to 30 ring carbon atoms; a substituted or unsubstituted alkylthio group having 1 to 30 carbon atoms; a substituted or unsubstituted arylthio group having 6 to 30 ring carbon atoms; a substituted or unsubstituted silyl group; a cyano group; and a halogen atom, $R_{11}$, $R_{21}$, $R_{22}$, $R_{31}$ and $R_{32}$ are each independently selected from the group consisting of: a hydrogen atom; a substituted or unsubstituted alkyl group having 1 to 30 carbon atoms; a substituted or unsubstituted alkenyl group having 2 to 30 carbon atoms; a substituted or unsubstituted alkynyl group having 2 to 30 carbon atoms; a substituted or unsubstituted aryl group having 6 to 30 ring carbon atoms; a substituted or unsubstituted heterocyclic group having 5 to 30 ring atoms; and a substituted or unsubstituted alkoxy group having 1 to 30 carbon atoms; a substituted or unsubstituted aryloxy group having 6 to 30 ring carbon atoms; a substituted or unsubstituted alkylthio group having 1 to 30 carbon atoms; a substituted or unsubstituted arylthio group having 6 to 30 ring carbon atoms; a substituted or unsubstituted silyl group;

a cyano group; and a halogen atom, $L_1$ is a single bond or a linking group selected from the group consisting of: a substituted or unsubstituted aromatic hydrocarbon group having 6 to 30 ring carbon atoms; a substituted or unsubstituted heterocyclic group having 5 to 30 ring atoms; a substituted or unsubstituted linear or branched hydrocarbon group having a carbon-carbon double bond and 2 to 30 carbon atoms; and a substituted or unsubstituted linear or branched hydrocarbon group having a carbon-carbon triple bond and 2 to 30 carbon atoms, $L_2$ is a linking group selected from the group consisting of: a substituted or unsubstituted aromatic hydrocarbon group having 6 to 30 ring carbon atoms; m is an integer ranging from 0 to 2, a plurality of $R_1$ may be mutually the same or different when m is 2; a plurality of $R_2$ may be mutually the same or different; $R_1$ and $R_2$ may be bonded to form a ring structure; p is an integer ranging from 0 to 4, a plurality of $R_{21}$ may be mutually the same or different when p is an integer in a range from 2 to 4; the plurality of $R_{21}$ may be bonded to each other to form a ring structure; q is an integer ranging from 0 to 3, a plurality of $R_{22}$ may be mutually the same or different when q is 2 or 3; the plurality of $R_{22}$ may be bonded to each other to form a ring structure; a is an integer ranging from 1 to 5 and the plurality of first moieties in parentheses parenthesized by a may be mutually the same or different when the plurality of first moieties are bonded to $L_2$; and b is an integer ranging from 1 to 5 and the plurality of second moieties in parentheses parenthesized by b may be mutually the same or different when the plurality of second moieties are bonded to $L_1$.

It should be noted that $R_1$ and $L_2$ are respectively bonded to different carbon atoms forming the six-membered ring of the first moiety, $R_{11}$, $L_1$ and $L_2$ are respectively bonded to different carbon atoms forming the six-membered ring of the third moiety, $R_{21}$ are respectively bonded to different carbon atoms forming the six-membered ring of the second moiety, and $R_{22}$ and $L_2$ are bonded to respectively different carbon atoms forming the six-membered ring of the second moiety, the six-membered ring bonded with $R_{21}$ being different from the six-membered ring bonded with $R_{22}$.

It is preferable that a and b are each independently an integer ranging from 1 to 3, more preferably 1 or 2, further more preferably 1. This is because the molecular weight of the compound becomes appropriate, so that processability during sublimation purification or film-formation process is improved.

Moreover, in the exemplary embodiment, it is also preferable that a is 1 and b is 2. In this case, the compound according to the exemplary embodiment is represented by a formula (1A) below.

[Formula 6]

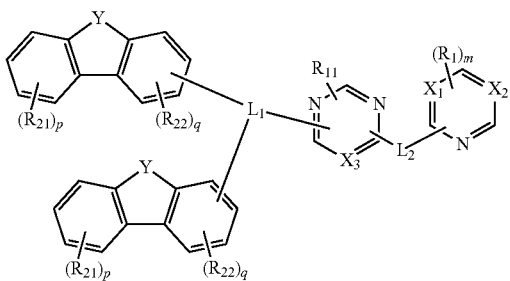

(1A)

In the above formula (1A), $X_1$, $X_2$, $X_3$, Y, $R_1$, $R_2$, $R_{11}$, $R_{21}$, $R_{22}$, $R_{31}$, $R_{32}$, $L_1$, $L_2$, m, p and q respectively are the same as $X_1$, $X_2$, $X_3$, Y, $R_1$, $R_2$, $R_{11}$, $R_{21}$, $R_{22}$, $R_{31}$, $R_{32}$, $L_1$, $L_2$, m, p and q in the above formula (1), the two Y being the same or different.

$L_2$ is preferably selected from the group consisting of a substituted or unsubstituted aromatic hydrocarbon groups having 6 to 18 ring carbon atoms, more preferably from the group consisting of substituted or unsubstituted phenylene group, substituted or unsubstituted naphthylene group and substituted or unsubstituted biphenyldiyl group. $L_2$ is further more preferably substituted or unsubstituted phenylene group. It should be noted that a phenylene group having a substituent herein (e.g. "substituted phenylene group") means that the phenylene group includes a bond to be bonded with the substituent in addition to two bonds. The same applies to the other divalent group having a substituent (s).

$R_{11}$, $R_{21}$, $R_{22}$, $R_{31}$ and $R_{32}$ are preferably each independently selected from the group consisting of a hydrogen atom, a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted silyl group, a cyano group and a halogen atom.

$R_{11}$ is preferably a substituted or unsubstituted aromatic hydrocarbon group having 6 to 30 ring carbon atoms, more preferably a substituted or unsubstituted aromatic hydrocarbon group having 6 to 18 ring carbon atoms.

Further, $R_{11}$ is preferably a group selected from the group consisting of a substituted or unsubstituted phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group. More preferably, $R_{11}$ is a substituted or unsubstituted phenyl group.

$X_1$ and $X_2$ are each preferably a carbon atom bonded with $R_2$, the two $R_2$ being the same or different.

$X_3$ is preferably a carbon atom bonded with $R_2$.

$X_3$ is also preferably a nitrogen atom.

It is preferable that the plurality of $R_1$ are each independently a substituted or unsubstituted aromatic hydrocarbon group having 6 to 30 ring carbon atoms. It is also preferable that m is 0.

Y is preferably an oxygen atom or a sulfur atom.

$L_1$ is preferably a substituted or unsubstituted aromatic hydrocarbon groups having 6 to 30 ring carbon atoms, more preferably a substituted or unsubstituted aromatic hydrocarbon group having 6 to 18 ring carbon atoms, further preferably selected from the group consisting of a substituted or unsubstituted phenylene group, a substituted or unsubstituted naphthylene group and a substituted or unsubstituted biphenyldiyl group. L1 is further more preferably a substituted or unsubstituted phenylene group.

The compound of the exemplary embodiment is also preferably represented by a formula (10) below.

[Formula 7]

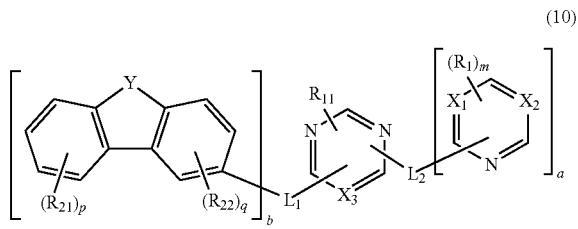

(10)

In the above formula (10), $X_1$, $X_2$, $X_3$, Y, $R_1$, $R_2$, $R_{11}$, $R_{21}$, $R_{22}$, $R_{31}$, $R_{32}$, $L_1$, $L_2$, m, p, q, a and b respectively are the same as $X_1$, $X_2$, $X_3$, Y, $R_1$, $R_2$, $R_{11}$, $R_{21}$, $R_{22}$, $R_{31}$, $R_{32}$, $L_1$, $L_2$, m, p, q, a and b in the above formula (1).

The compound of the exemplary embodiment is also preferably represented by a formula (11) below.

[Formula 8]

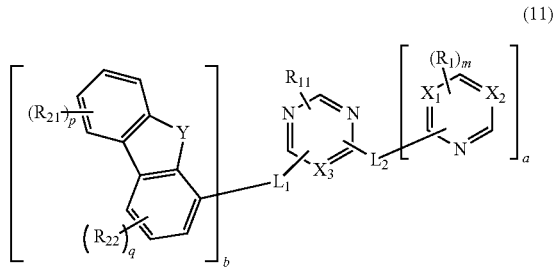

(11)

In the above formula (11), $X_1$, $X_2$, $X_3$, Y, $R_1$, $R_2$, $R_{11}$, $R_{21}$, $R_{22}$, $R_{31}$, $R_{32}$, $L_1$, $L_2$, m, p, q, a and b respectively are the same as $X_1$, $X_2$, $X_3$, Y, $R_1$, $R_2$, $R_{11}$, $R_{21}$, $R_{22}$, $R_{31}$, $R_{32}$, $L_1$, $L_2$, m, p, q, a and b in the above formula (1).

The compound of the exemplary embodiment is also preferably represented by a formula (1B) below.

[Formula 9]

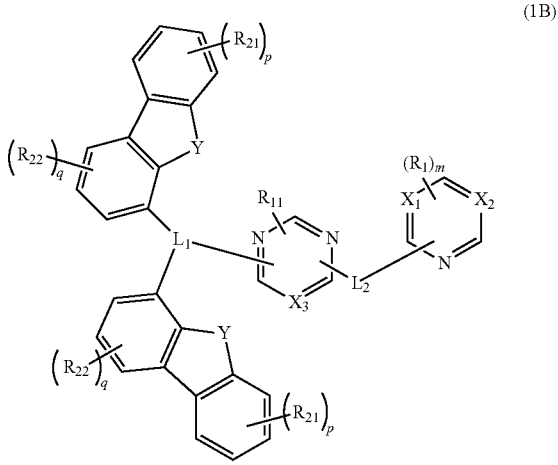

(1B)

In the above formula (1B), $X_1$, $X_2$, $X_3$, Y, $R_1$, $R_2$, $R_{11}$, $R_{21}$, $R_{22}$, $R_{31}$, $R_{32}$, $L_1$, $L_2$, p and q respectively are the same as $X_1$, $X_2$, $X_3$, Y, $R_1$, $R_2$, $R_{11}$, $R_{21}$, $R_{22}$, $R_{31}$, $R_{32}$, $L_1$, $L_2$, m, p and q in the above formula (1), the two Y being the same or different.

The compound of the exemplary embodiment is also preferably represented by a formula (1C) below.

[Formula 10]

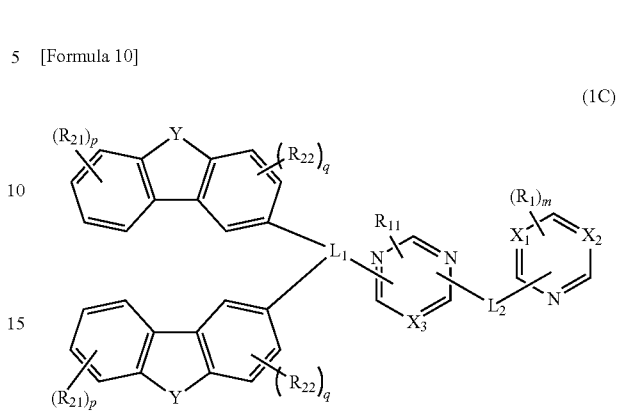

(1C)

In the above formula (1C), $X_1$, $X_2$, $X_3$, Y, $R_1$, $R_2$, $R_{11}$, $R_{21}$, $R_{22}$, $R_{31}$, $R_{32}$, $L_1$, $L_2$, m, p and q respectively are the same as $X_1$, $X_2$, $X_3$, Y, $R_1$, $R_2$, $R_{11}$, $R_{21}$, $R_{22}$, $R_{31}$, $R_{32}$, $L_1$, $L_2$, m, p and q in the above formula (1), the two Y being the same or different.

When $R_1$ or $R_2$ is a substituent, the substituent is preferably selected from the group consisting of an unsubstituted alkyl group having 1 to 30 carbon atoms, an unsubstituted alkenyl group having 2 to 30 carbon atoms, an unsubstituted alkynyl group having 2 to 30 carbon atoms, an unsubstituted aromatic hydrocarbon group having 6 to 30 ring carbon atoms, an unsubstituted alkoxy group having 1 to 30 carbon atoms, an unsubstituted aryloxy group having 6 to 30 ring carbon atoms, an unsubstituted alkylthio group having 1 to 30 carbon atoms, an unsubstituted arylthio group having 6 to 30 ring carbon atoms, an unsubstituted silyl group, a cyano group and a halogen atom.

$R_1$ and $R_2$ are preferably each independently selected from the group consisting of a hydrogen atom, a substituted or unsubstituted alkyl group having 1 to 30 carbon atoms, a substituted or unsubstituted aryl group having 6 to 30 ring carbon atoms, a substituted or unsubstituted silyl group, a cyano group and a halogen atom.

In the compound according to the exemplary embodiment, Y is preferably an oxygen atom or a sulfur atom, $L_1$ and $L_2$ are each independently preferably selected from the group consisting of a substituted or unsubstituted phenylene group, a substituted or unsubstituted naphthylene group and a substituted or unsubstituted biphenyldiyl group, $R_{11}$ is preferably selected from the group consisting of a phenyl group, a biphenyl group, a terphenyl group, a naphthyl group, an anthryl group, a phenanthryl group, a fluorenyl group, a pyrenyl group, a chrysenyl group, a fluoranthenyl group, a benzo[a]anthryl group, a benzo[c]phenanthryl group, a triphenylenyl group, a benzo[k]fluoranthenyl group, a benzo[g]chrysenyl group, a benzo[b]triphenylenyl group, a picenyl group and a perylenyl group, $R_{21}$ and $R_{22}$ are each independently preferably selected from the group consisting of a hydrogen atom, a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring carbon atoms, a substituted or unsubstituted silyl group, a cyano group and a halogen atom, and $R_1$ and $R_2$ are each independently preferably selected from the group consisting of a hydrogen atom, a substituted or unsubstituted alkyl group having 1 to 30 carbon atoms, a substituted or unsubstituted aryl group having 6 to 30 ring carbon atoms, a substituted or unsubstituted silyl group, a cyano group and a halogen atom.

When $R_1$ has a substituent, the substituent is preferably selected from the group consisting of an alkyl group having 1 to 30 carbon atoms, an aryl group having 6 to 30 ring carbon atoms, an alkoxy group having 1 to 30 carbon atoms, an aryloxy group having 6 to 30 ring carbon atoms, an alkylthio group having 1 to 30 carbon atoms, an arylthio group having 6 to 30 ring carbon atoms, an alkylsilyl group having 3 to 30 carbon atoms, an arylsilyl group having 6 to 30 ring carbon atoms, a cyano group and a halogen atom.

When $R_2$ has a substituent, the substituent is preferably selected from the group consisting of an alkyl group having 1 to 30 carbon atoms, an aryl group having 6 to 30 ring carbon atoms, an alkoxy group having 1 to 30 carbon atoms, an aryloxy group having 6 to 30 ring carbon atoms, an alkylthio group having 1 to 30 carbon atoms, an arylthio group having 6 to 30 ring carbon atoms, an alkylsilyl group having 3 to 30 carbon atoms, an arylsilyl group having 6 to 30 ring carbon atoms, a cyano group and a halogen atom.

The first moiety represented by a formula (100c) below in the compound represented by the formula (100) according to the exemplary embodiment is also preferably represented by a formula (100c-1) or a formula (100c-2) below.

[Formula 11]

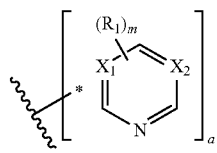

(100c)

[Formula 12]

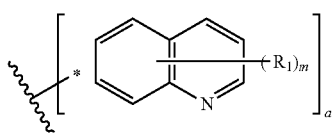

(100c-1)

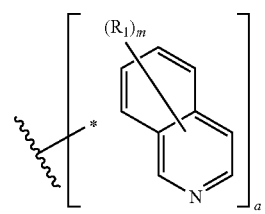

(100c-2)

In the formulae (100c-1) and (100c-2), $R_1$, m and a are respectively the same as $R_1$, m and a in the formula (100), a plurality of $R_1$ being optionally bonded to form a ring structure. In the above formulae (100c-1) and (100c-2), m is preferably 6. It is also preferable in the above formulae (100c-1) and (100c-2) that $R_1$ is a hydrogen atom.

The first moiety of the compound according to the exemplary embodiment is preferably selected from the group consisting of monocyclic structures represented by formulae (10c-1) to (10c-7) below and fused ring structures represented by formulae (10c-8) to (10c-27) below.

[Formula 13]

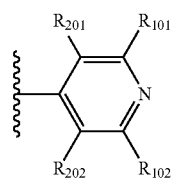

(10c-1)

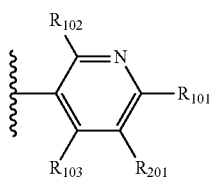

(10c-2)

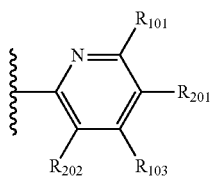

(10c-3)

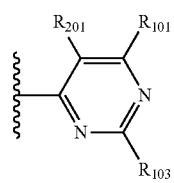

(10c-4)

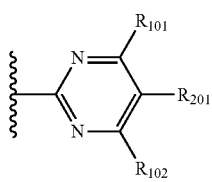

(10c-5)

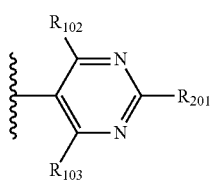

(10c-6)

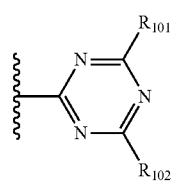

(10c-7)

[Formula 14]

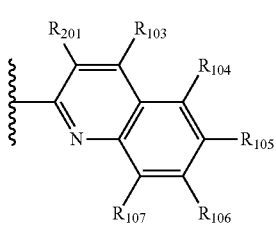

(10c-8)

-continued
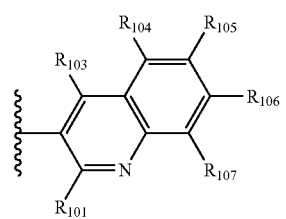
(10c-9)
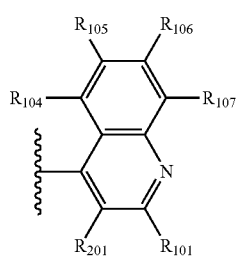
(10c-10)
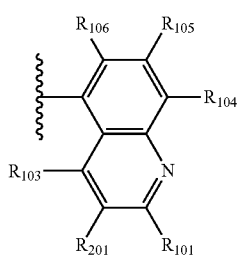
(10c-11)
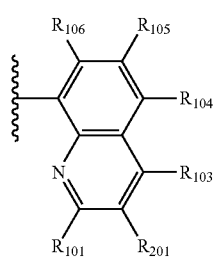
(10c-12)
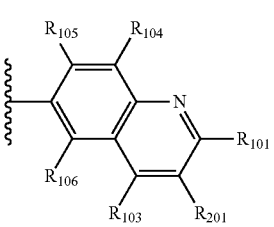
(10c-13)
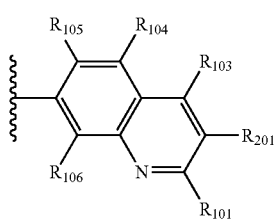
(10c-14)
[Formula 15]
-continued
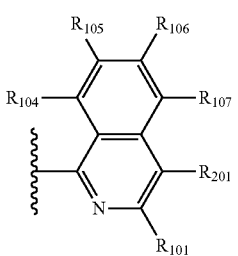
(10c-15)
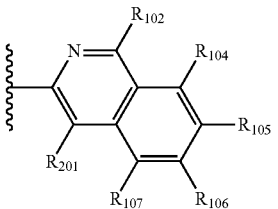
(10c-16)
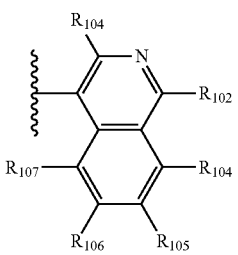
(10c-17)
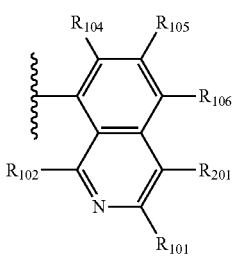
(10c-18)
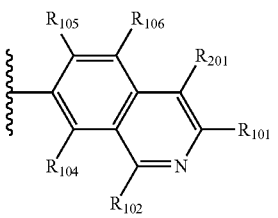
(10c-19)
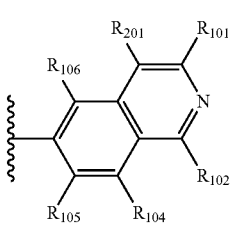
(10c-20)

(10c-21)
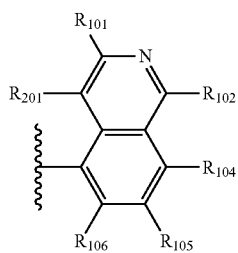

[Formula 16]

(10c-22)
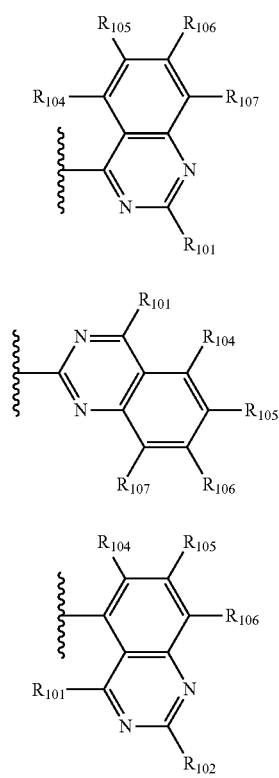

(10c-23)

(10c-24)

(10c-25)

(10c-26)

(10c-27)
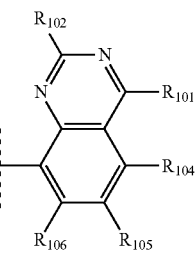

In the formulae (10c-1) to (10c-27), $R_{101}$ to $R_{107}$ and $R_{201}$ to $R_{202}$ each independently represent the same as $R_1$ and $R_2$ of the formula (100). Two or more groups among $R_{101}$ to $R_{107}$ and $R_{201}$ to $R_{202}$ may be mutually bonded to form a ring structure.

In the exemplary embodiment, $R_{101}$ to $R_{107}$ and $R_{201}$ to $R_{202}$ are each independently preferably a hydrogen atom or a substituted or unsubstituted aromatic hydrocarbon group having 6 to 14 ring carbon atoms, more preferably a hydrogen atom or a substituted or unsubstituted aromatic hydrocarbon group having 6 to 10 ring carbon atoms. $R_{101}$ to $R_{107}$ and $R_{201}$ to $R_{202}$ are each further preferably a hydrogen atom.

Manufacturing Method of Compound of Exemplary Embodiment

The compound according to the exemplary embodiment can be manufactured according to the method described in the later-described Examples. The compound according to the exemplary embodiment can be synthesized according to the method described in the Examples and using known substitution reactions and materials in accordance with a target compound.

Examples of the compound of the exemplary embodiment are shown below. It should be noted that the compound in the exemplary embodiment is not limited thereto.

[Formula 17]

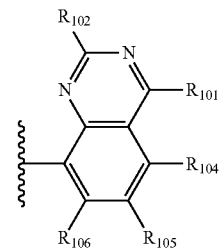

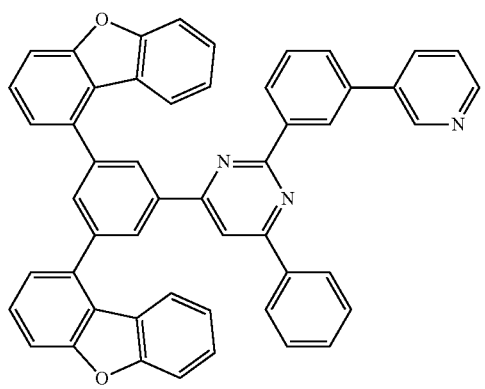
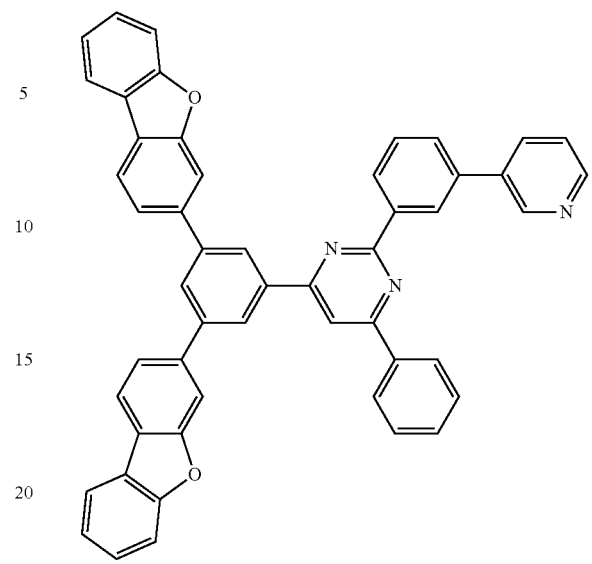
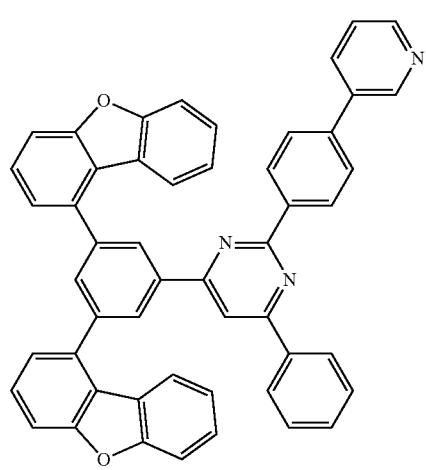
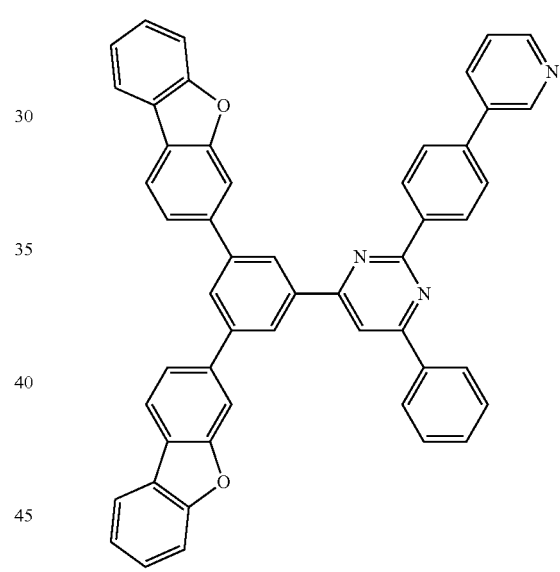
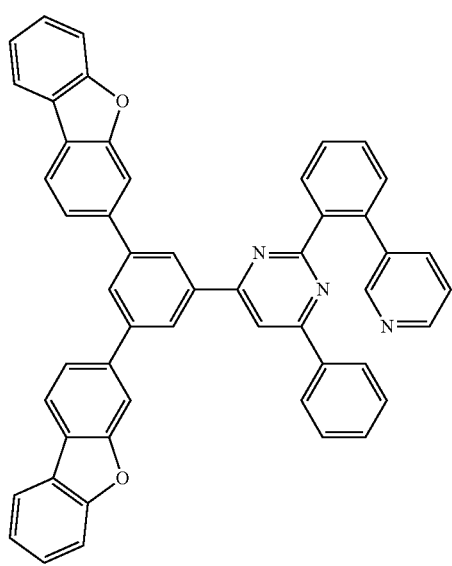
[Formula 18]
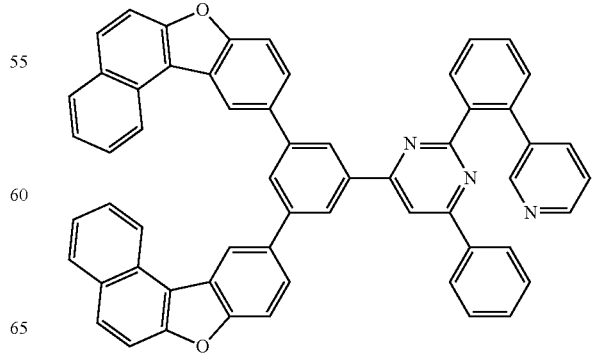

-continued
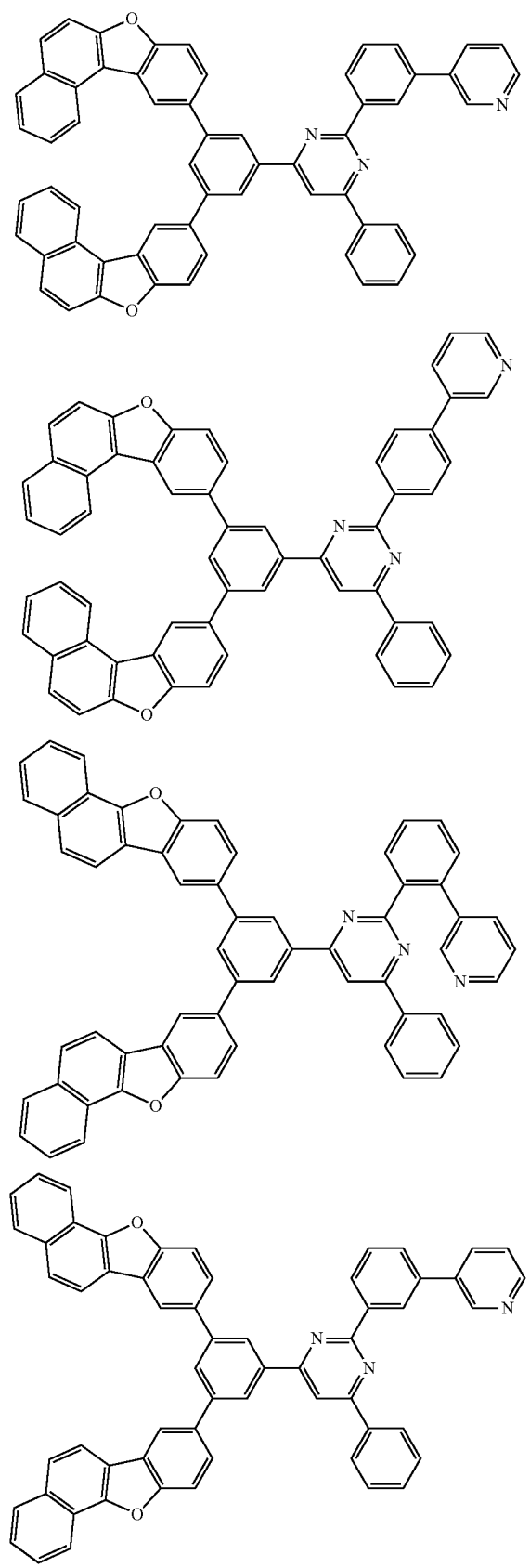
-continued
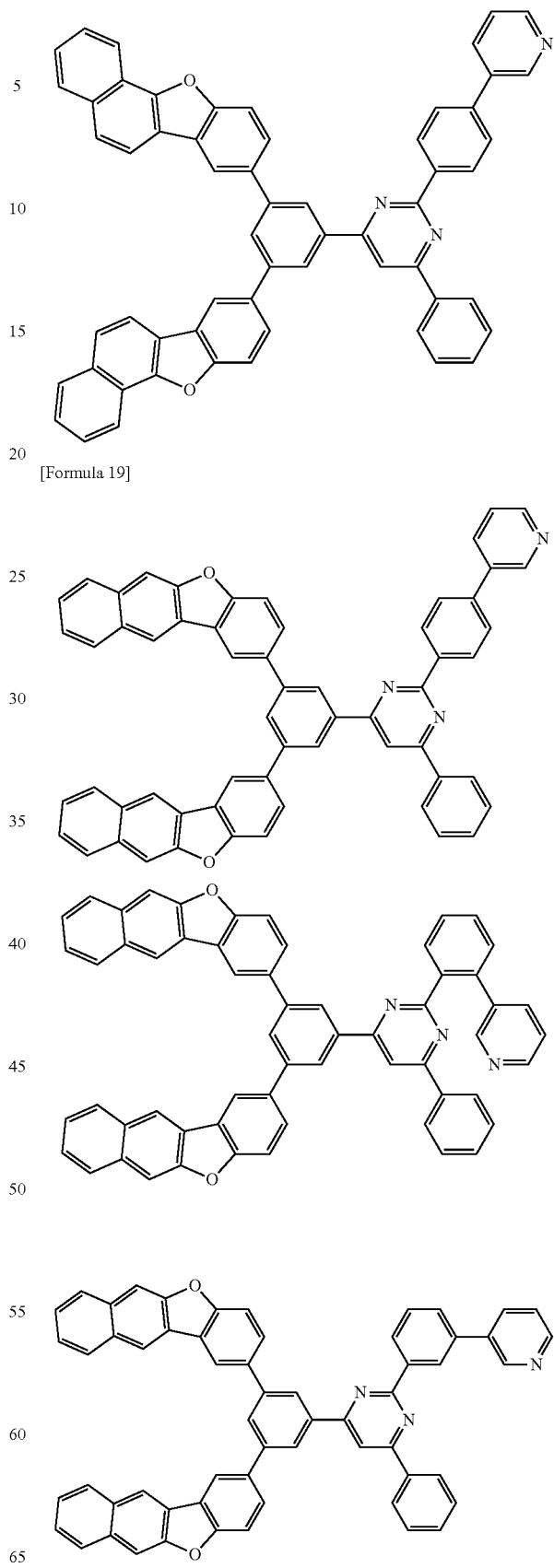
[Formula 19]

[Formula 20]
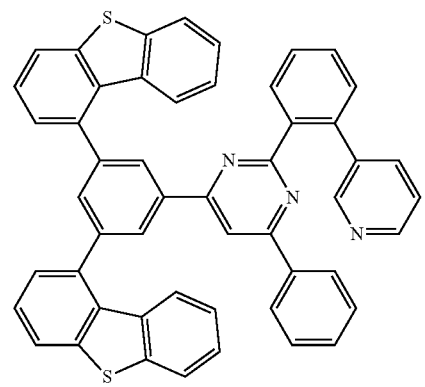
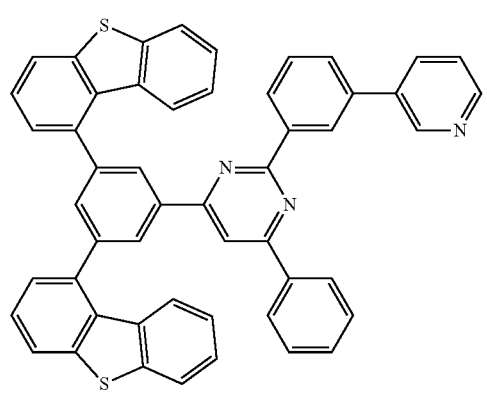
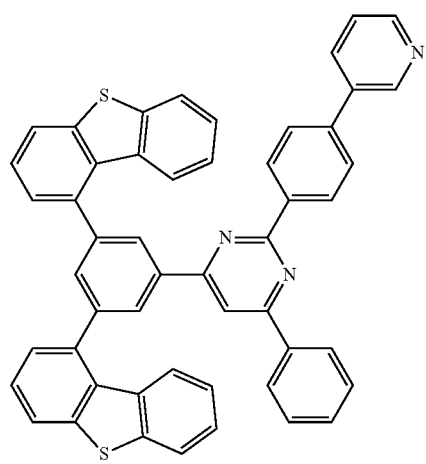
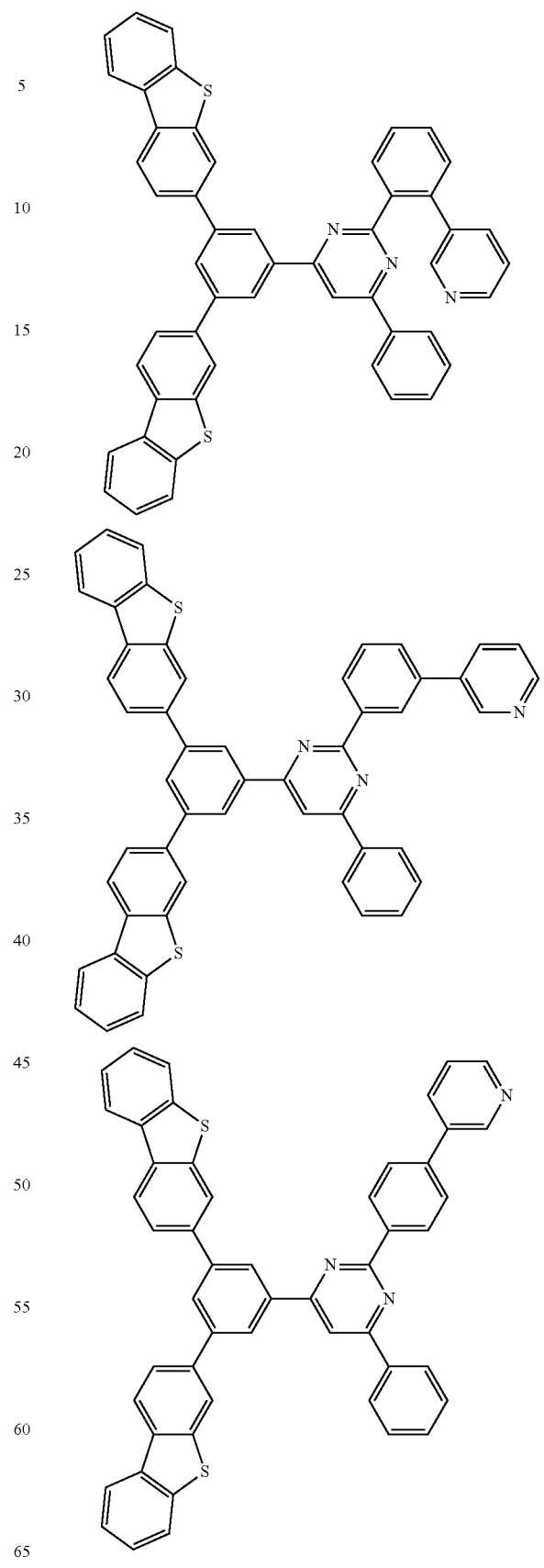

[Formula 21]
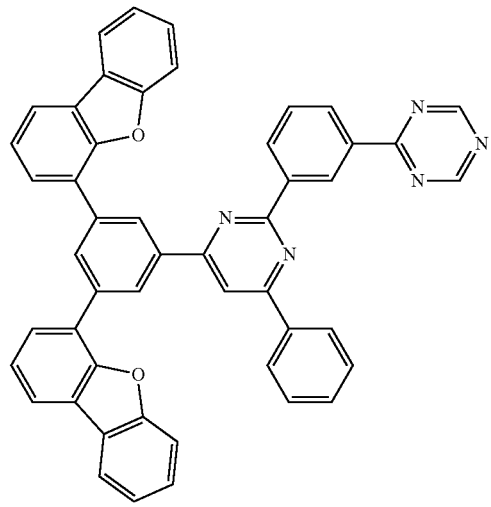
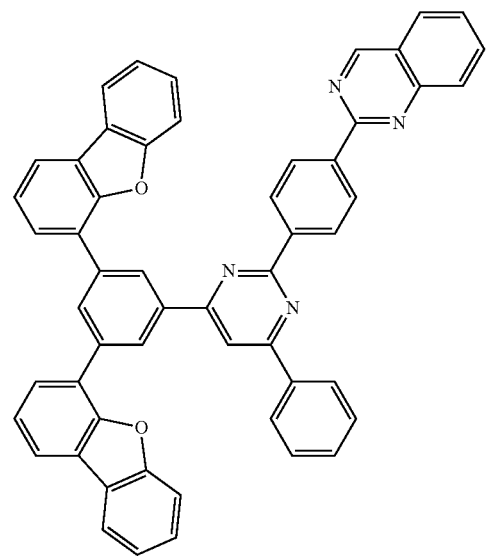
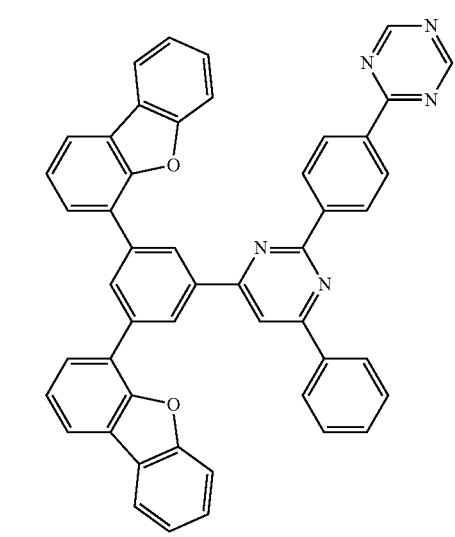
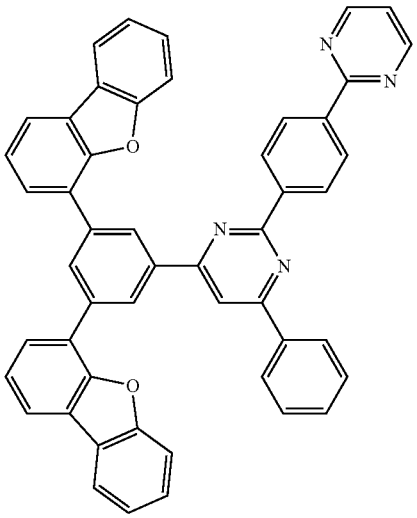
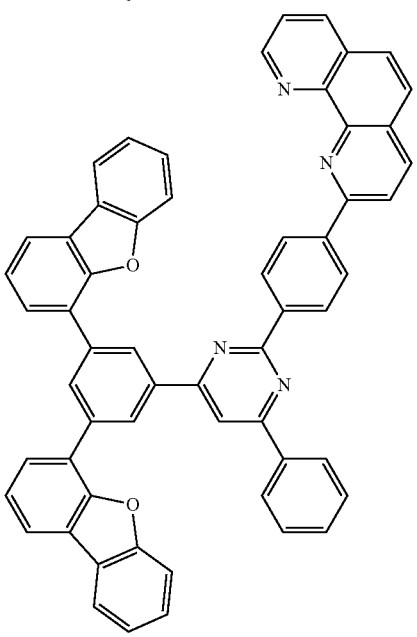
[Formula 22]
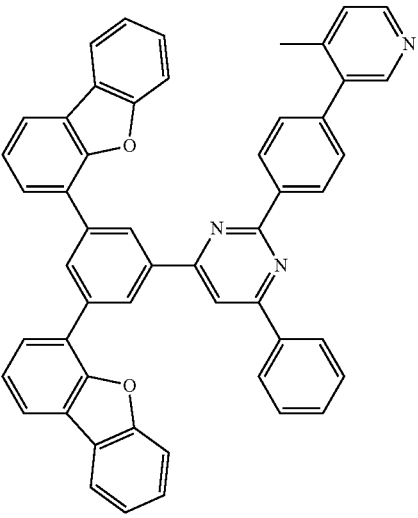

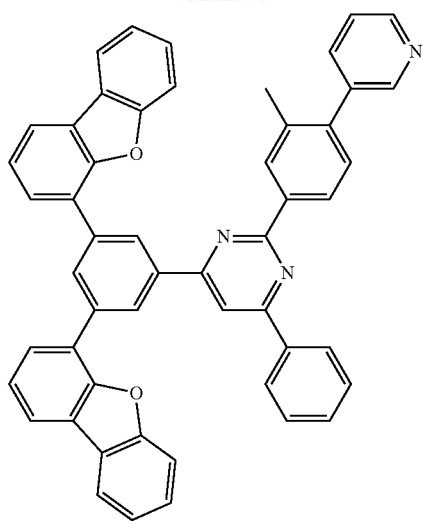
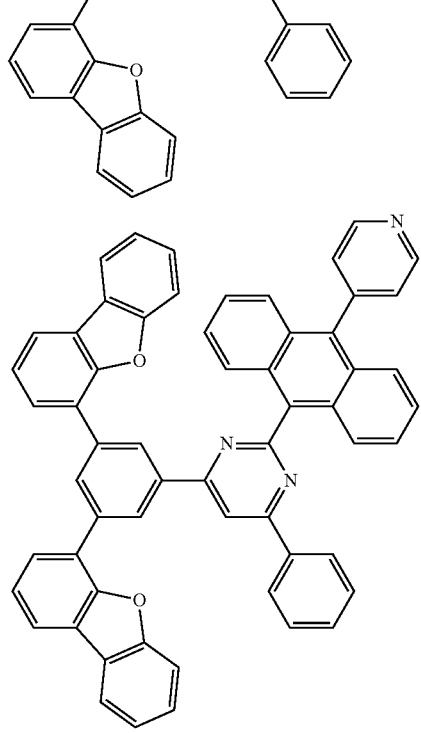
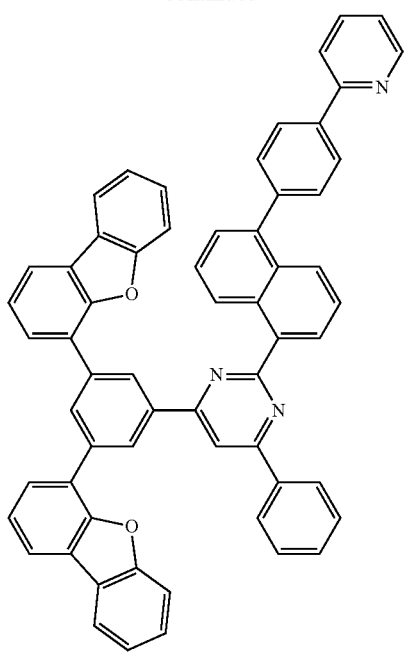
[Formula 23]
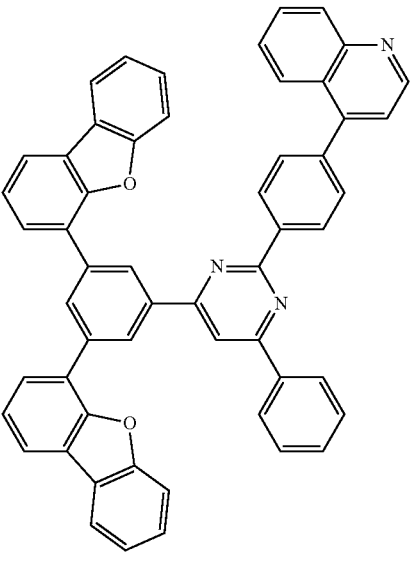

-continued
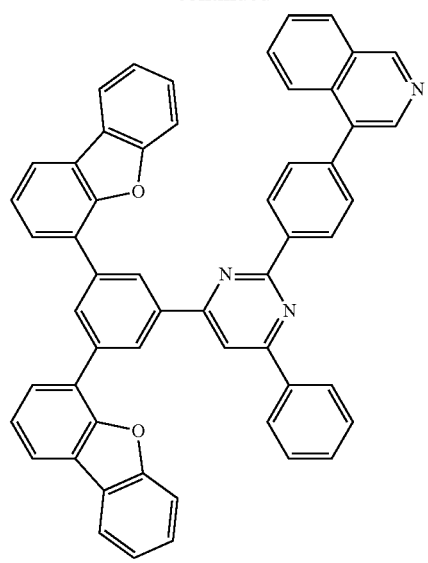
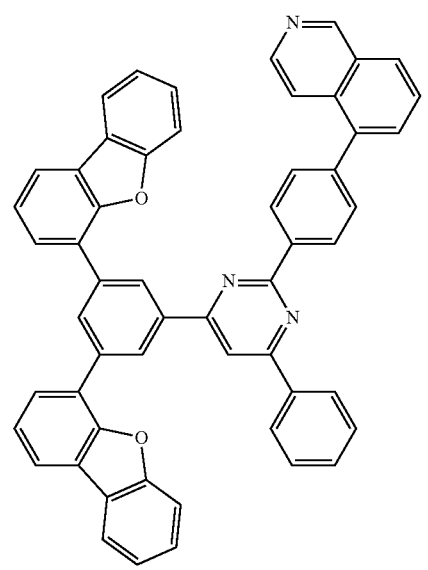
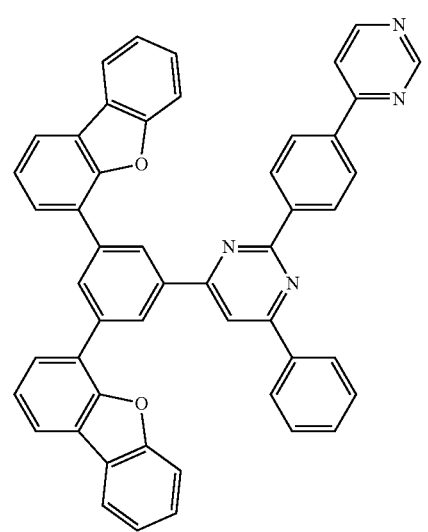
-continued
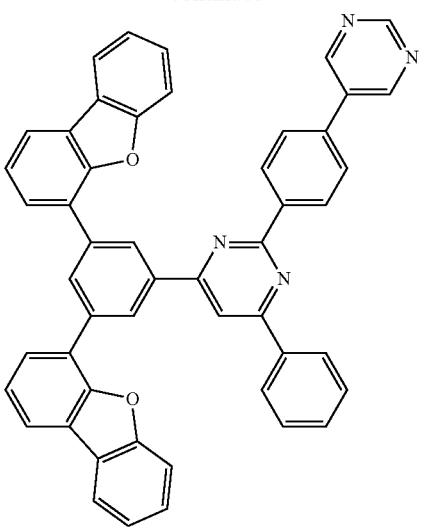
[Formula 24]
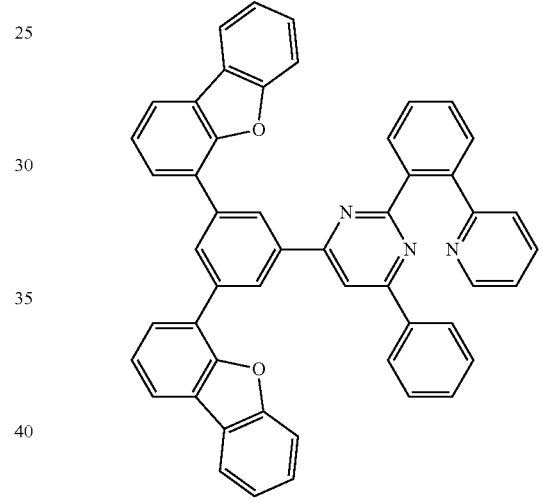
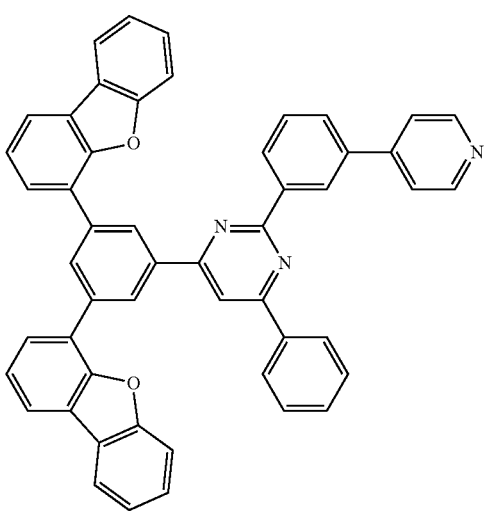

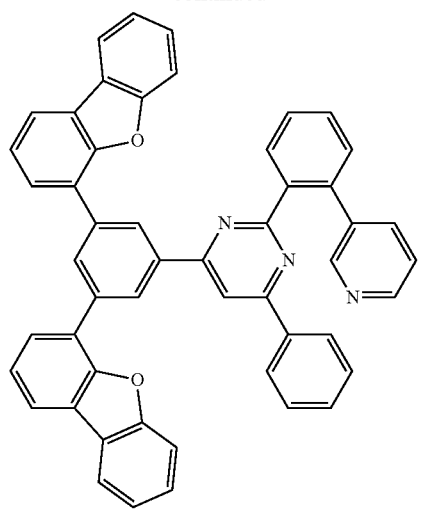
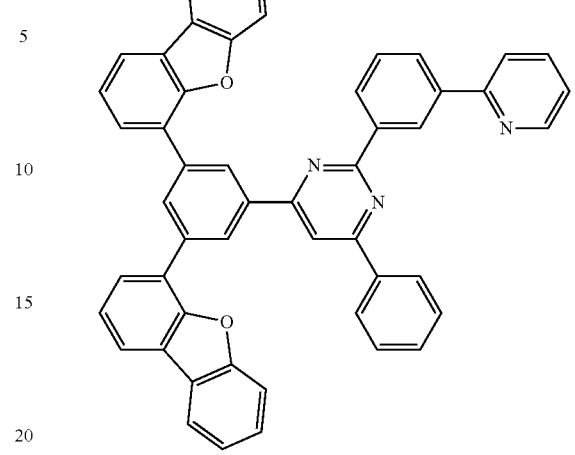
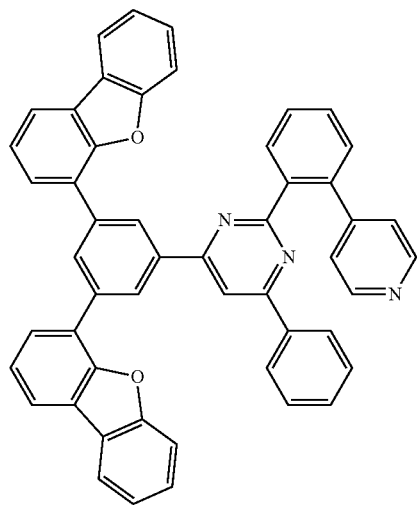
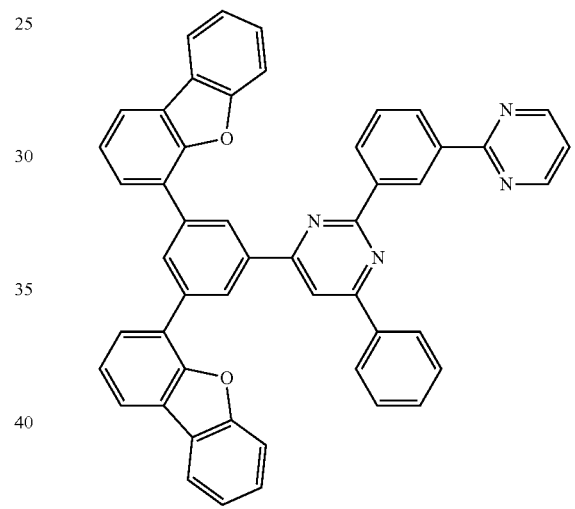
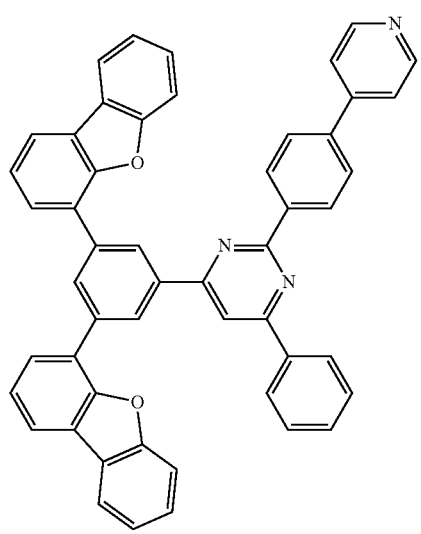
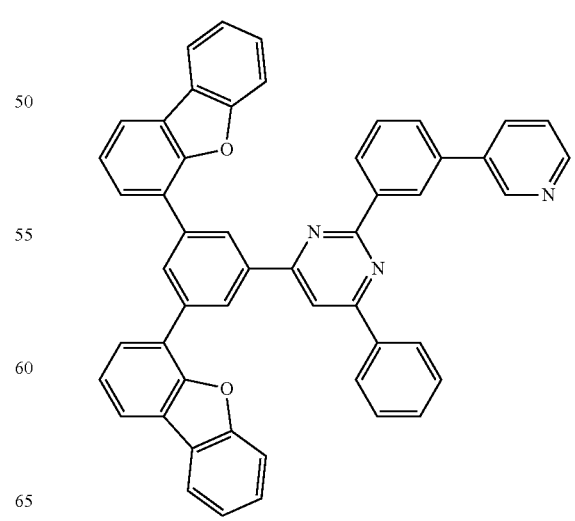

33
-continued
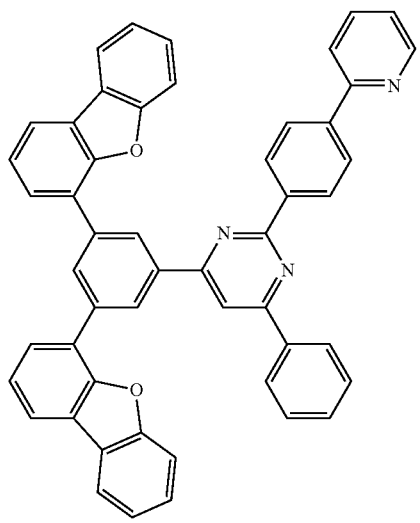
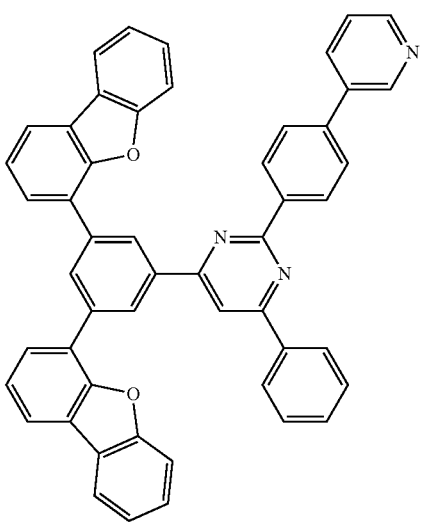
[Formula 25]
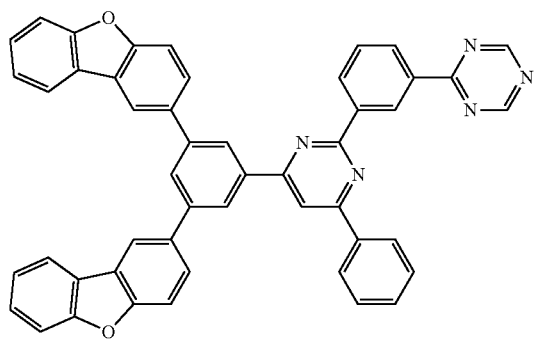
34
-continued
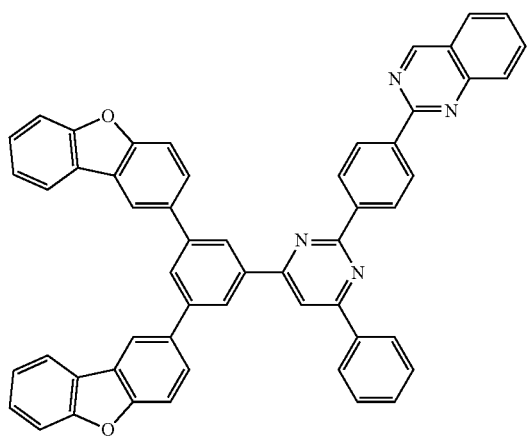
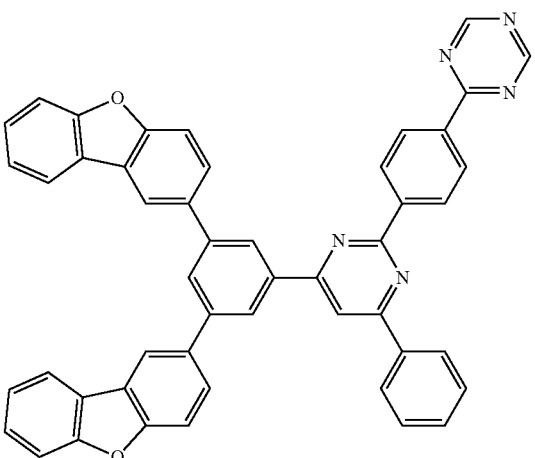
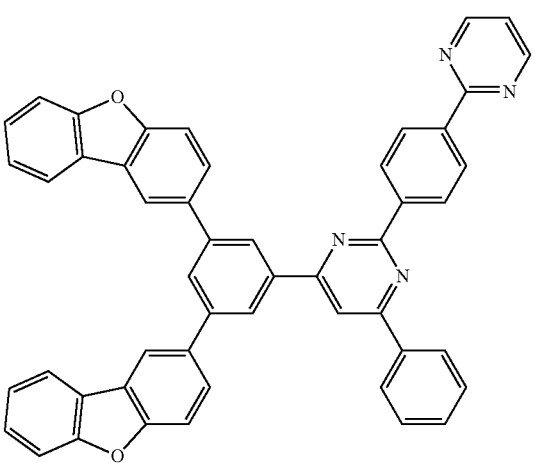

[Formula 26]
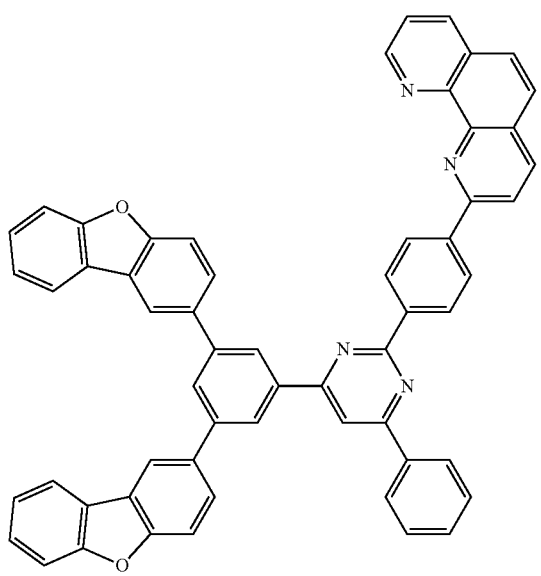
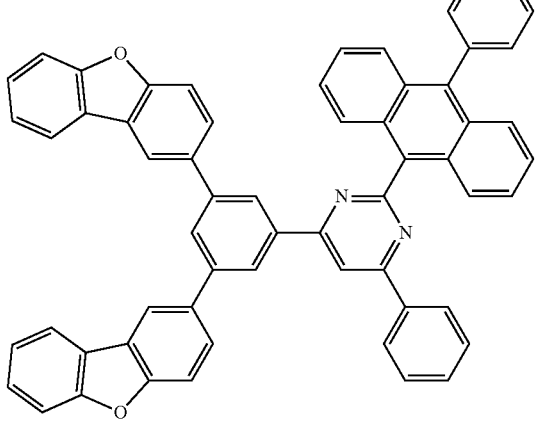
[Formula 27]
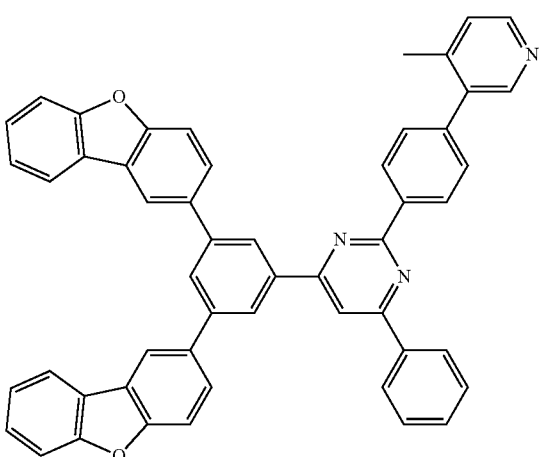
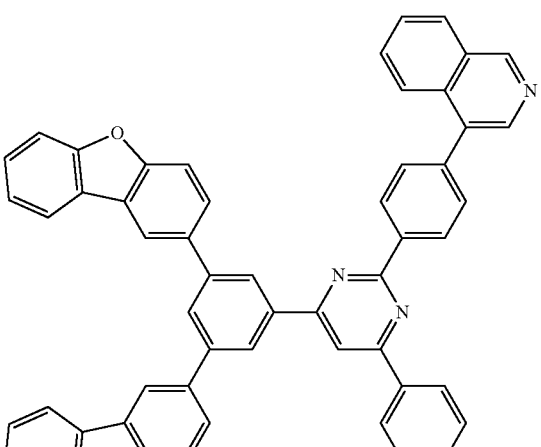
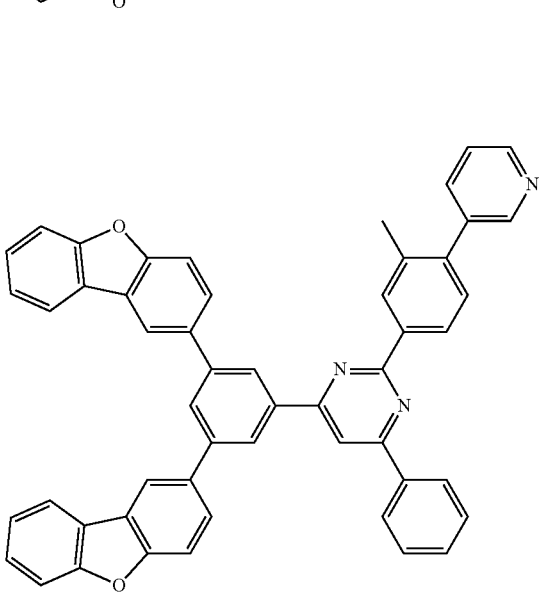
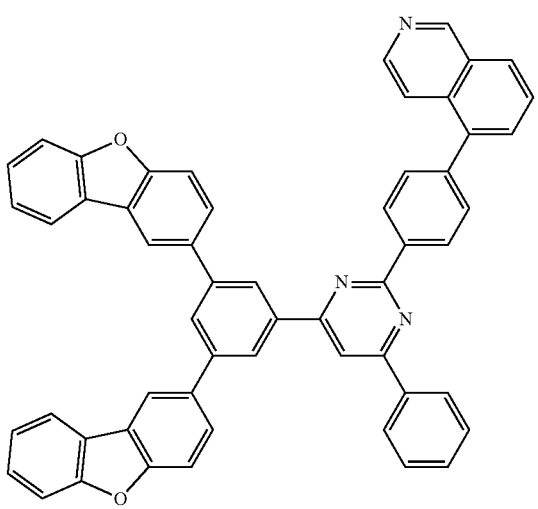

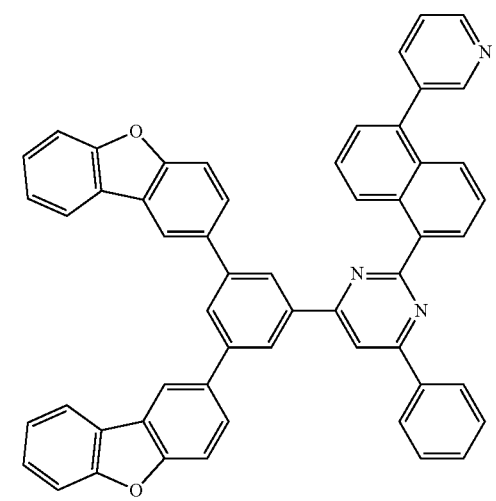
[Formula 28]
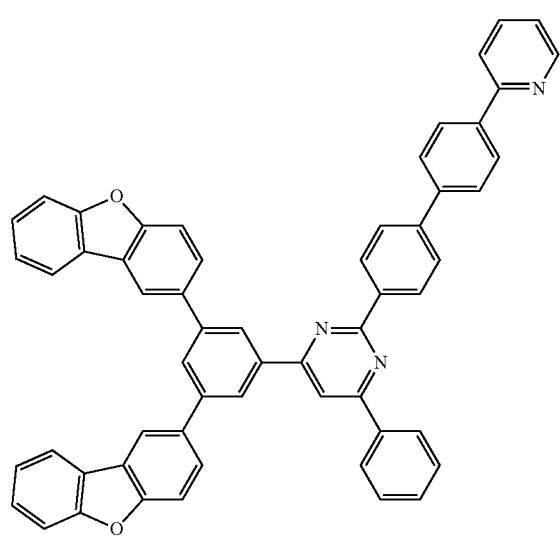
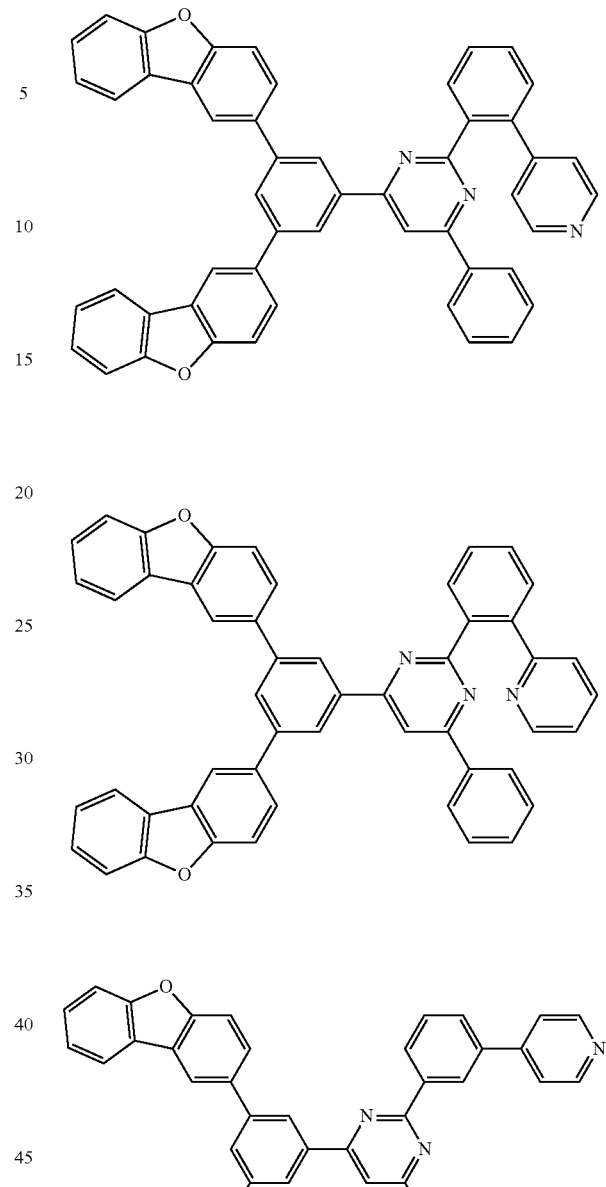
[Formula 29]
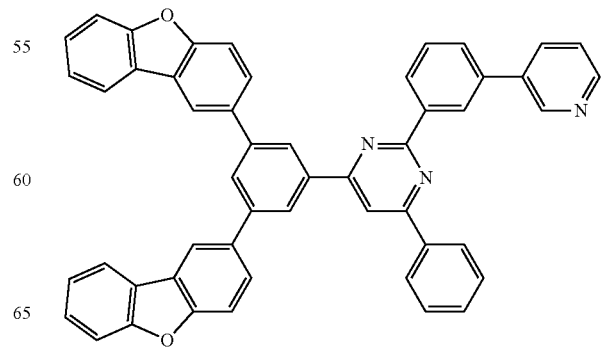

[Formula 30]
[Formula 31]
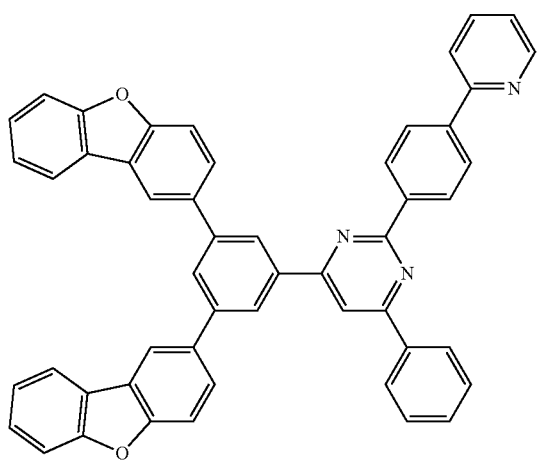
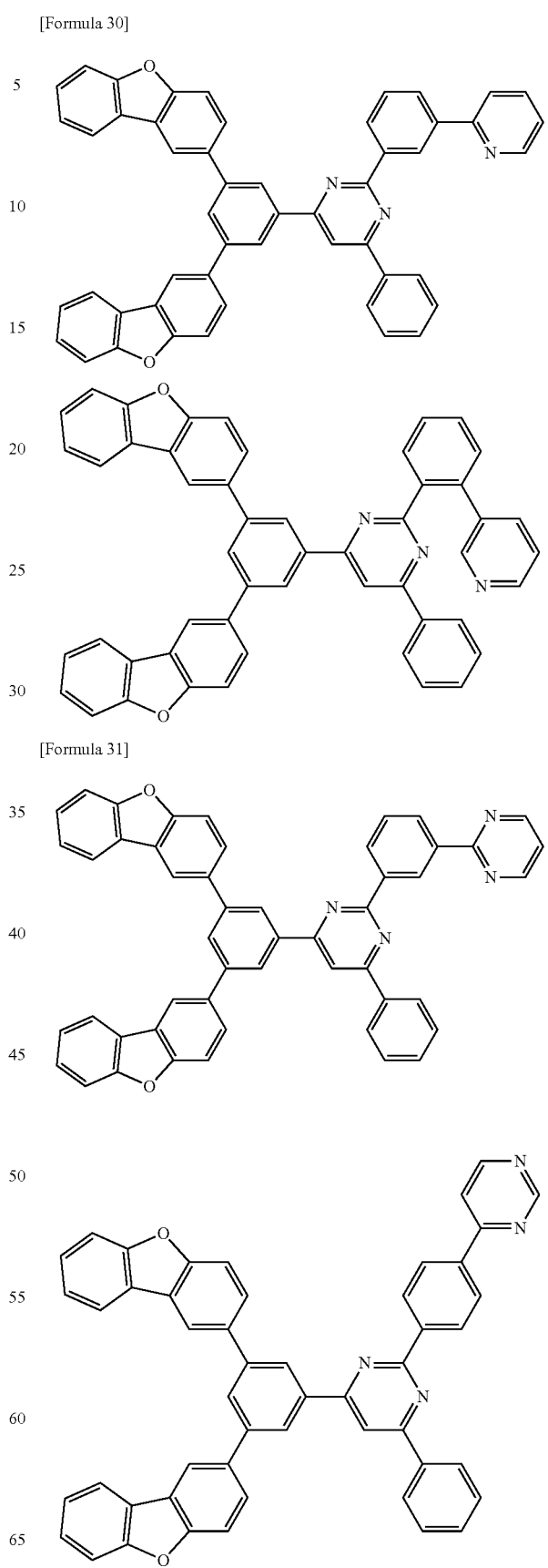

41
-continued
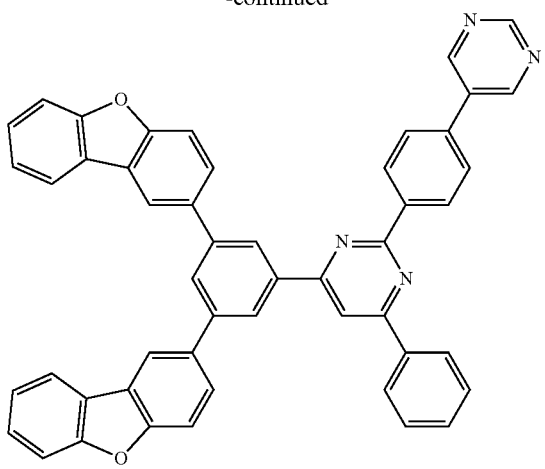
[Formula 32]
42
-continued
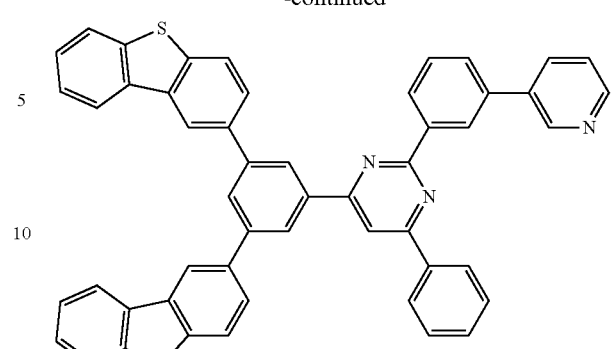
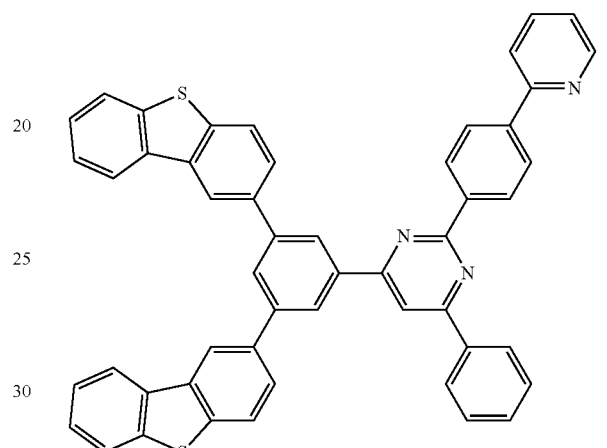
[Formula 33]
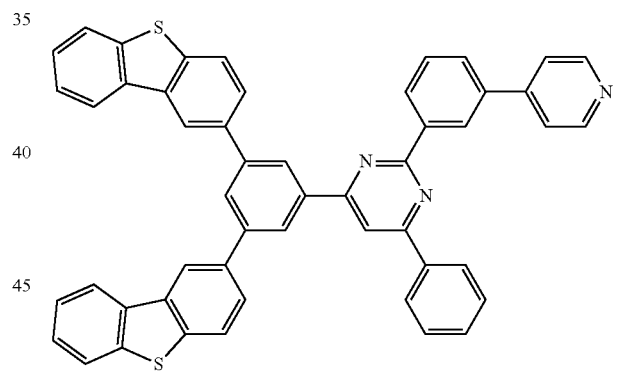
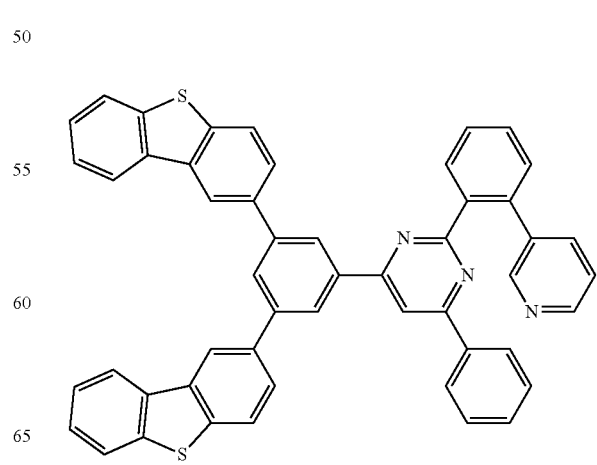

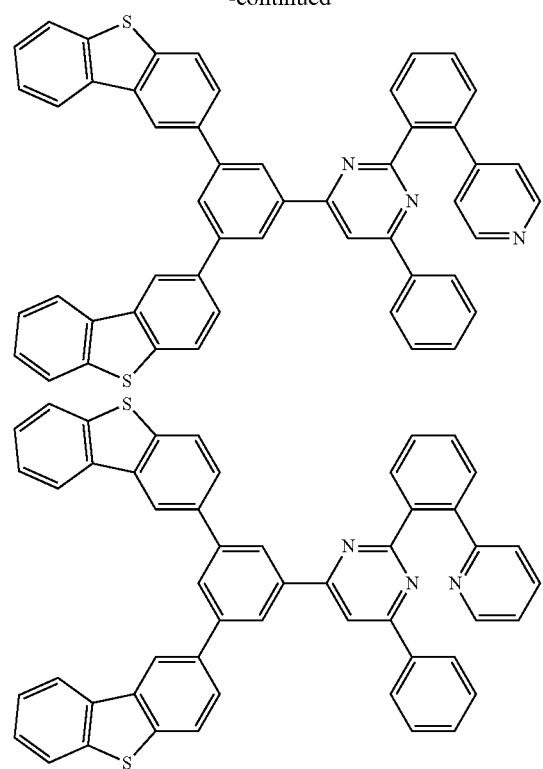
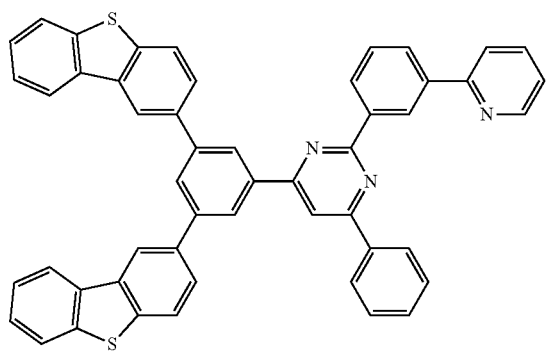
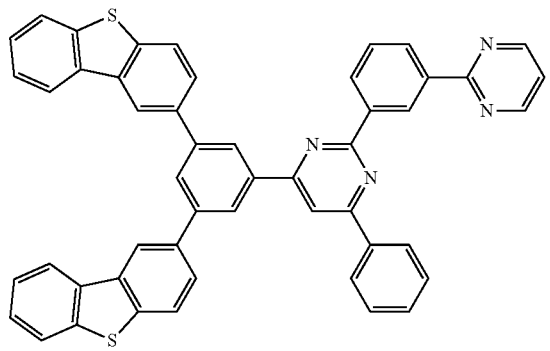
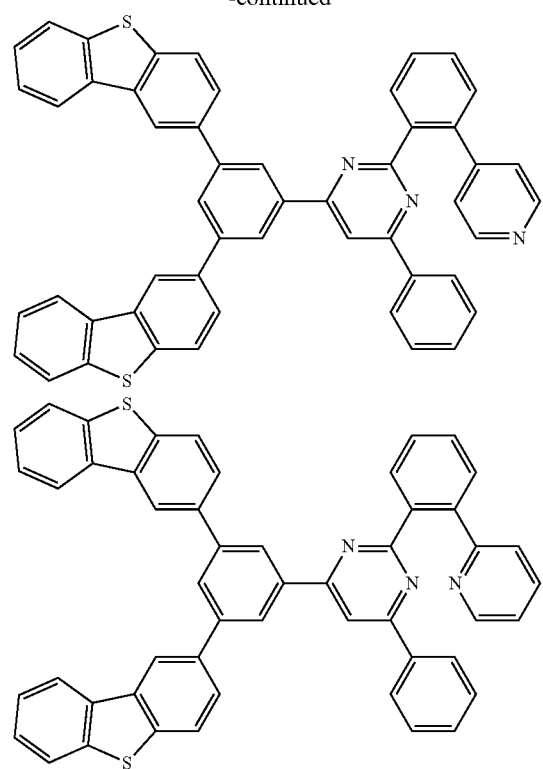
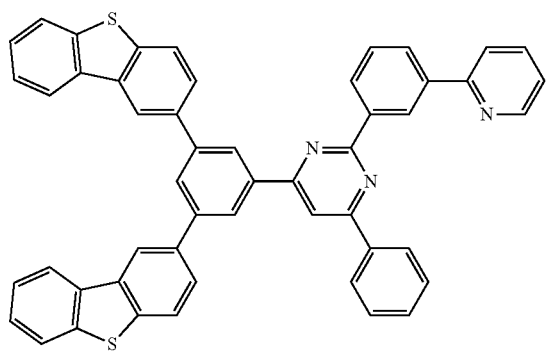
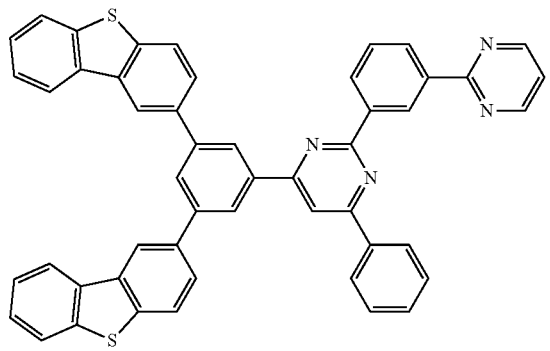
[Formula 34]
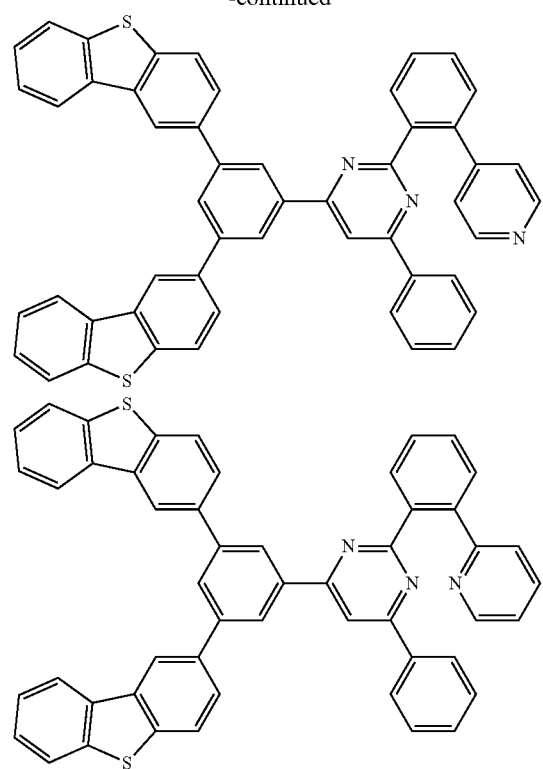

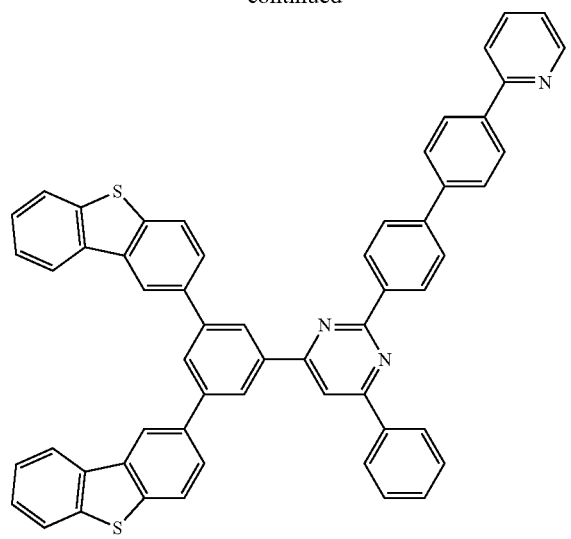
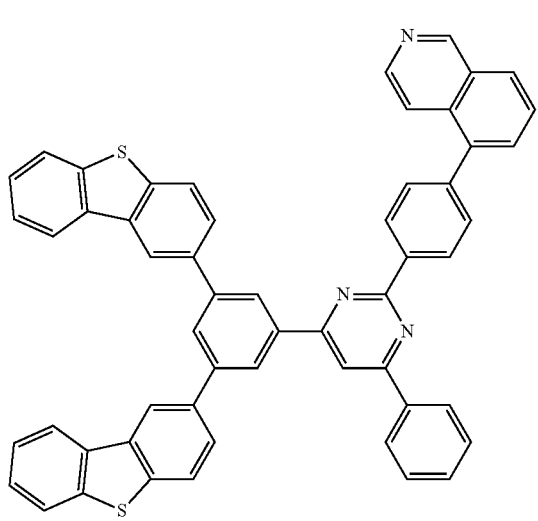
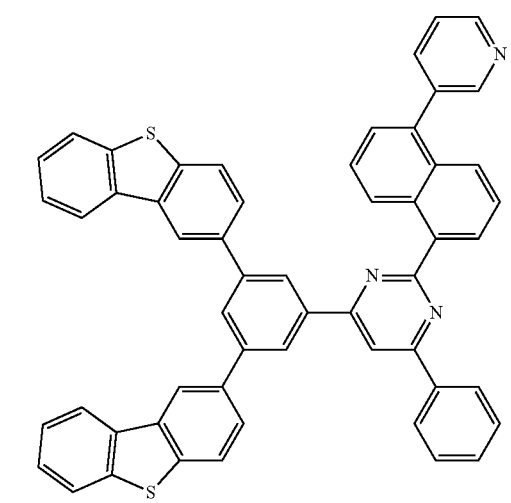
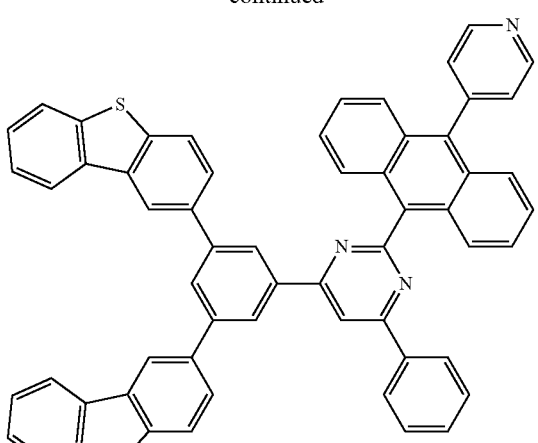
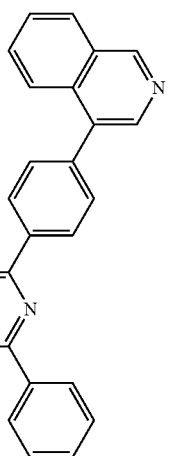
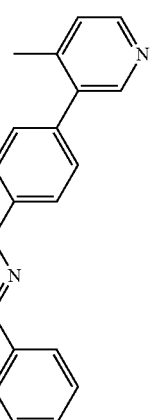

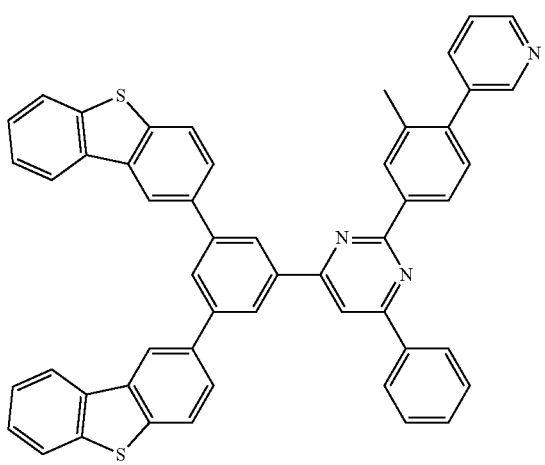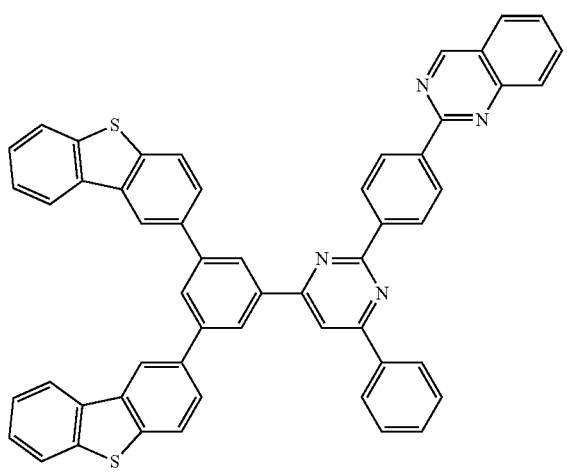
[Formula 35]
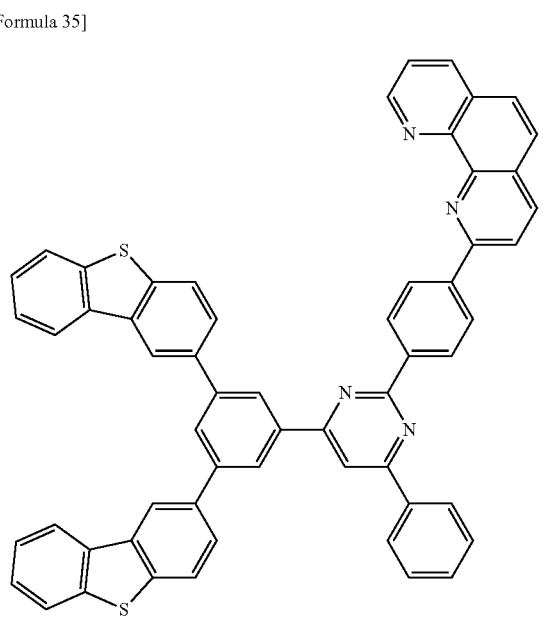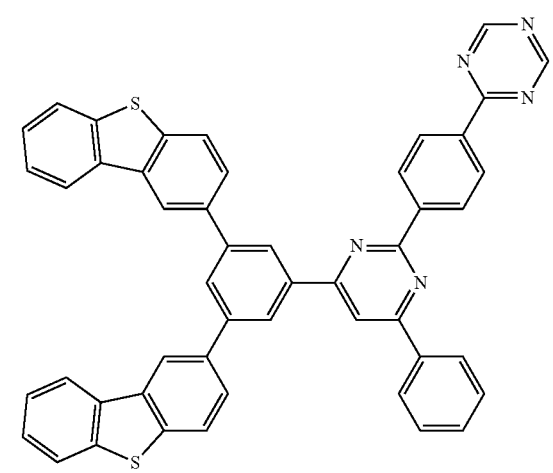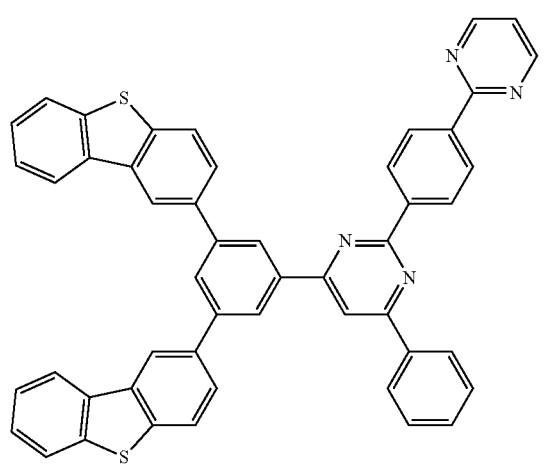

[Formula 36]
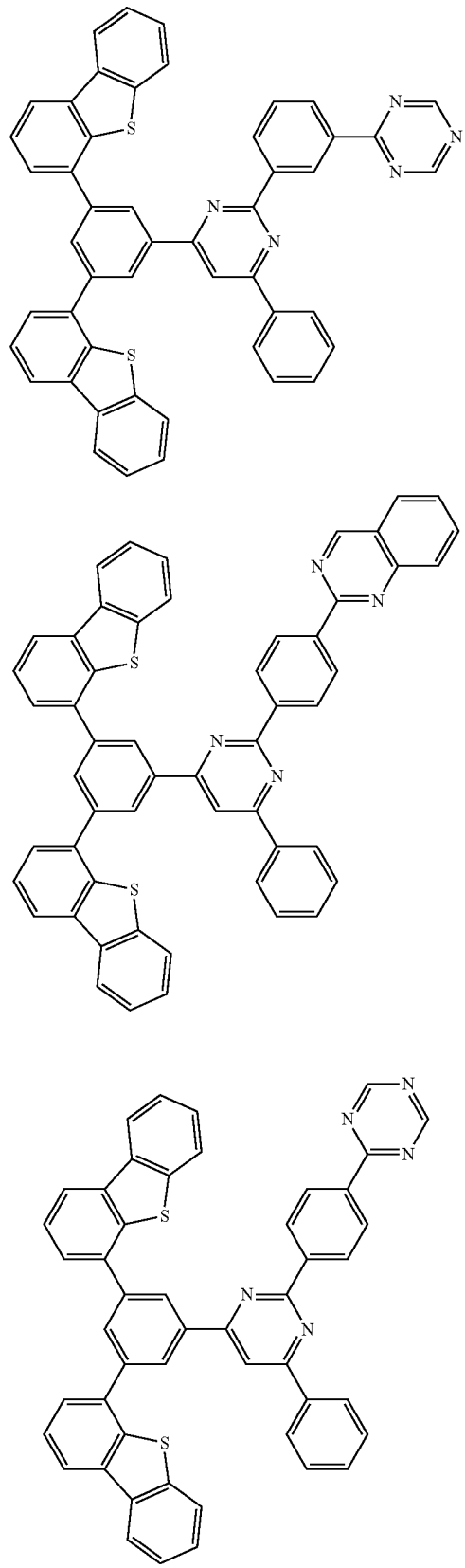
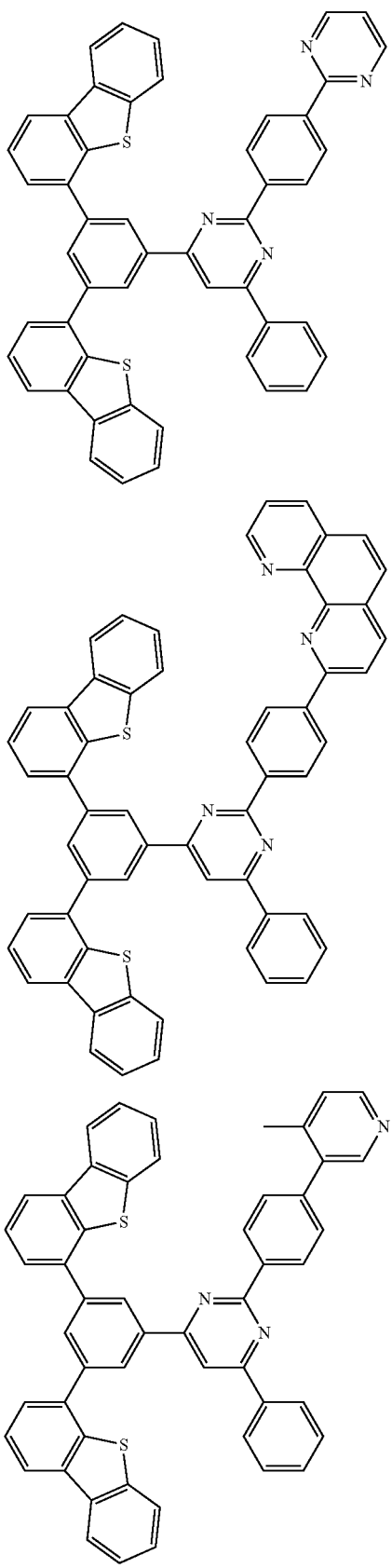

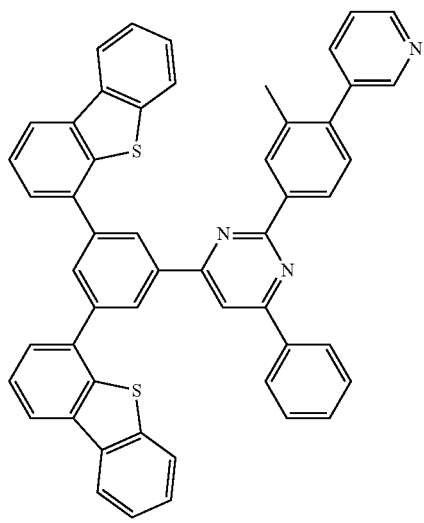
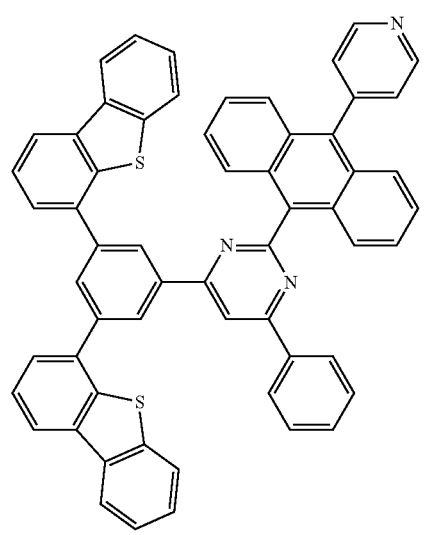
[Formula 37]
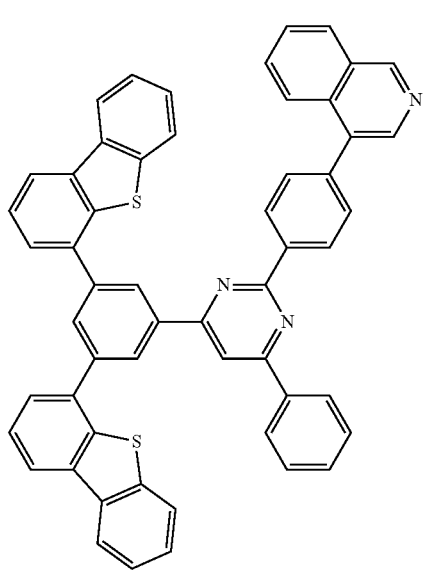
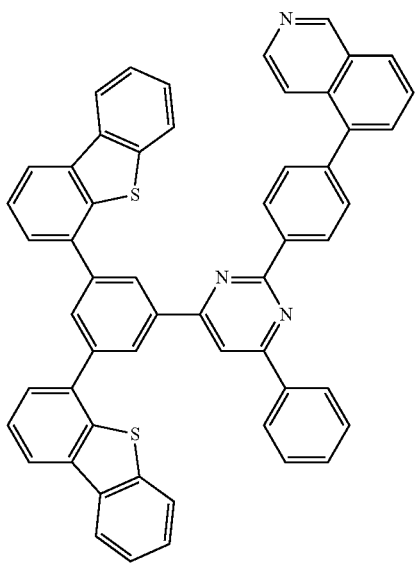
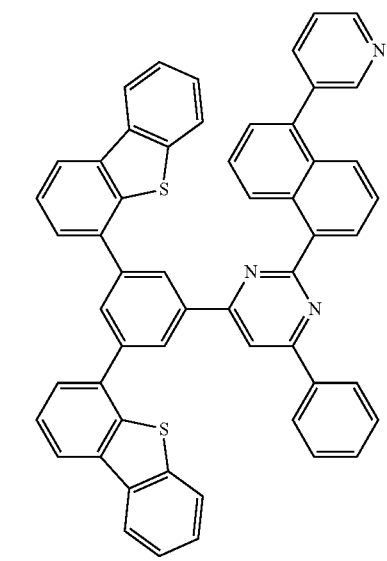

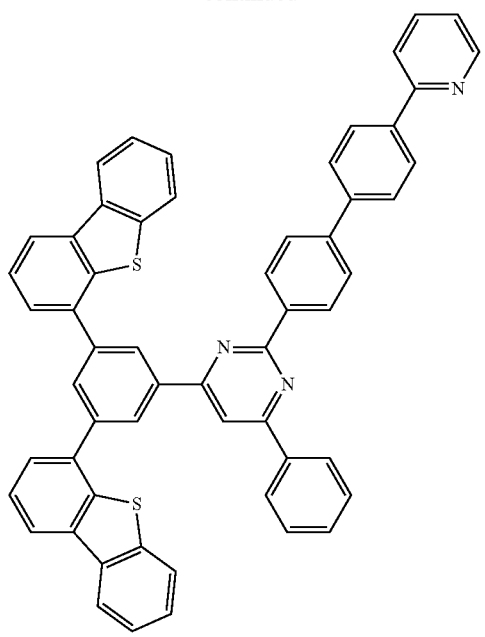
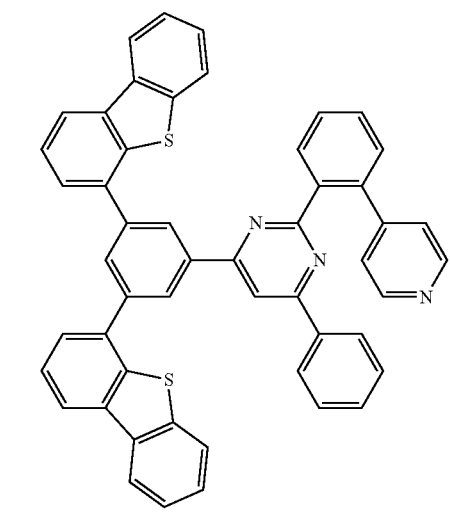
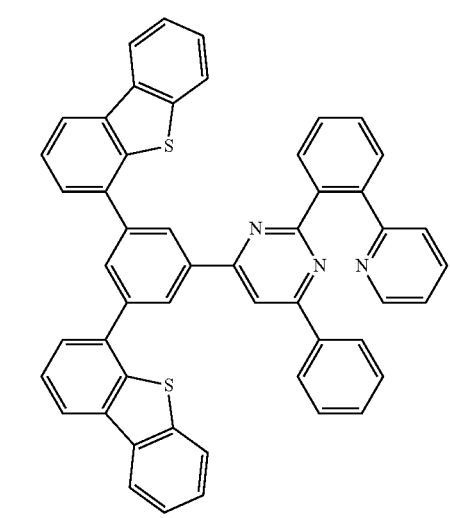
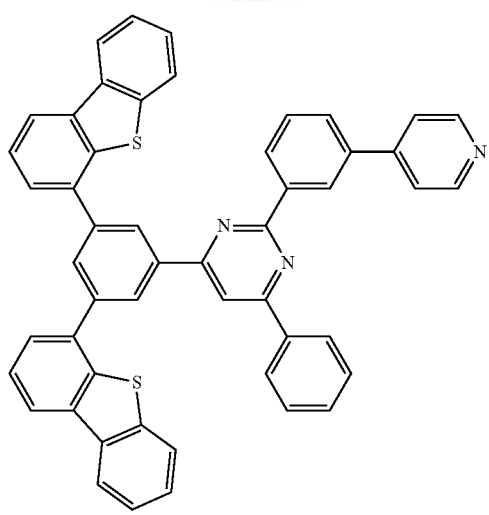
[Formula 38]
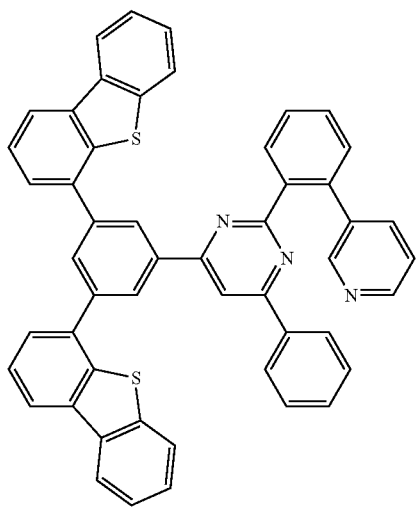
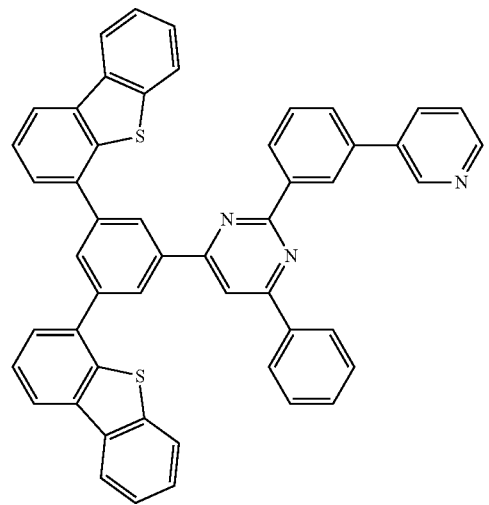

[Formula 39]
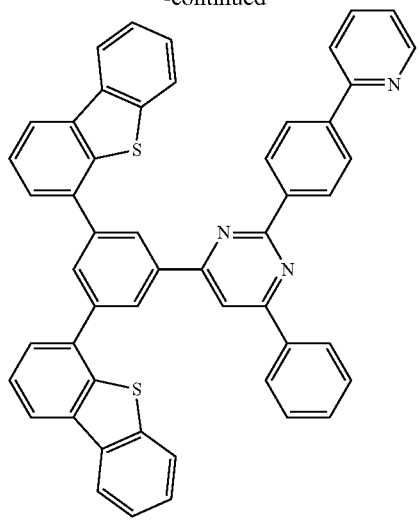
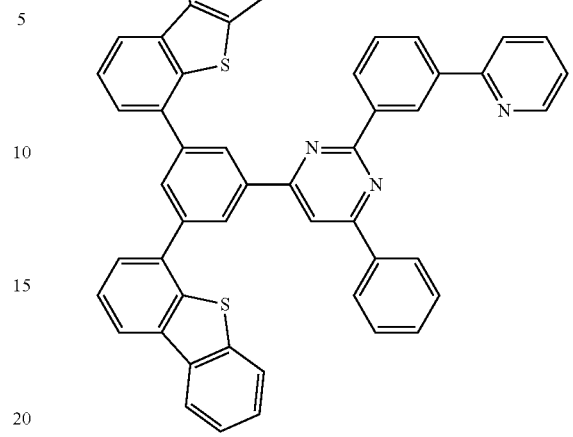
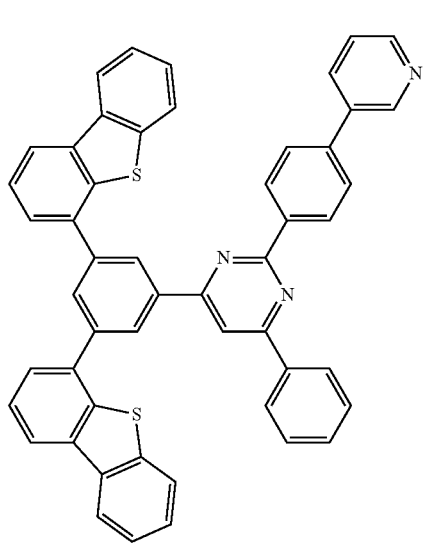
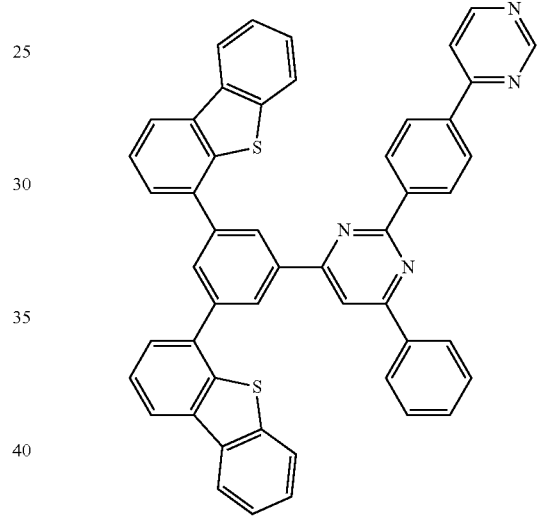
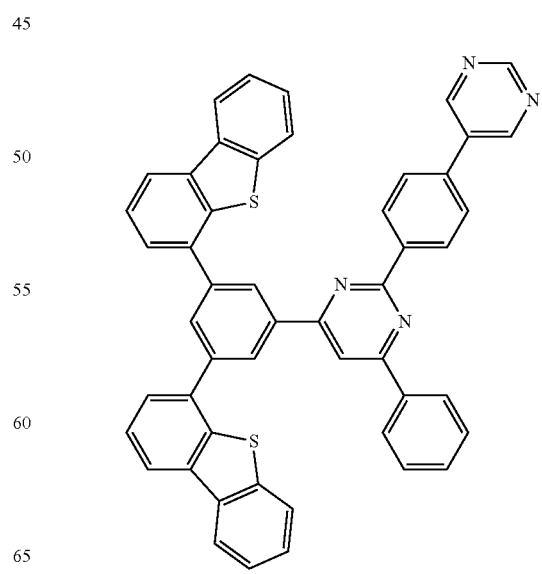

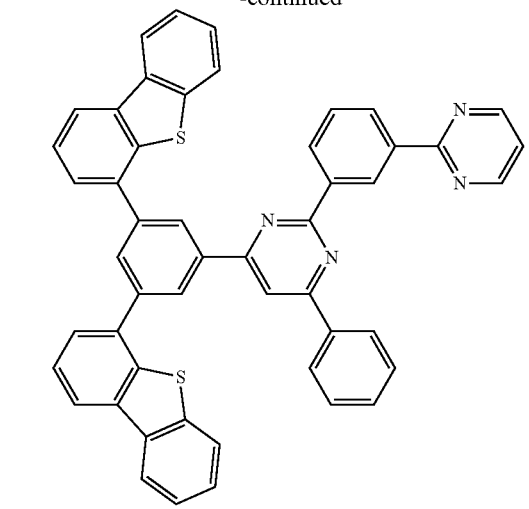
[Formula 40]
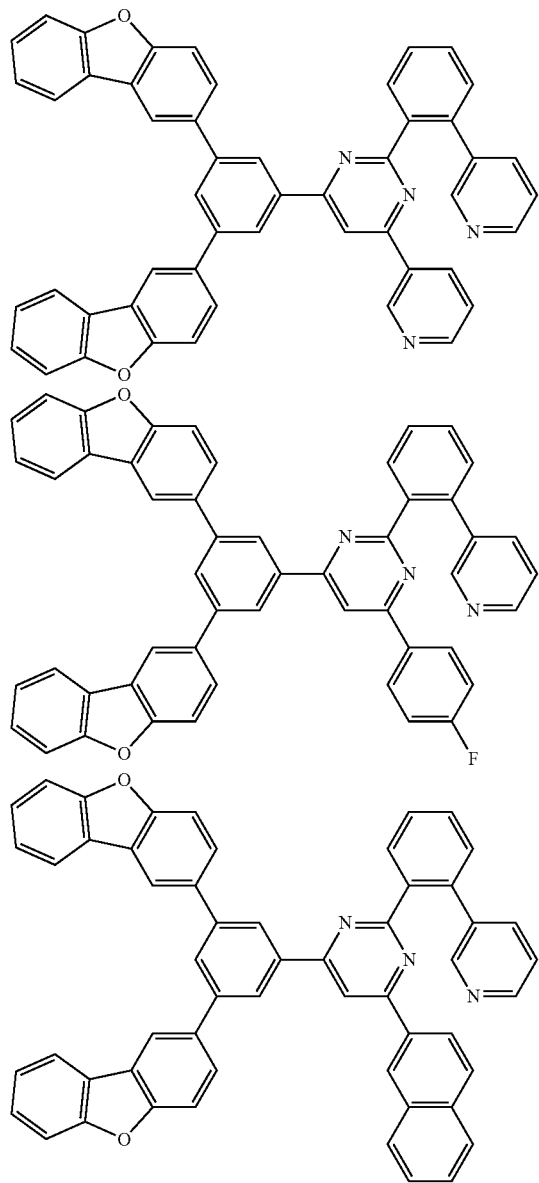
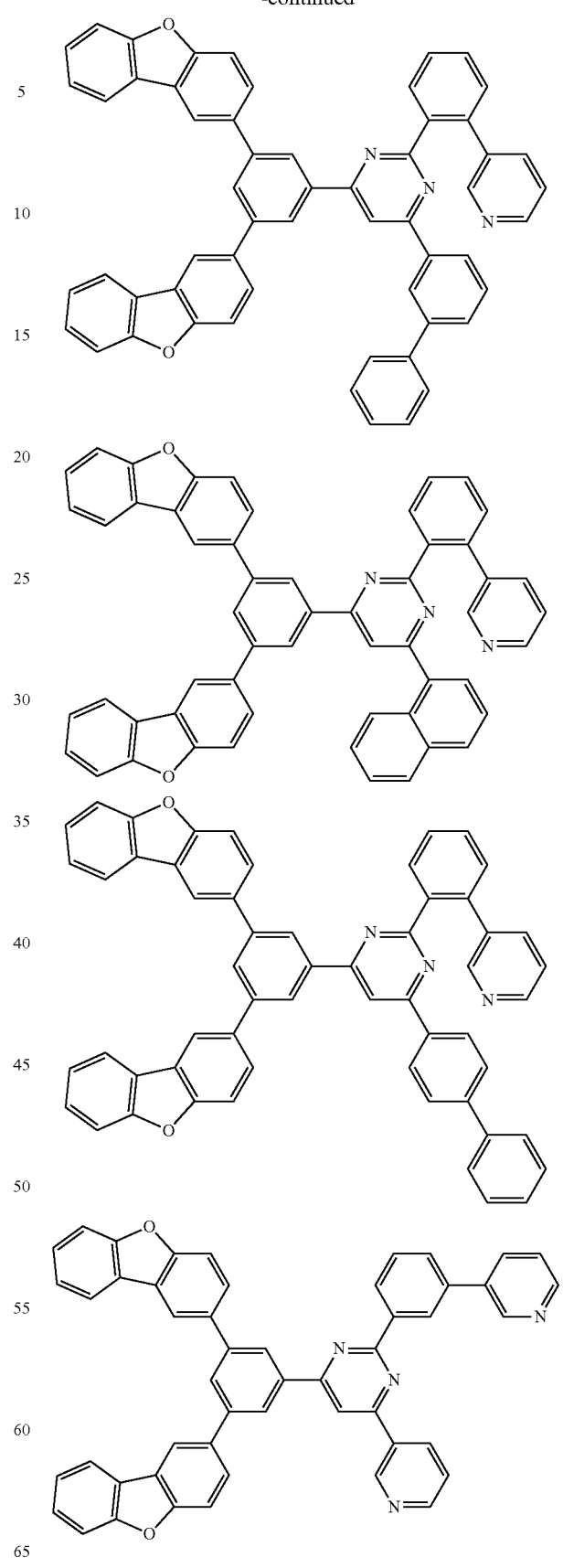

59
-continued
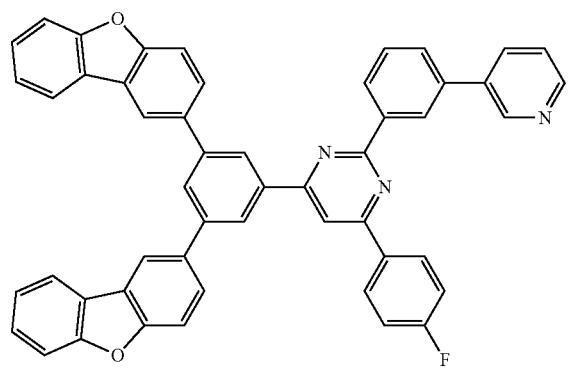
[Formula 41]
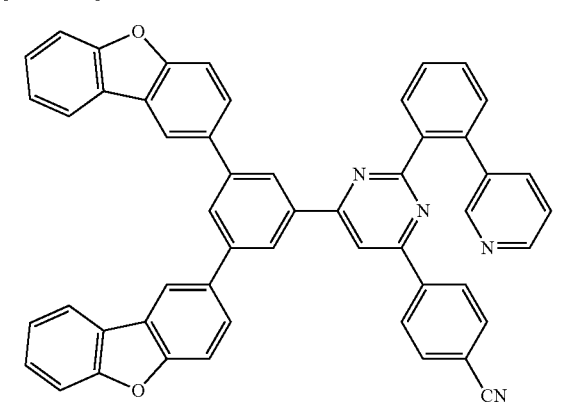
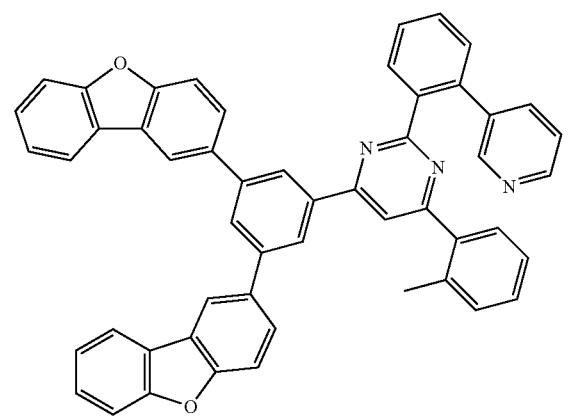
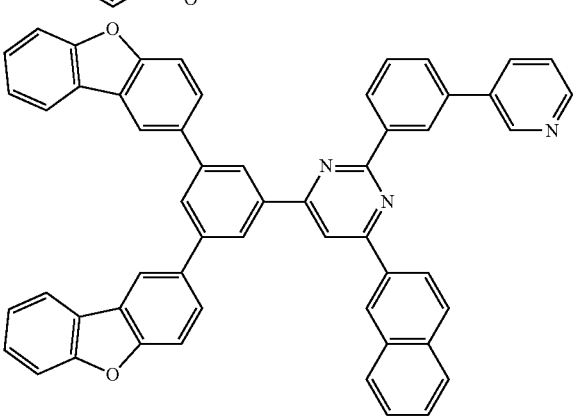
60
-continued
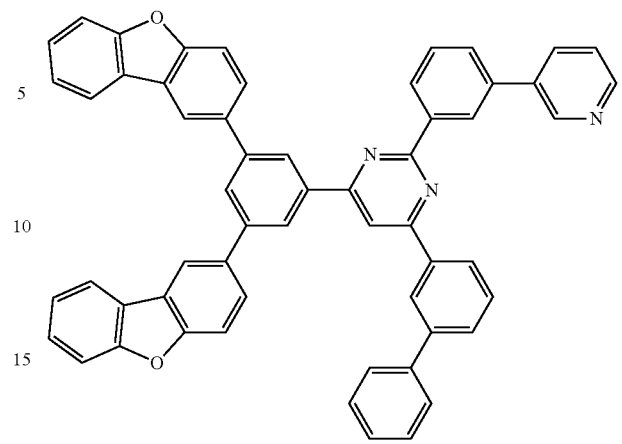
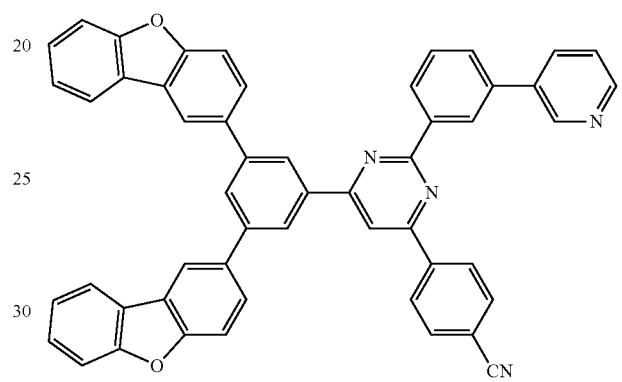
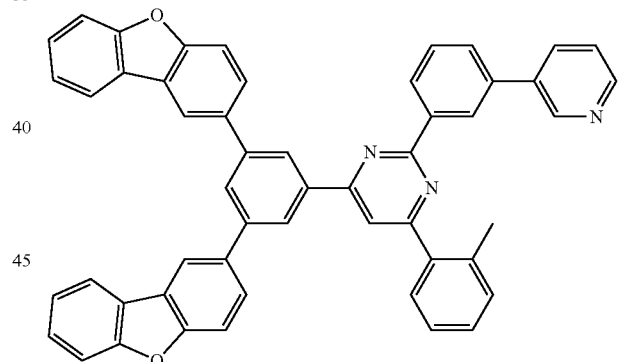
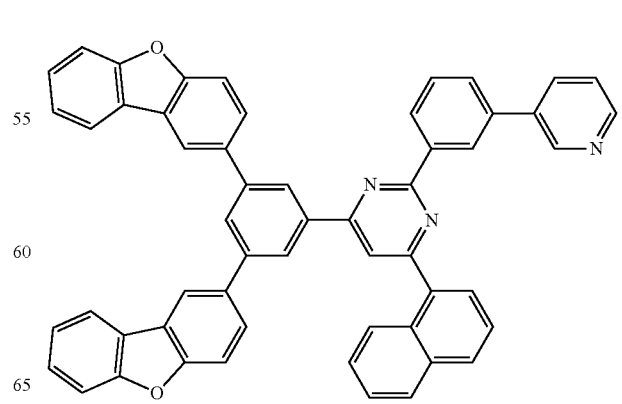

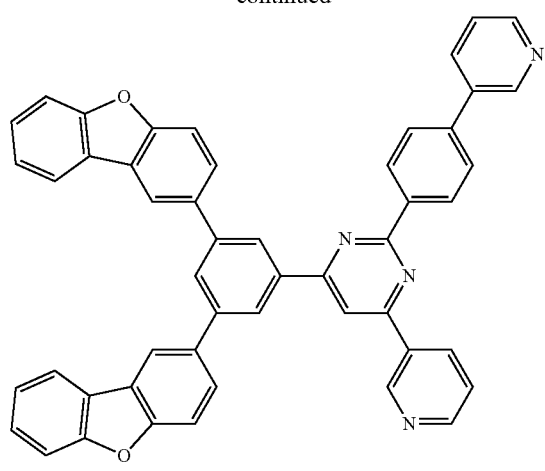
[Formula 42]
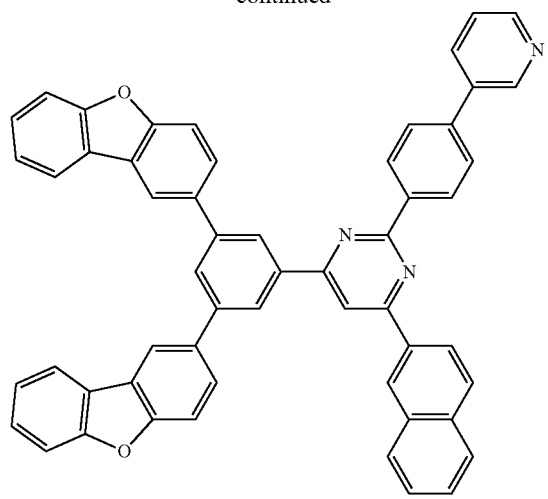
[Formula 43]
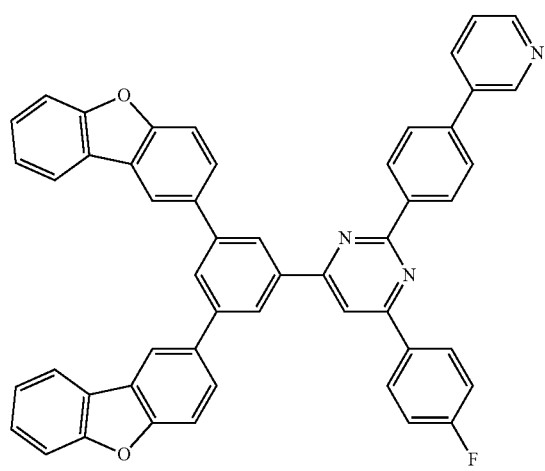
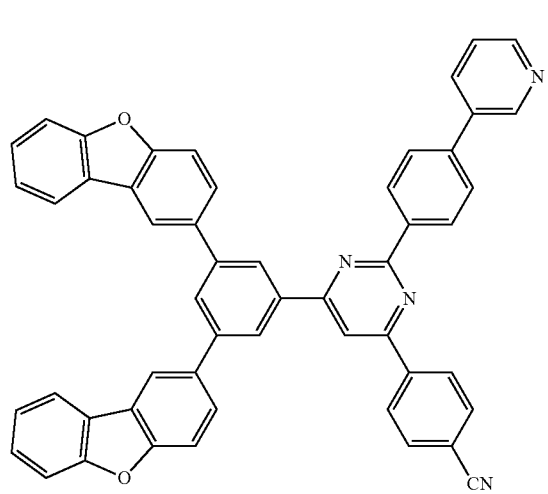

[Formula 44]
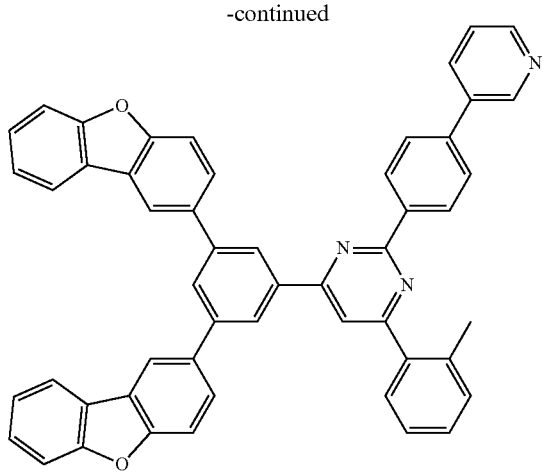
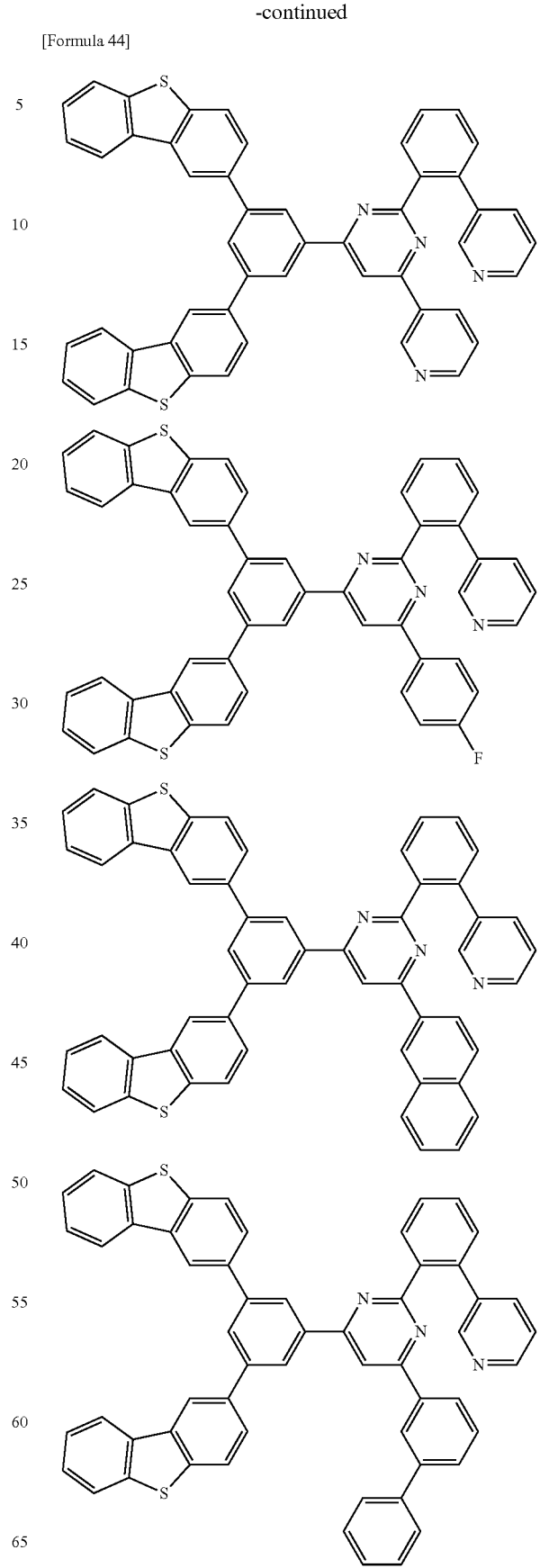

65
-continued
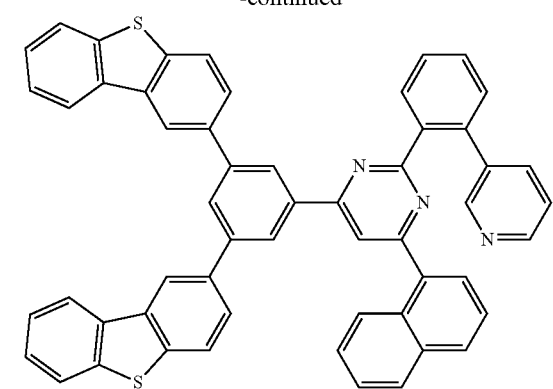
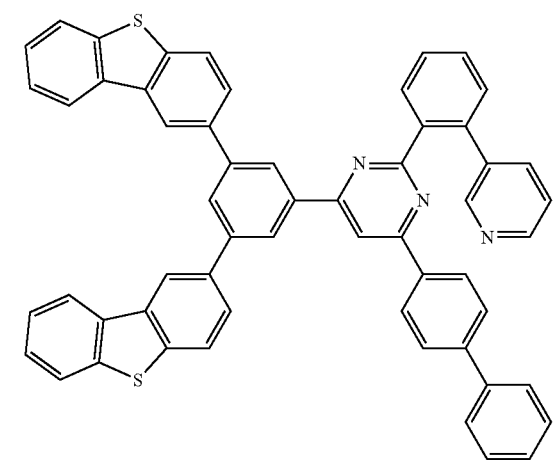
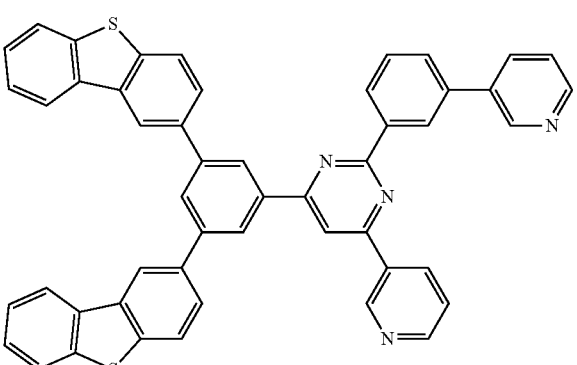
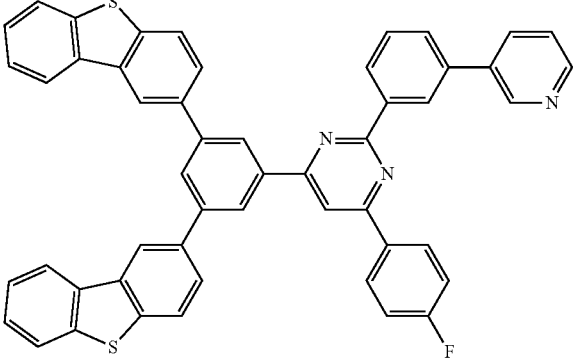
66
-continued
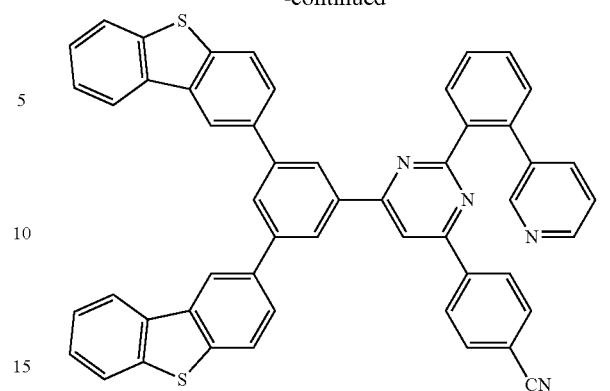
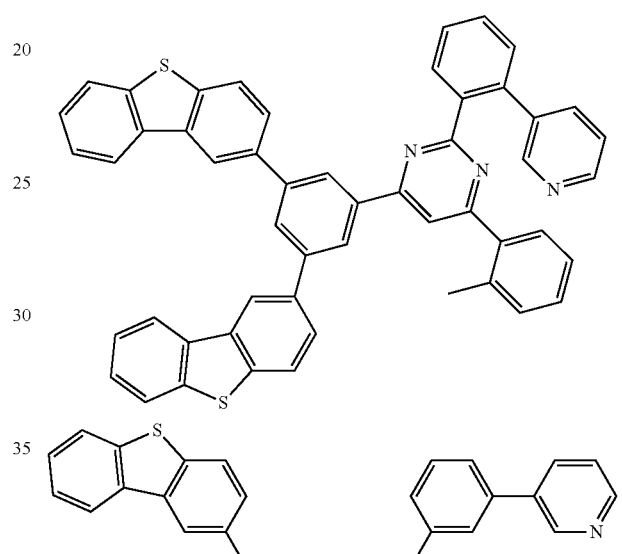
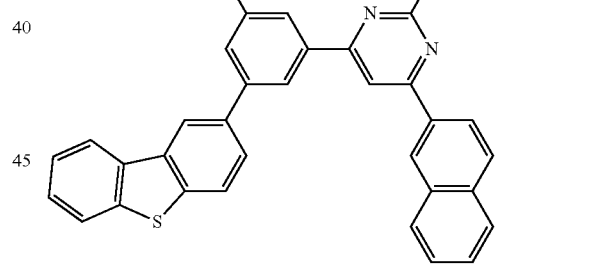
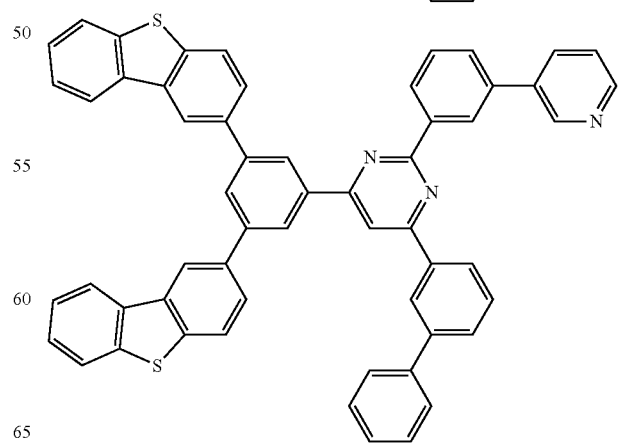

[Formula 45]
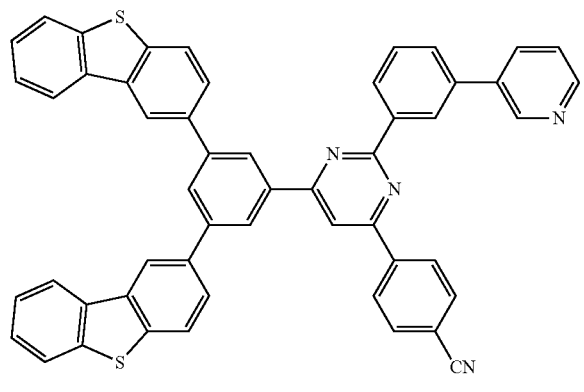
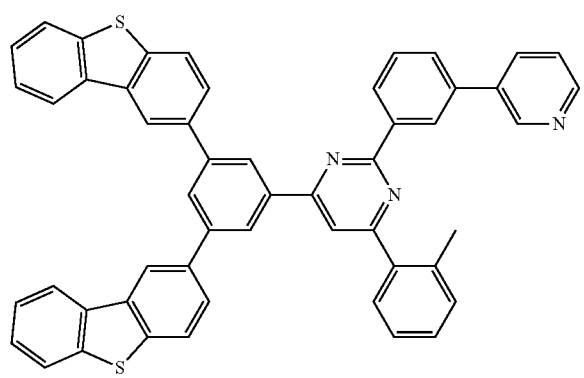
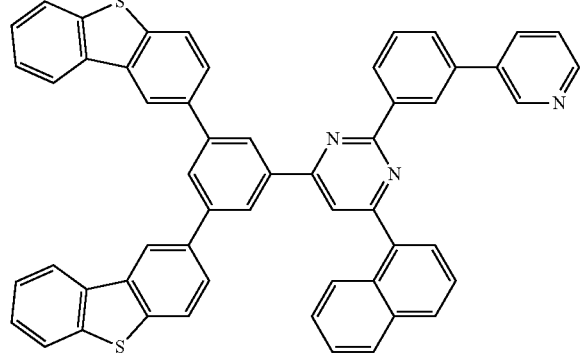
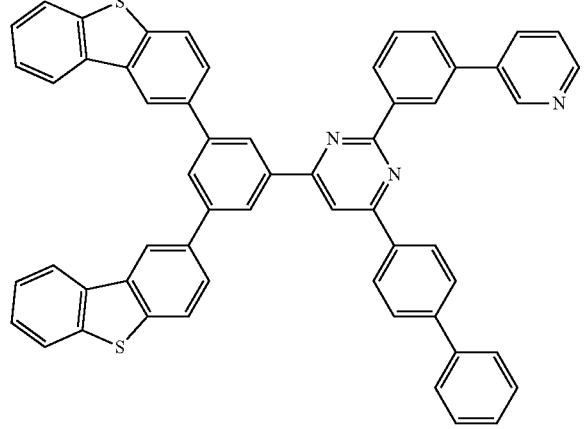
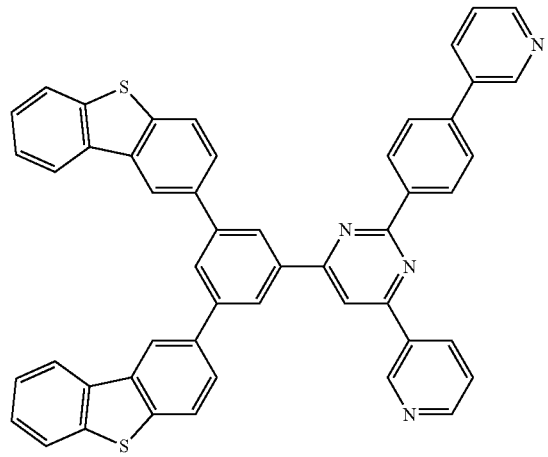
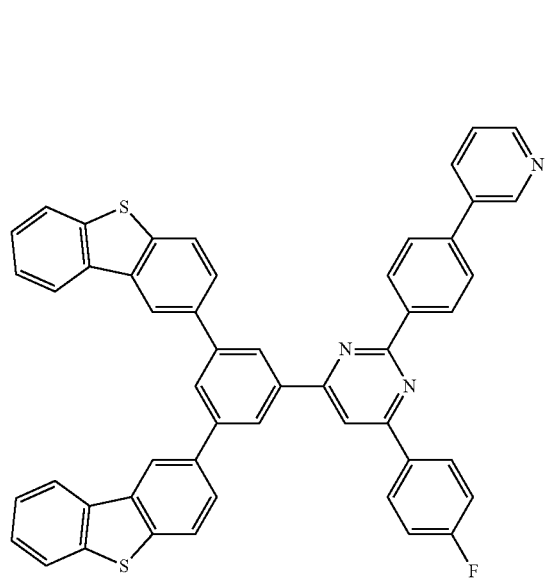
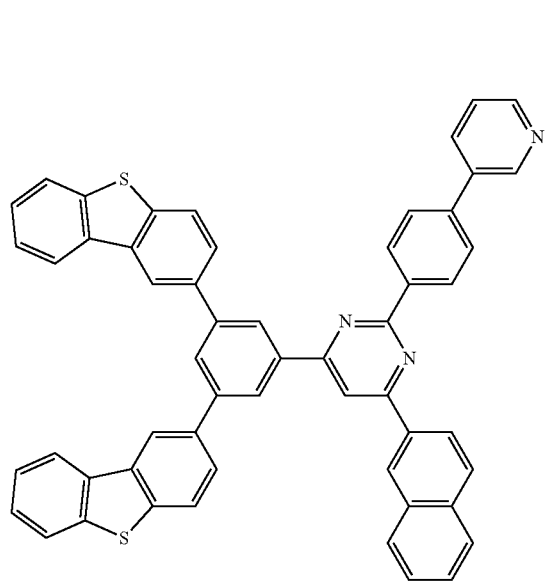

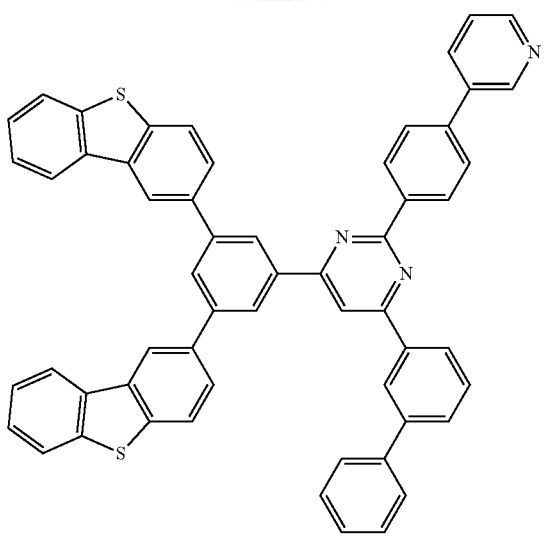
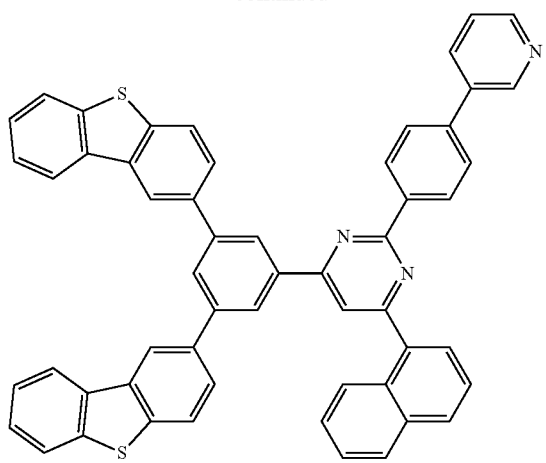
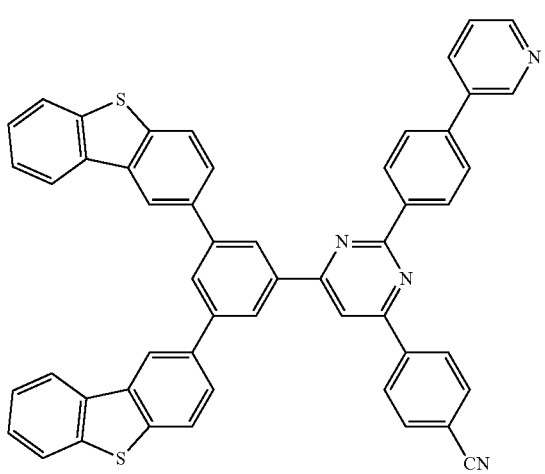
[Formula 46]
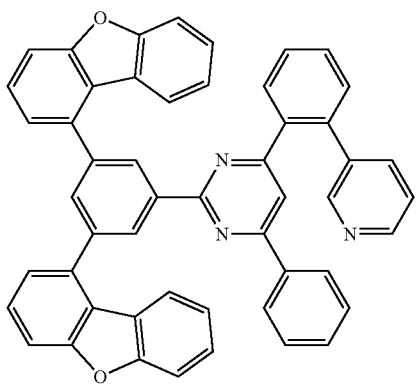

71
-continued
72
-continued
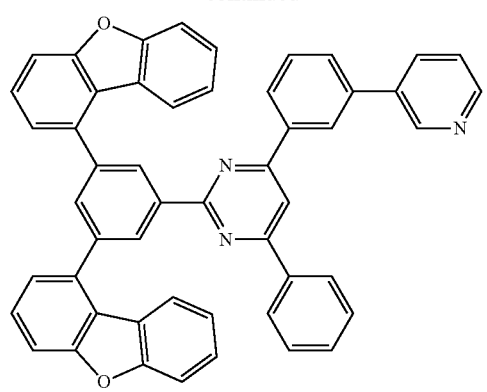
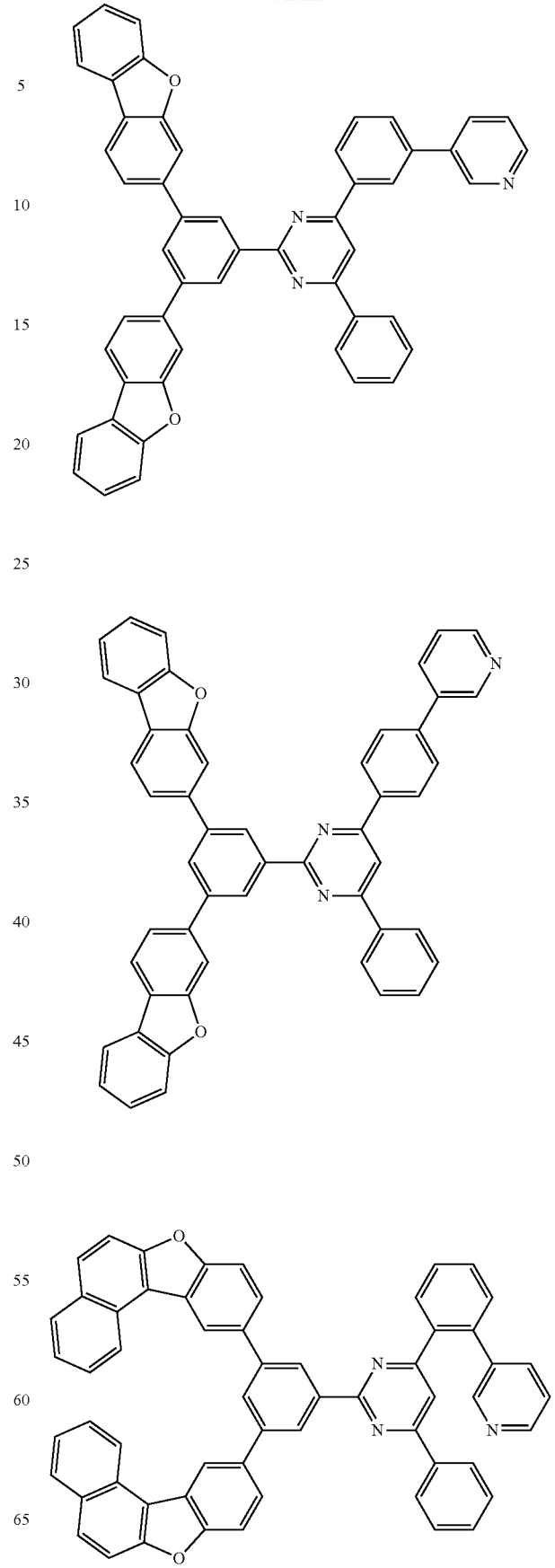

-continued
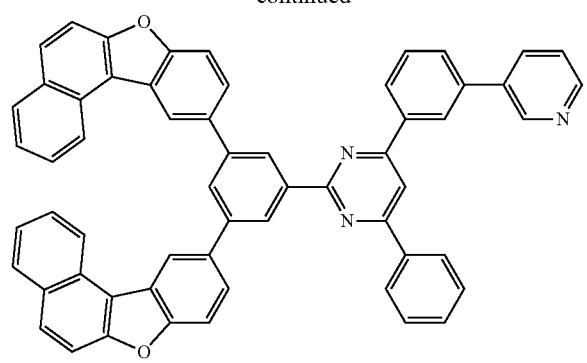

[Formula 47]
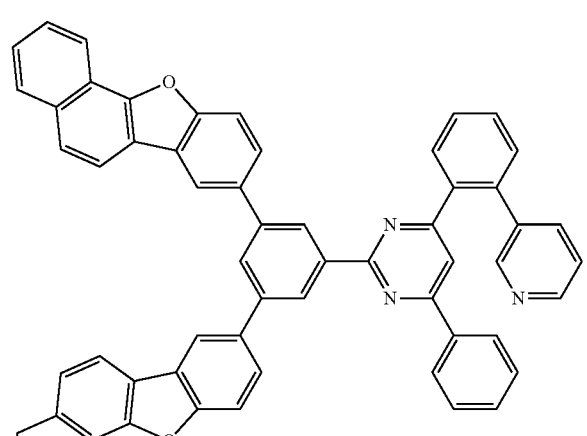
-continued
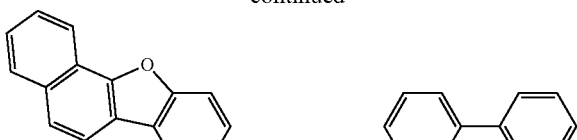
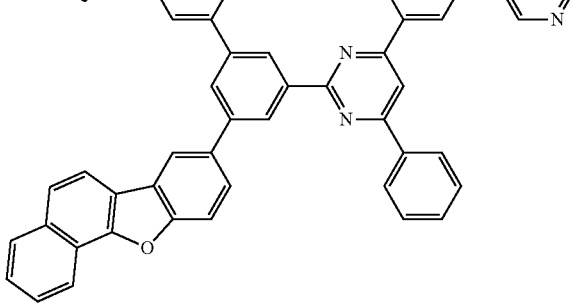
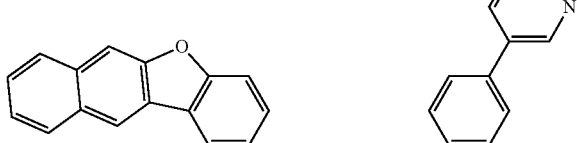

75
-continued
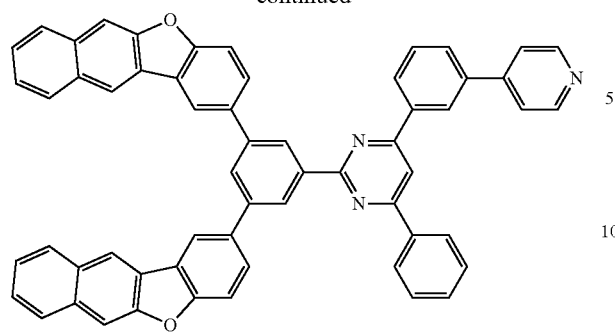
[Formula 48]
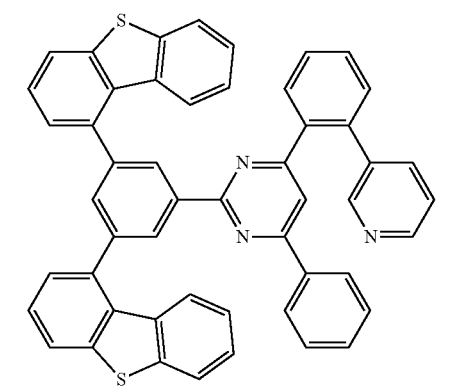
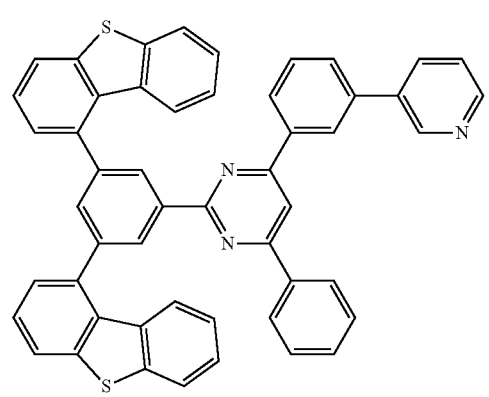
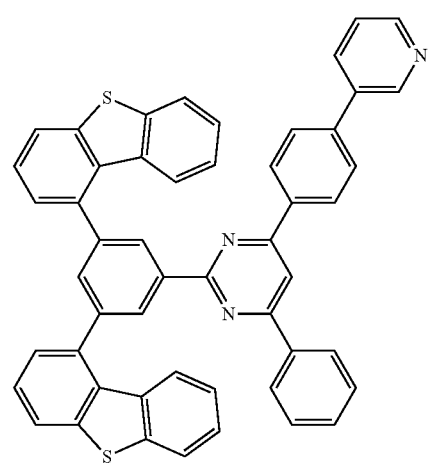
76
-continued
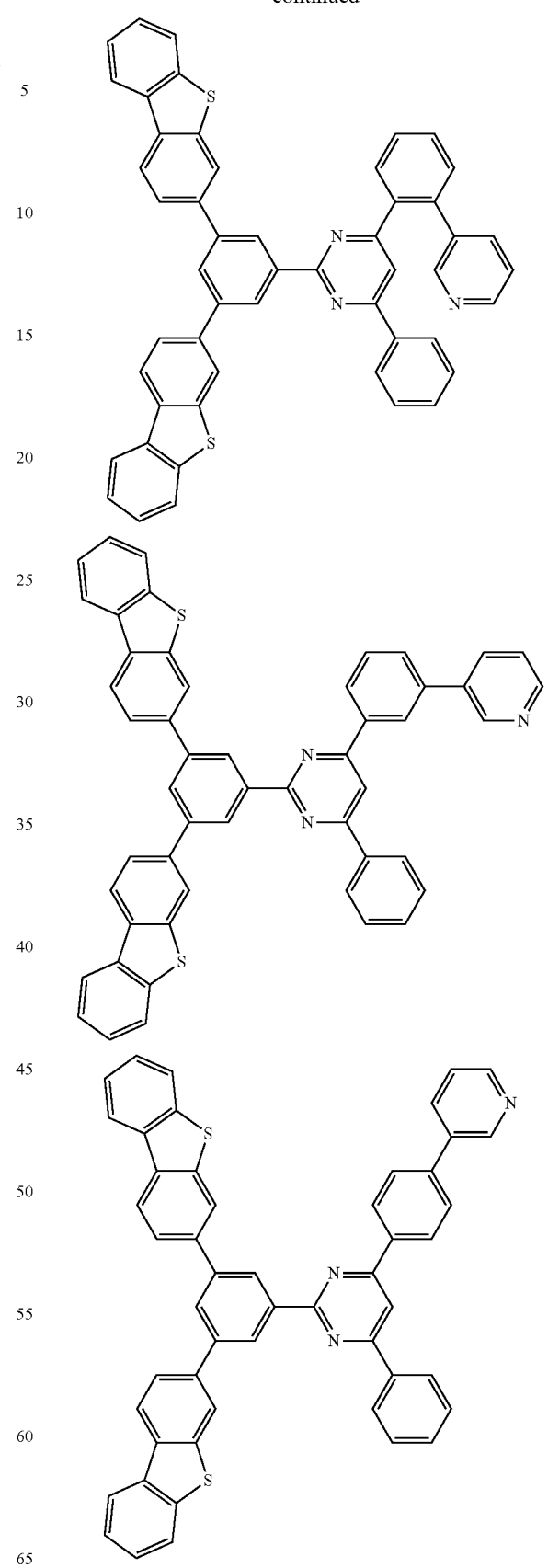

[Formula 49]
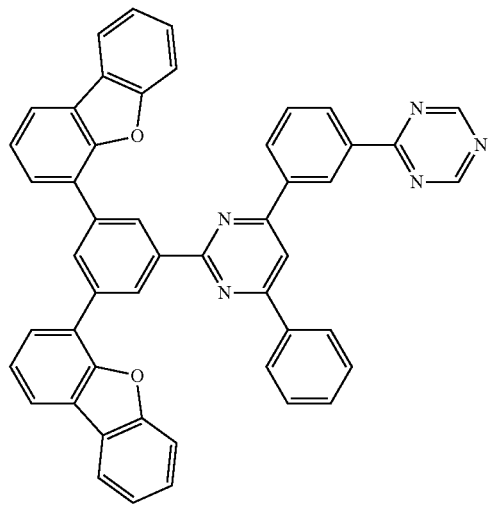
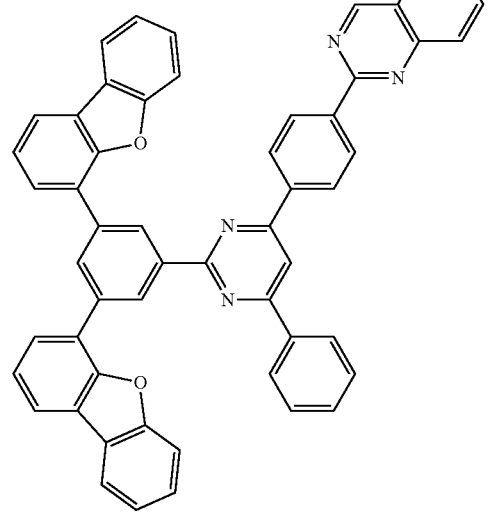
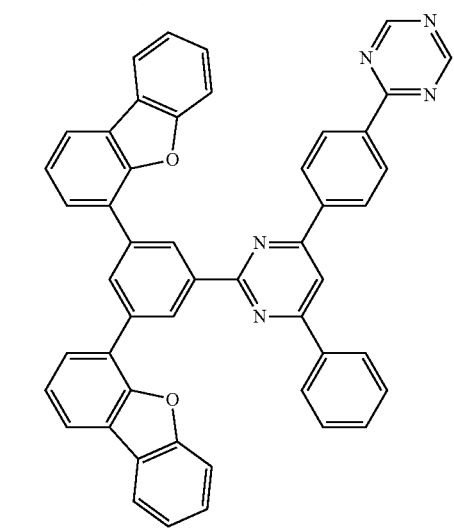
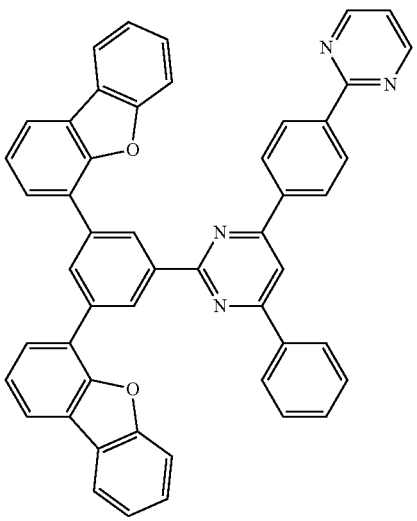
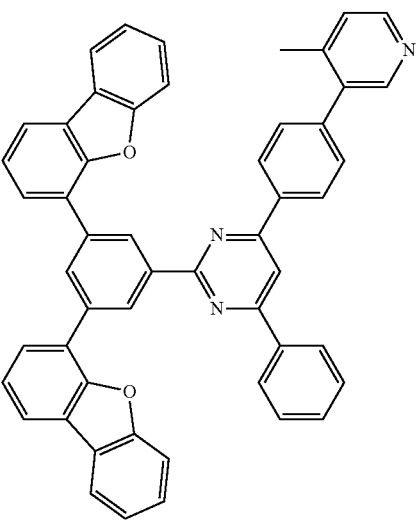
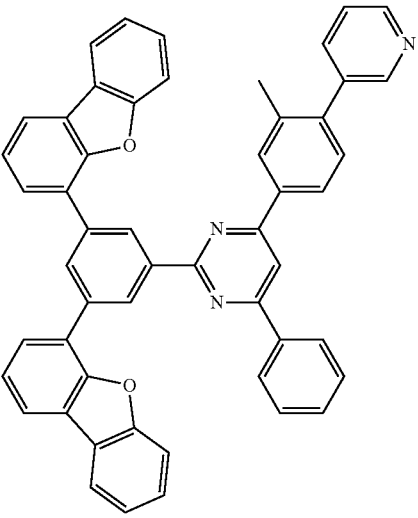

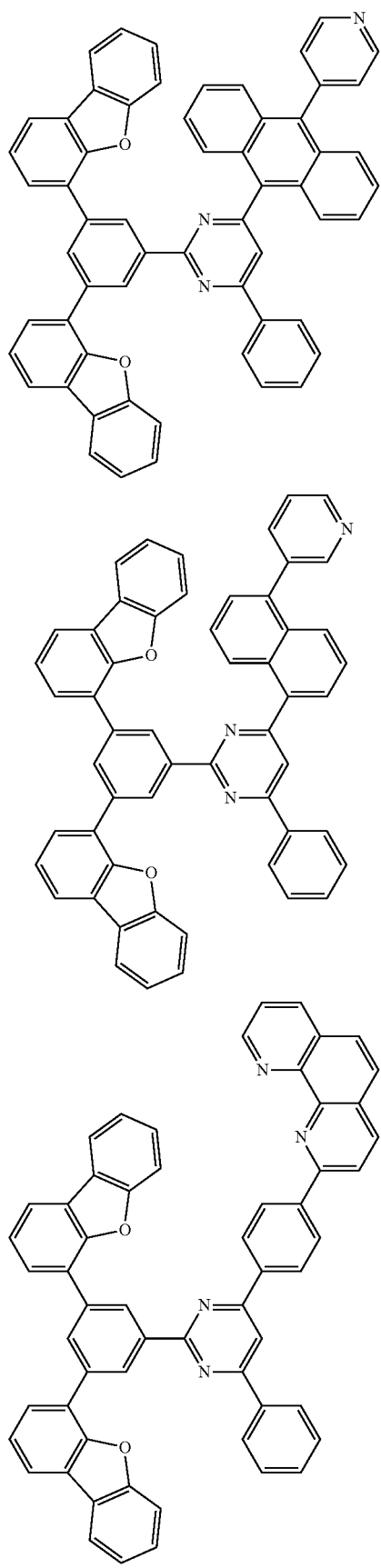 [SMILES: c1ccc(-c2cc(-c3c4ccccc4c(-c4ccncc4)c4ccccc34)nc(-c3cc(-c4cccc5c4oc4ccccc45)cc(-c4cccc5c4oc4ccccc45)c3)n2)cc1 ; c1ccc(-c2cc(-c3cccc4c(-c5cccnc5)cccc34)nc(-c3cc(-c4cccc5c4oc4ccccc45)cc(-c4cccc5c4oc4ccccc45)c3)n2)cc1 ; c1ccc(-c2cc(-c3ccc(-c4ccc5ccc6cccnc6c5n4)cc3)nc(-c3cc(-c4cccc5c4oc4ccccc45)cc(-c4cccc5c4oc4ccccc45)c3)n2)cc1]
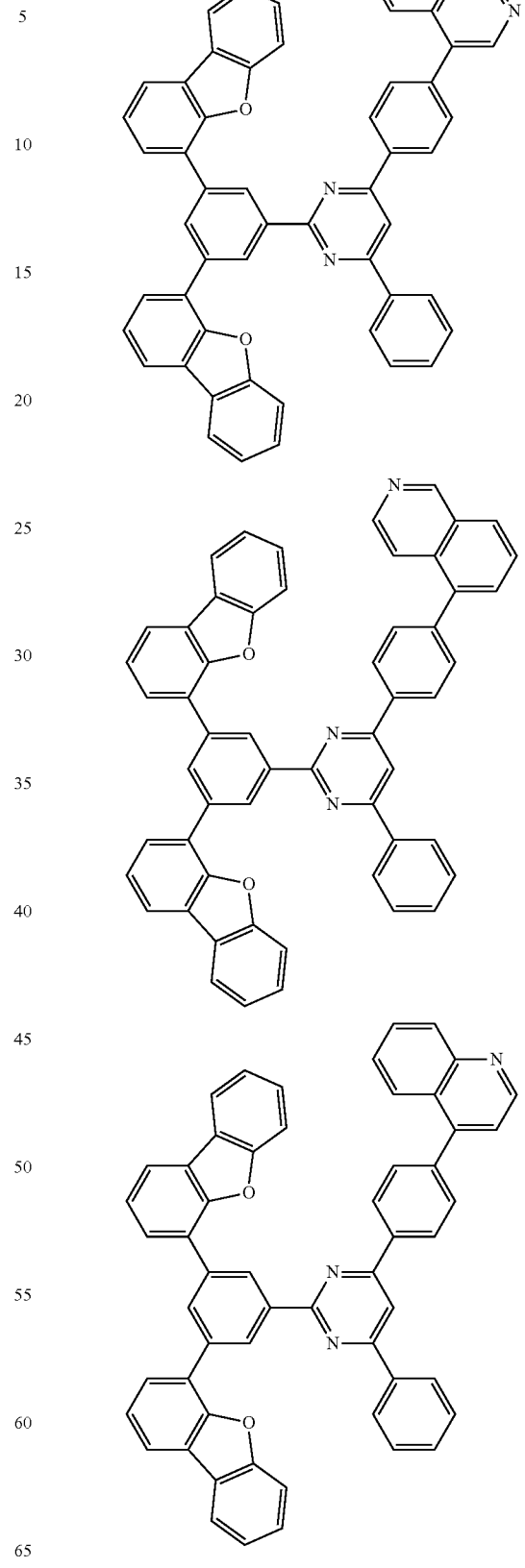

[Formula 50]
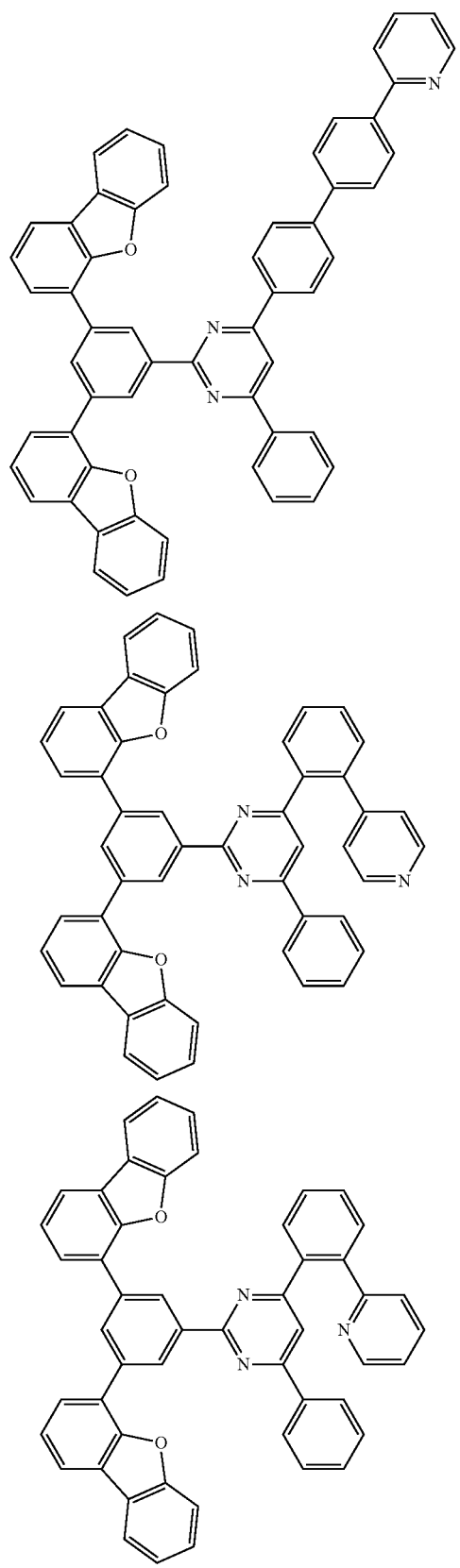
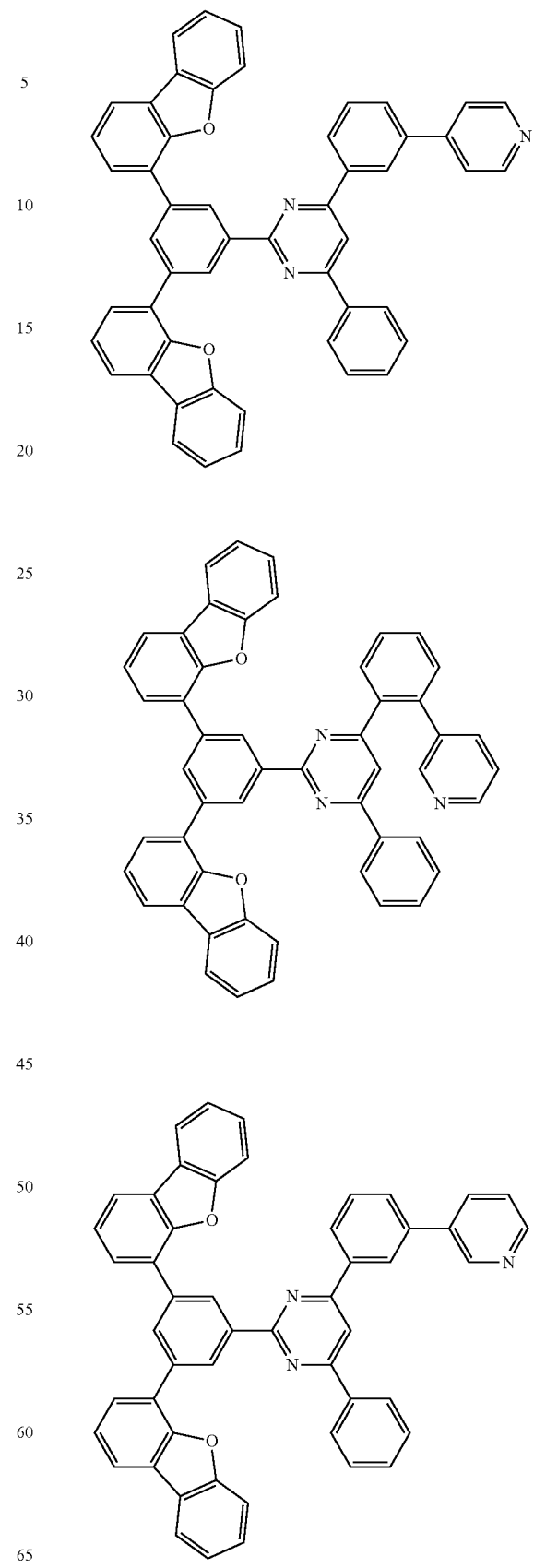

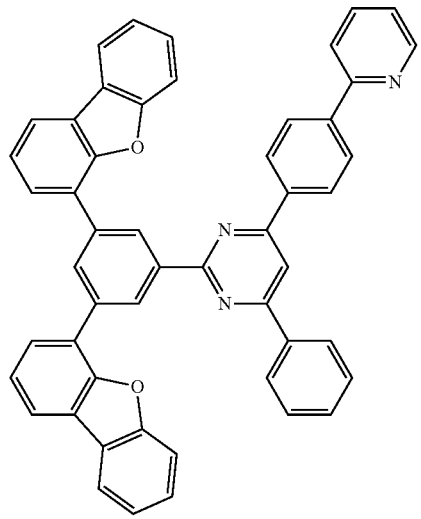
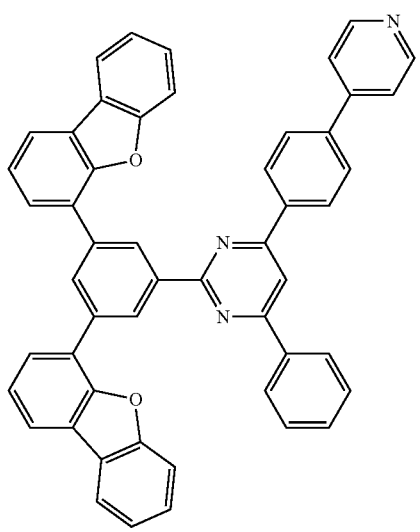
[Formula 51]
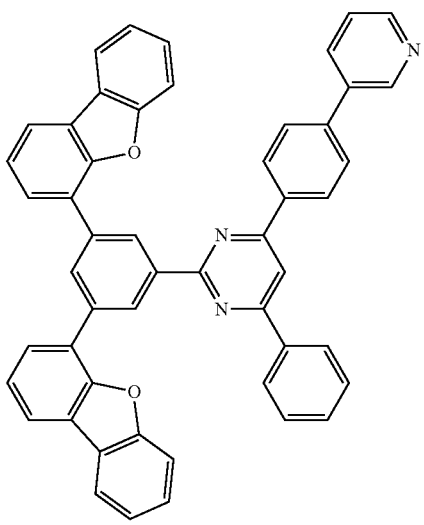
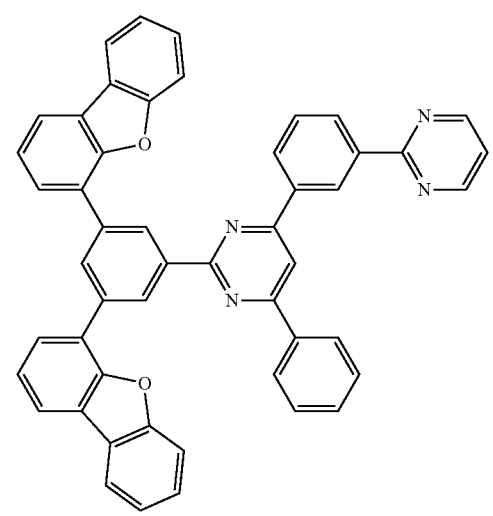
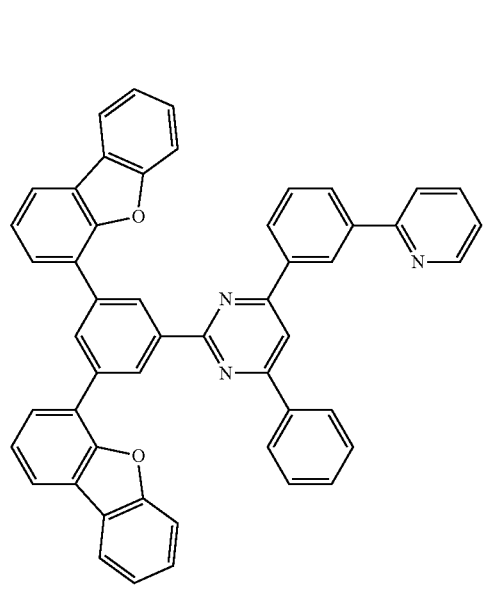
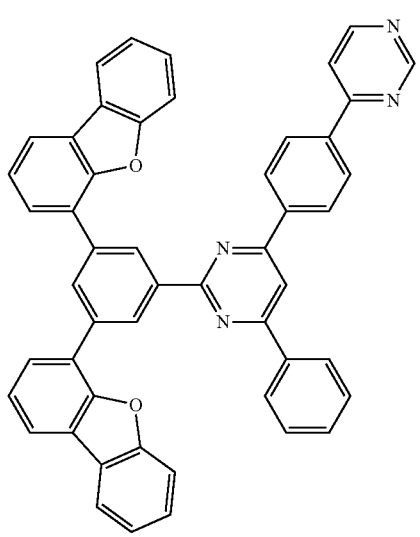

85
-continued
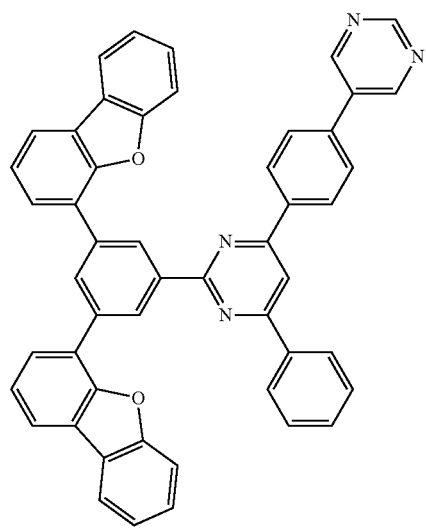
[Formula 52]
86
-continued
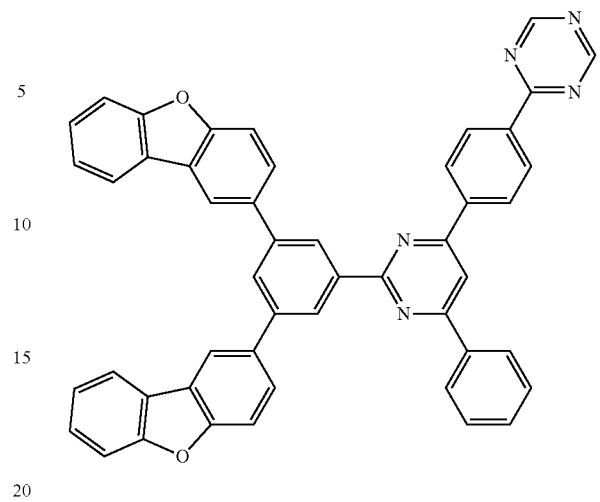
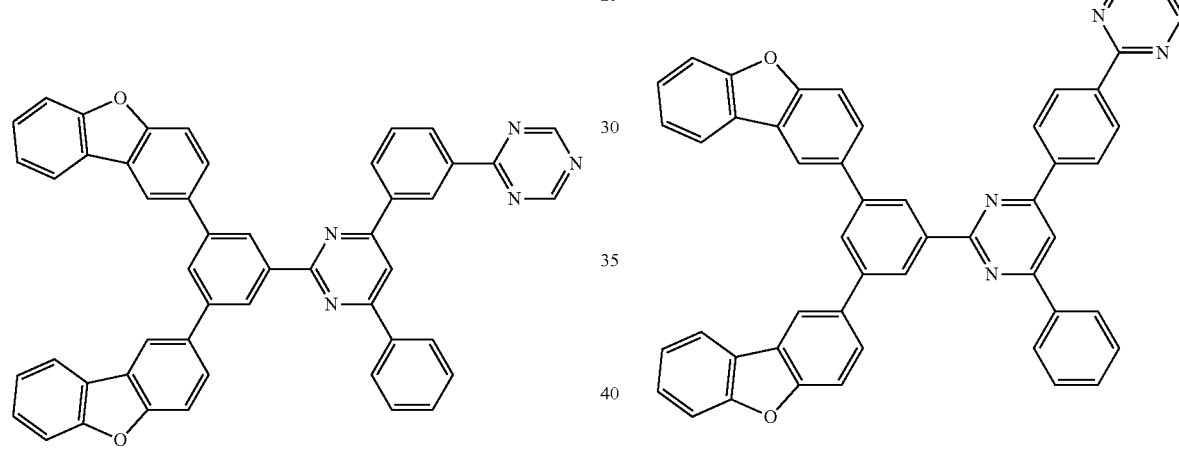
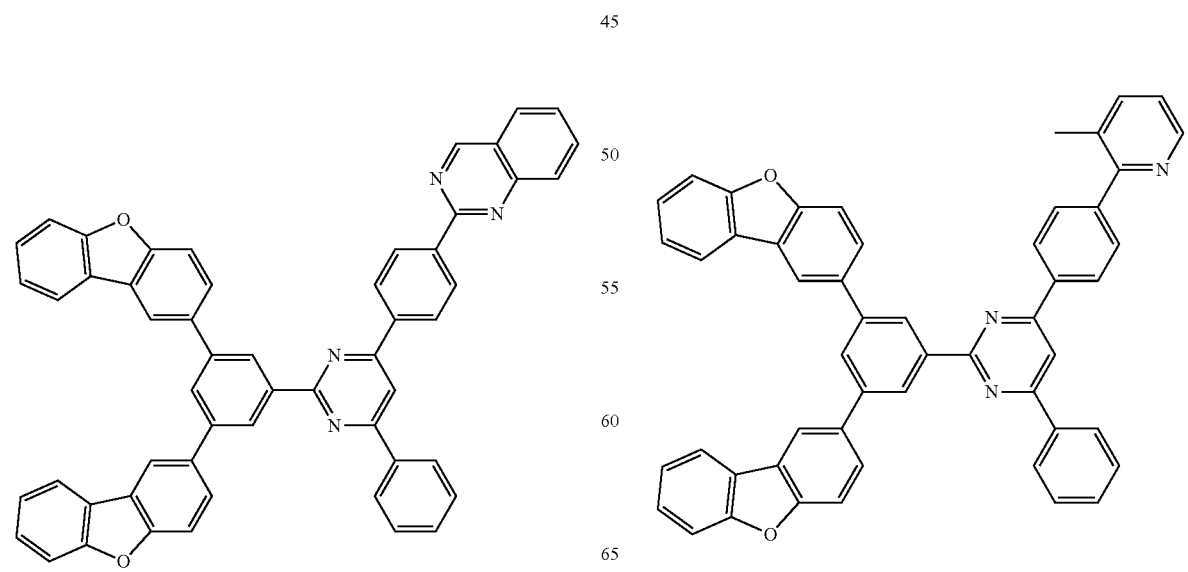

87
-continued
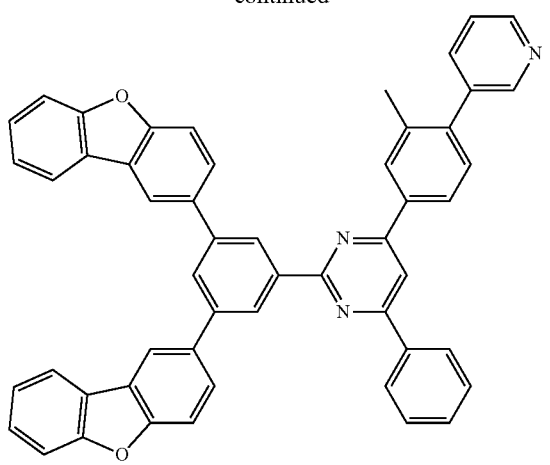
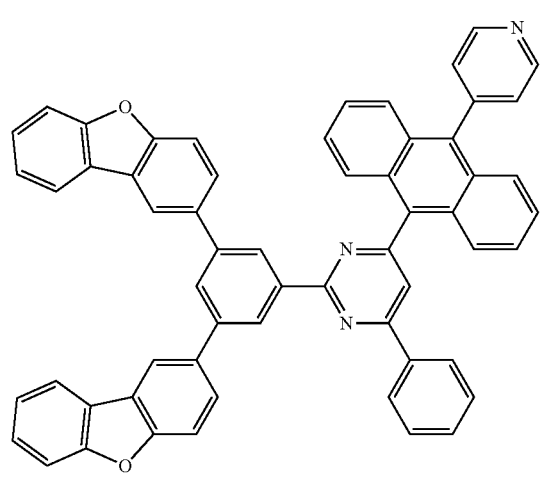
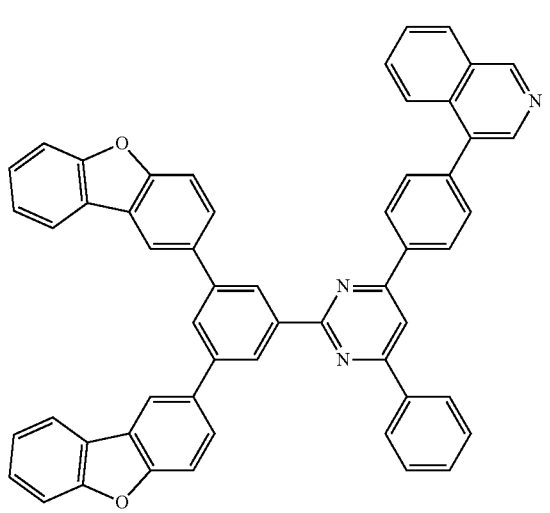
88
-continued
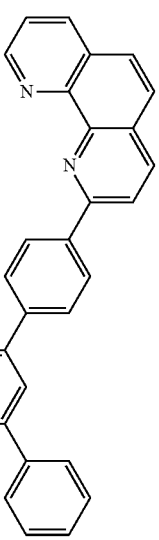
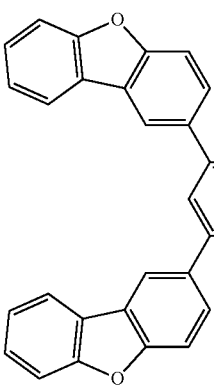
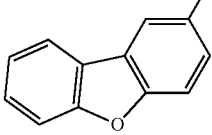
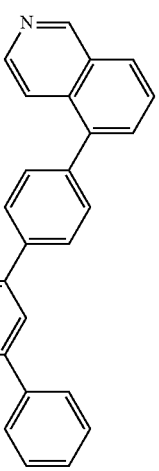
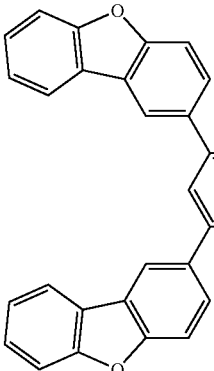
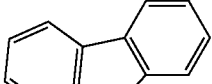
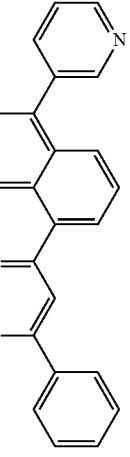
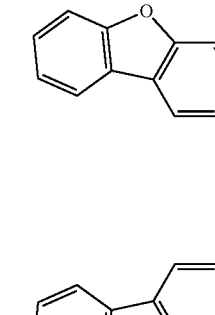
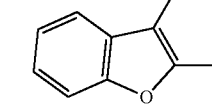

[Formula 53]
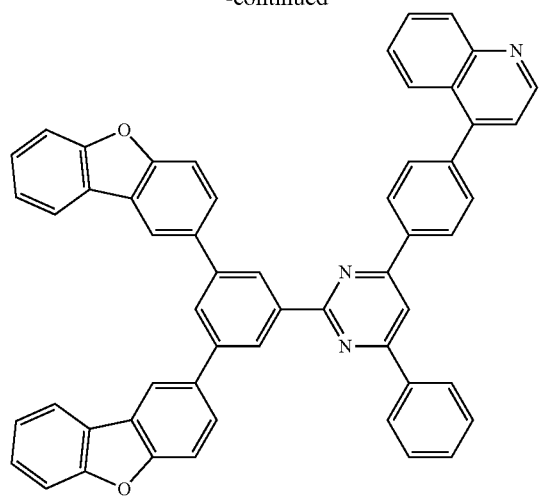
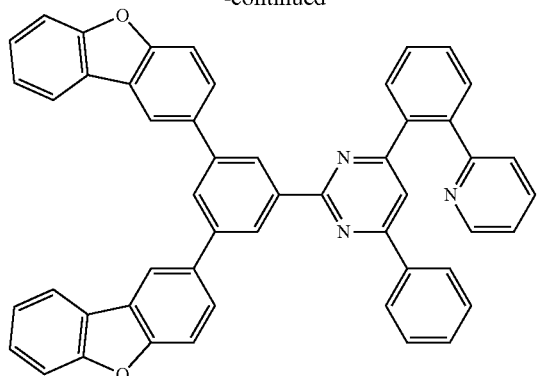
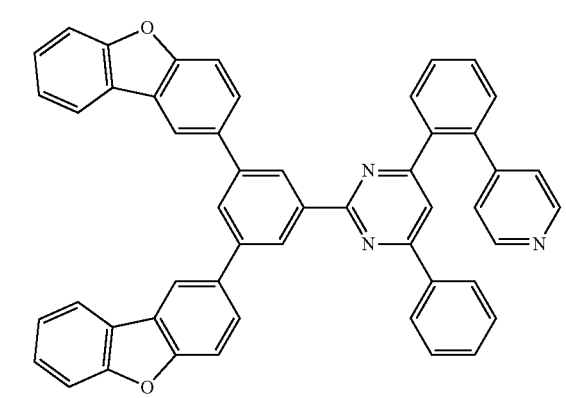

91
-continued
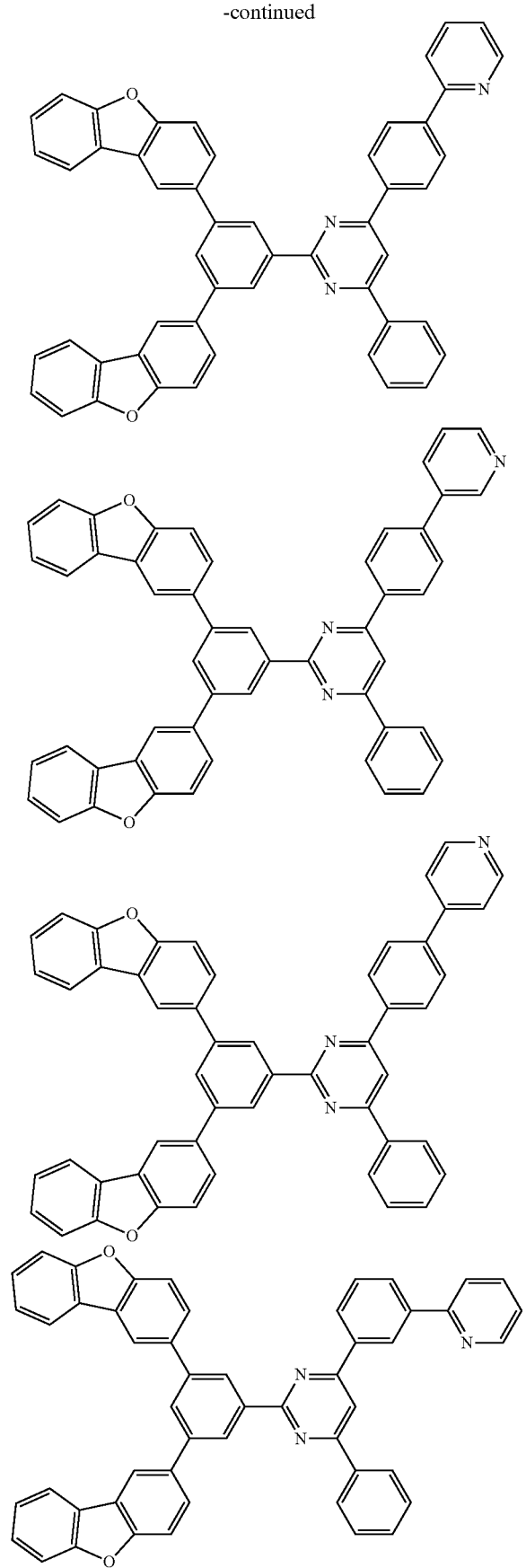
92
-continued
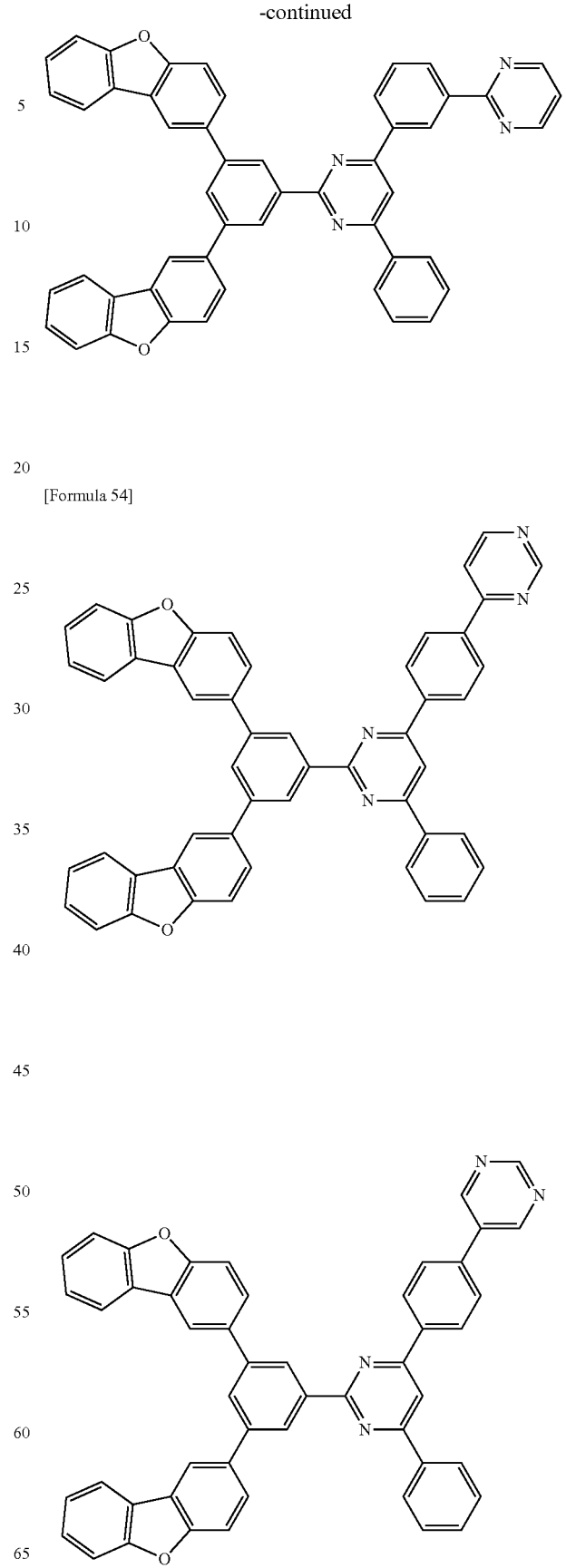
[Formula 54]

[Formula 55]
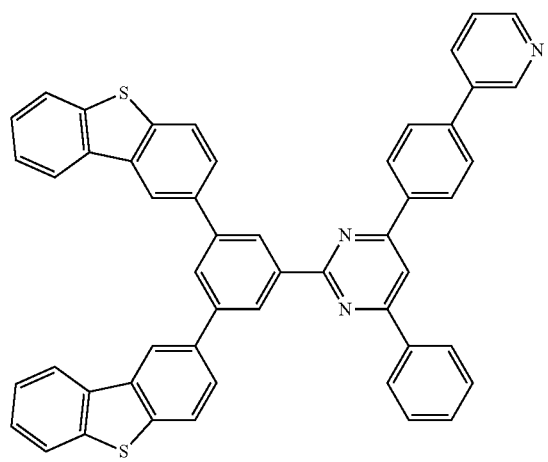
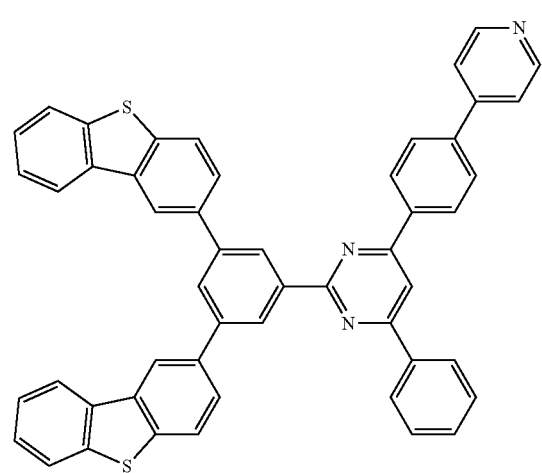
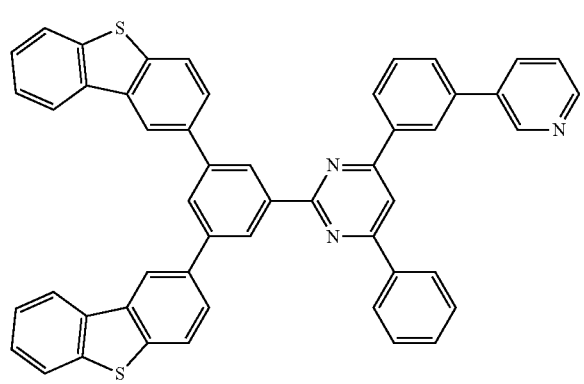
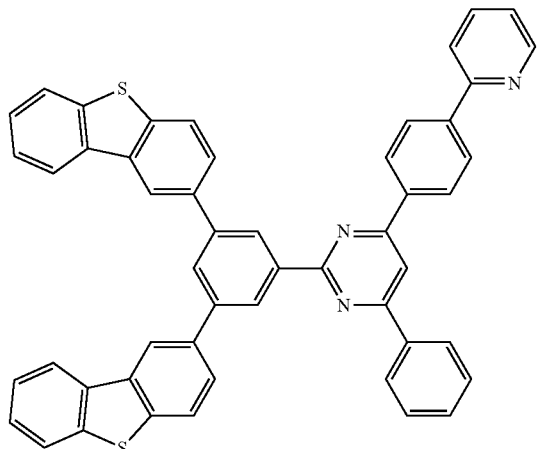
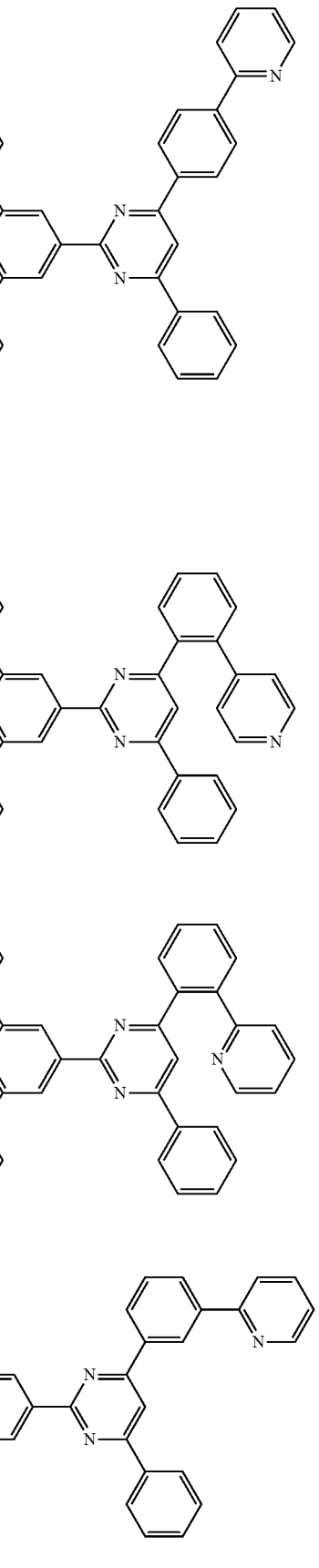

95
-continued
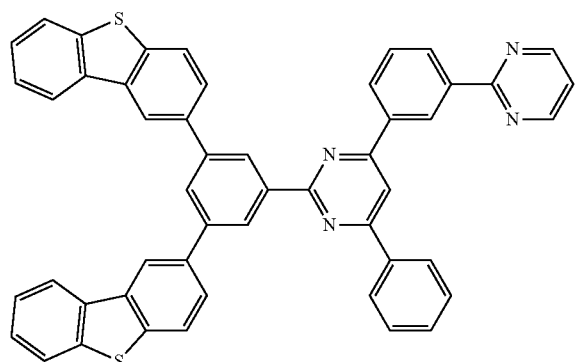
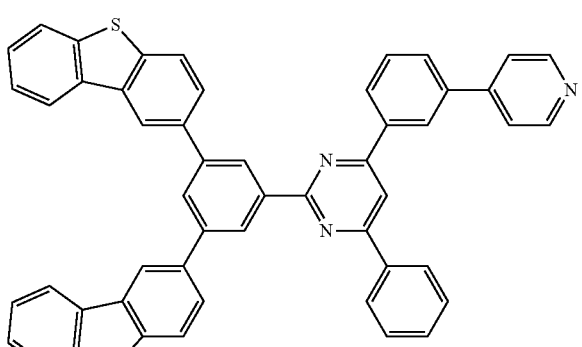
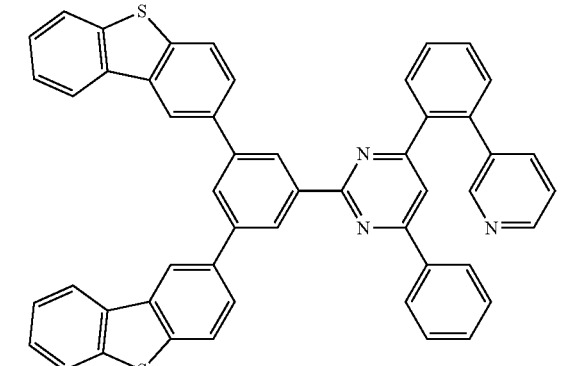
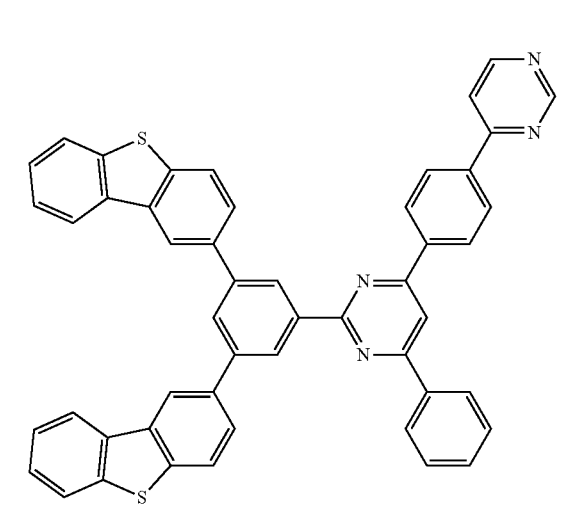
96
-continued
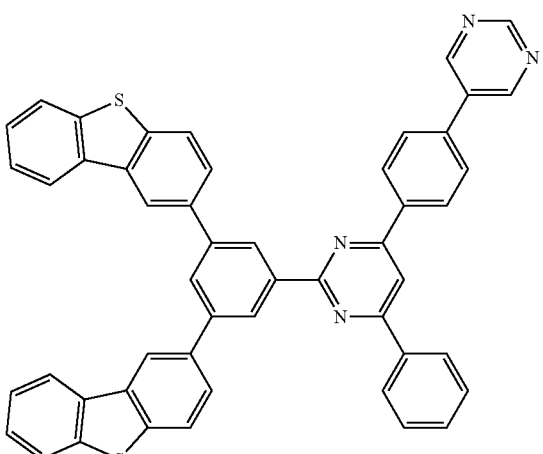
[Formula 56]
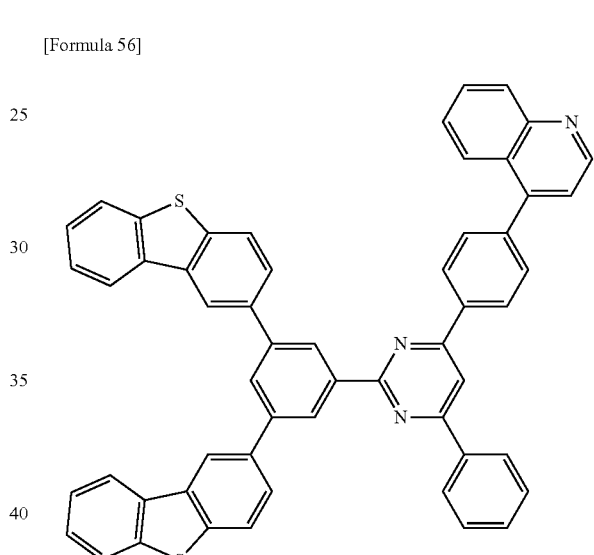
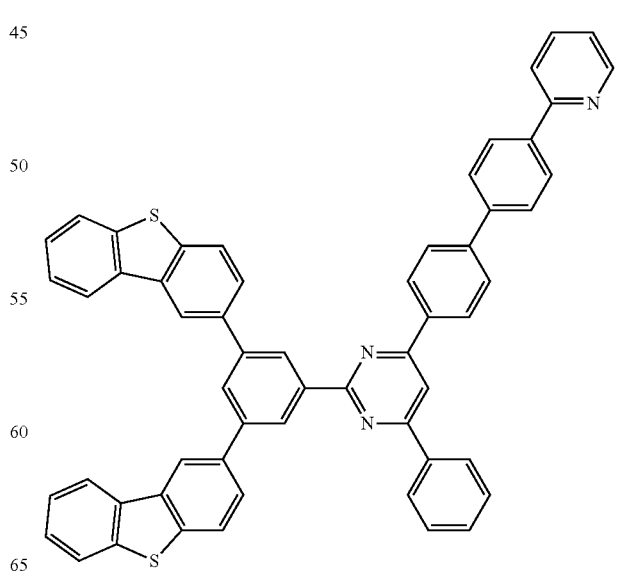

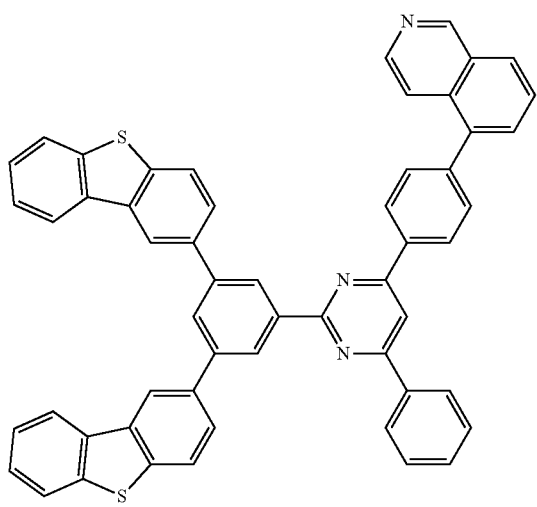
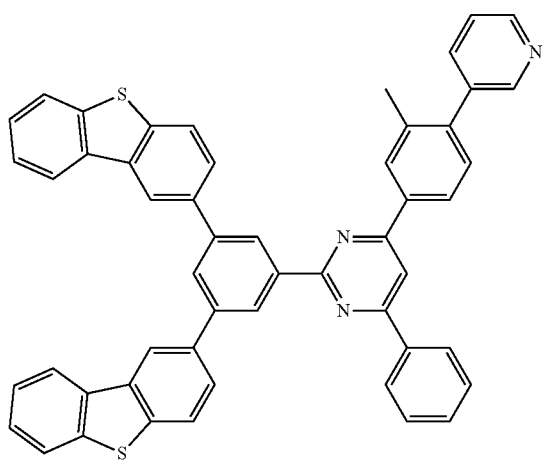
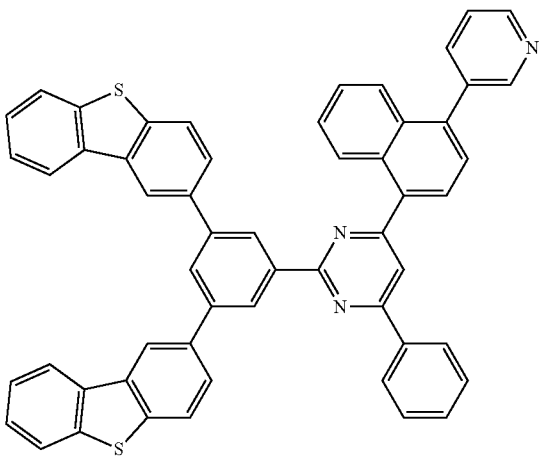
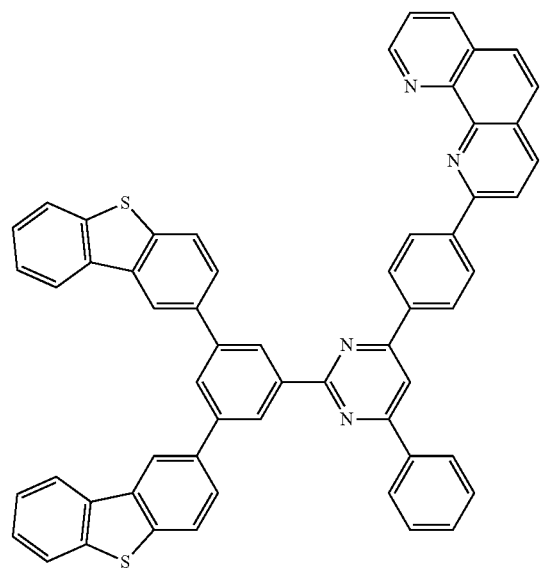
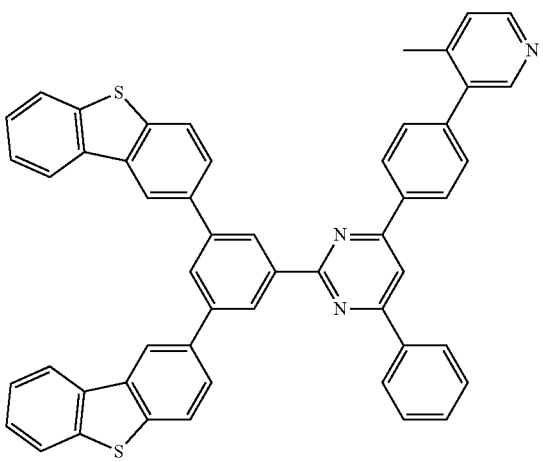
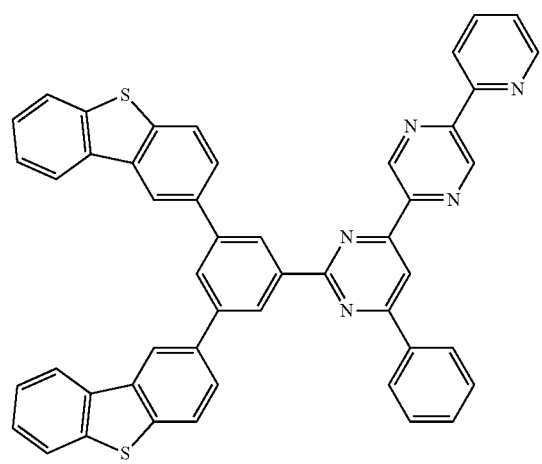

[Formula 57]
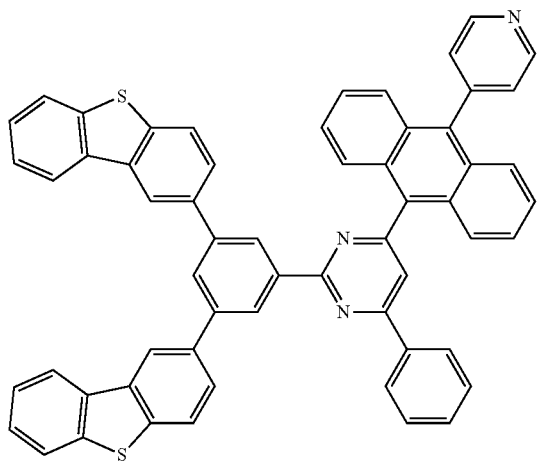
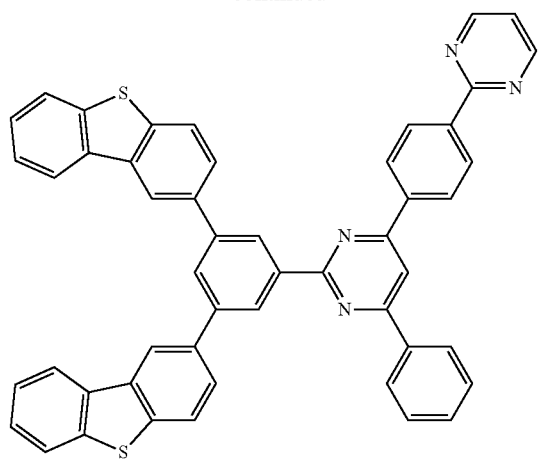
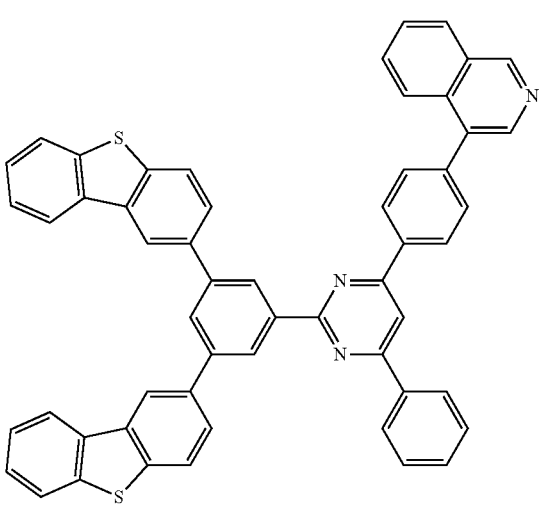
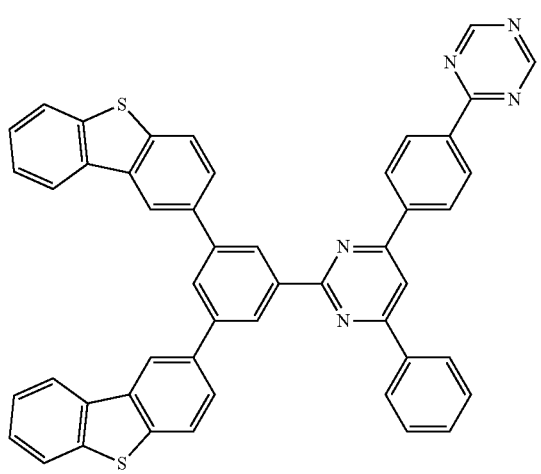
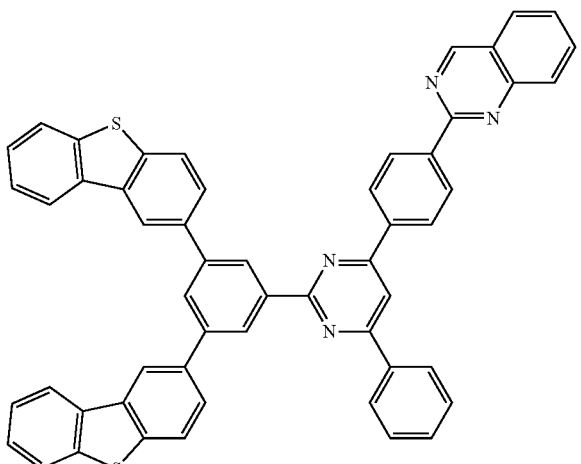

[Formula 58]
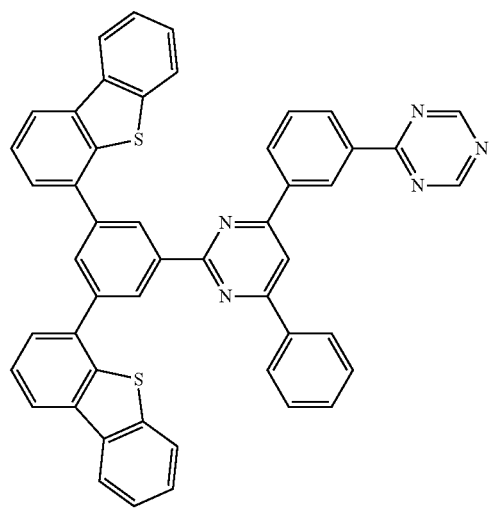
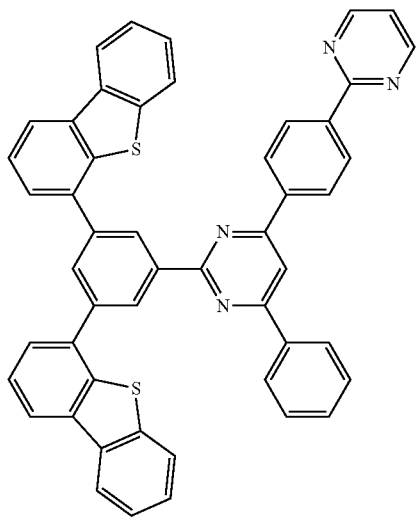
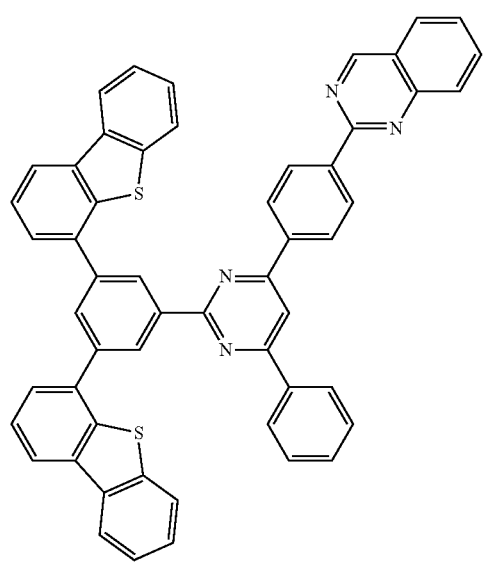
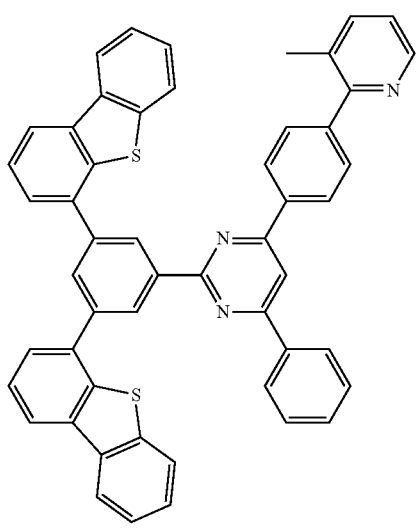
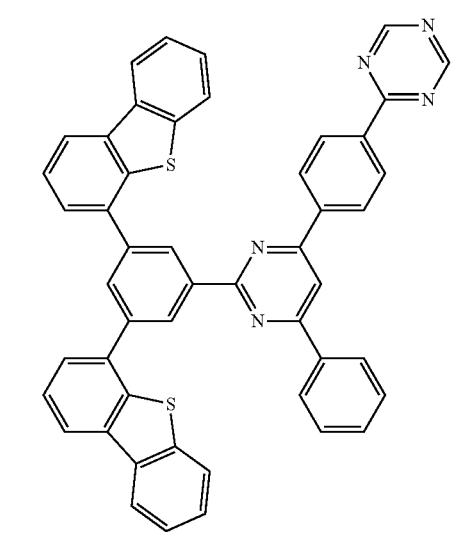
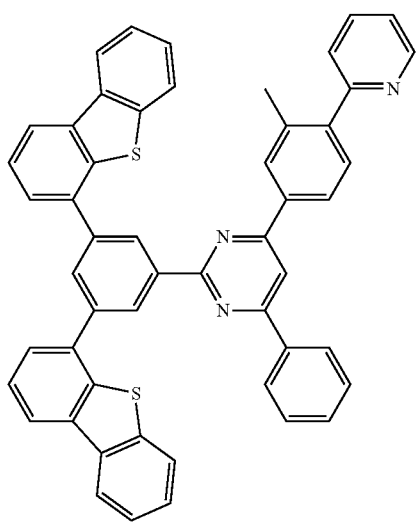

103
-continued
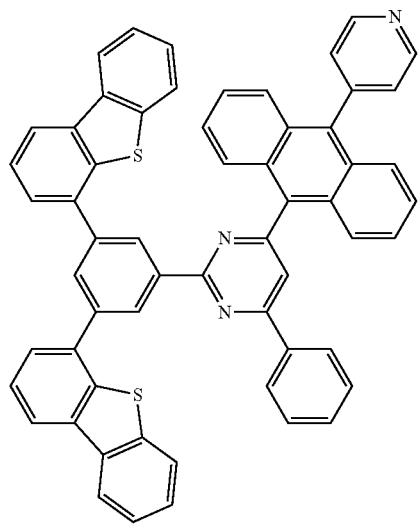
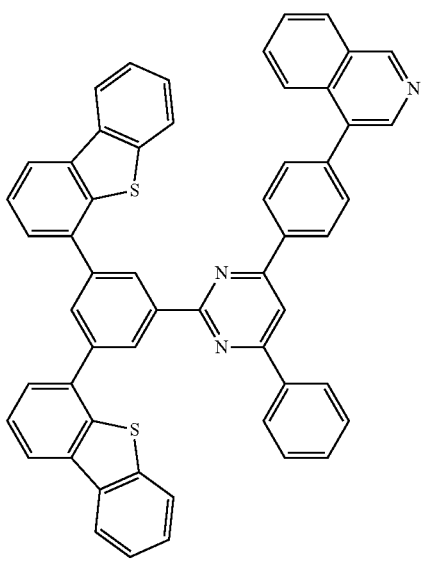
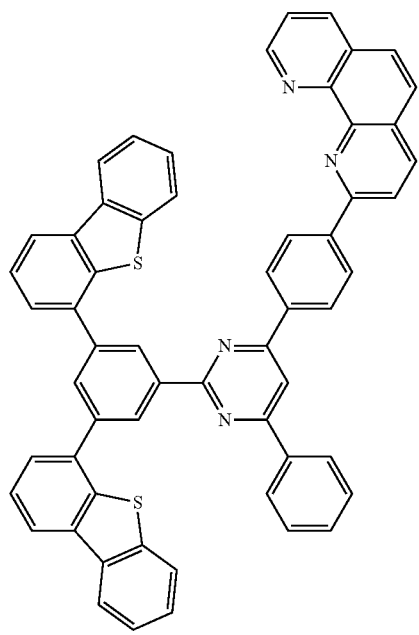
104
-continued
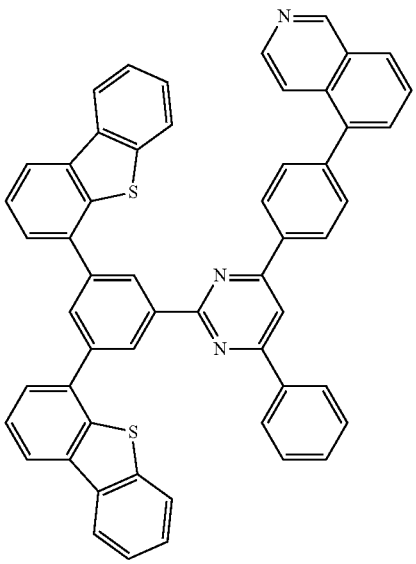
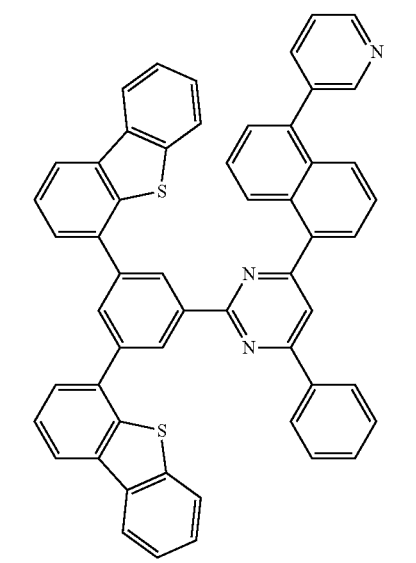
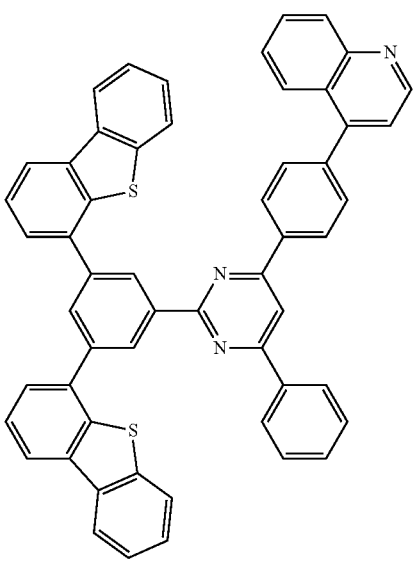

[Formula 59]
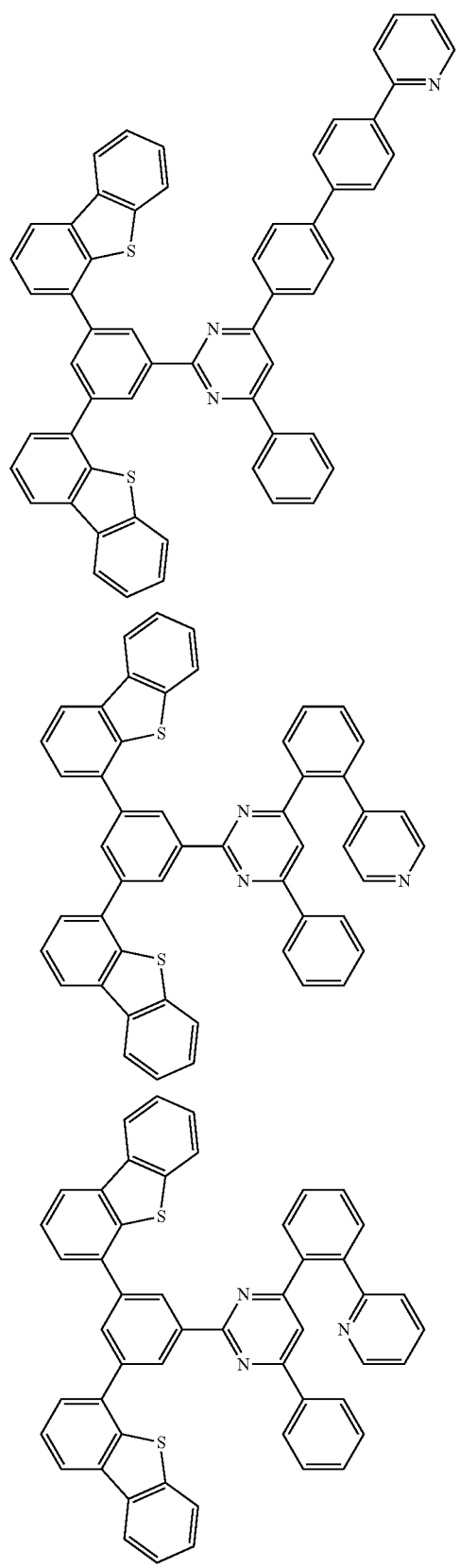
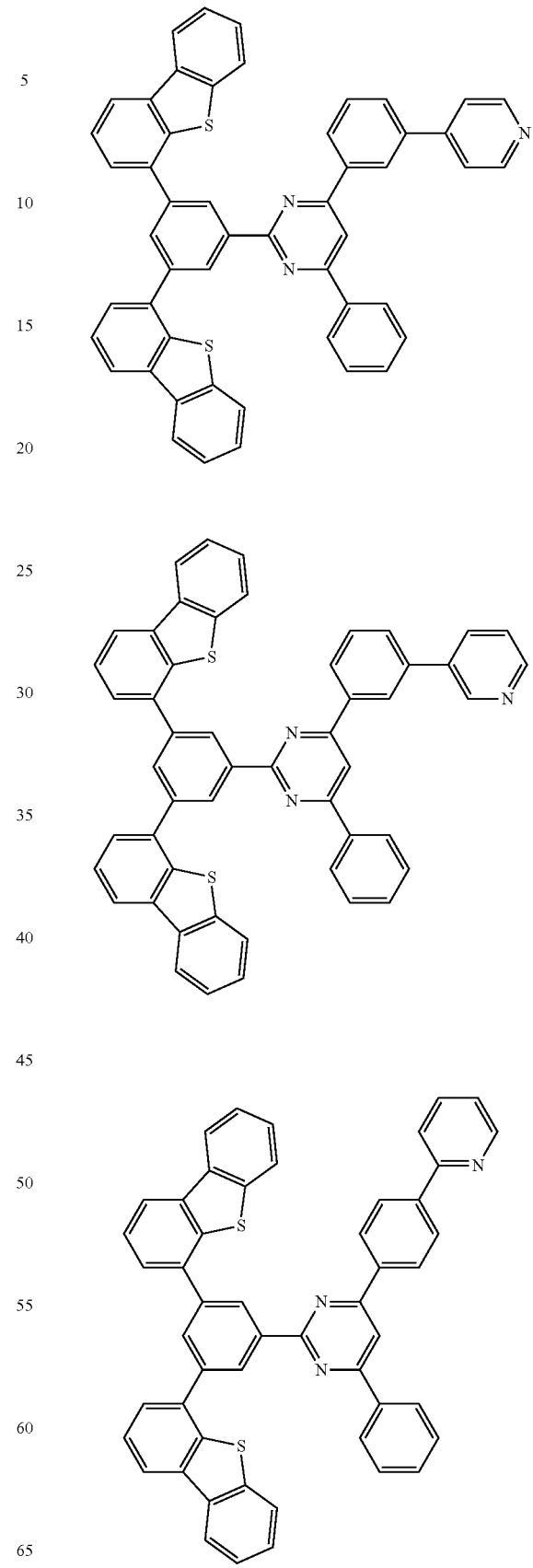

107
-continued
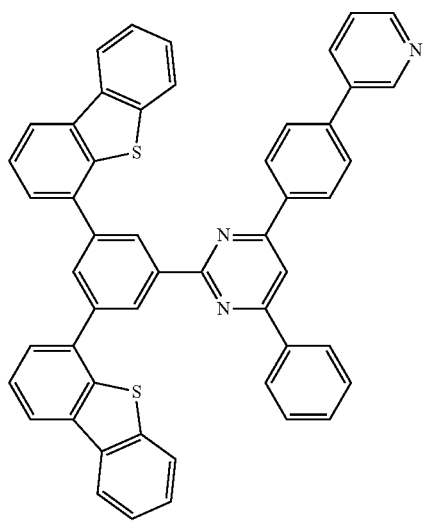
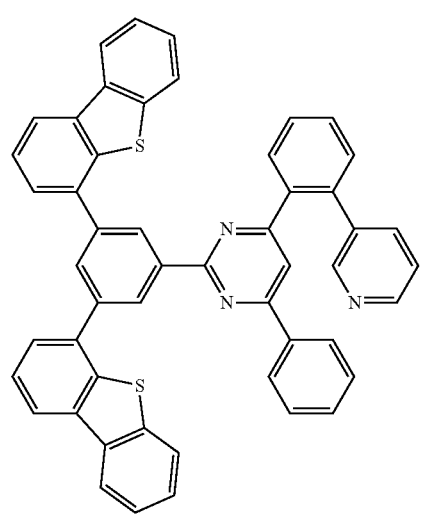
108
-continued
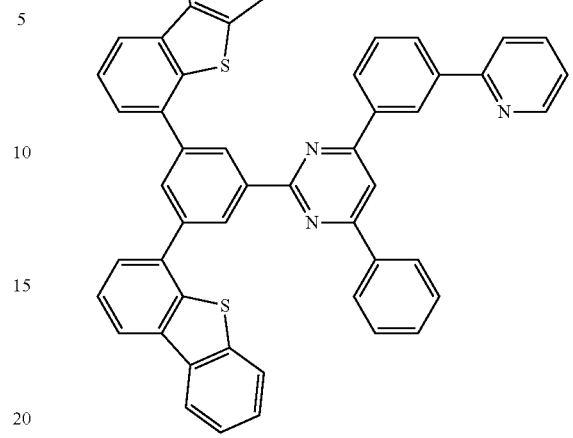
[Formula 60]
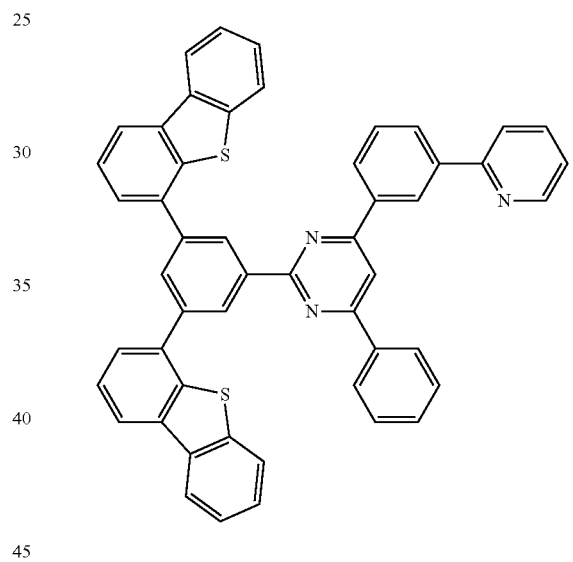
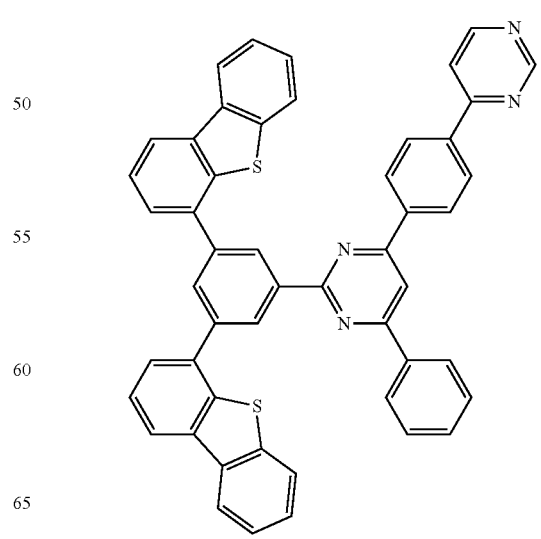

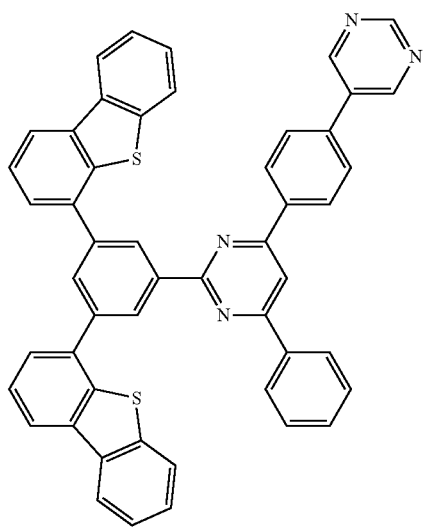
[Formula 61]
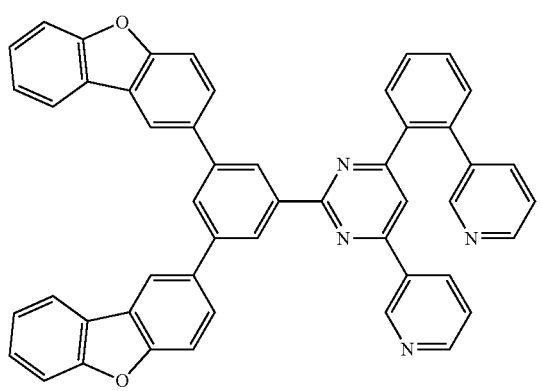
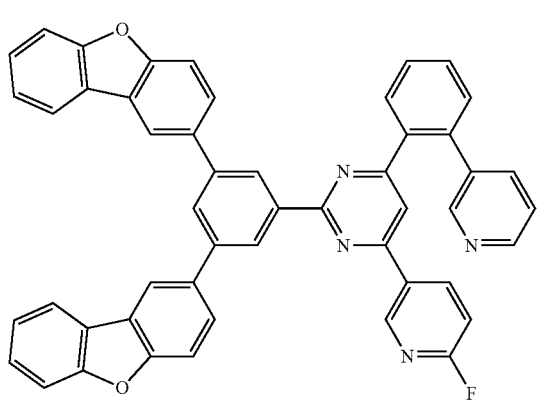
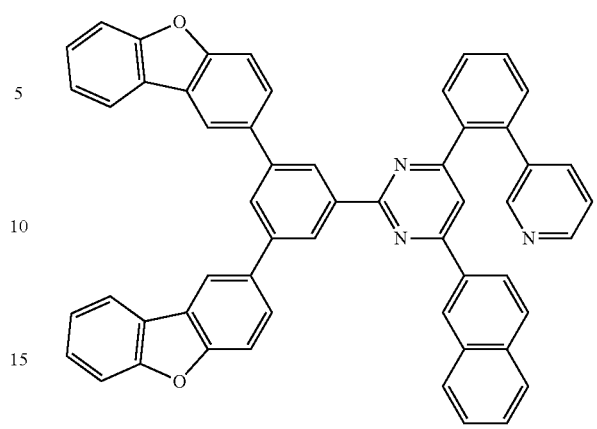
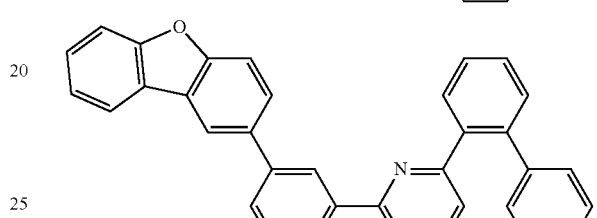
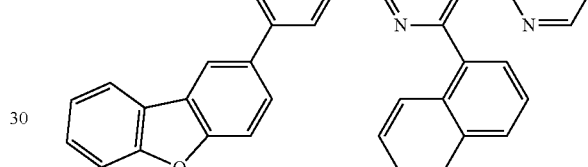
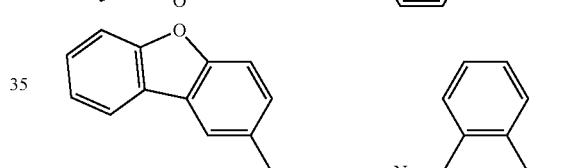
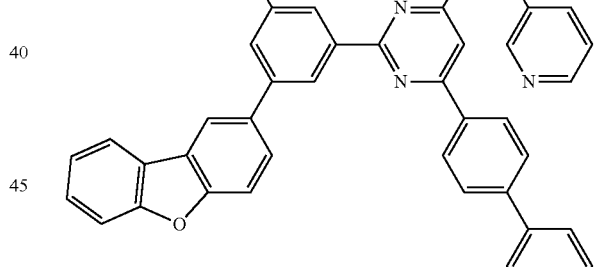
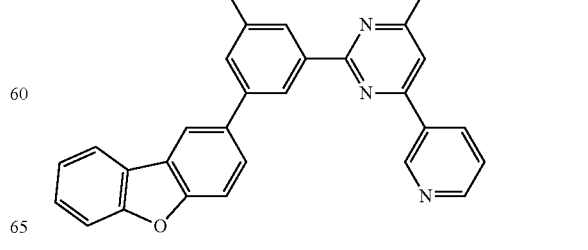

[Formula 62]
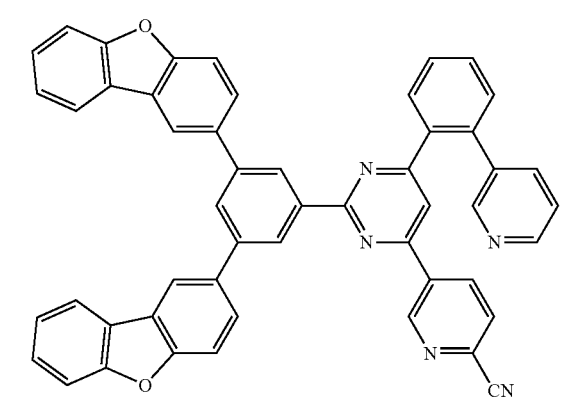
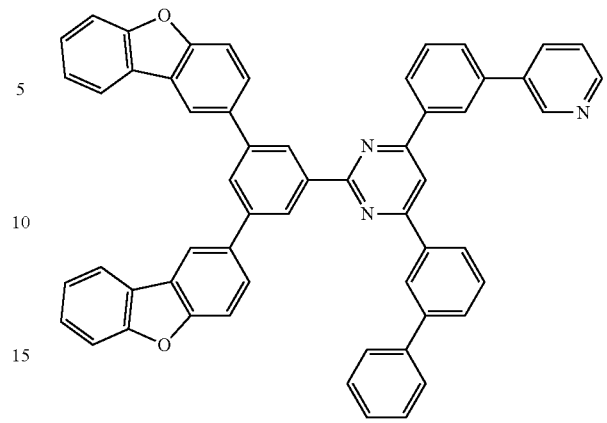
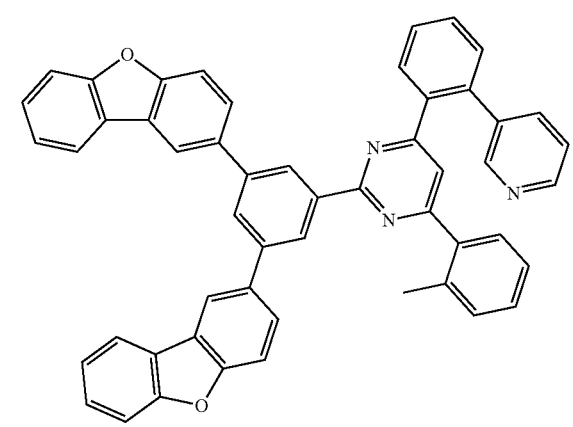
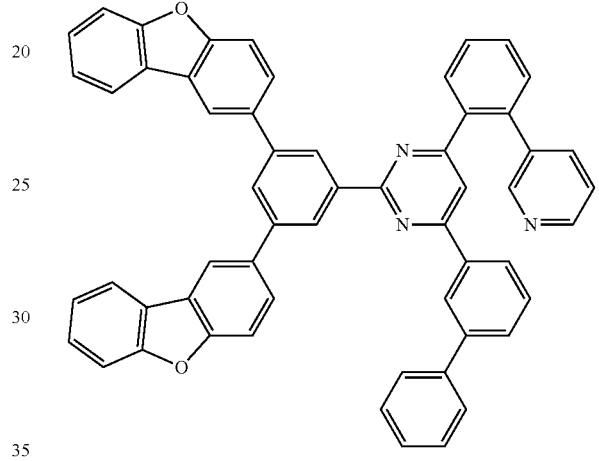
[Formula 63]
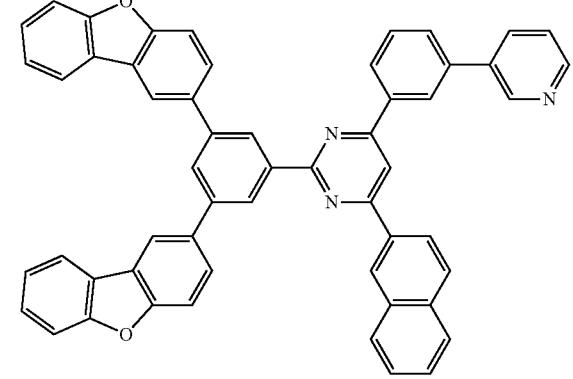
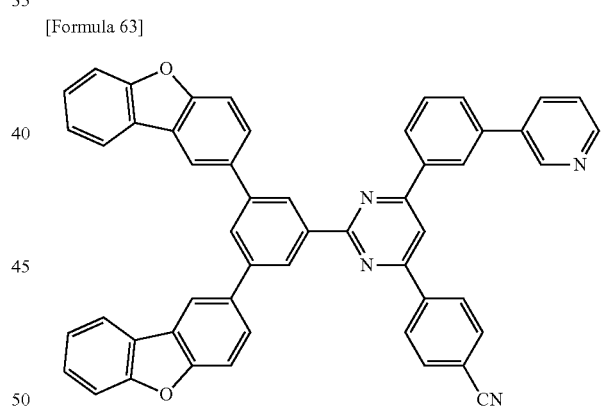
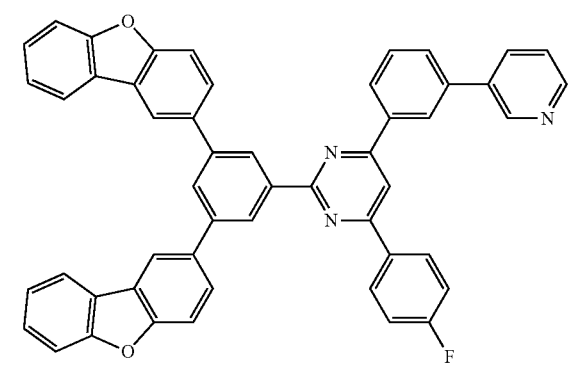
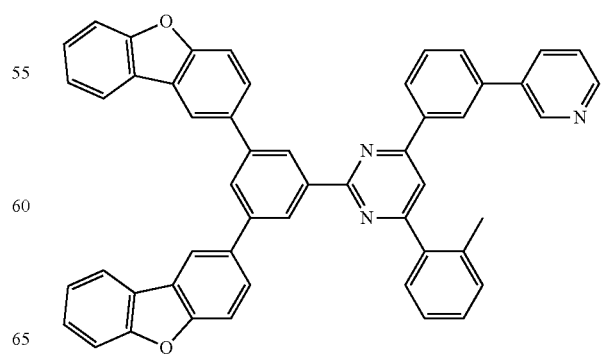

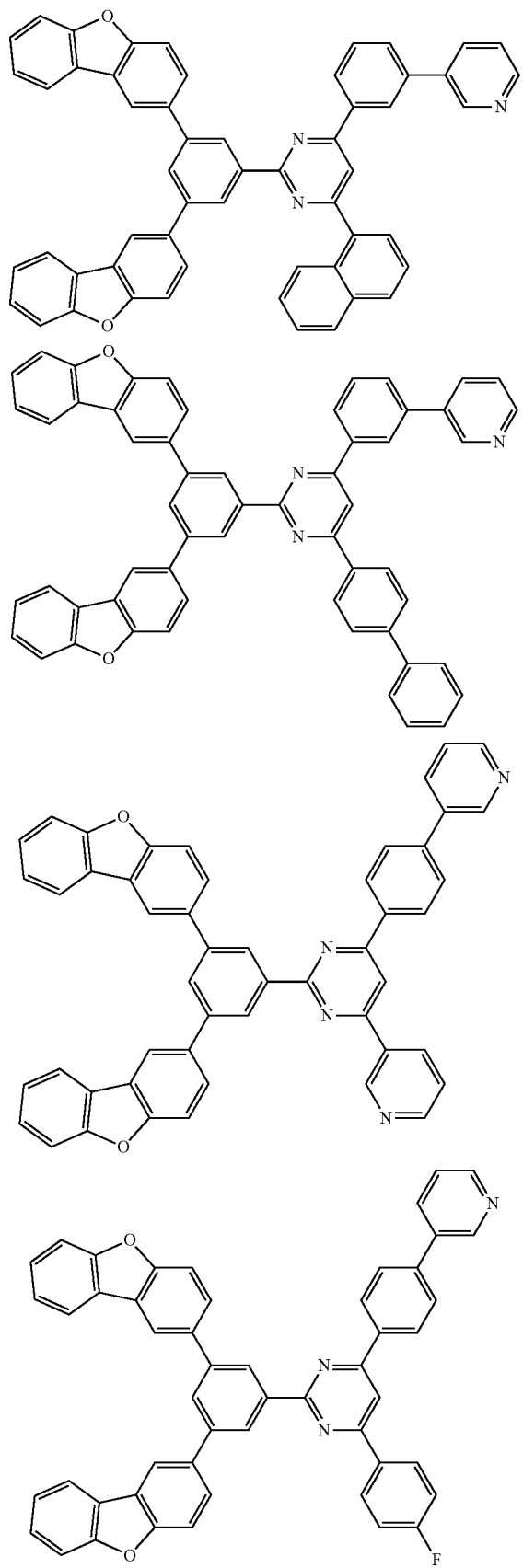
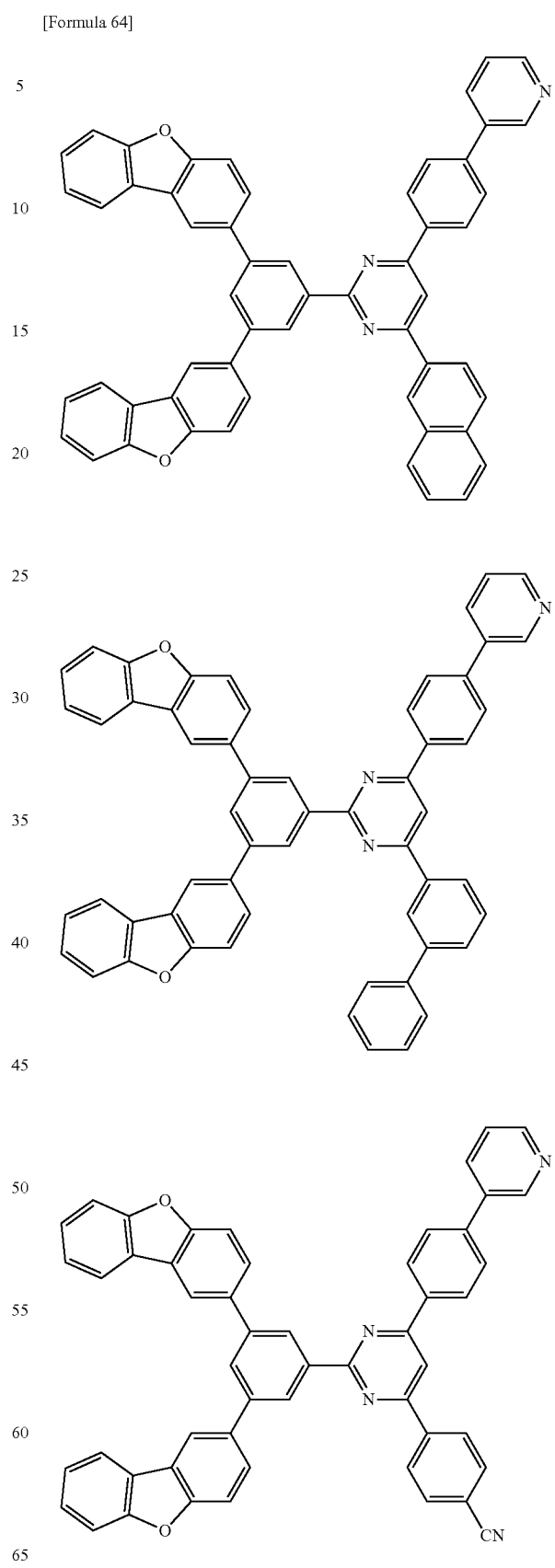

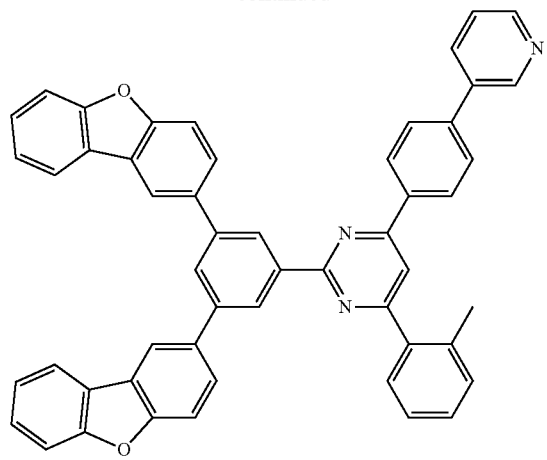
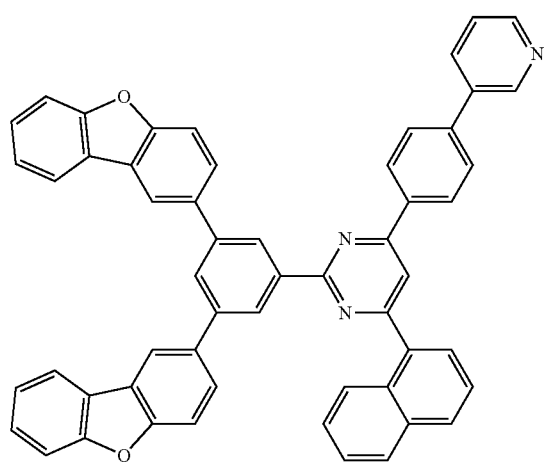
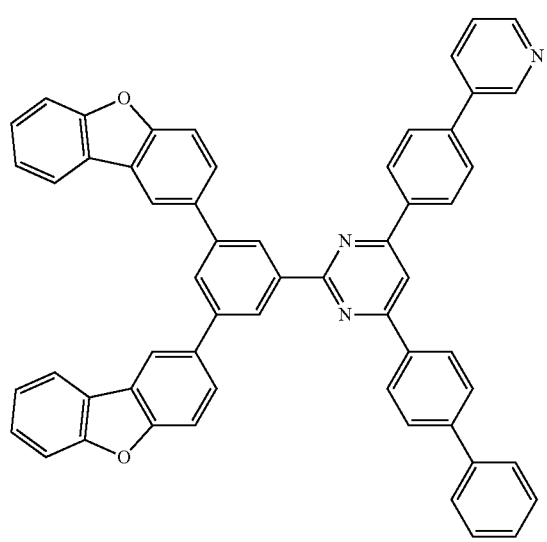
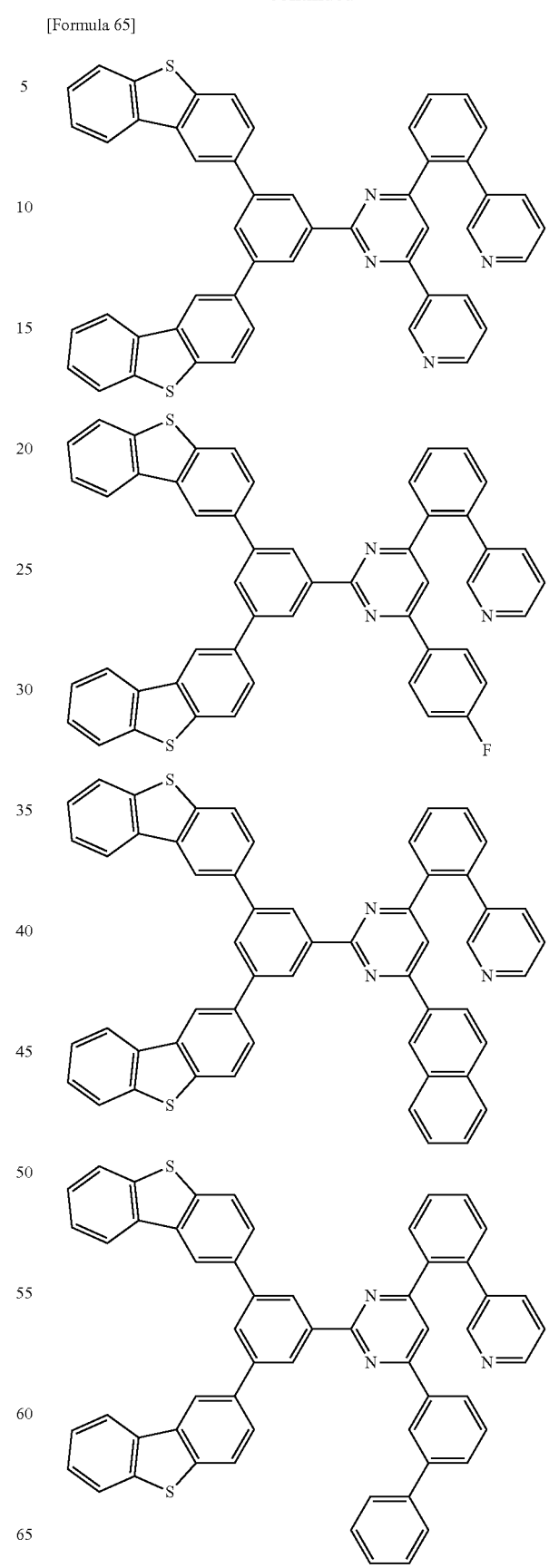

117
-continued
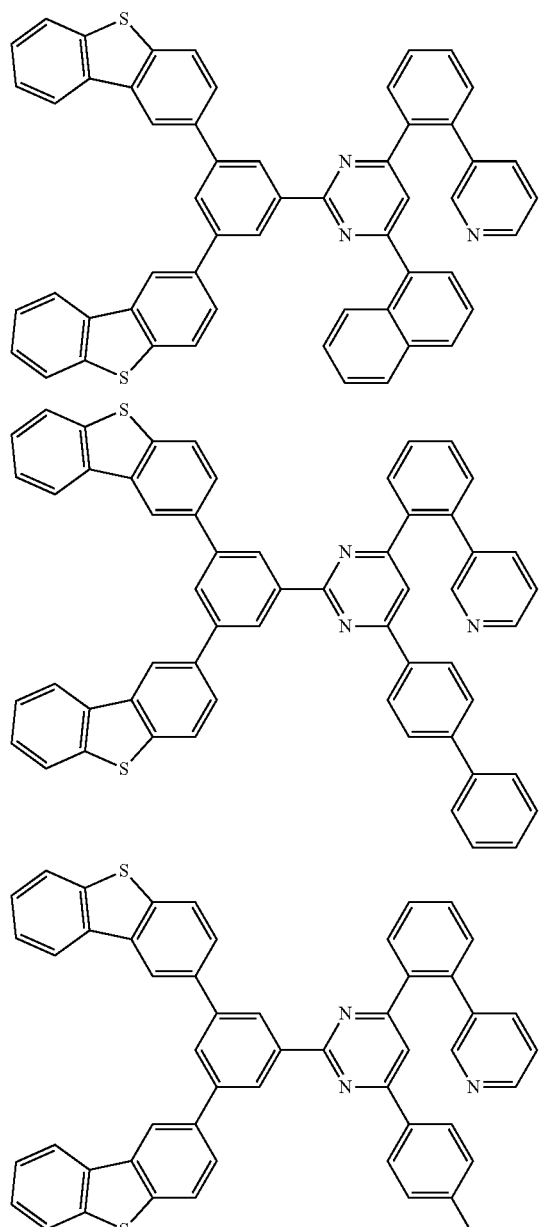
118
-continued
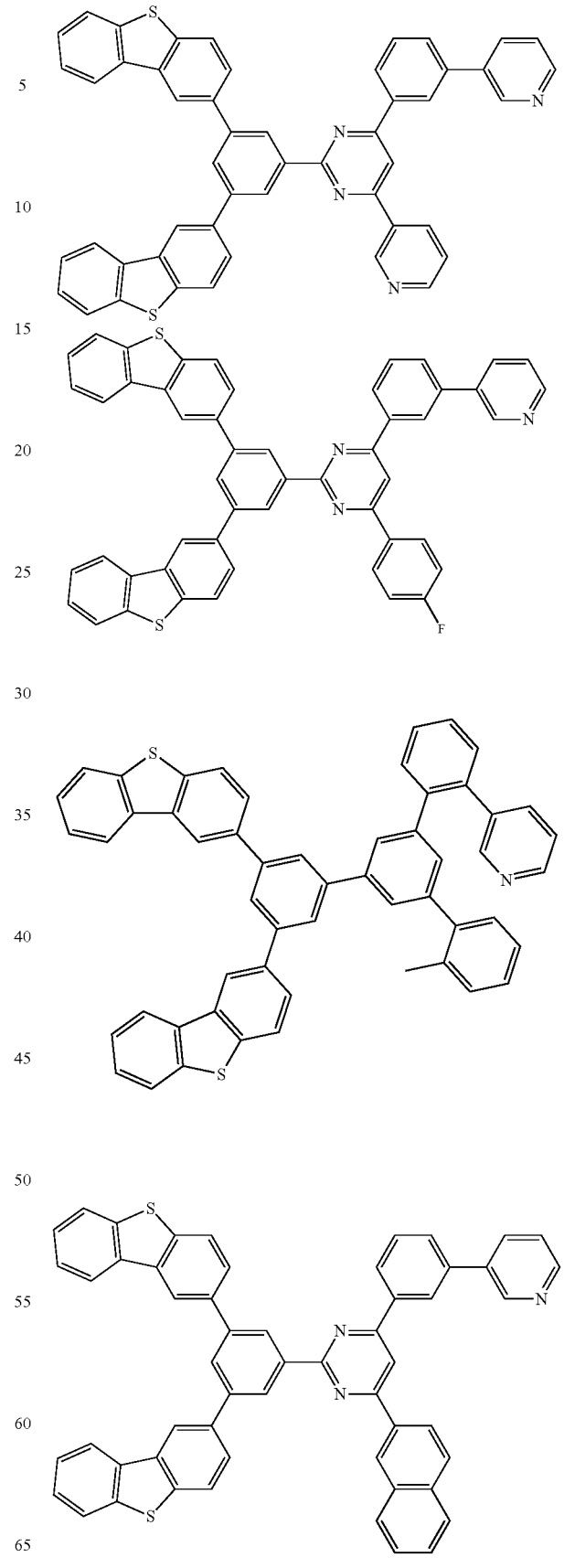

[Formula 66]
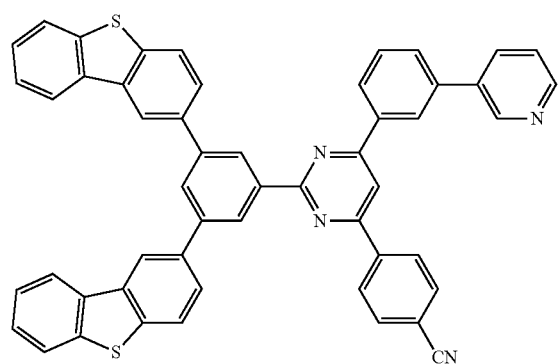
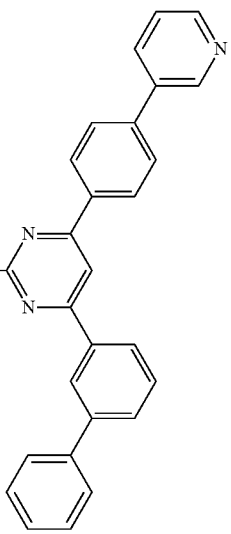
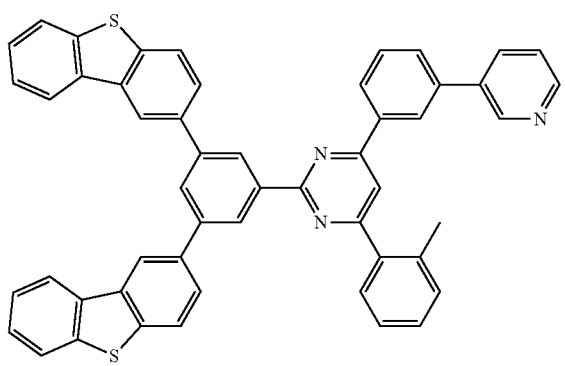
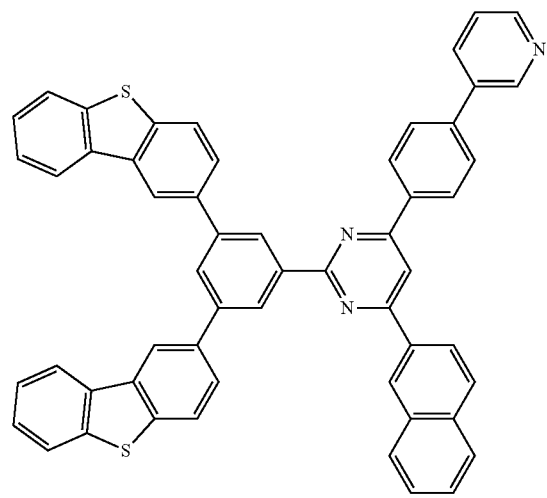
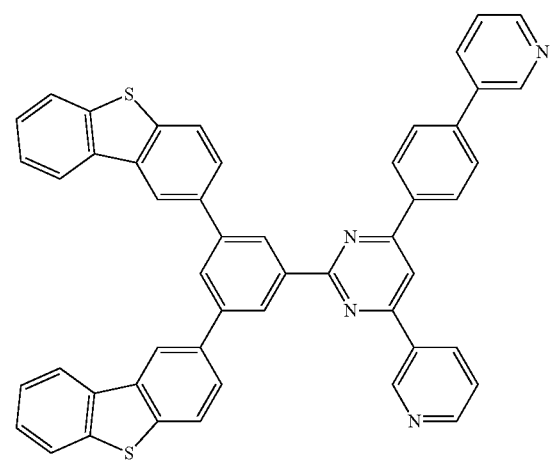

121
-continued
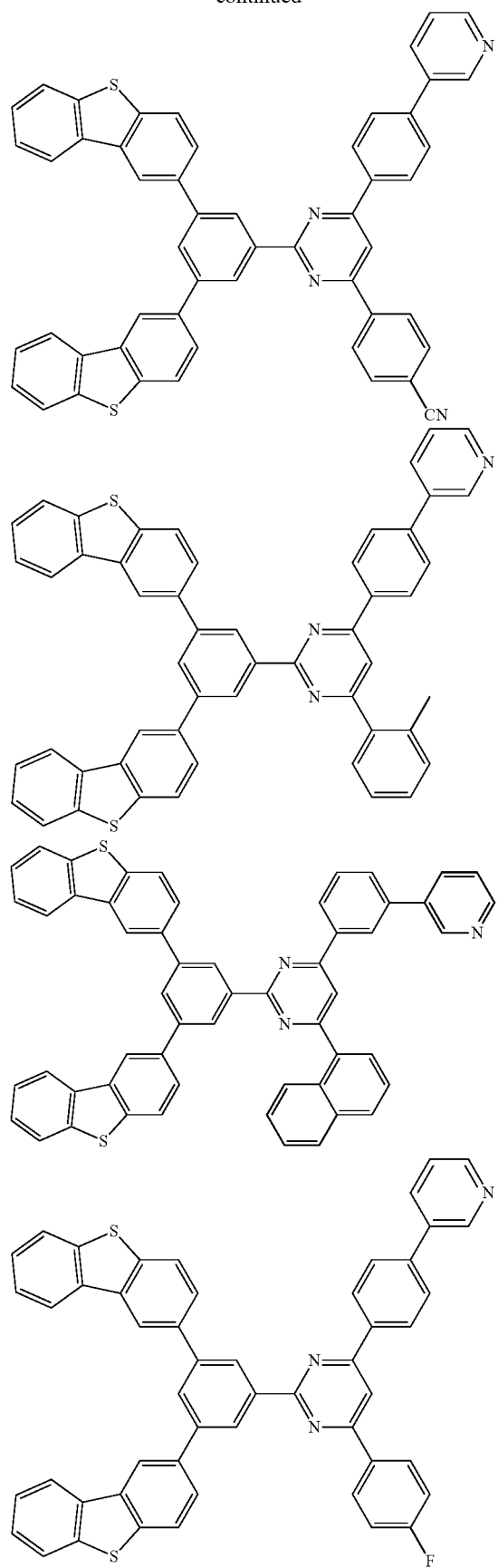
122
-continued
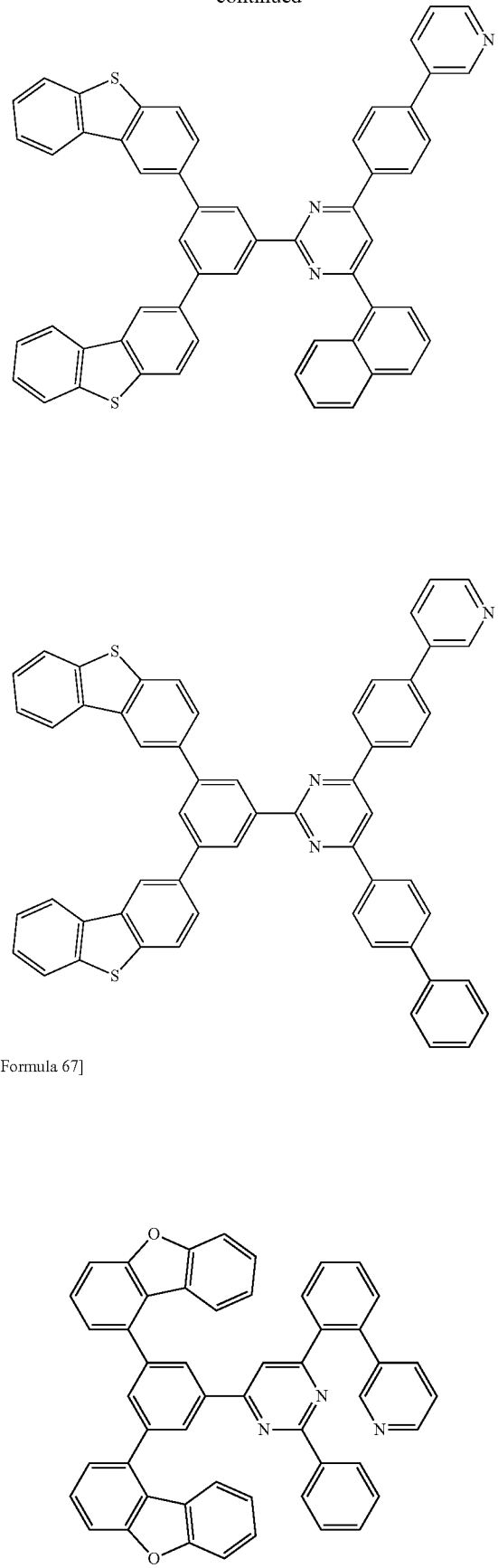
[Formula 67]

123
-continued
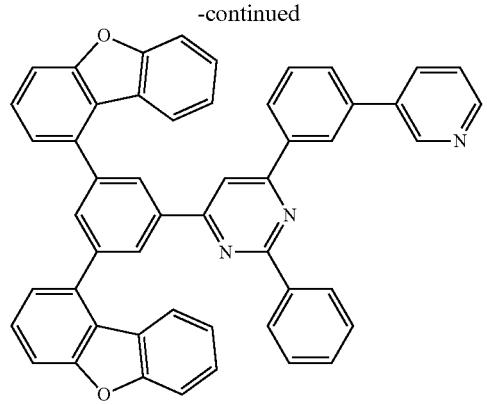
124
-continued
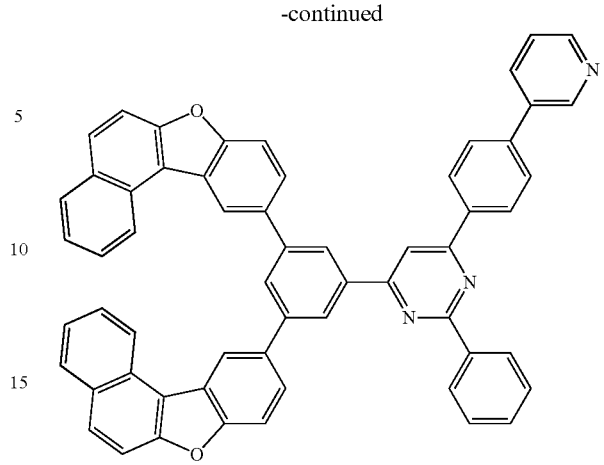
[Formula 68]
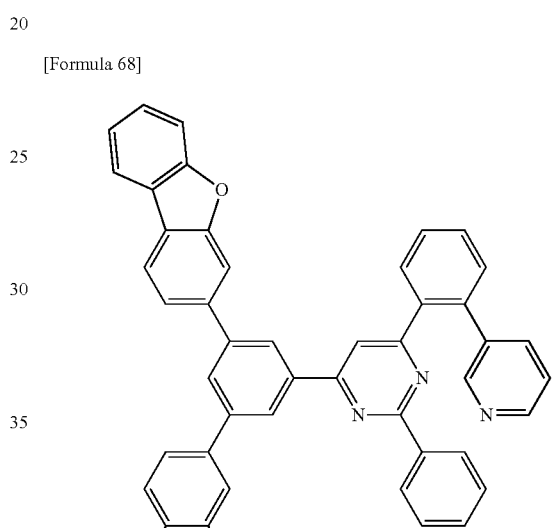
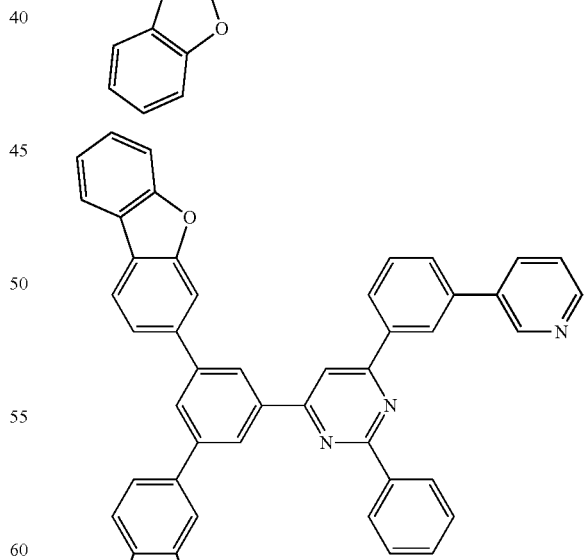

125
-continued
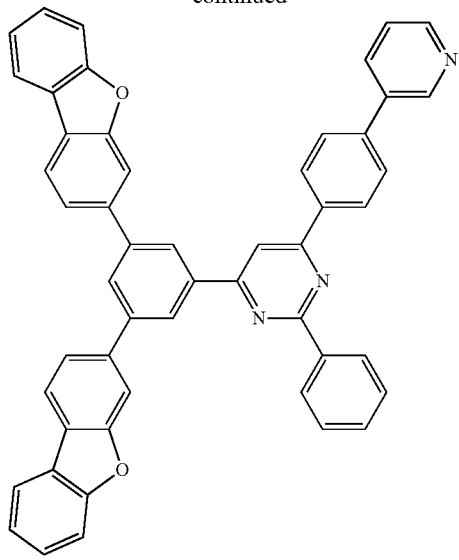
[Formula 69]
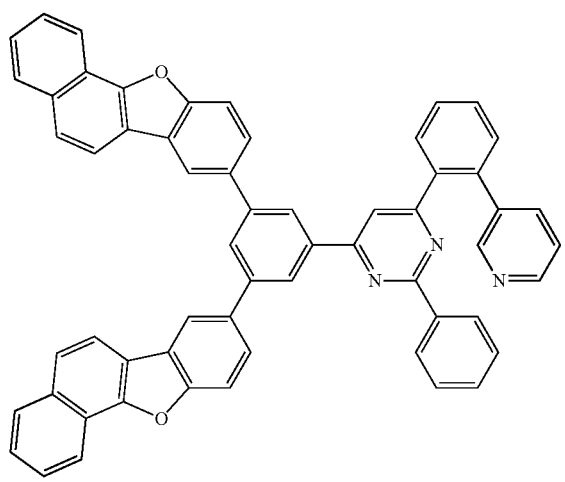
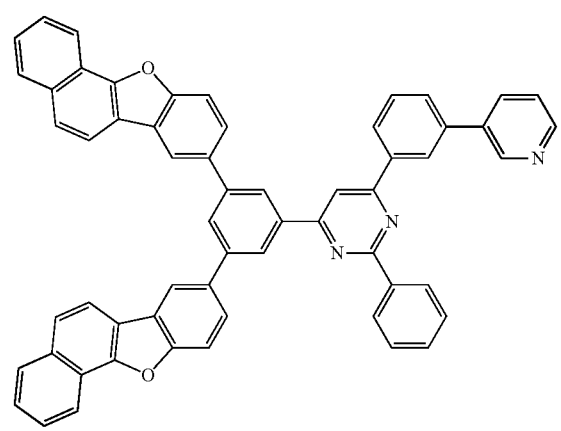
126
-continued
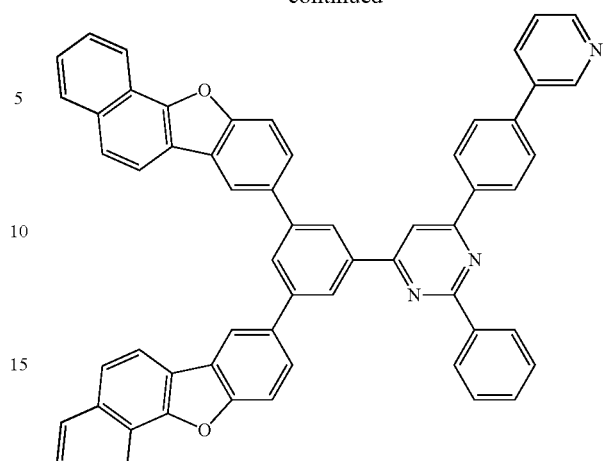
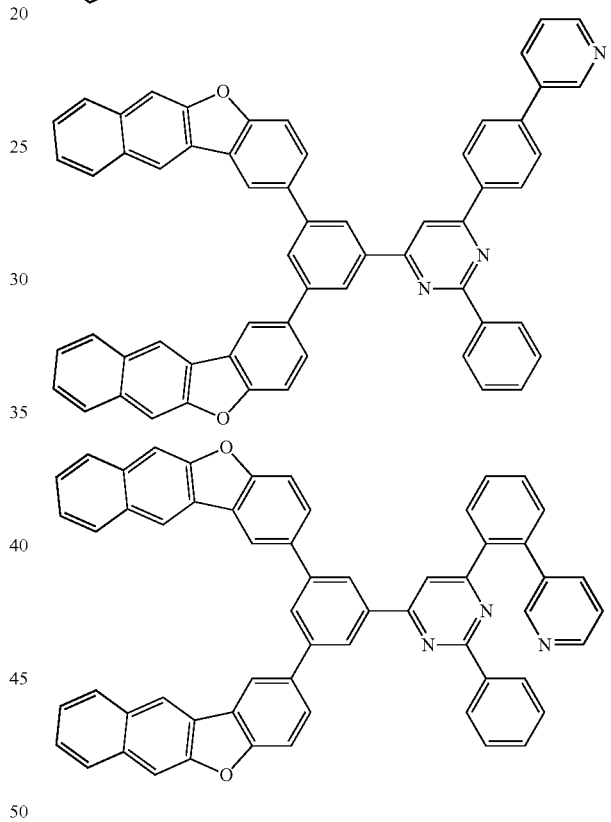
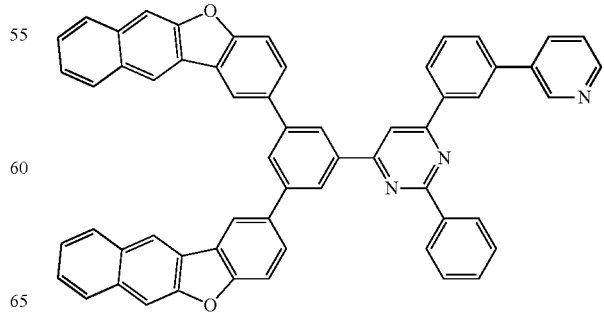

[Formula 70]
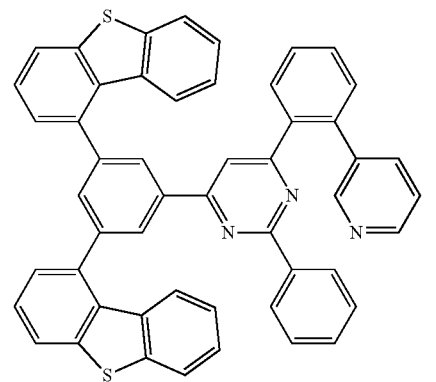
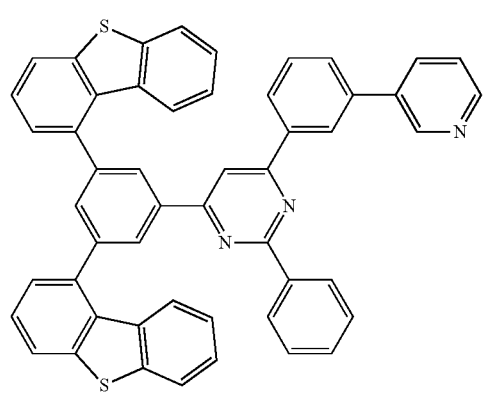
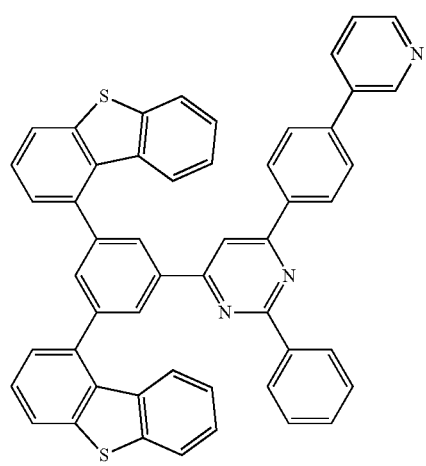
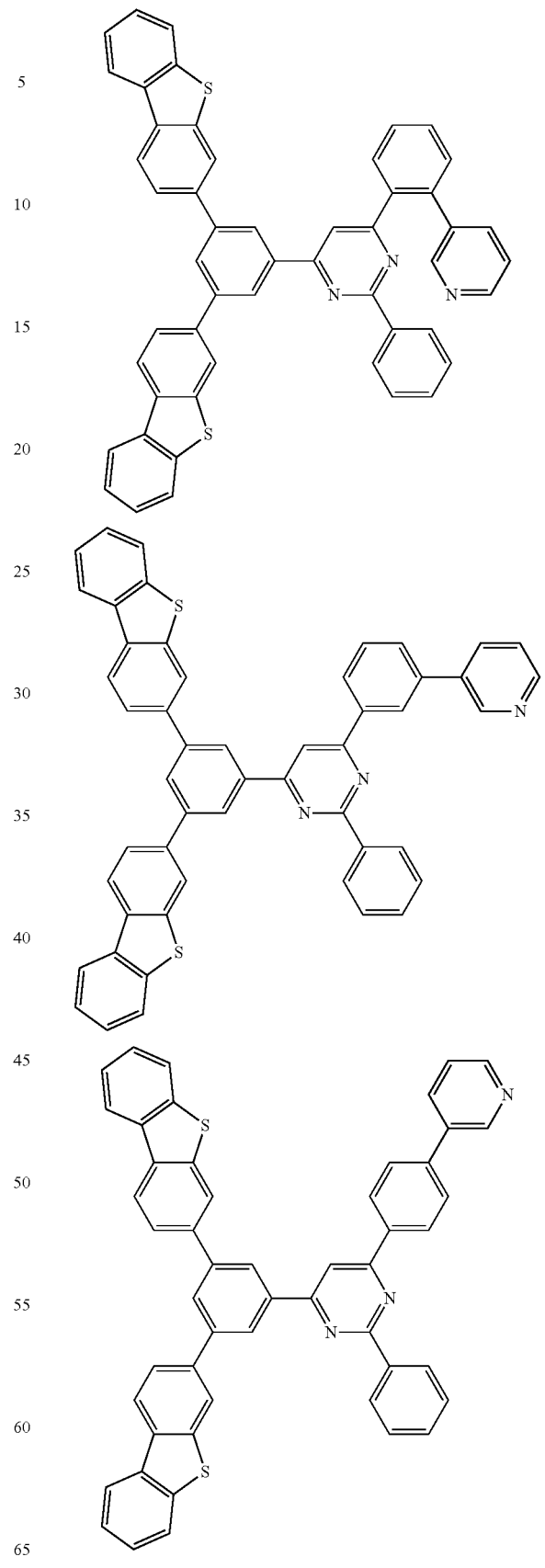

[Formula 71]
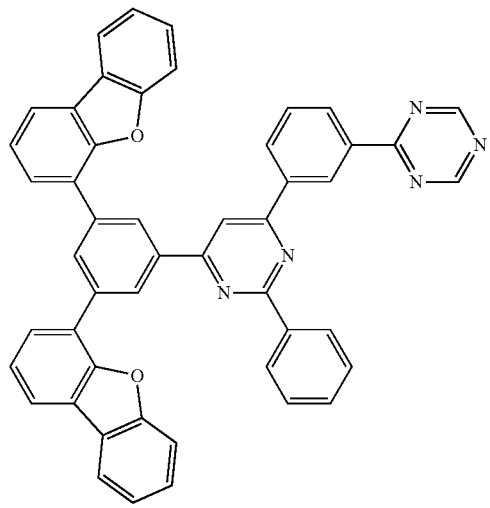
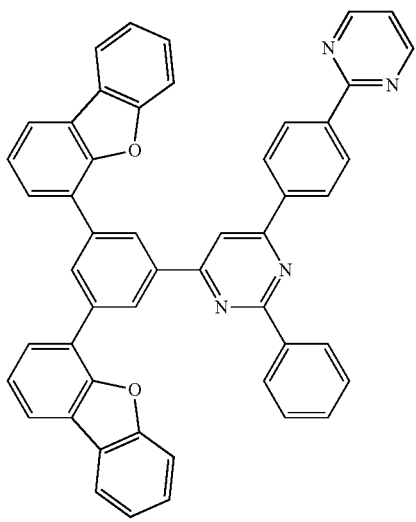
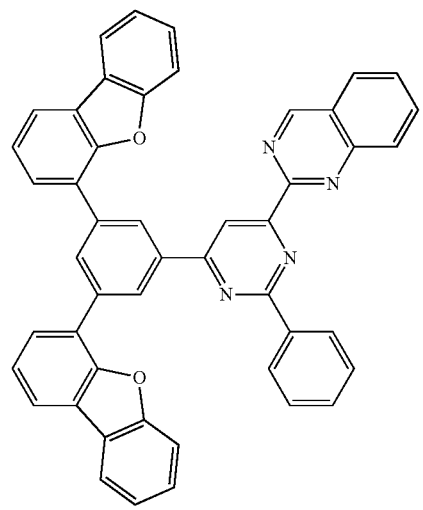
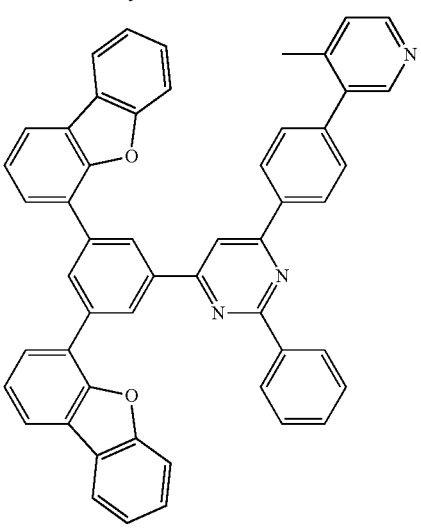
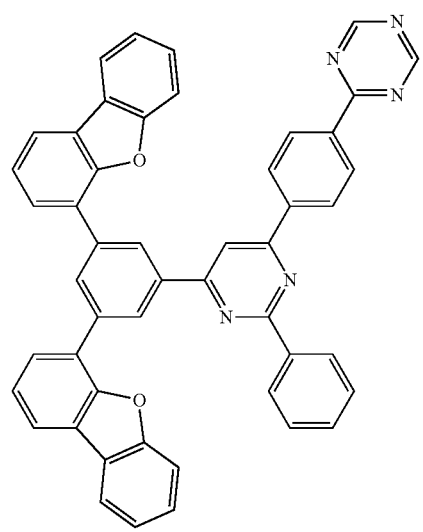
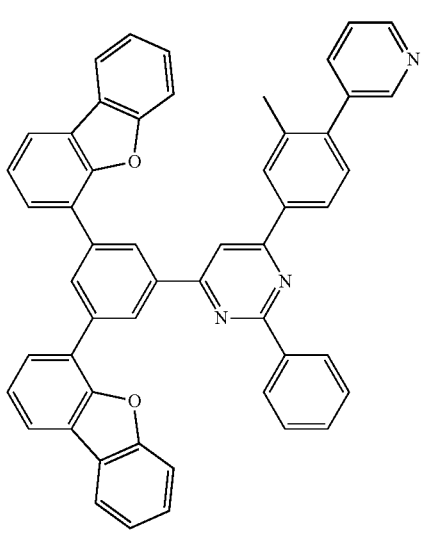

131
-continued
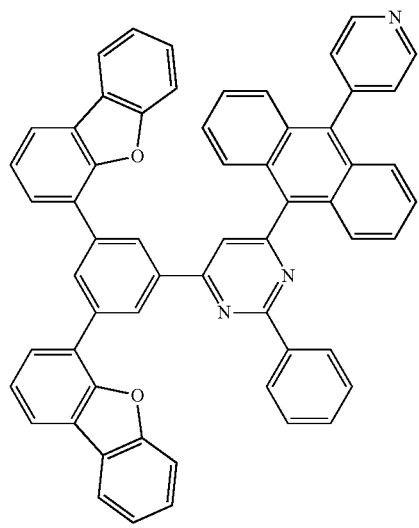
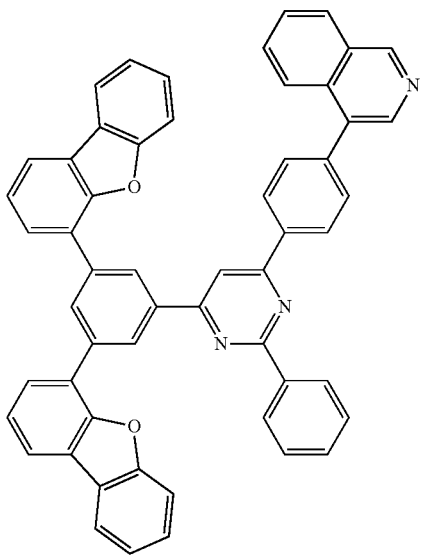
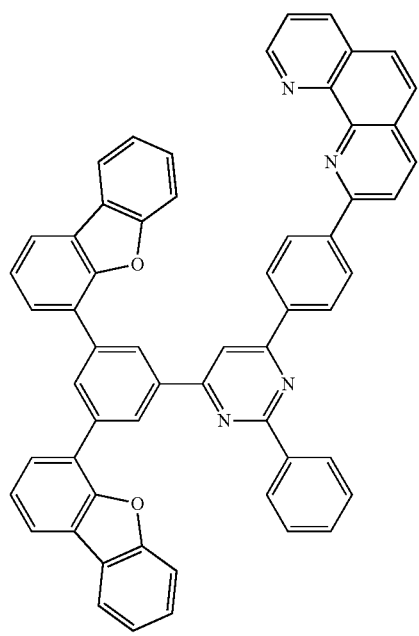
132
-continued
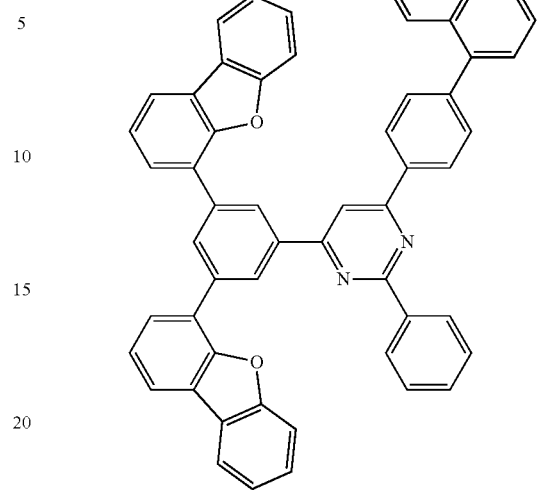
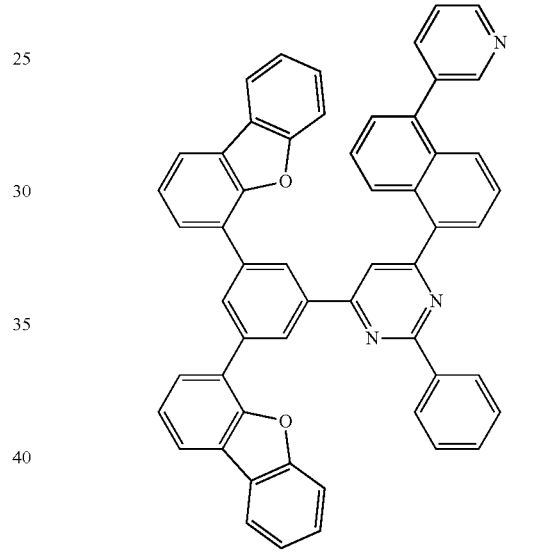
[Formula 72]
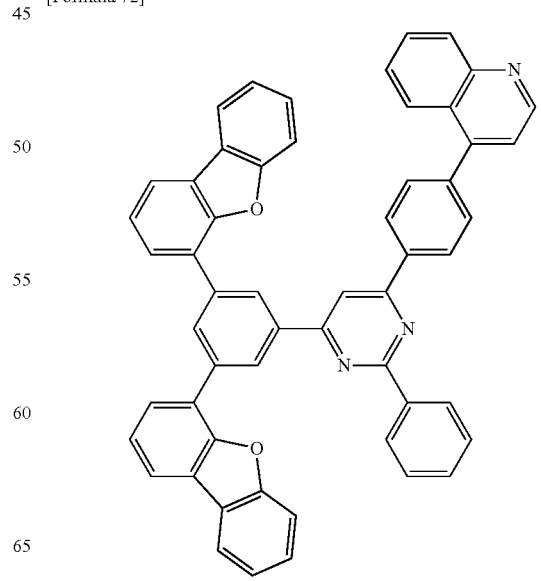

133
-continued
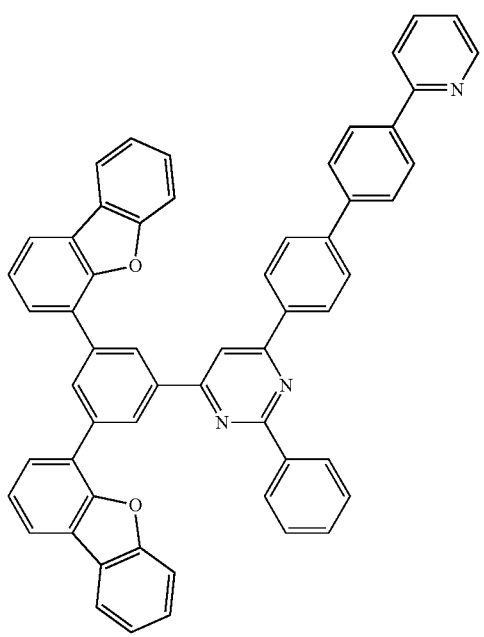
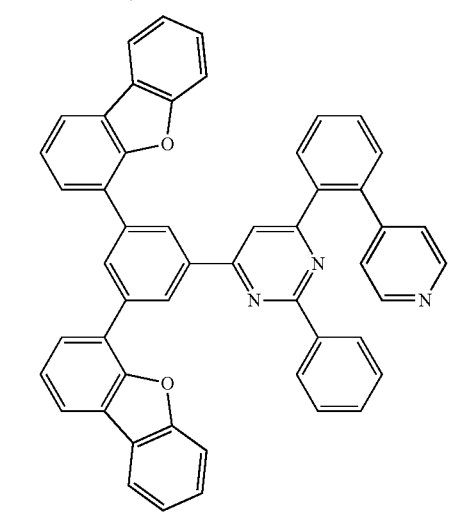
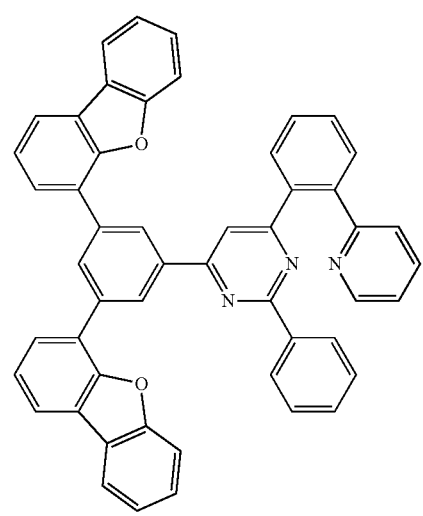
134
-continued
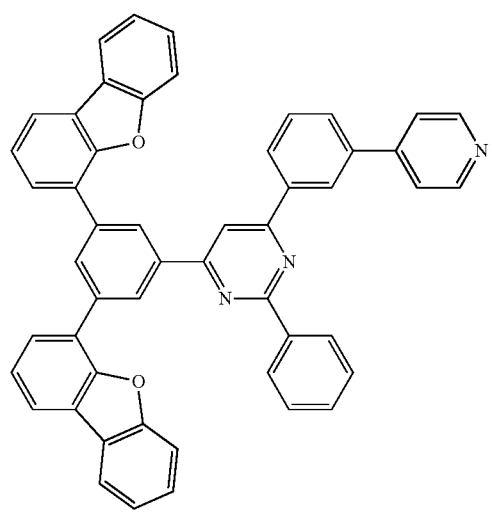
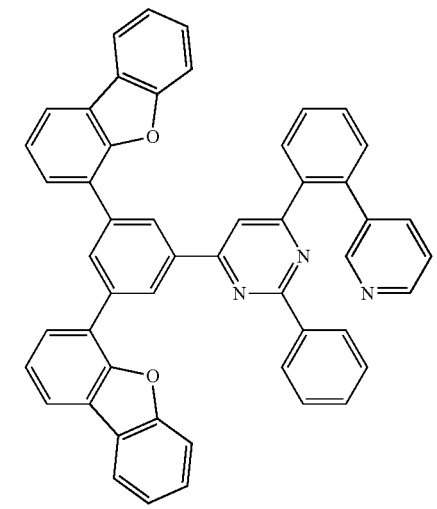
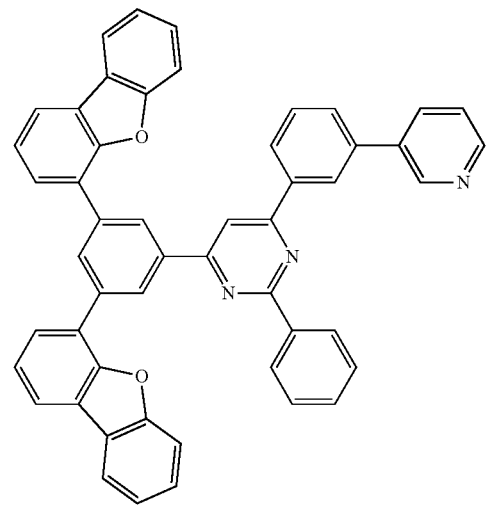

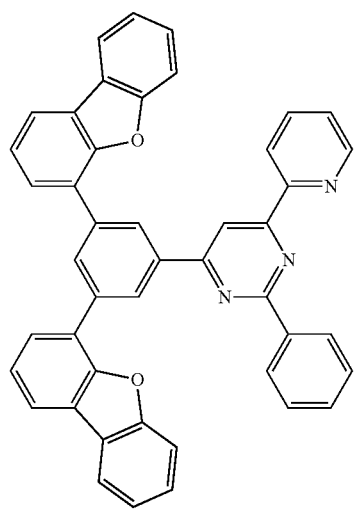
[Formula 73]
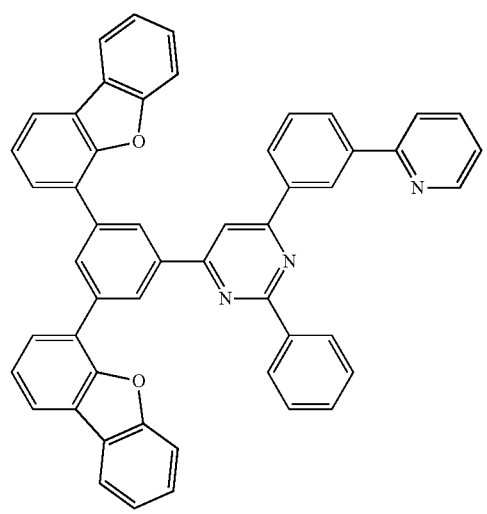
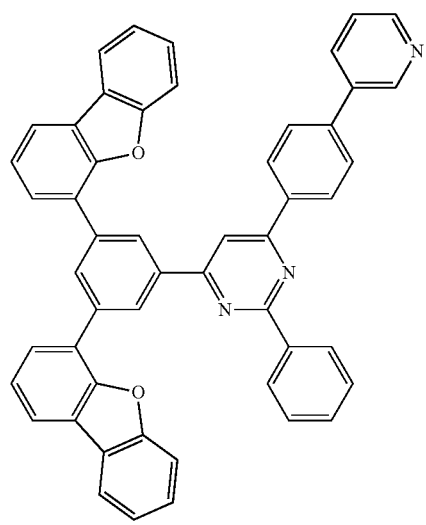
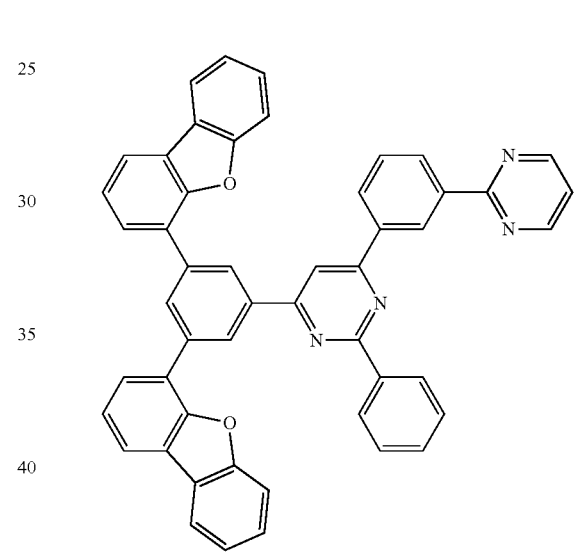
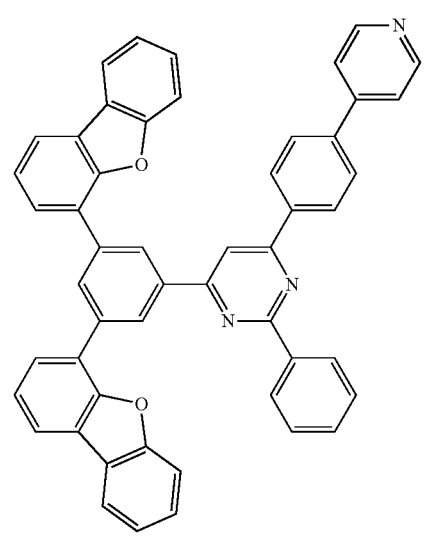
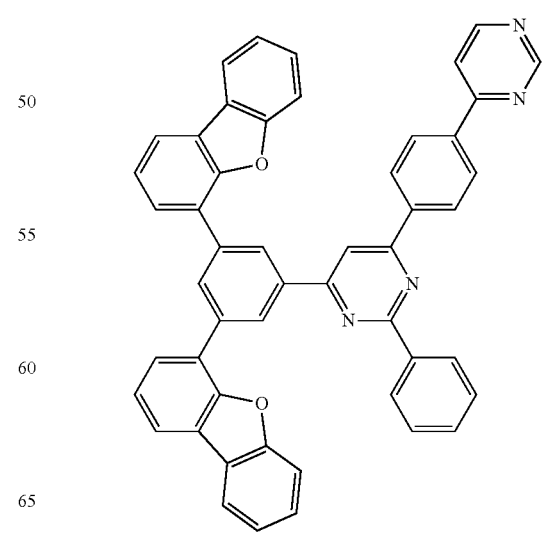

137
-continued
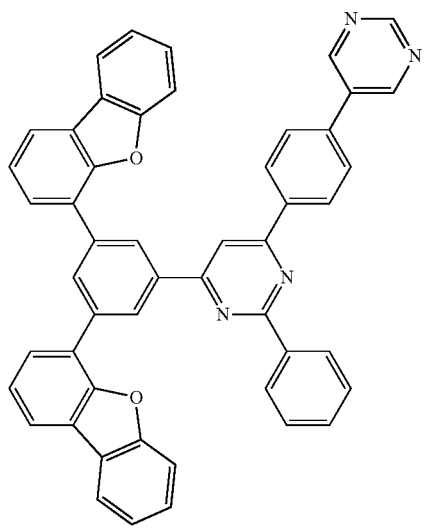 [SMILES: c1ccc(-c2nc(-c3ccc(-c4cncnc4)cc3)cc(-c3cc(-c4cccc5c4oc4ccccc45)cc(-c4cccc5c4oc4ccccc45)c3)n2)cc1]
[Formula 74]
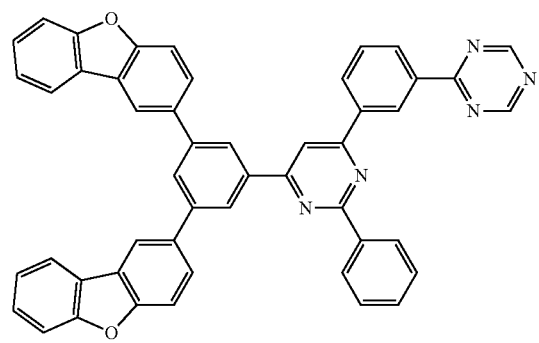
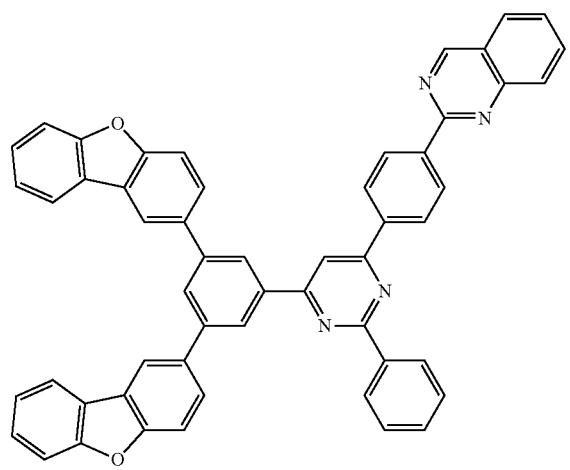
138
-continued
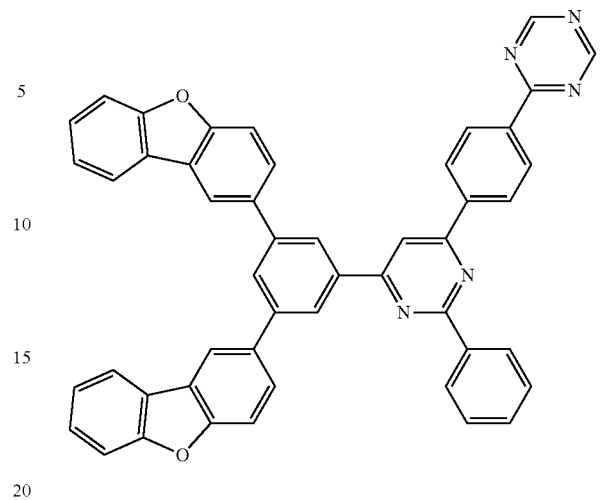
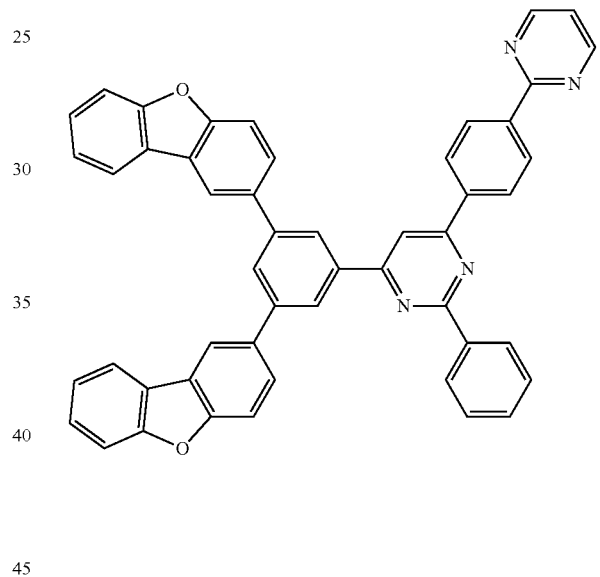
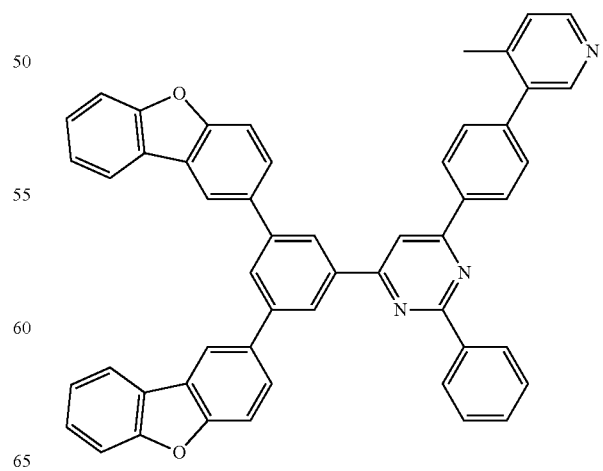

139
-continued
140
-continued
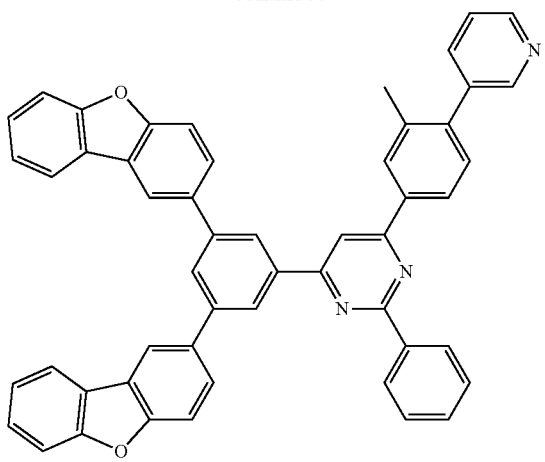
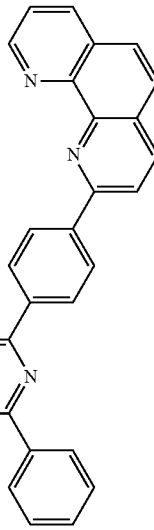

141
-continued
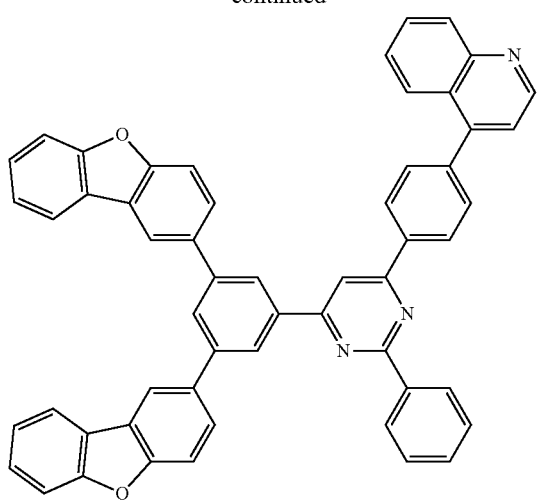
[Formula 75]
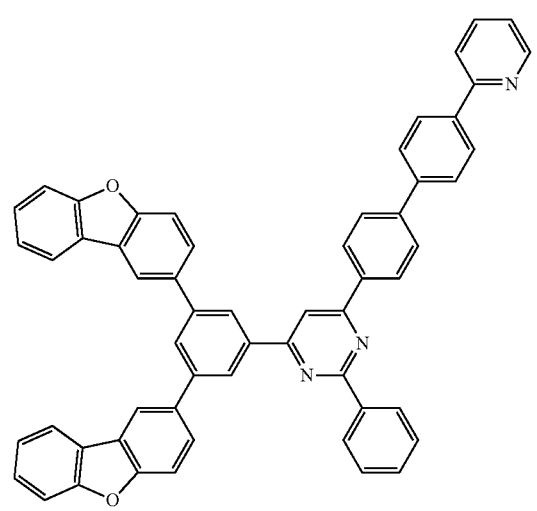
142
-continued
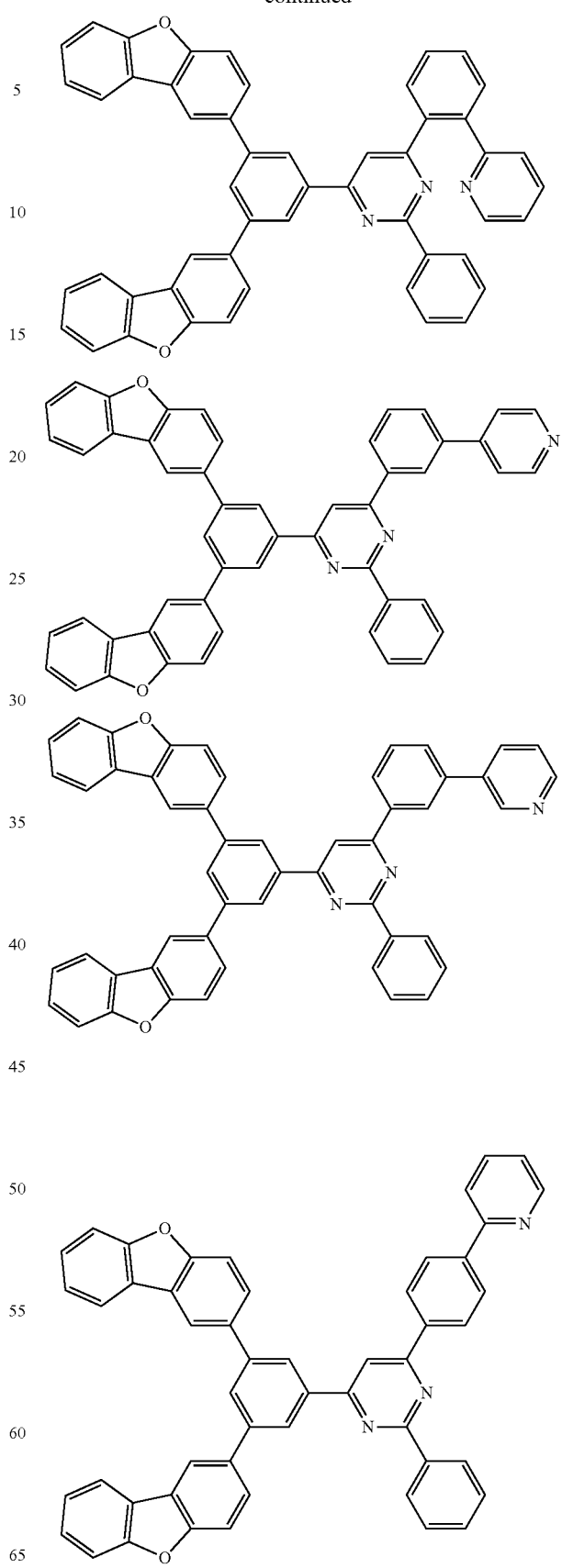

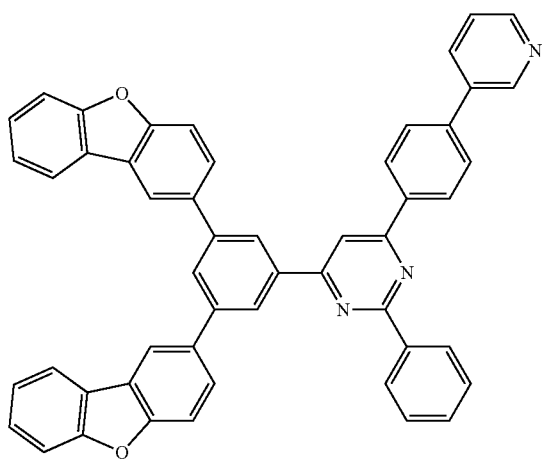
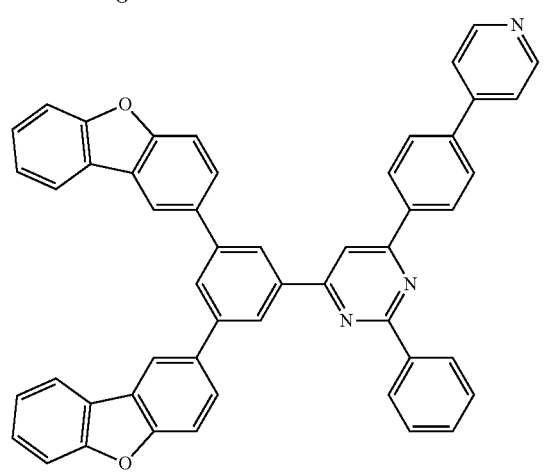
[Formula 76]
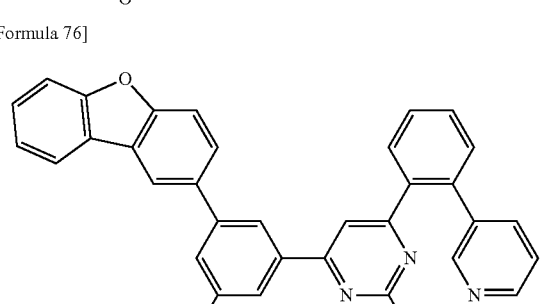
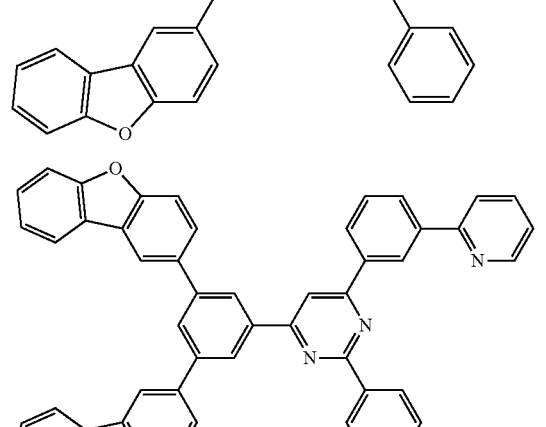
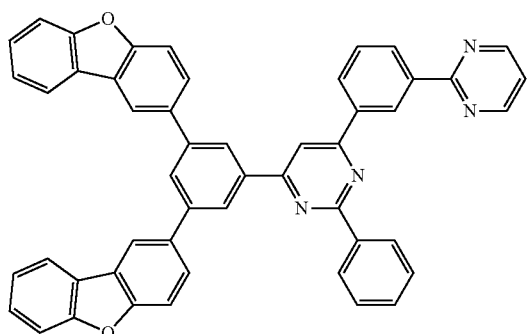
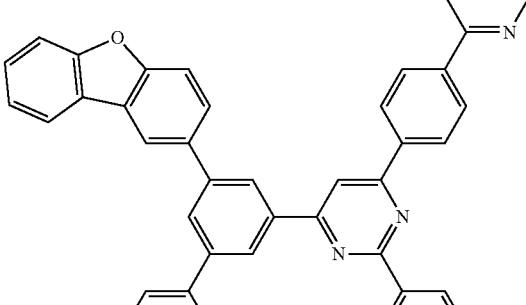
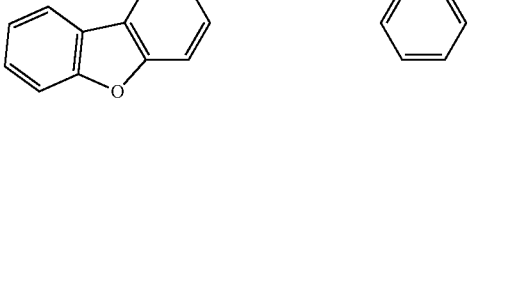
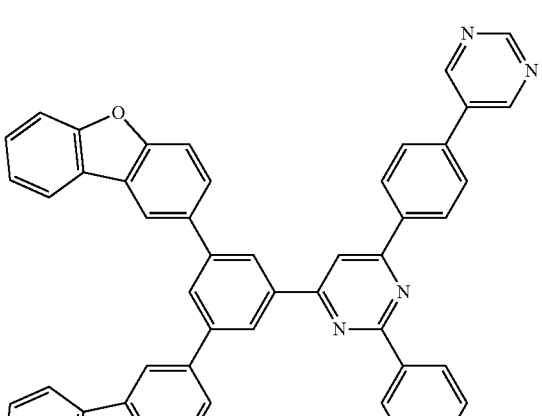

[Formula 77]
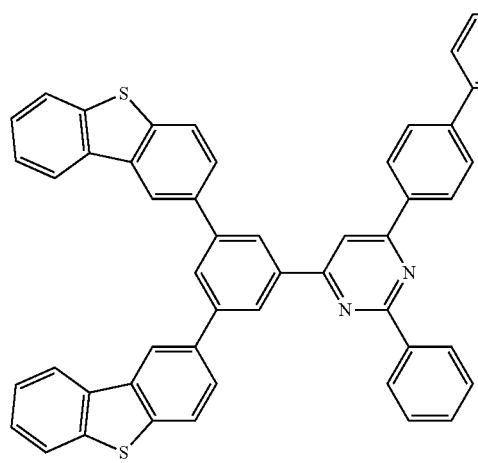
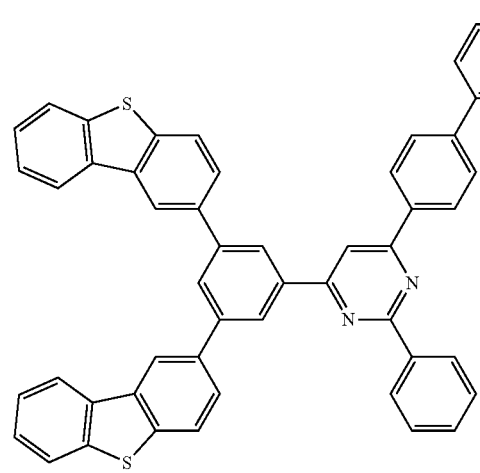
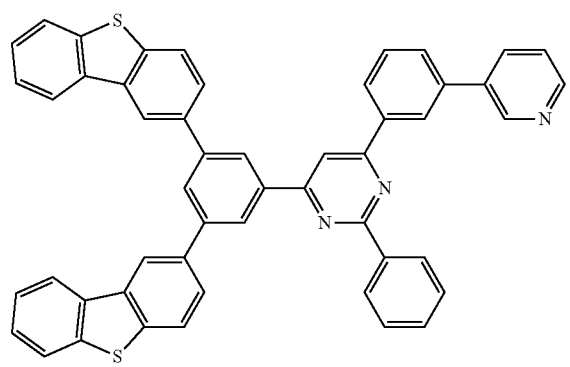
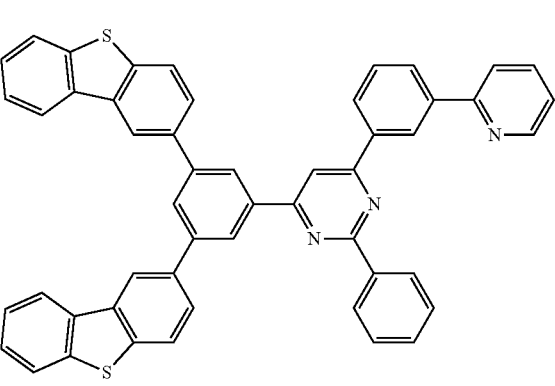

147
-continued
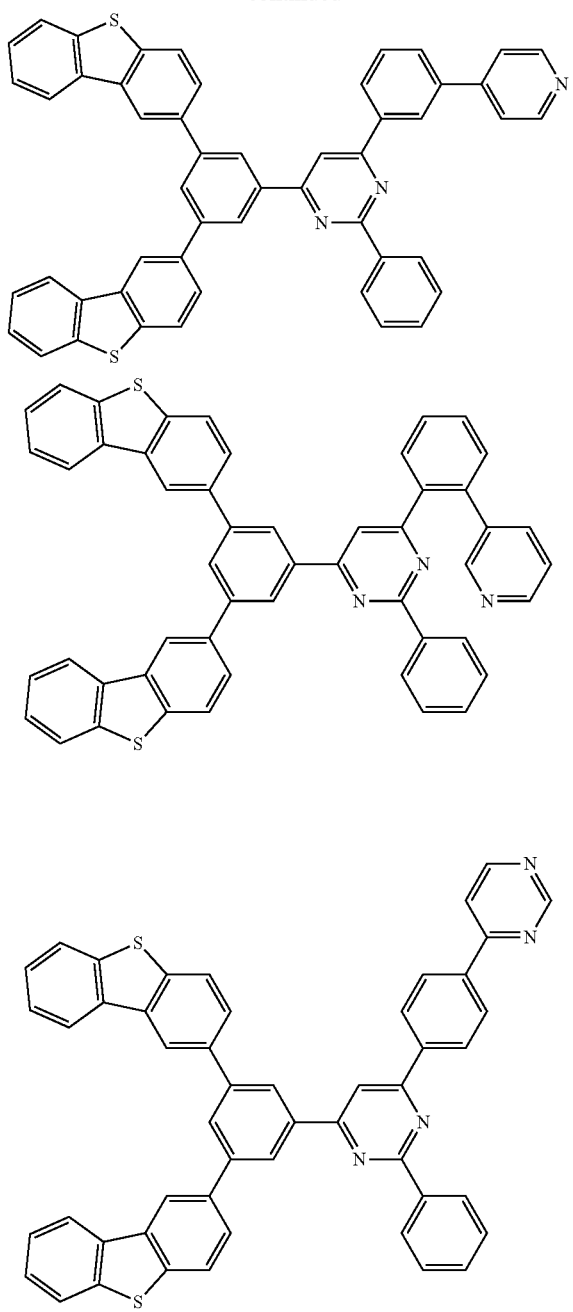
[Formula 78]
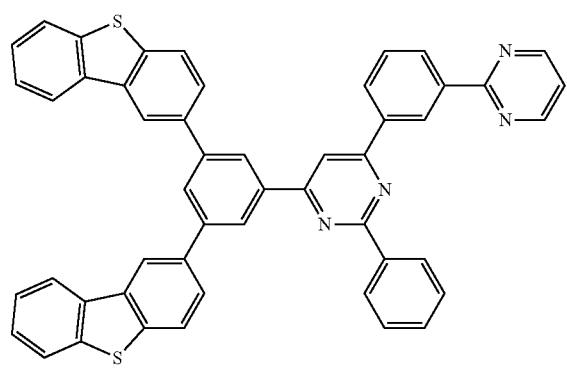
148
-continued
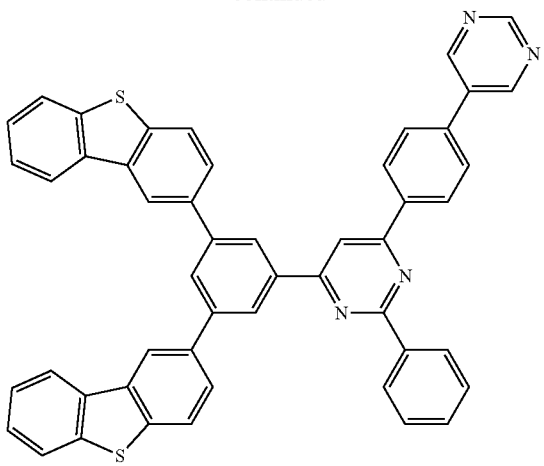
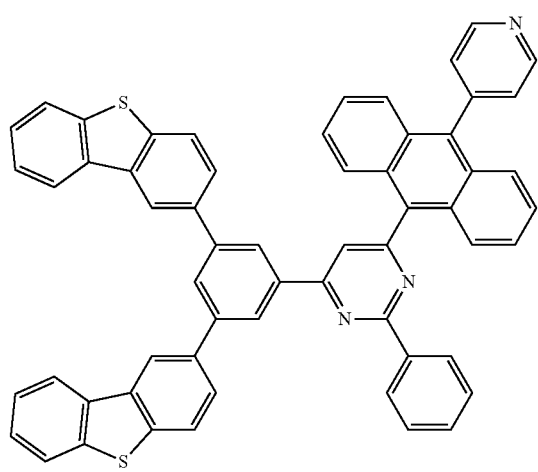
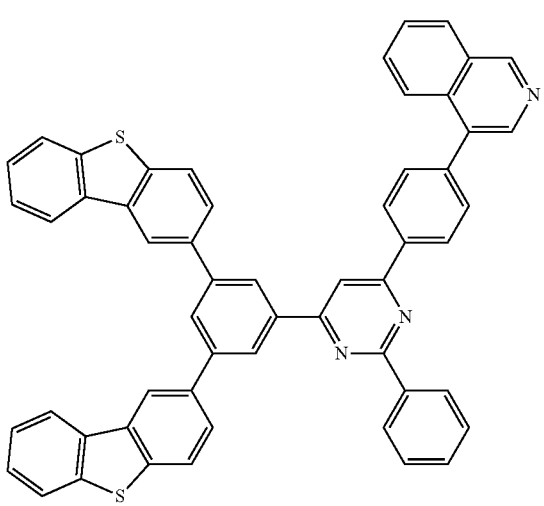

149
-continued
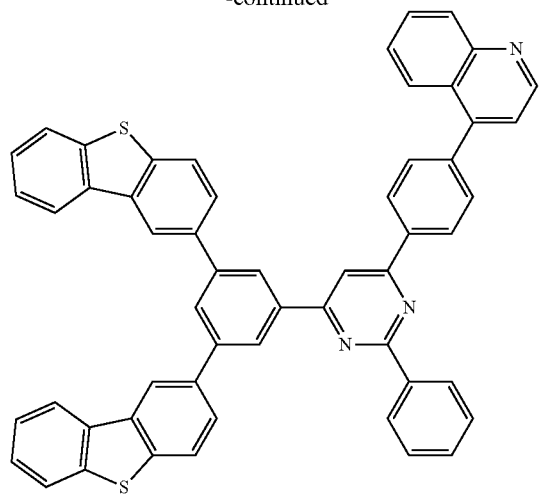
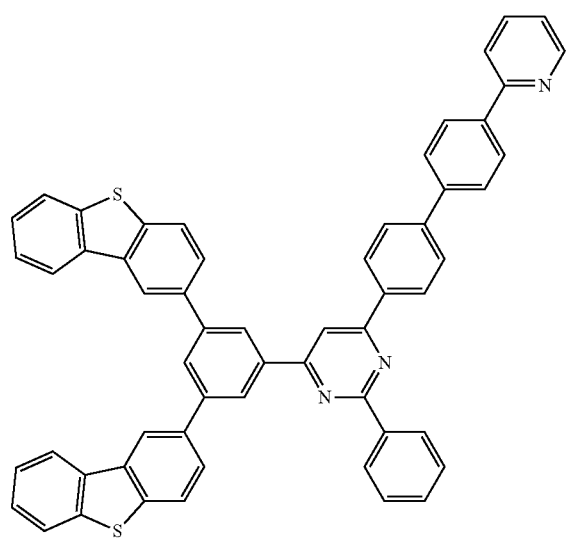
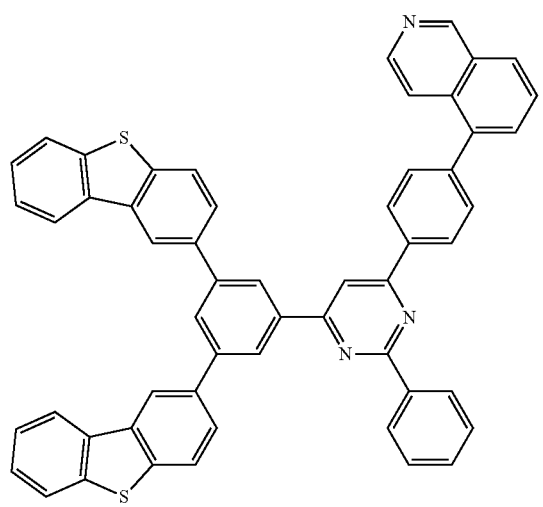
150
-continued
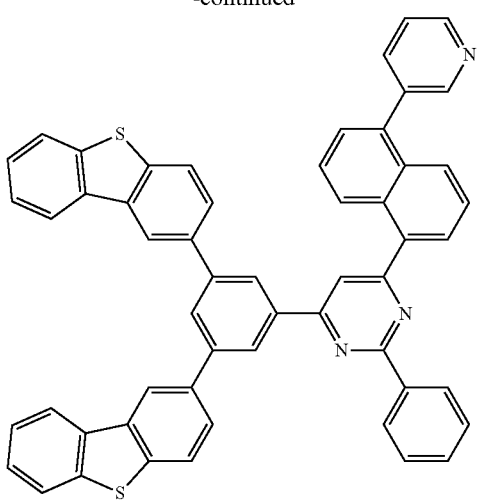
[Formula 79]
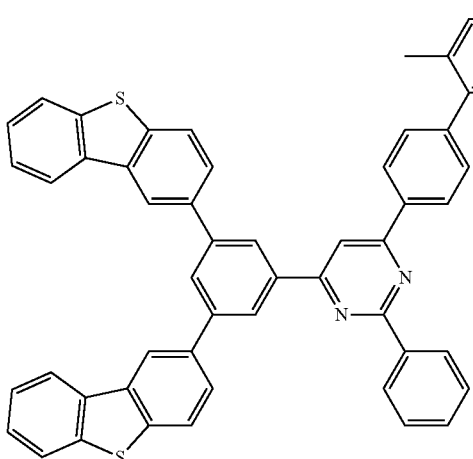
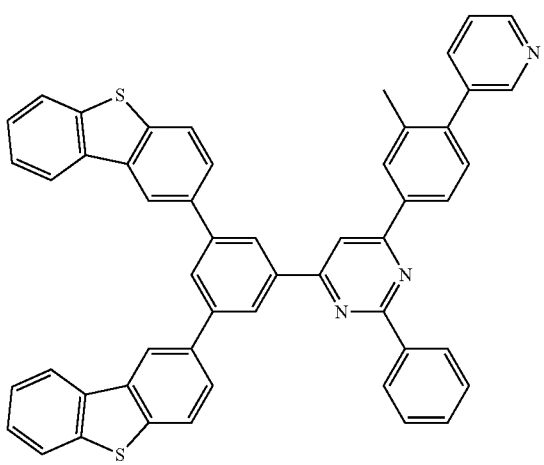

151
-continued
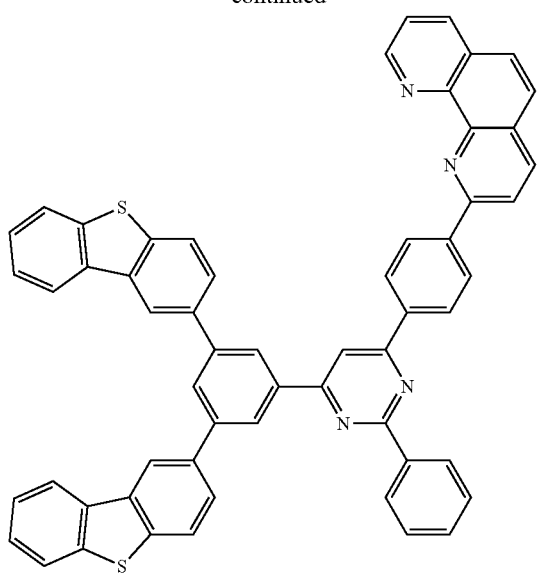
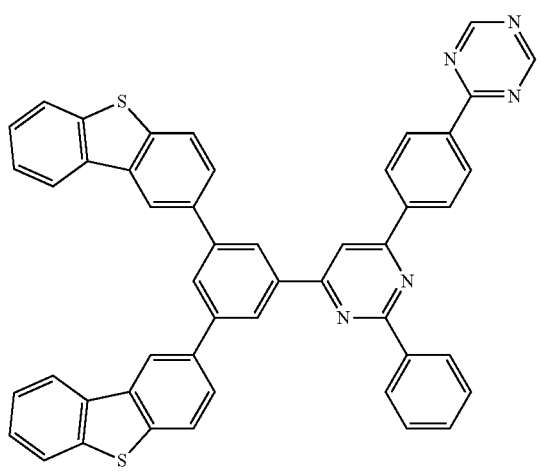
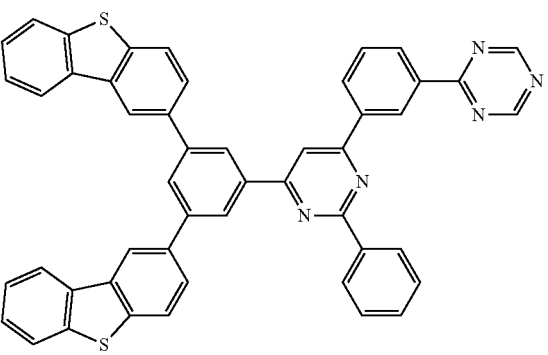
152
-continued
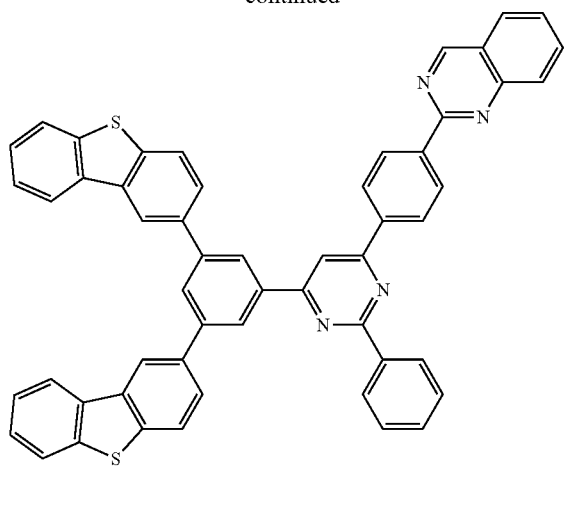
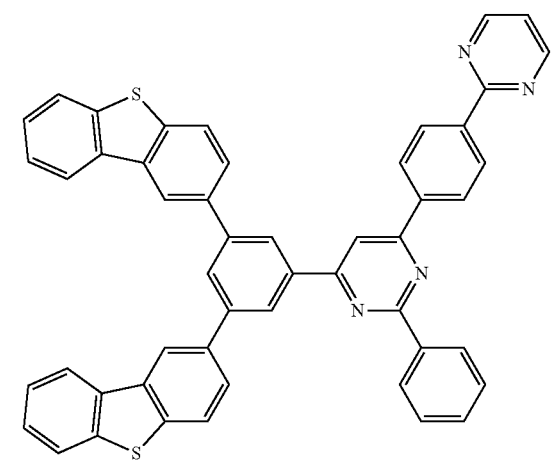
[Formula 80]
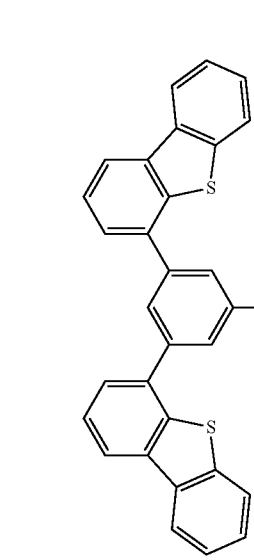

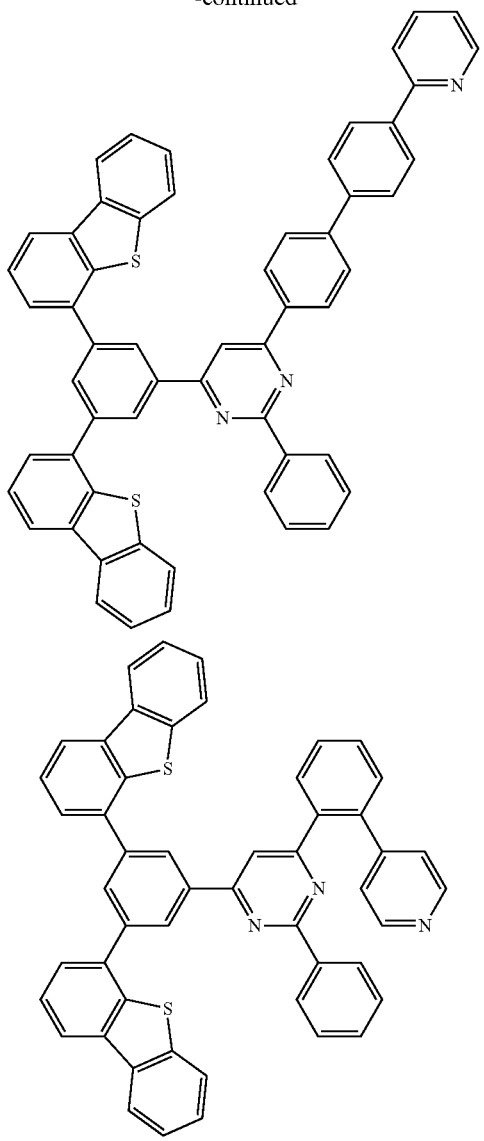
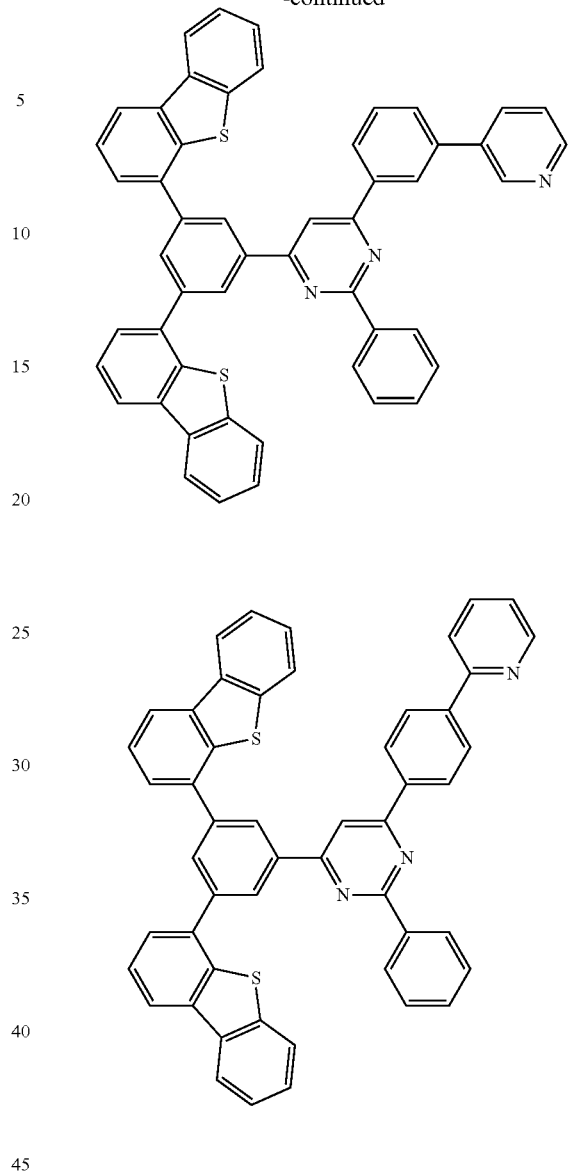
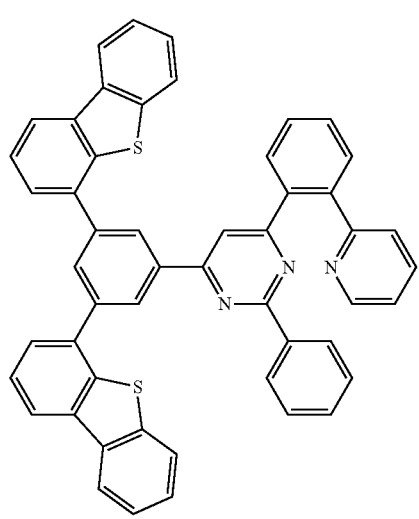
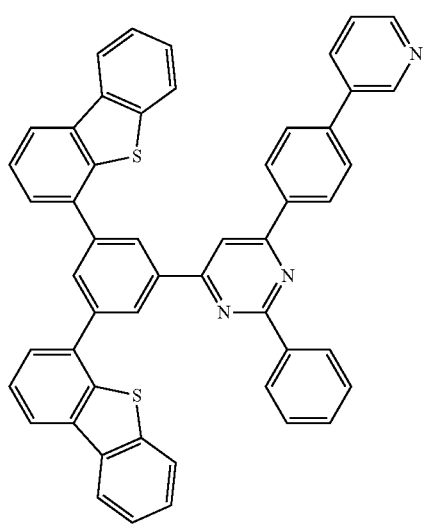

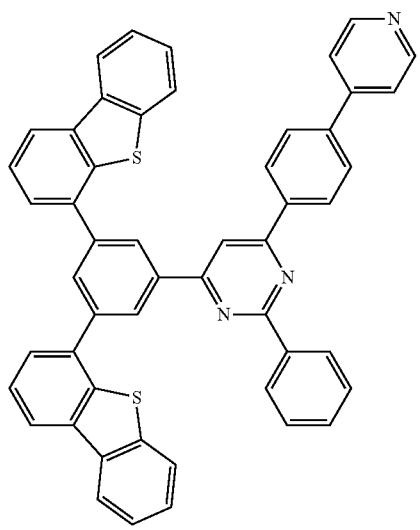
[Formula 81]
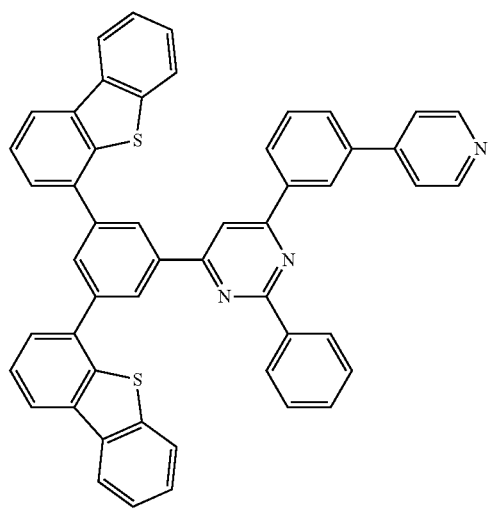
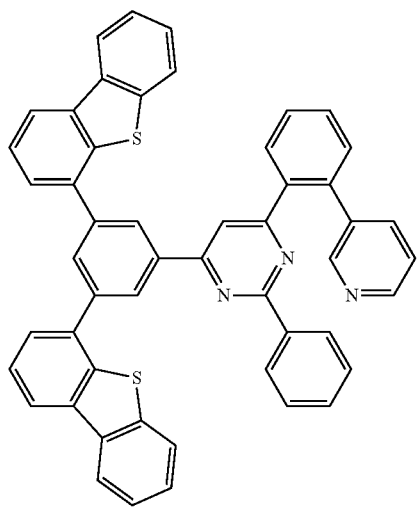
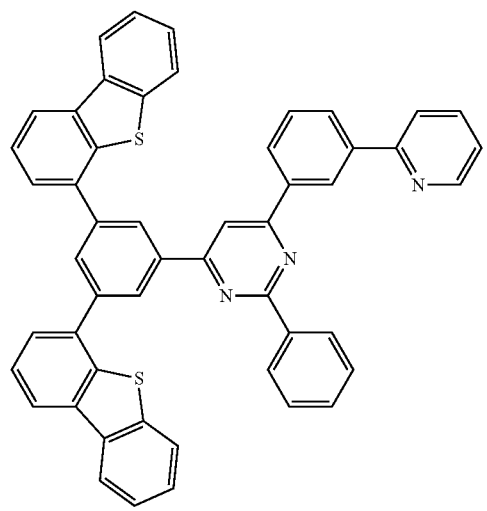
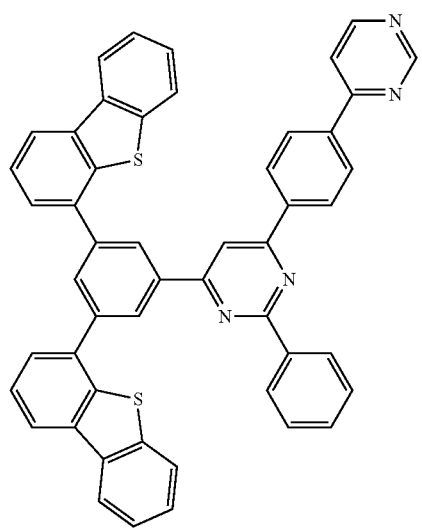
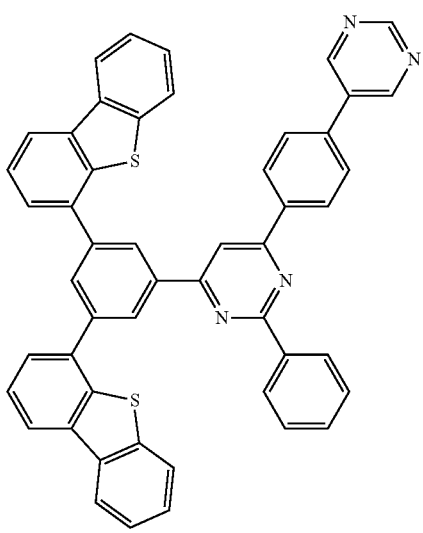

157
-continued
158
-continued
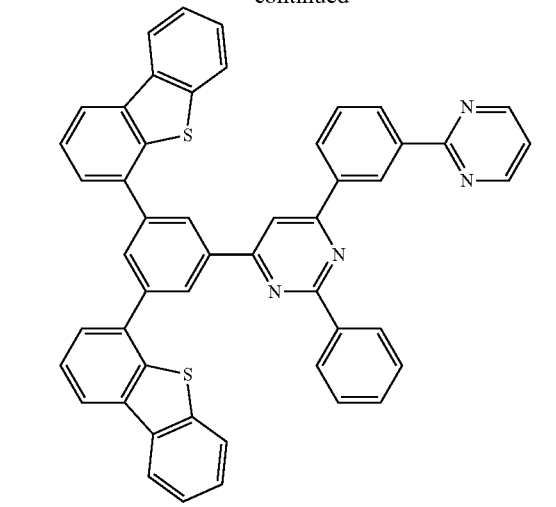
[Formula 82]
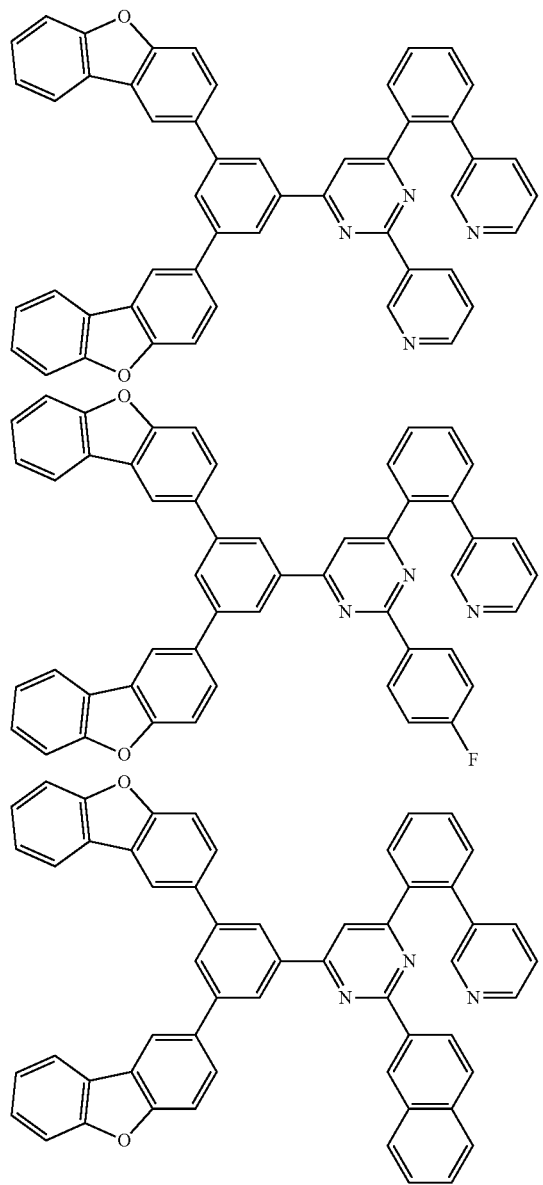
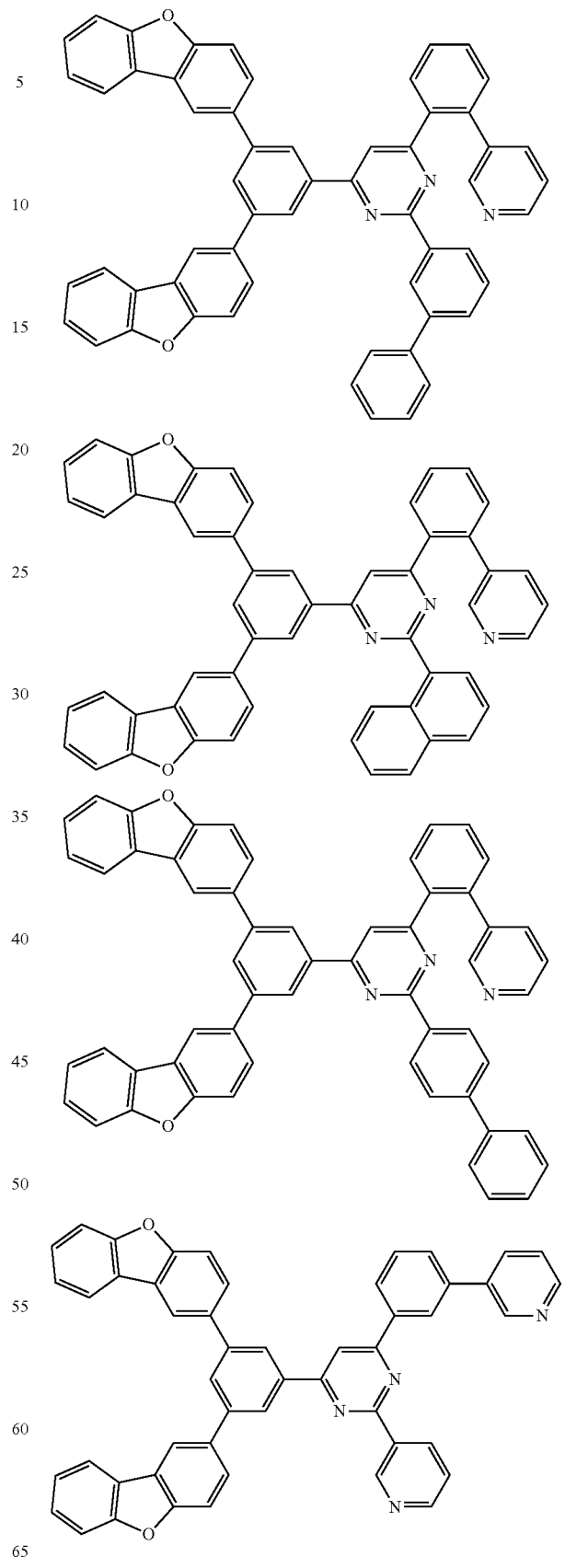

159
-continued
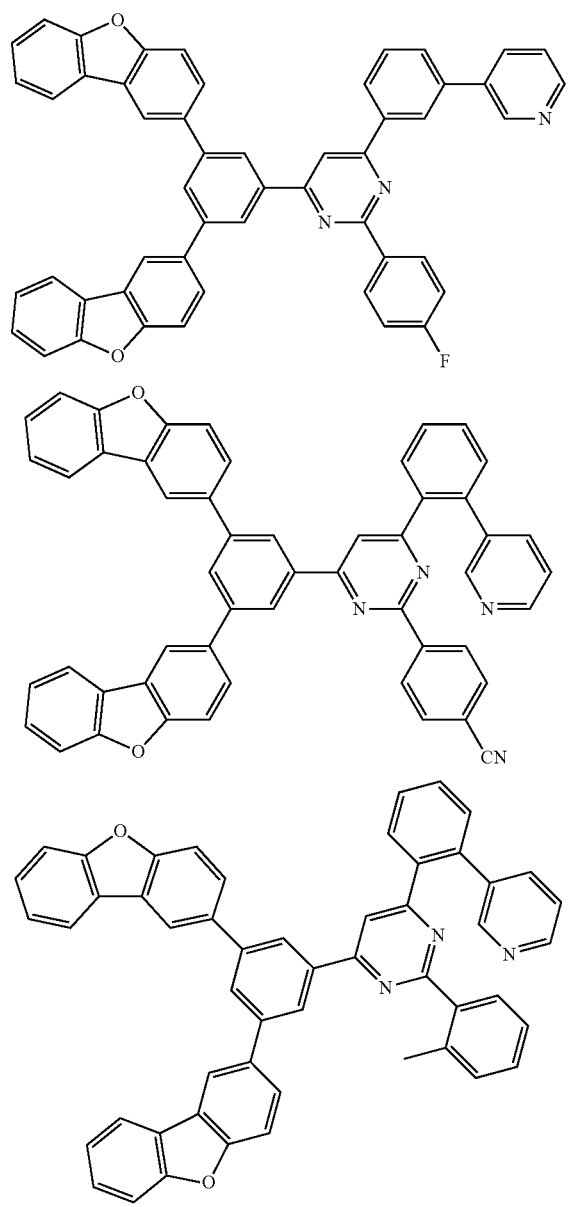
160
-continued
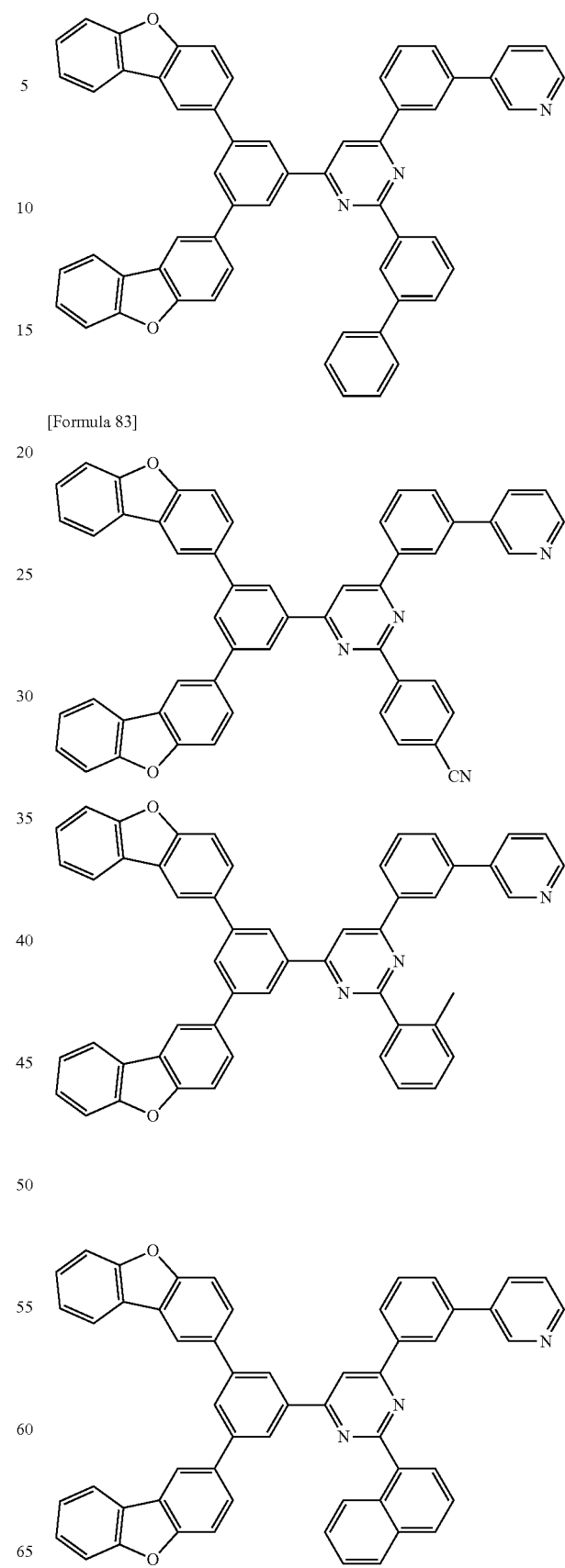
[Formula 83]

161
-continued
162
-continued
[Formula 84]
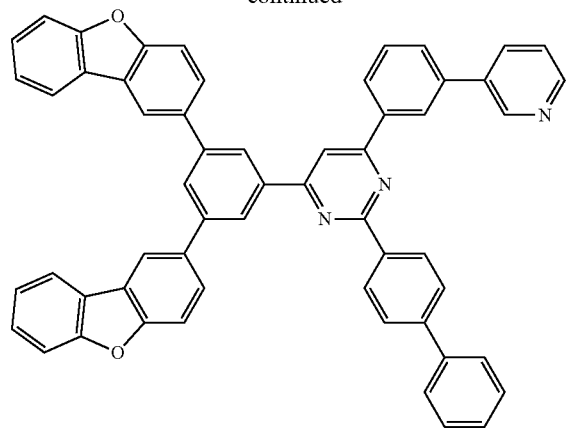
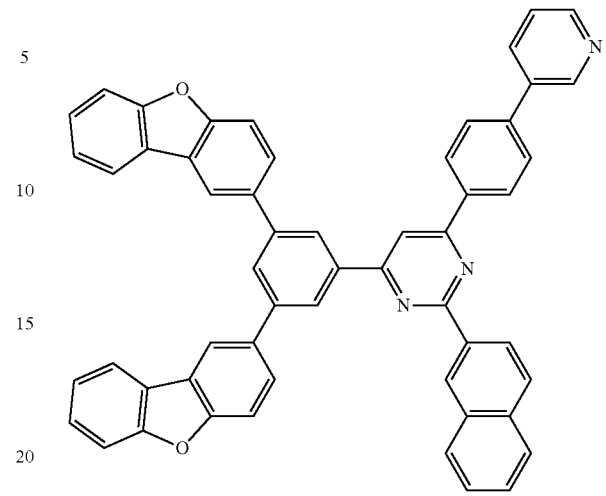
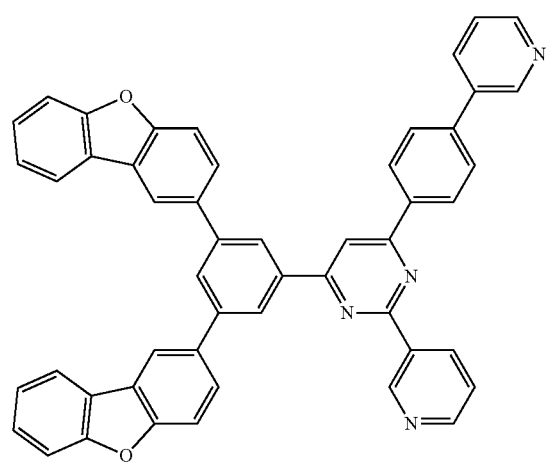
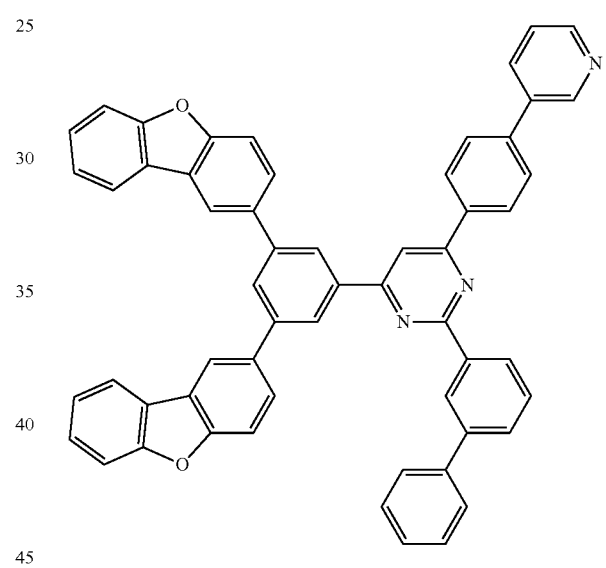
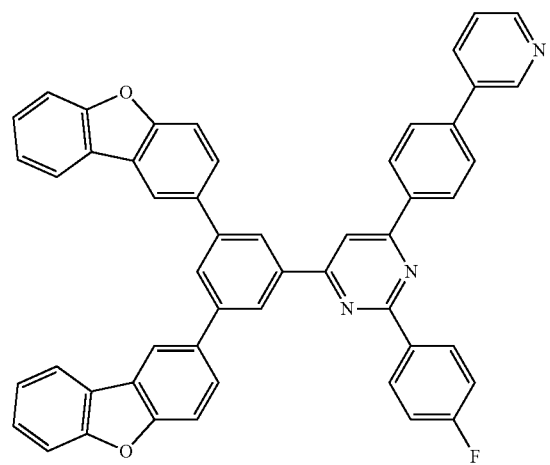
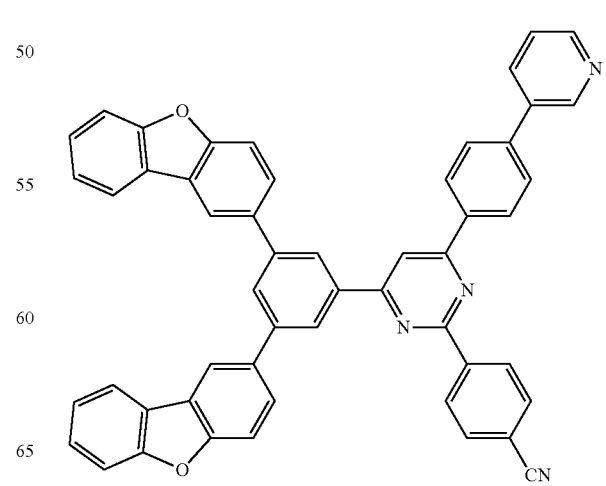

-continued
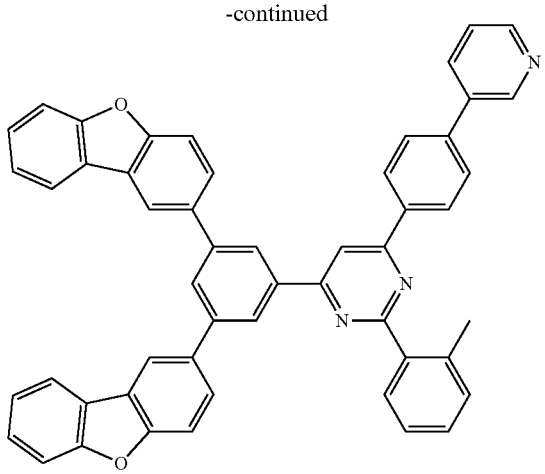
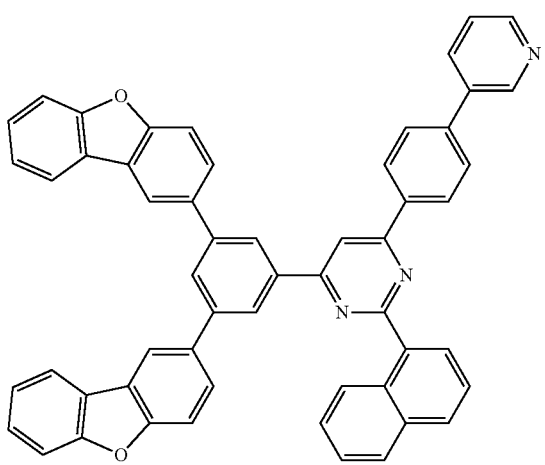
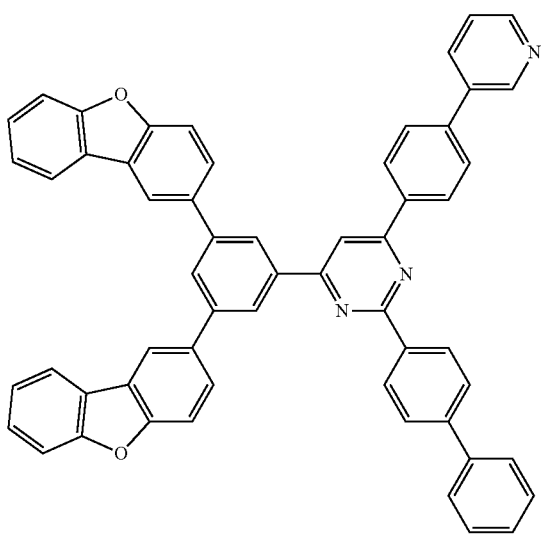
[Formula 85]
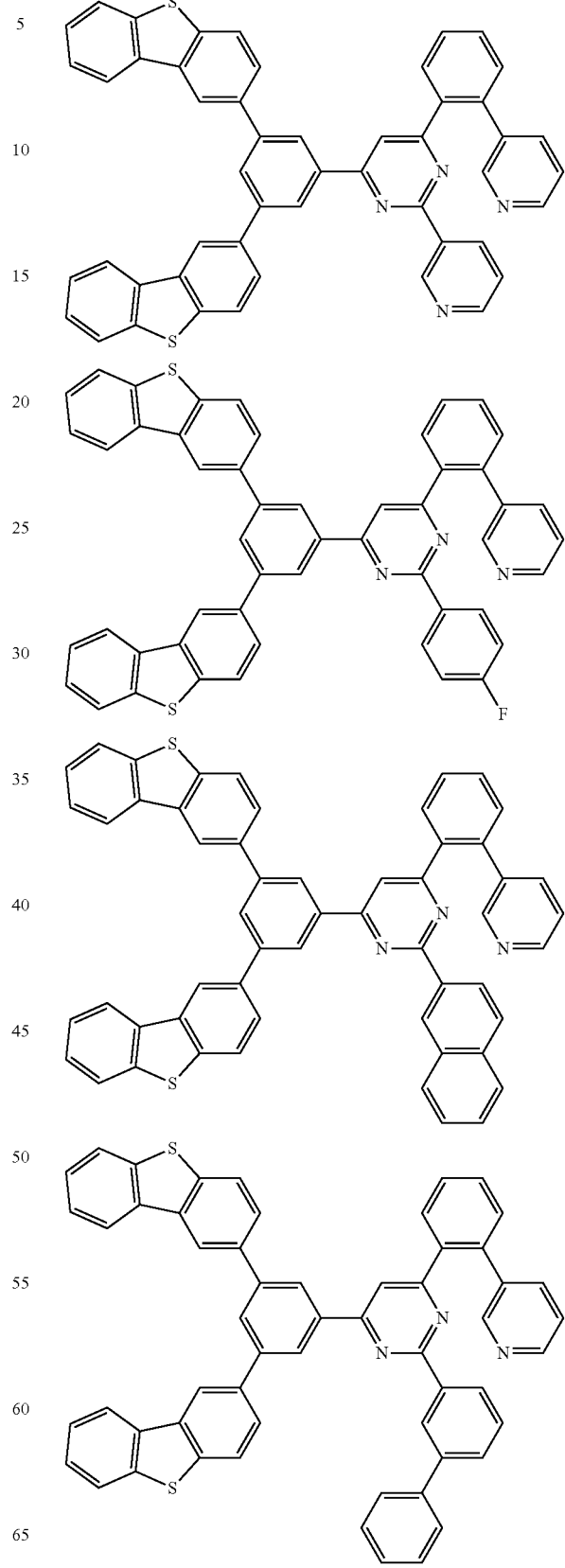

165
-continued
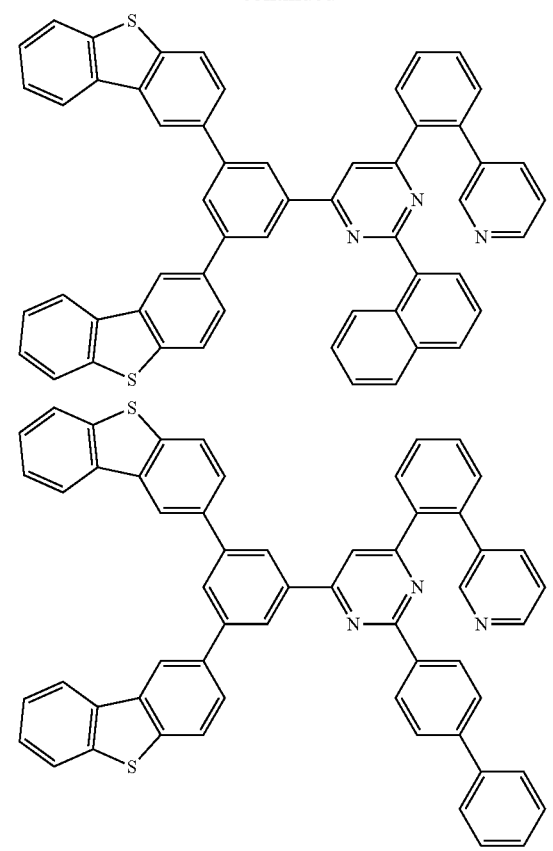
166
-continued
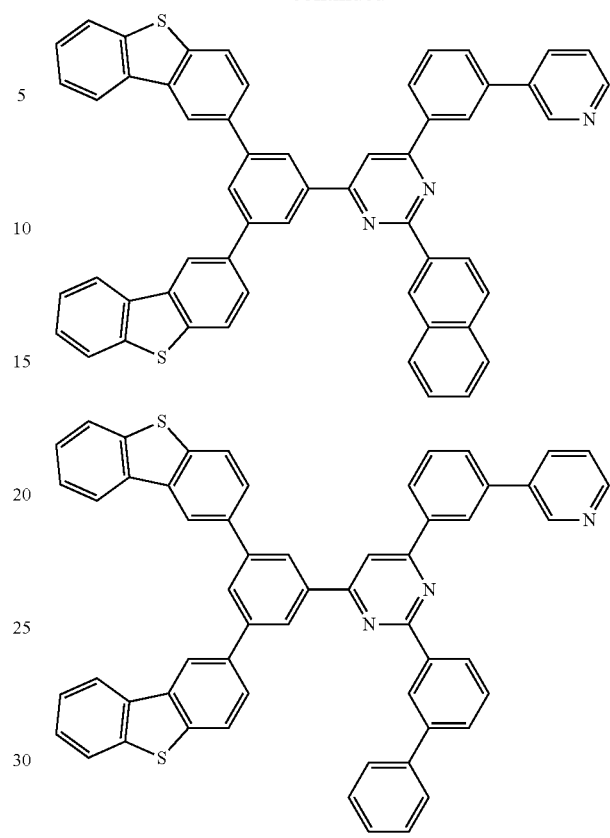
[Formula 86]
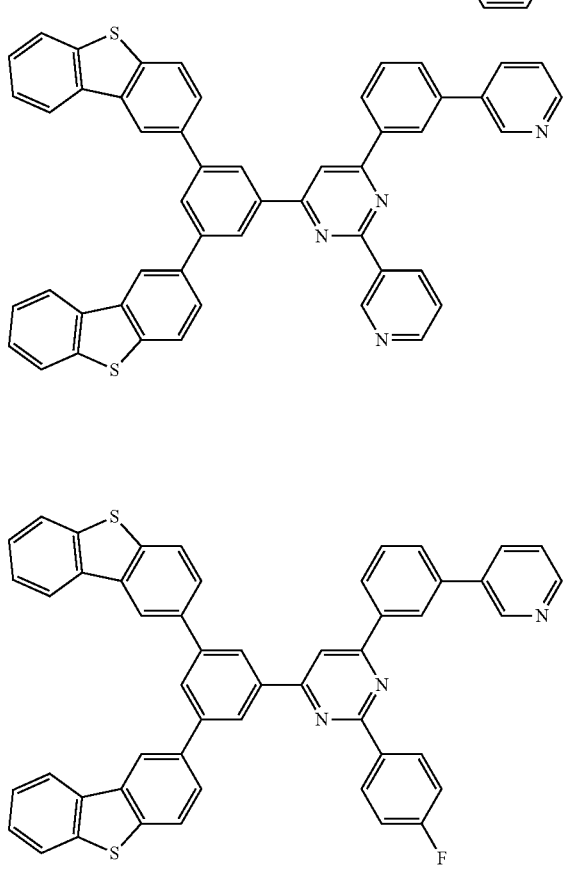
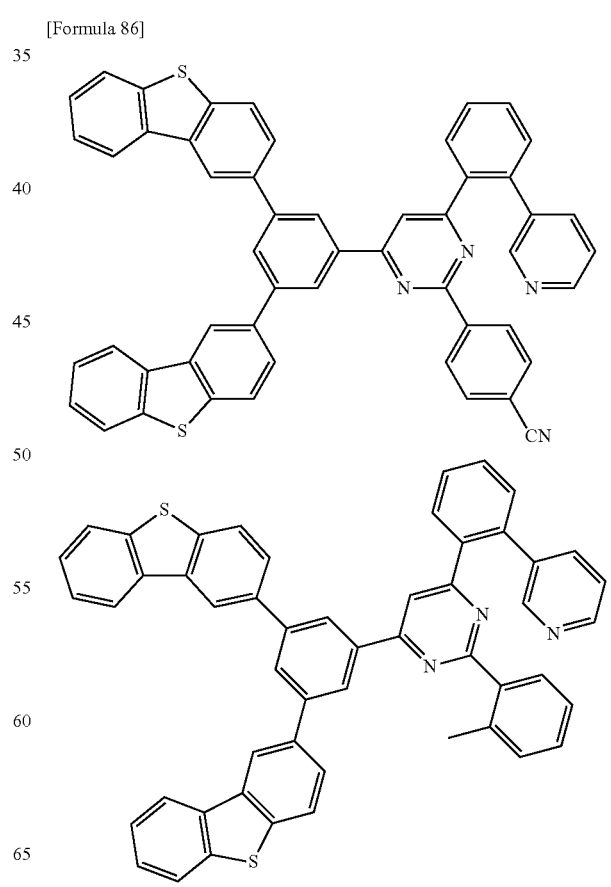

[Formula 87]
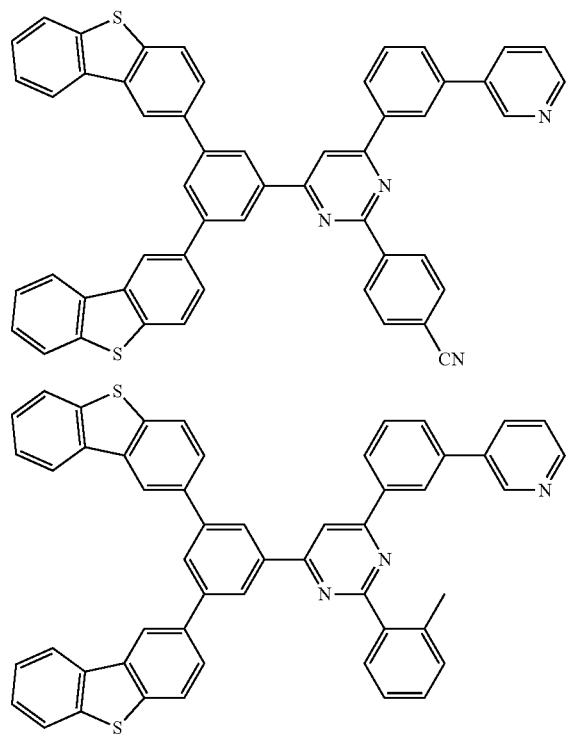
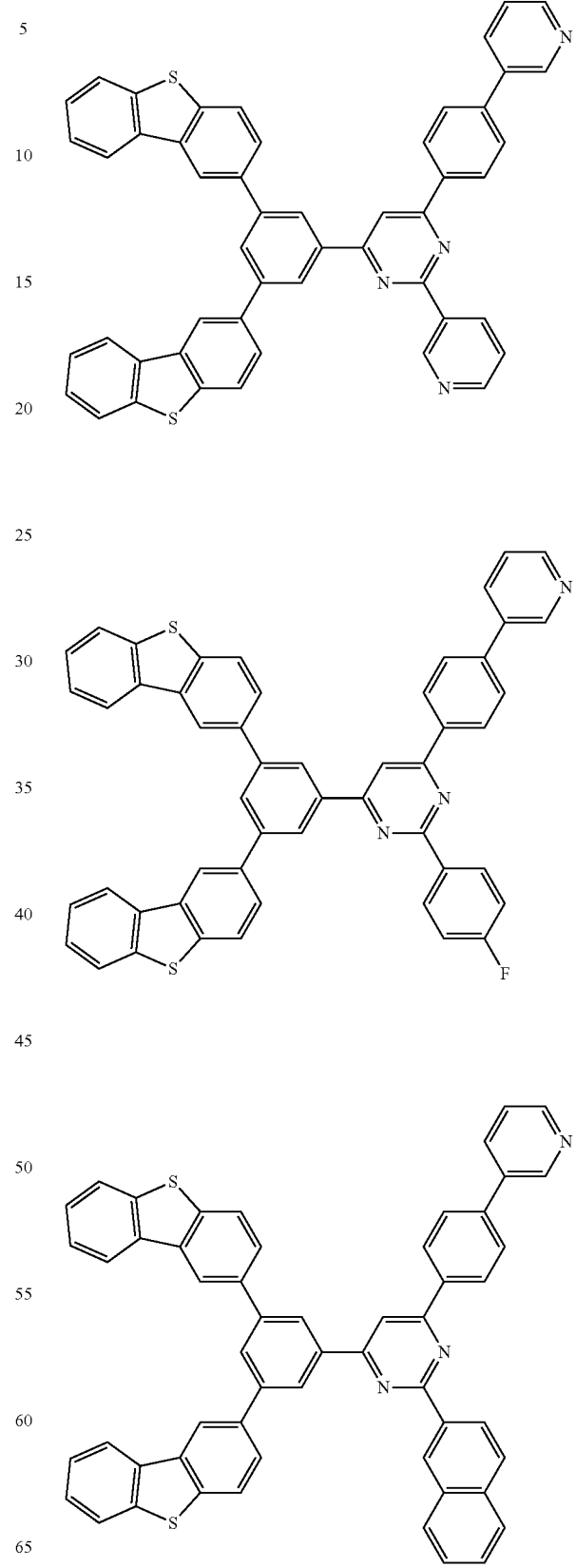

-continued
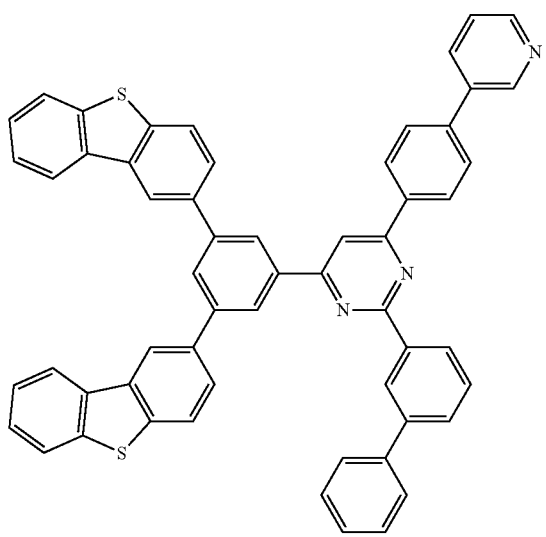
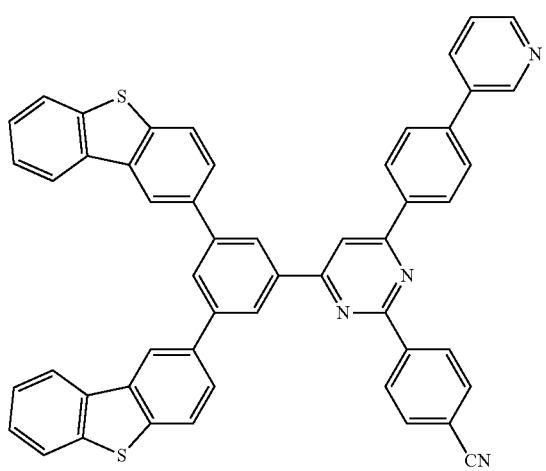
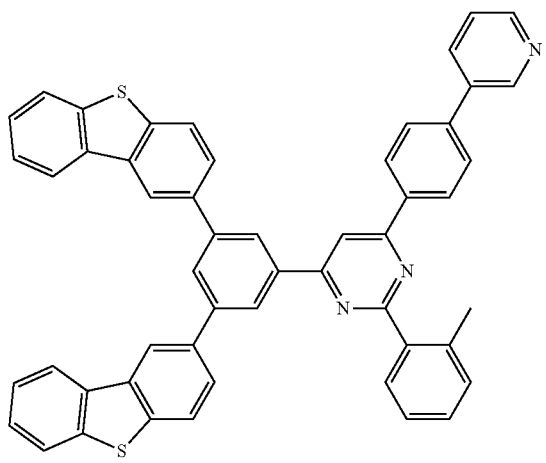
-continued
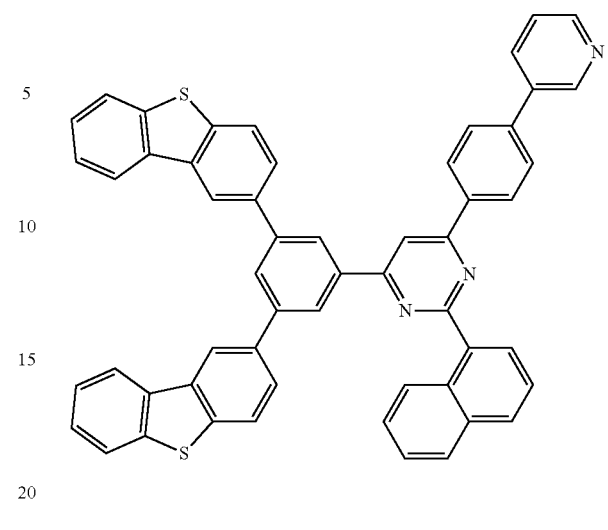
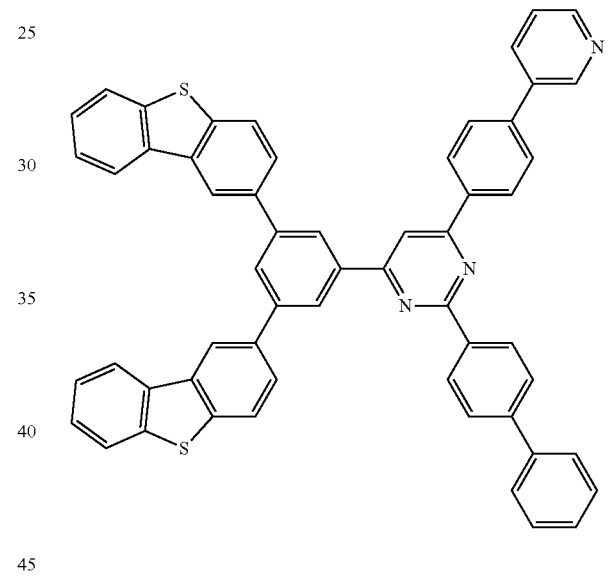
[Formula 88]
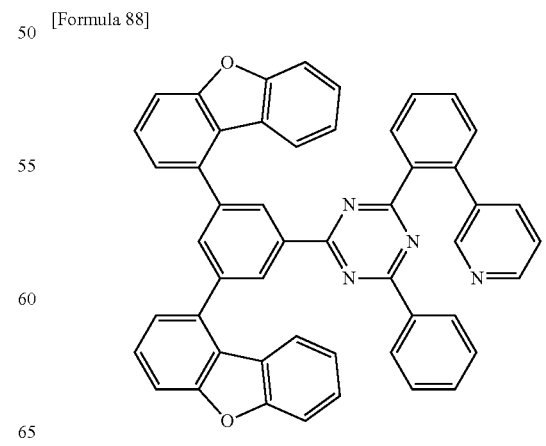

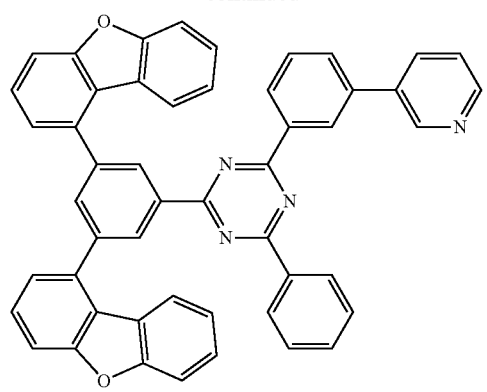
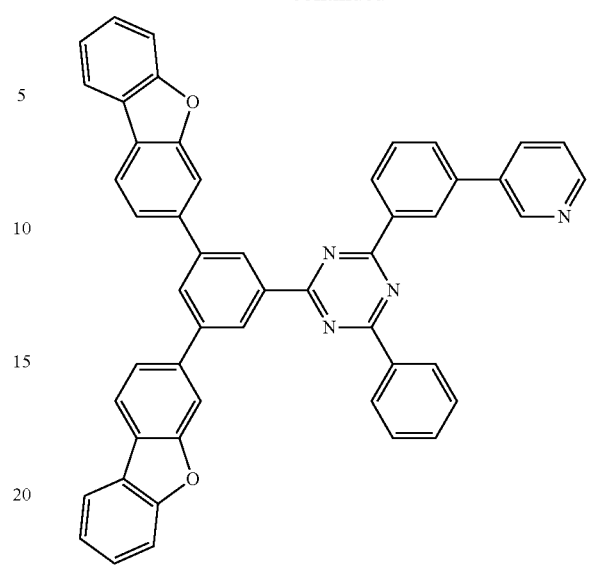
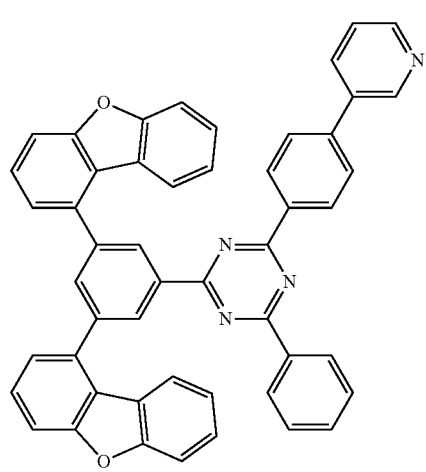
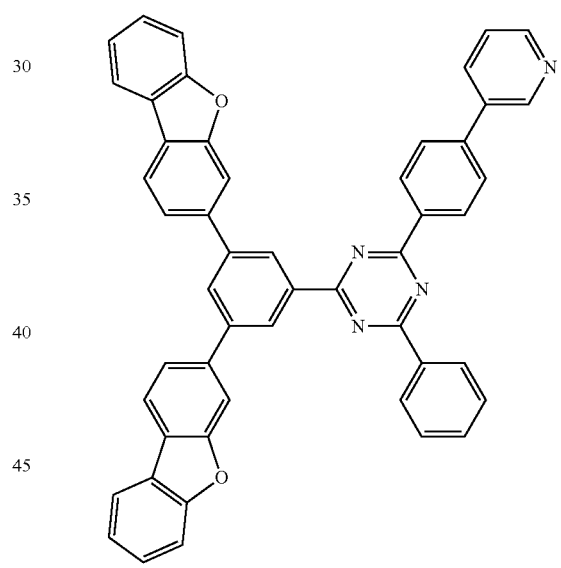
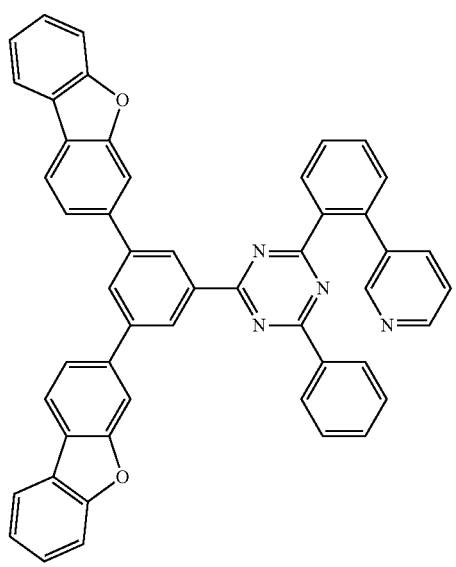
[Formula 89]
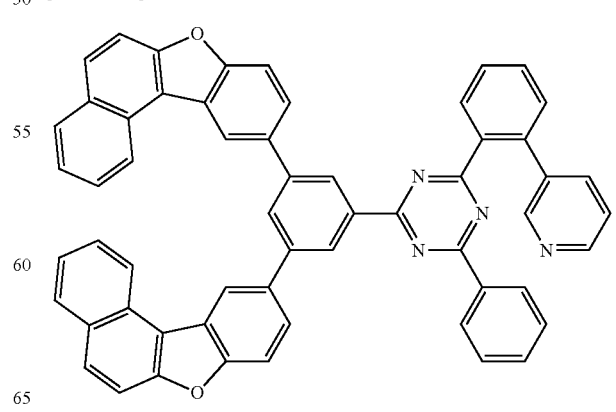

173
-continued
174
-continued
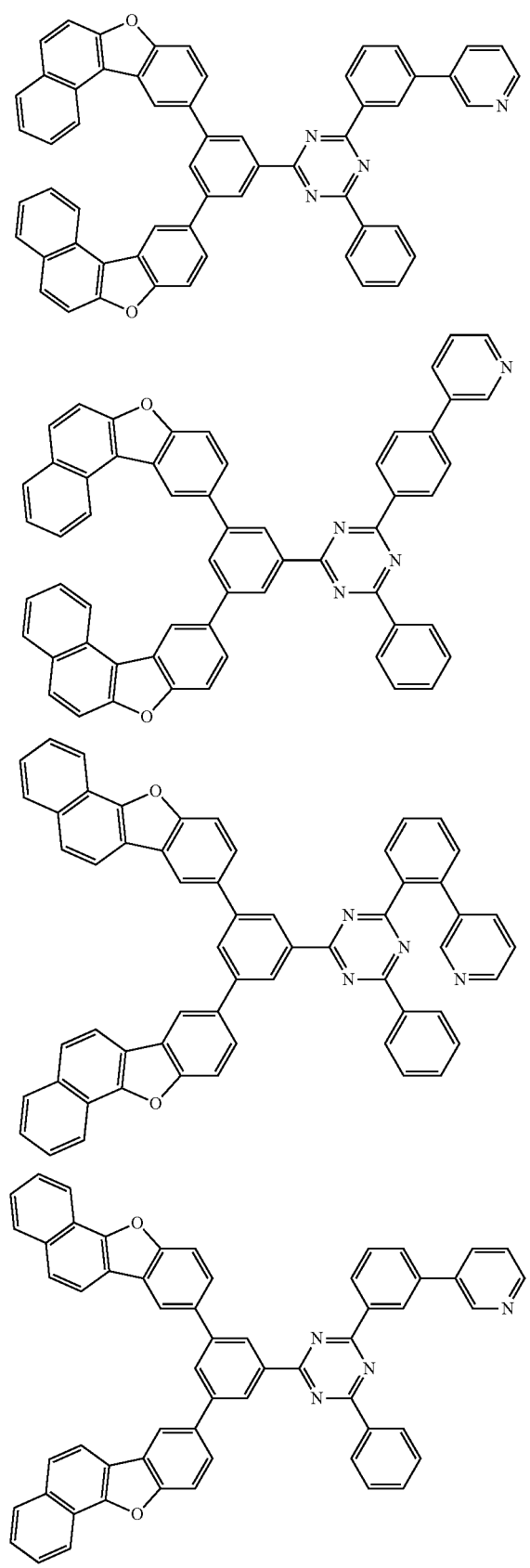
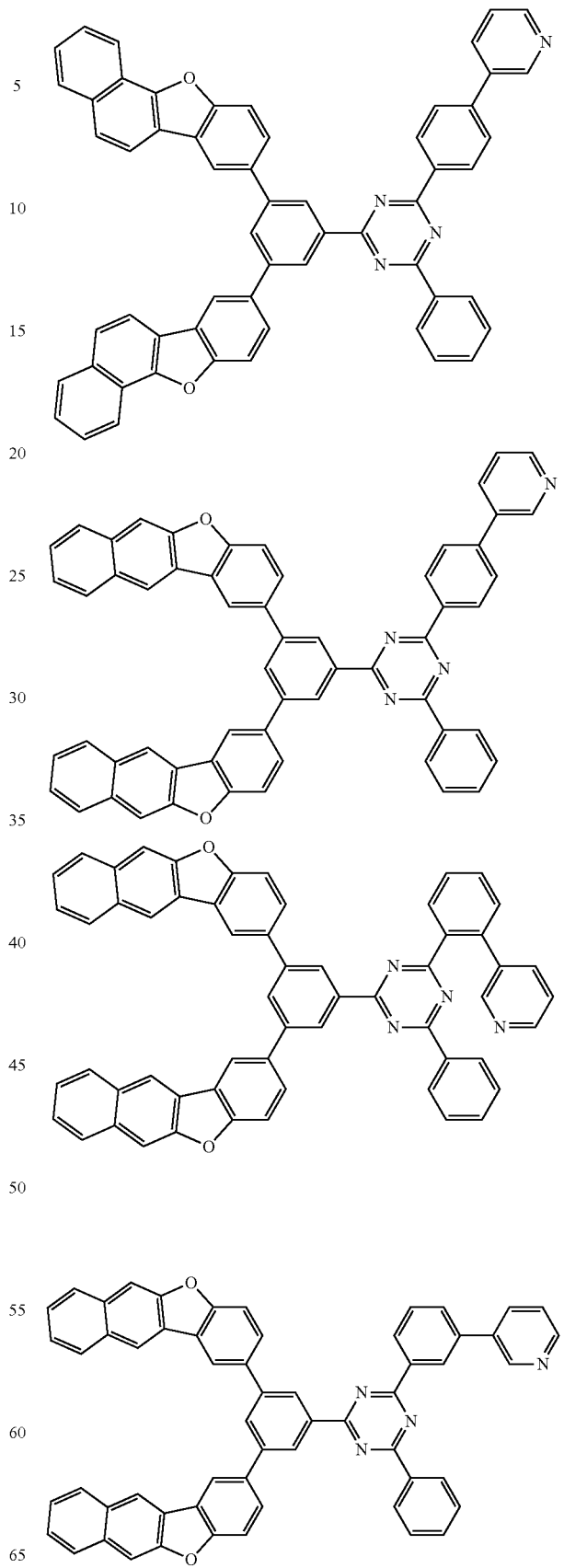

[Formula 90]
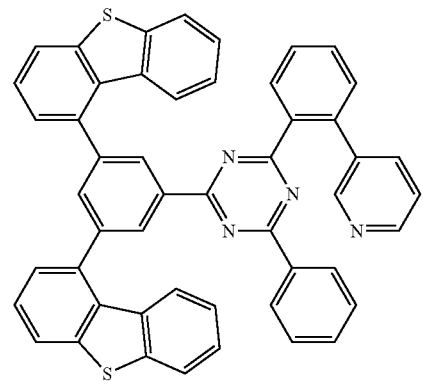
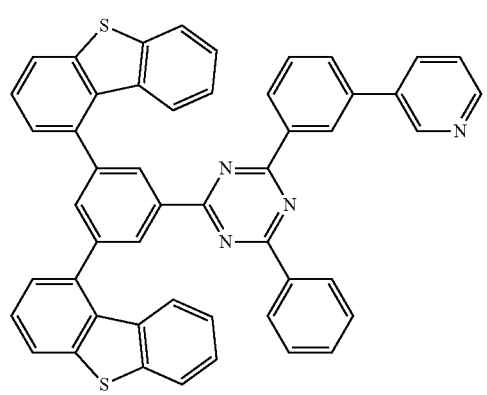
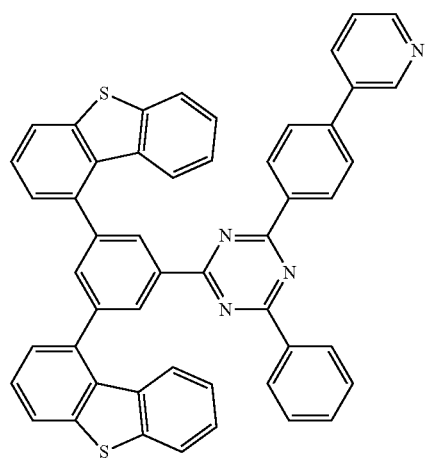
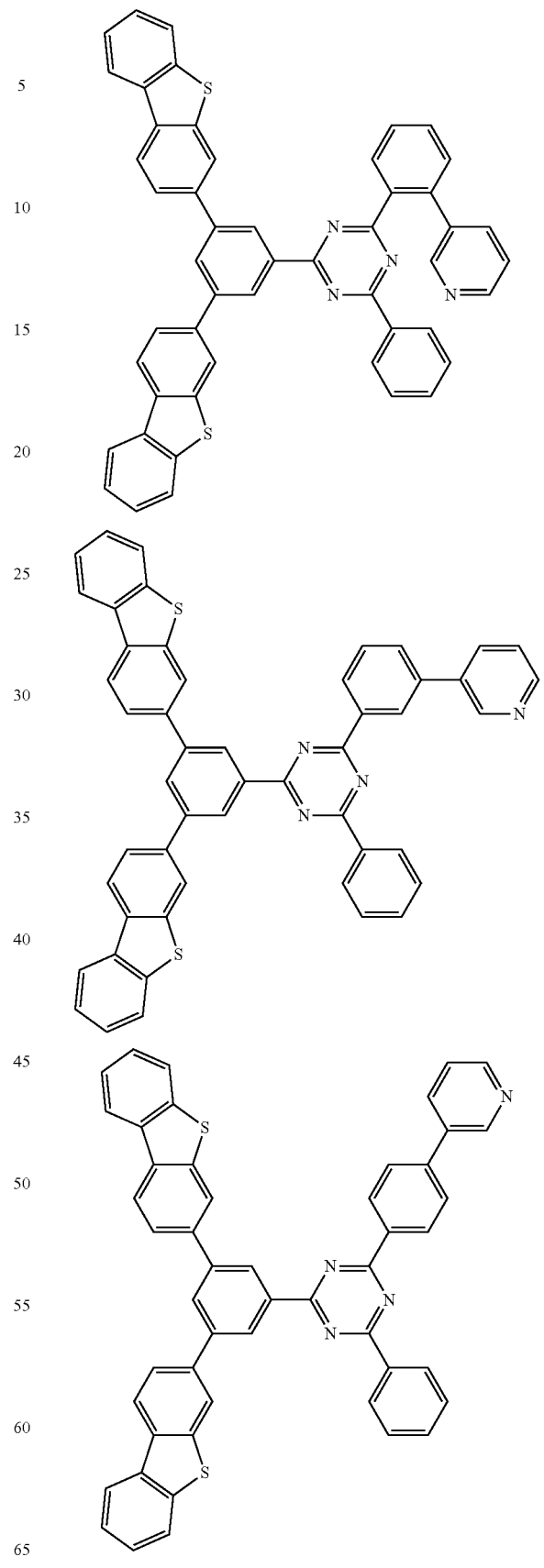

-continued
[Formula 91]
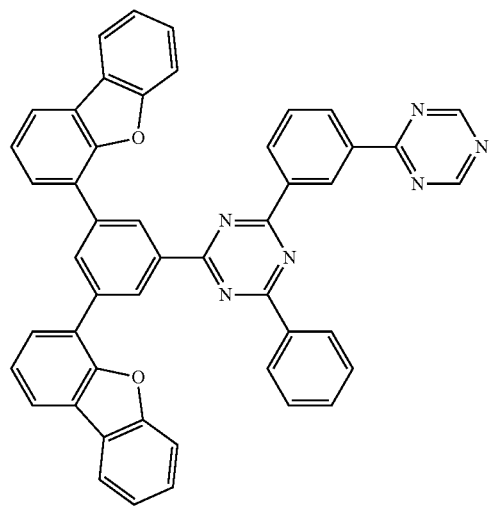
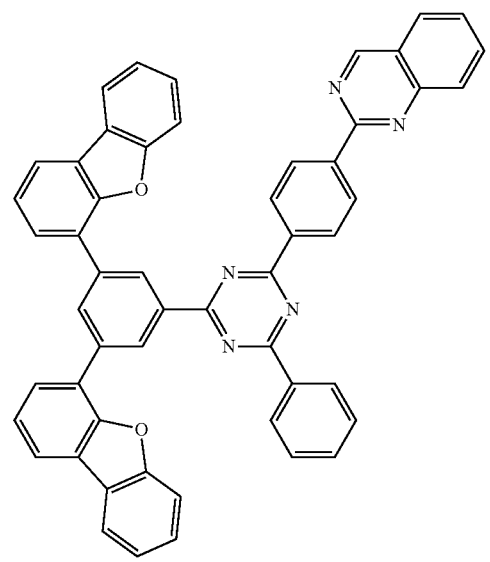
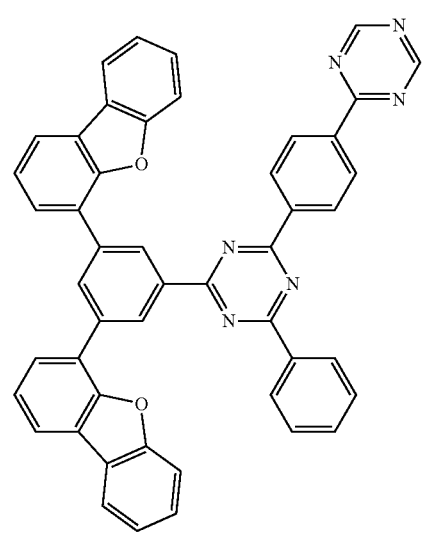
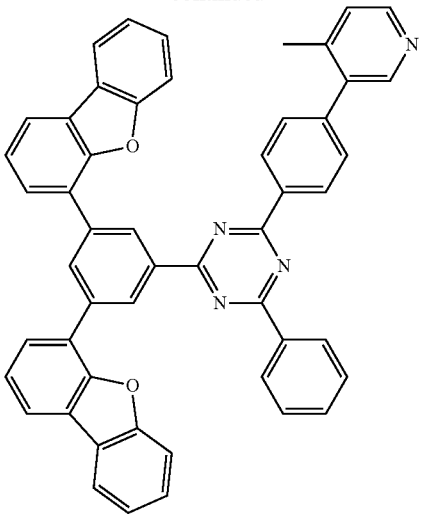
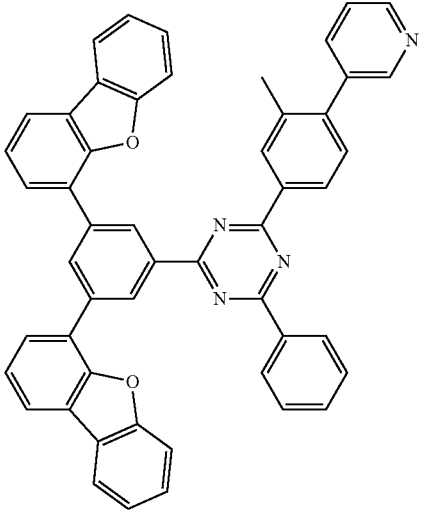
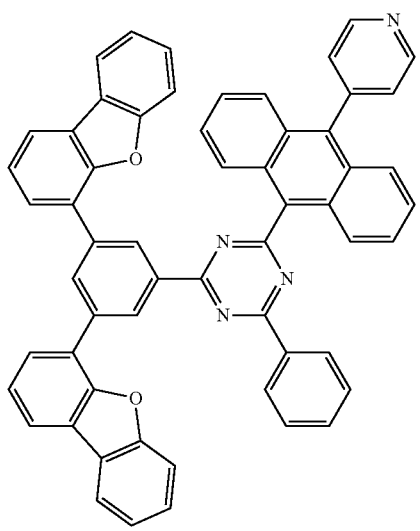

[Formula 92]
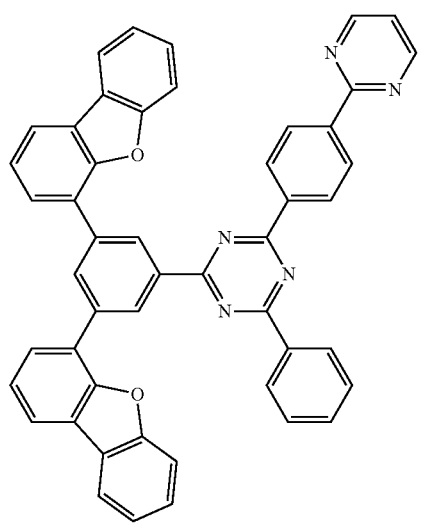
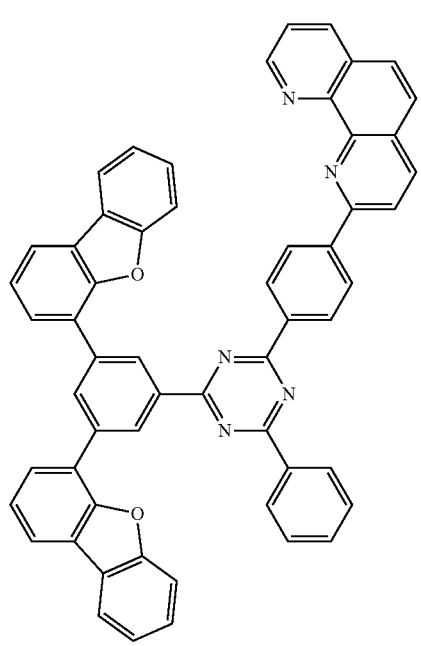
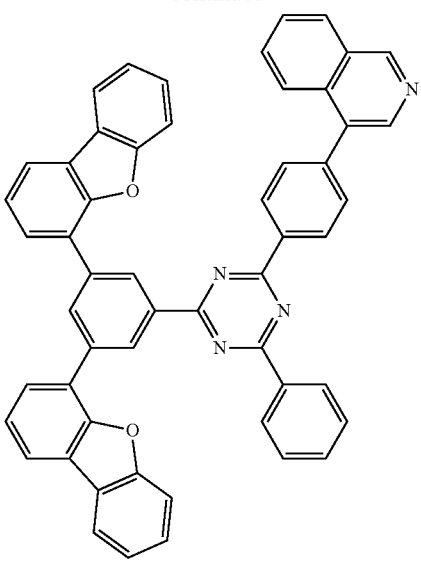
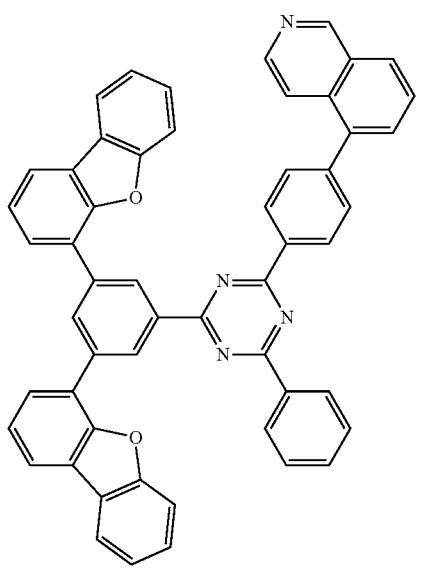
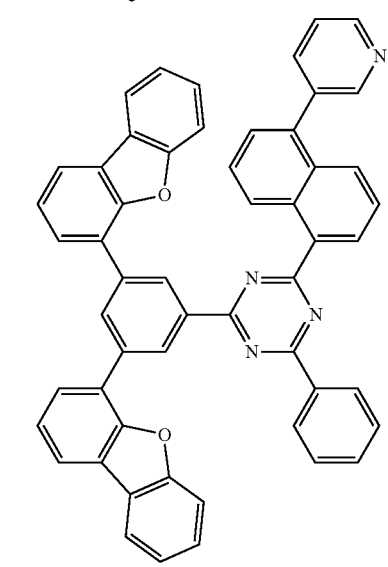

-continued
[Formula 93]
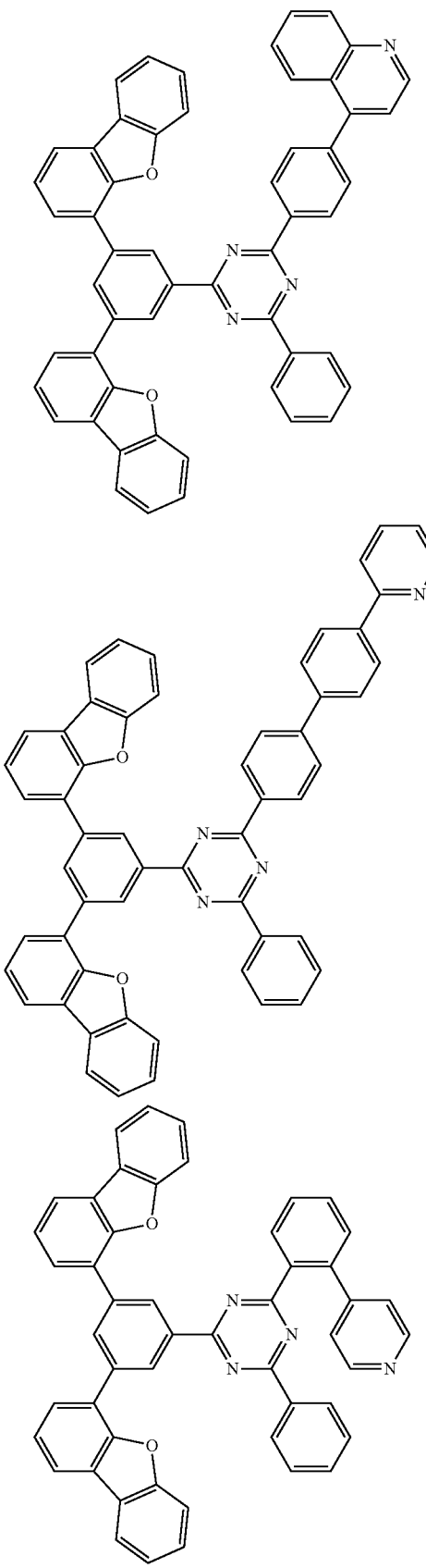
-continued
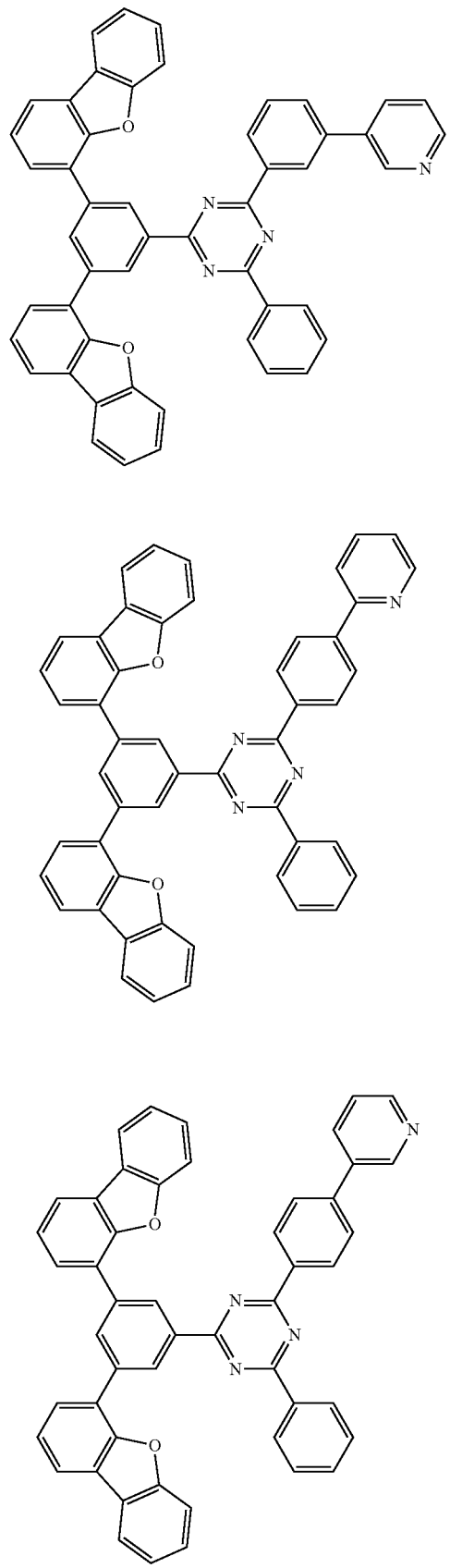 [SMILES: c1ccc(-c2nc(-c3cccc(-c4cccnc4)c3)nc(-c3cc(-c4cccc5c4sc4ccccc45)cc(-c4cccc5c4sc4ccccc45)c3)n2)cc1 ; c1ccc(-c2nc(-c3ccc(-c4ccccn4)cc3)nc(-c3cc(-c4cccc5c4sc4ccccc45)cc(-c4cccc5c4sc4ccccc45)c3)n2)cc1 ; c1ccc(-c2nc(-c3ccc(-c4cccnc4)cc3)nc(-c3cc(-c4cccc5c4sc4ccccc45)cc(-c4cccc5c4sc4ccccc45)c3)n2)cc1]

[Formula 94]
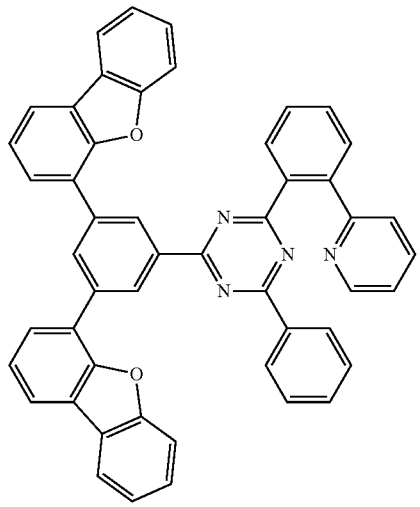
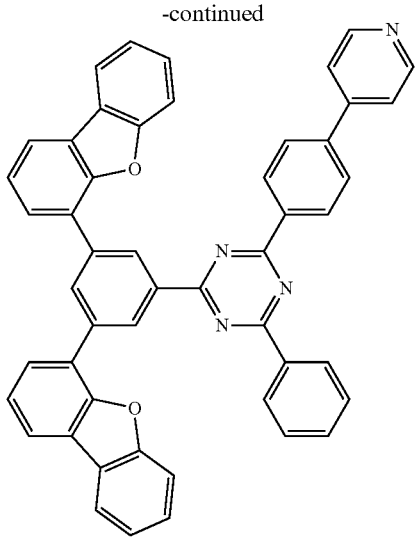
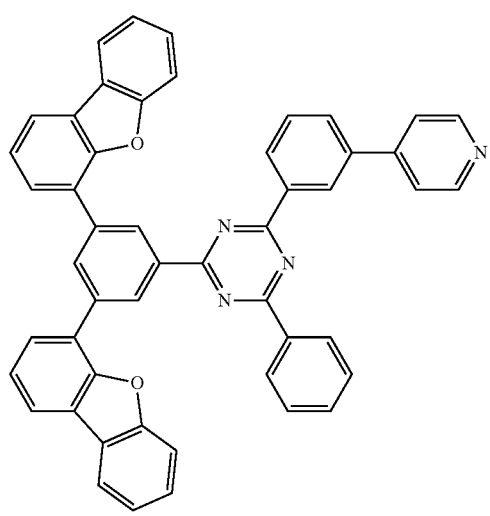
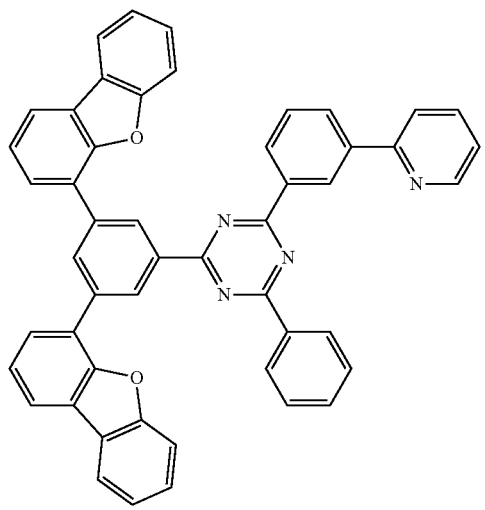
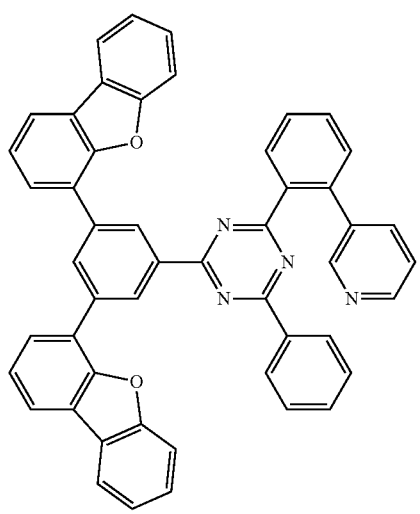
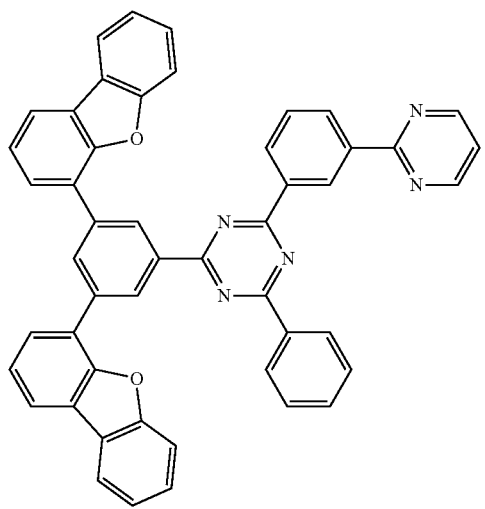

[Formula 95]
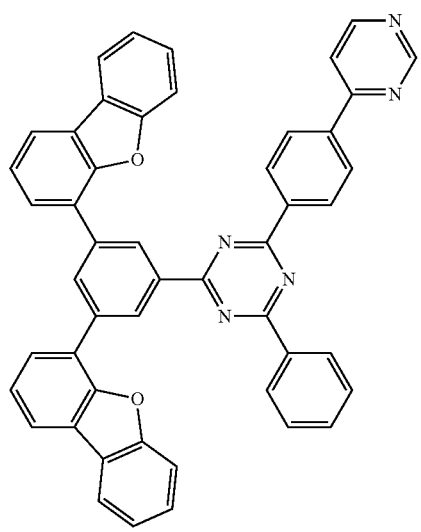
[Formula 96]
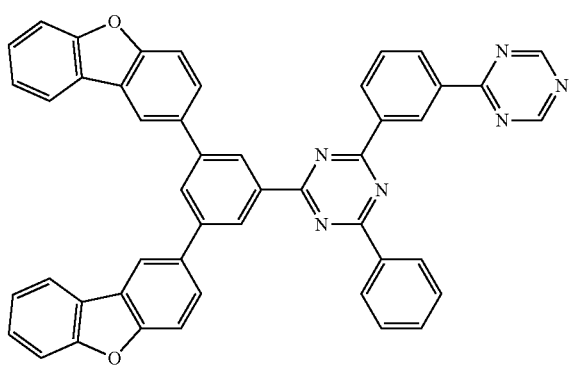
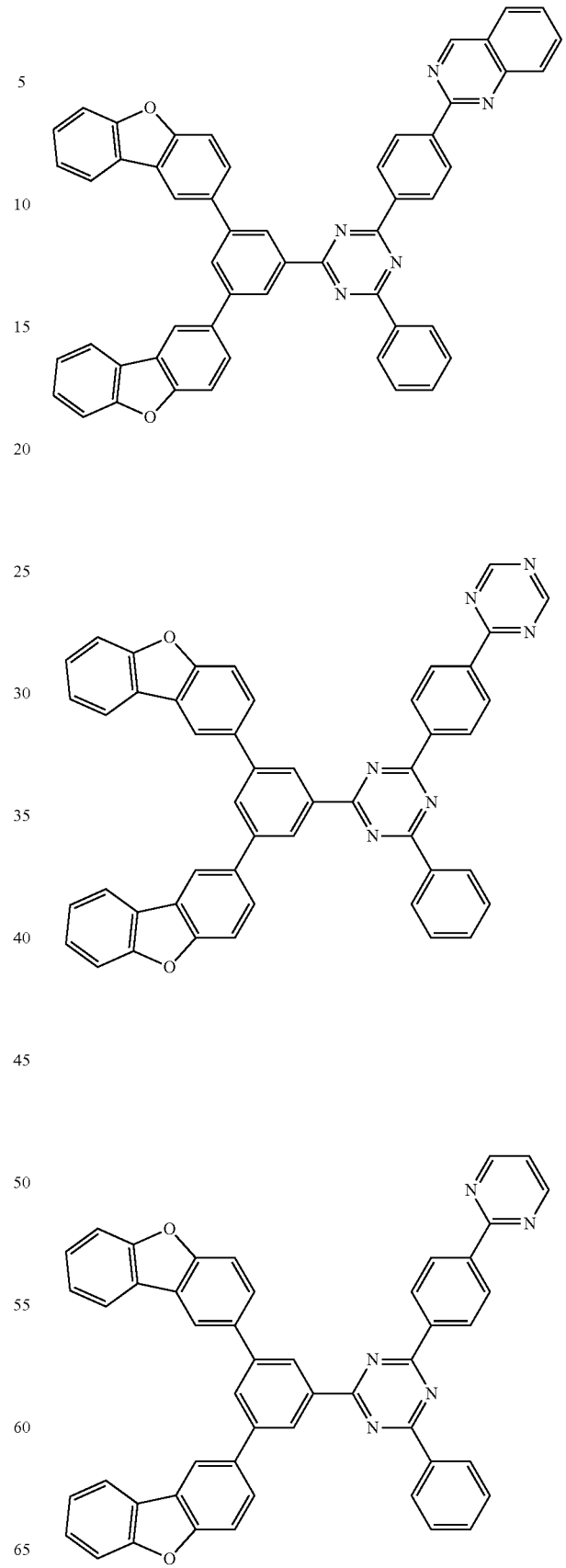

187
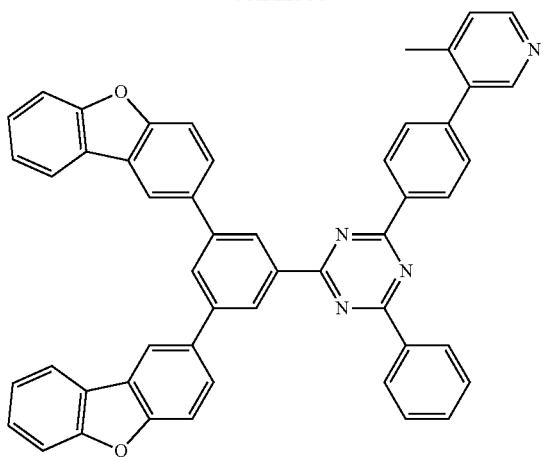
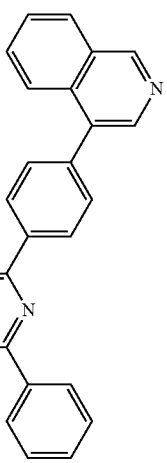
188
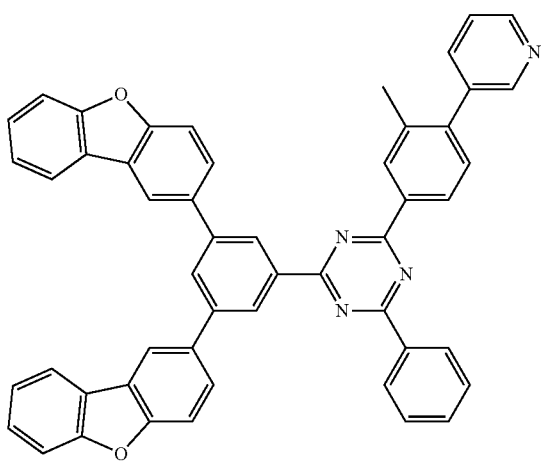
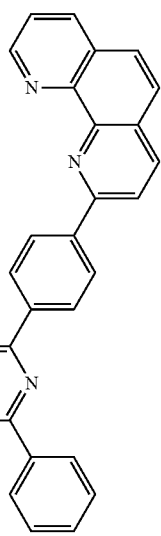
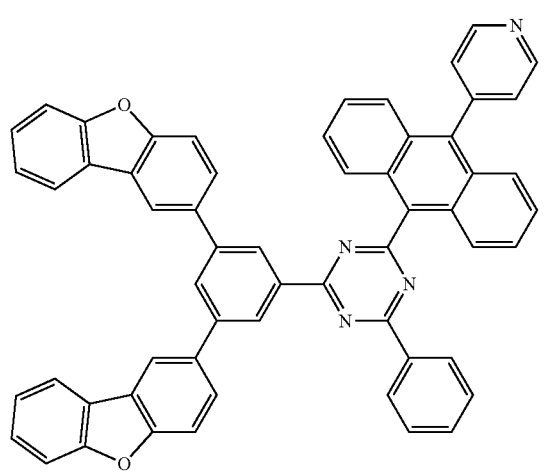
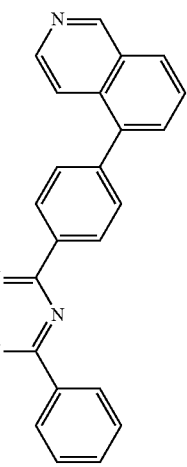

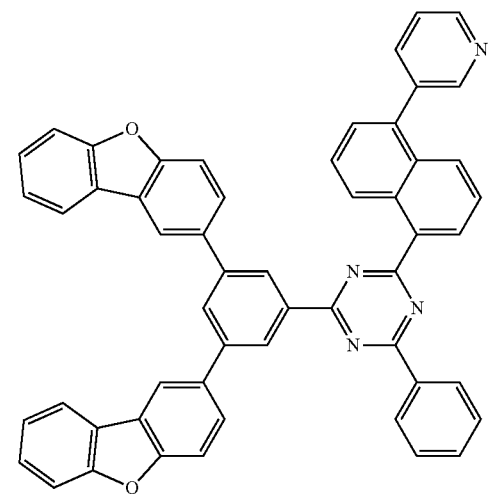
[Formula 97]
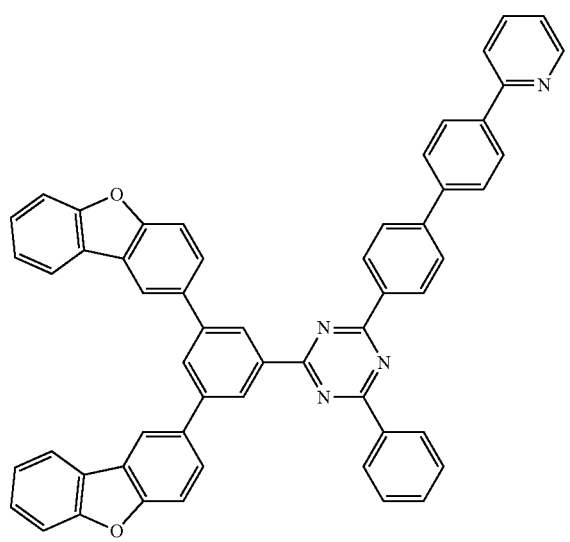
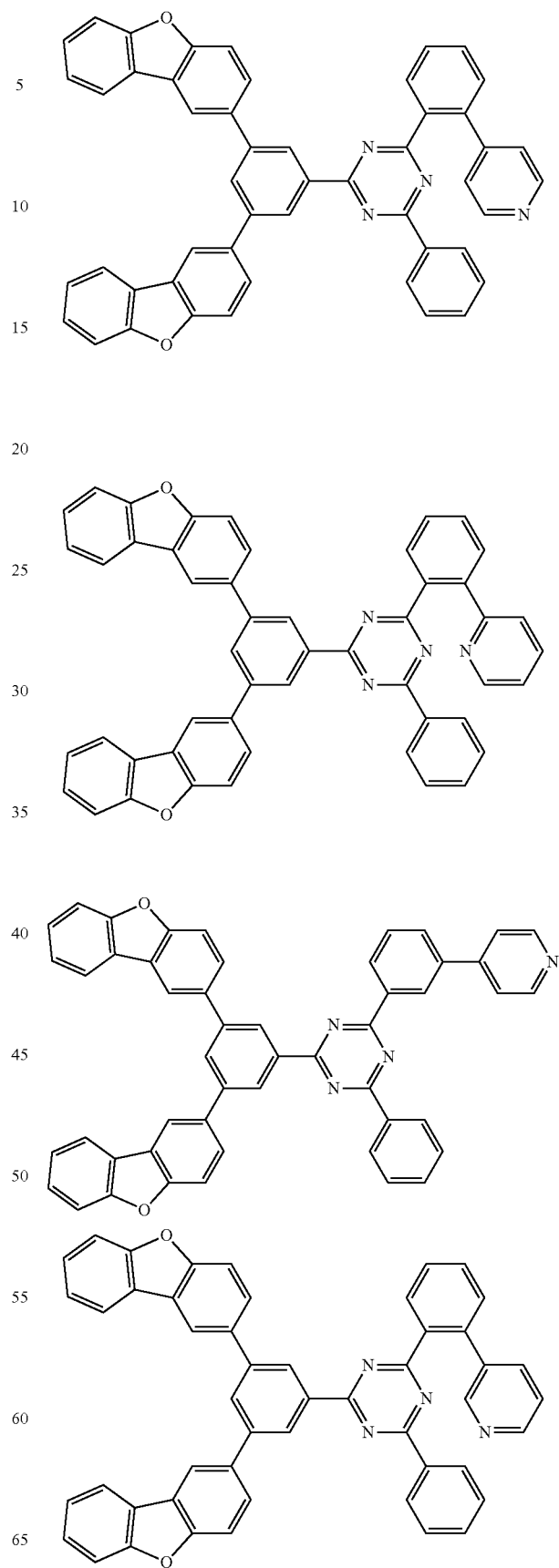

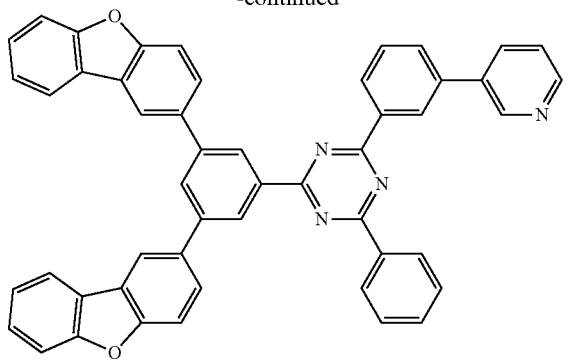
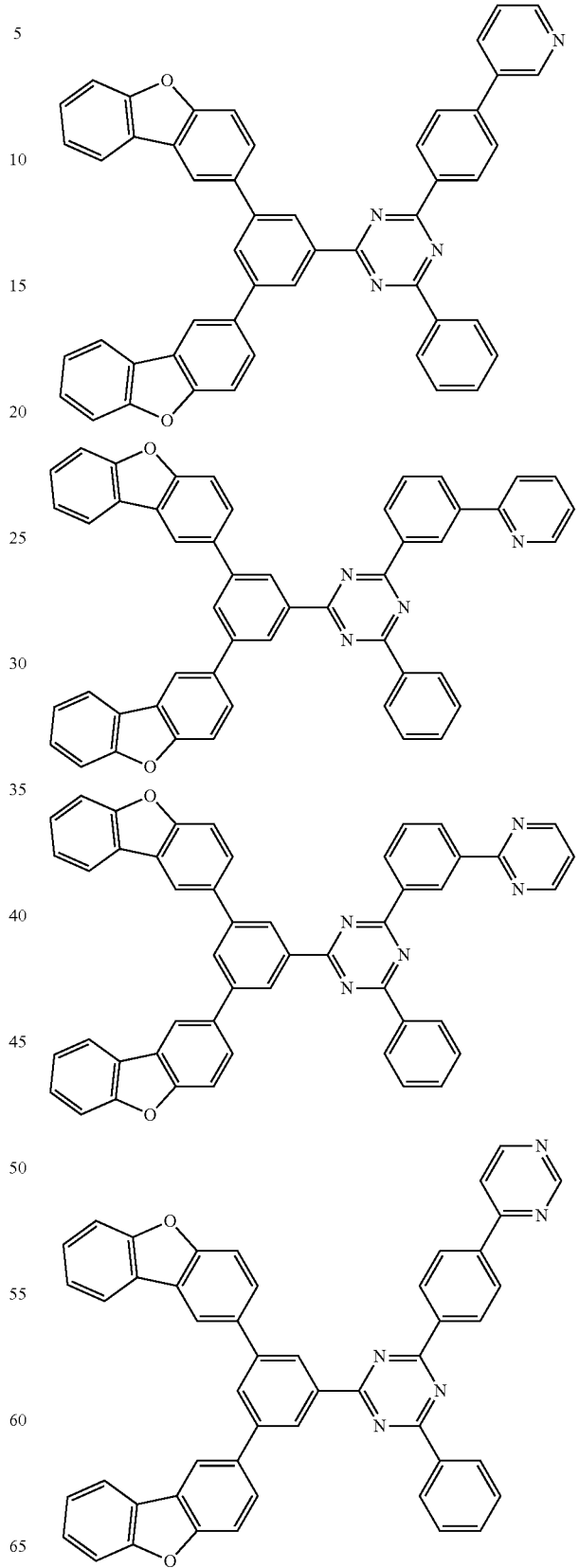

193
-continued
194
-continued
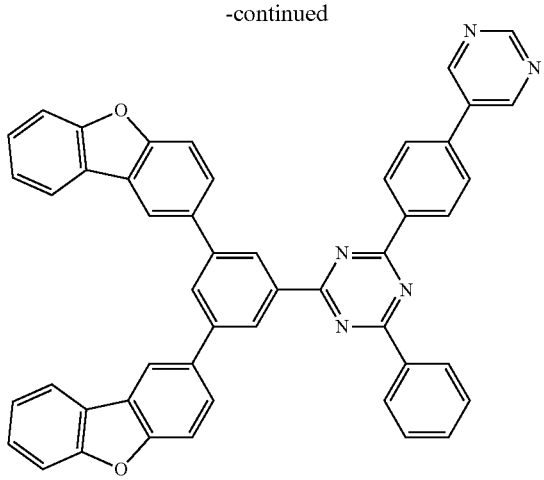
[Formula 99]
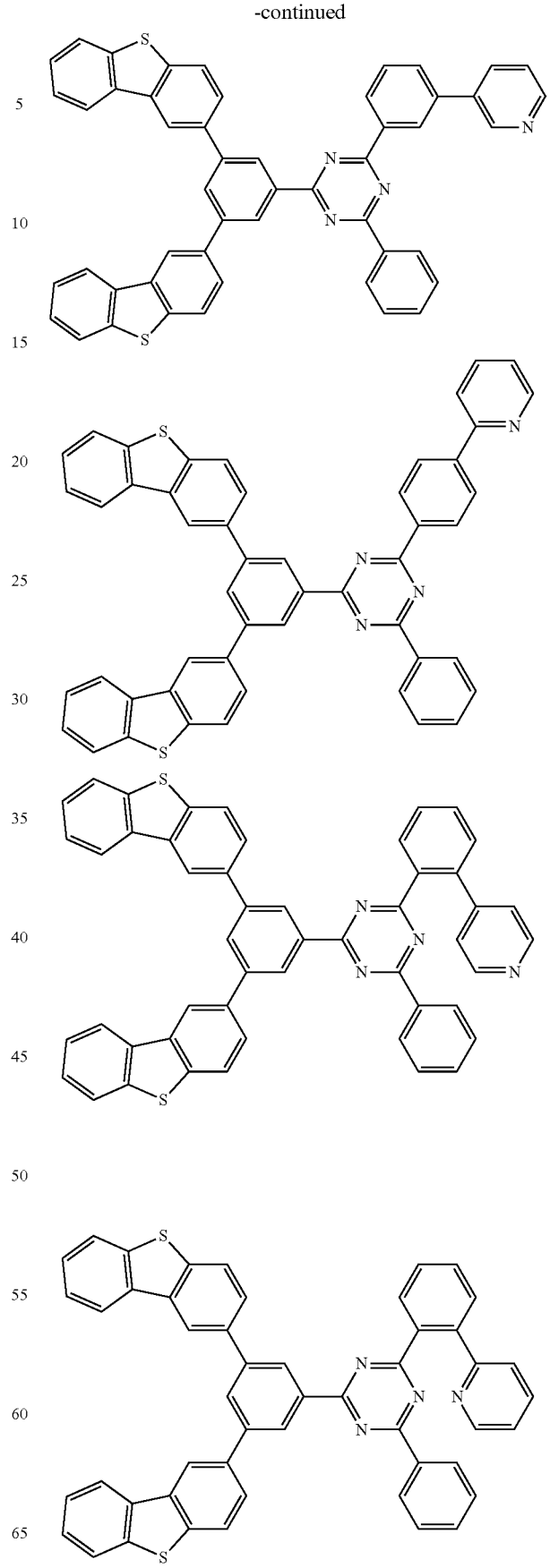

195
-continued
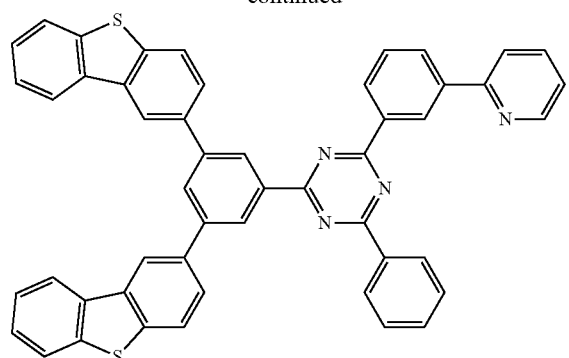
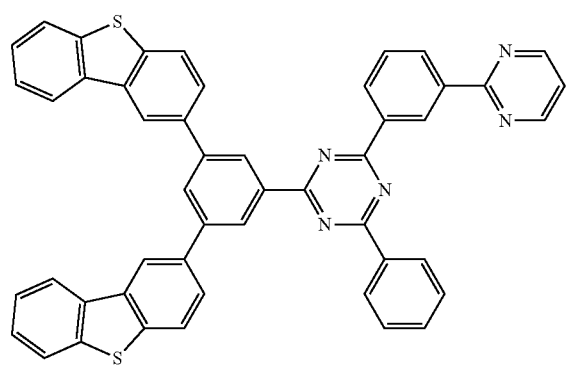
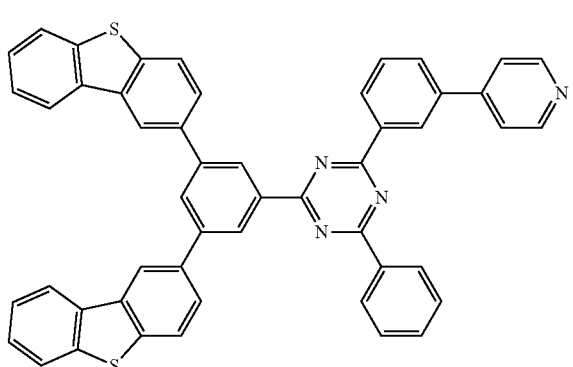
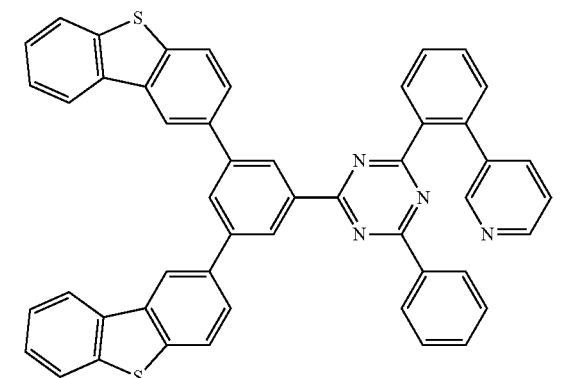
196
-continued
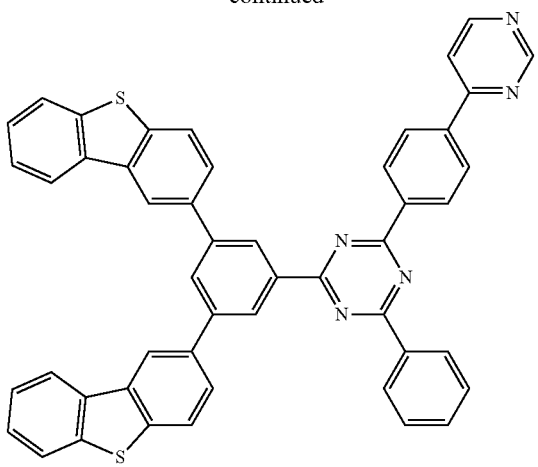
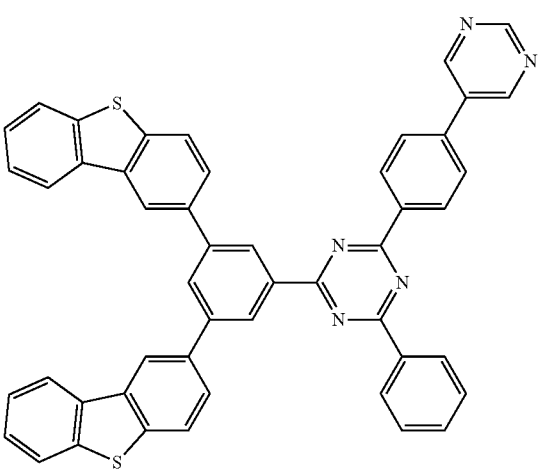
[Formula 100]
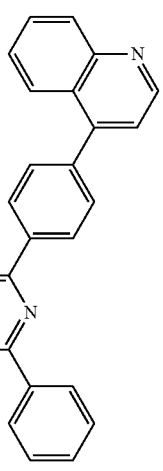

197
-continued
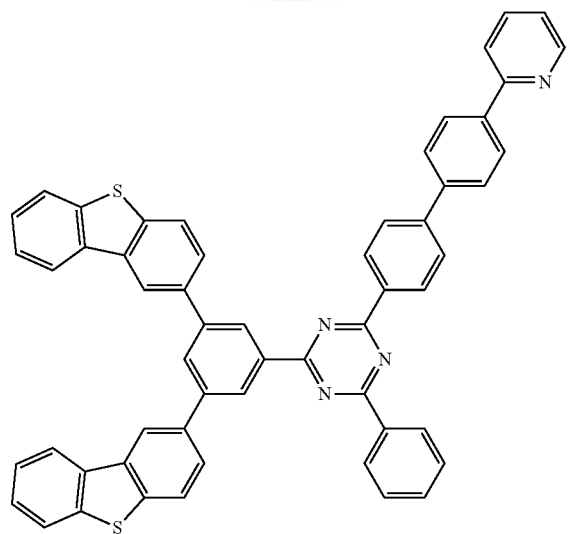
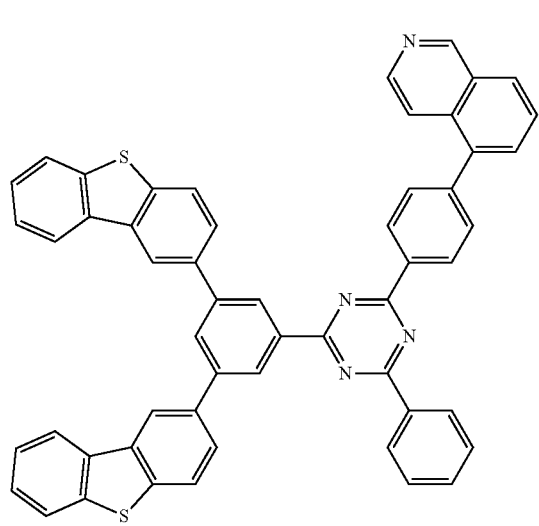
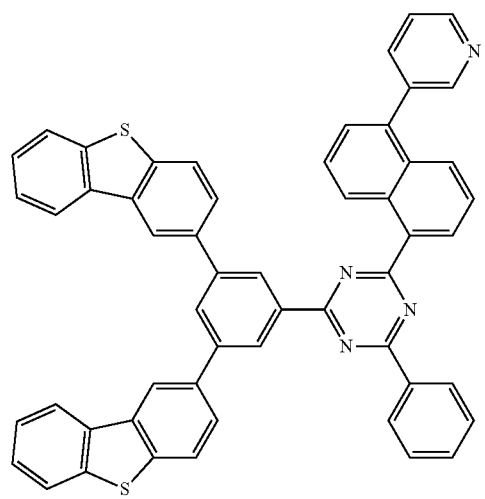
198
-continued
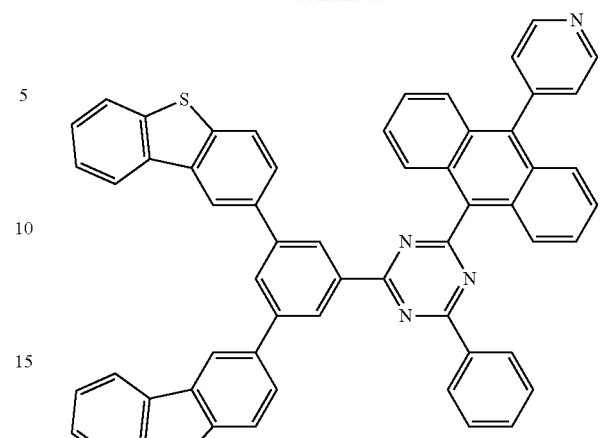
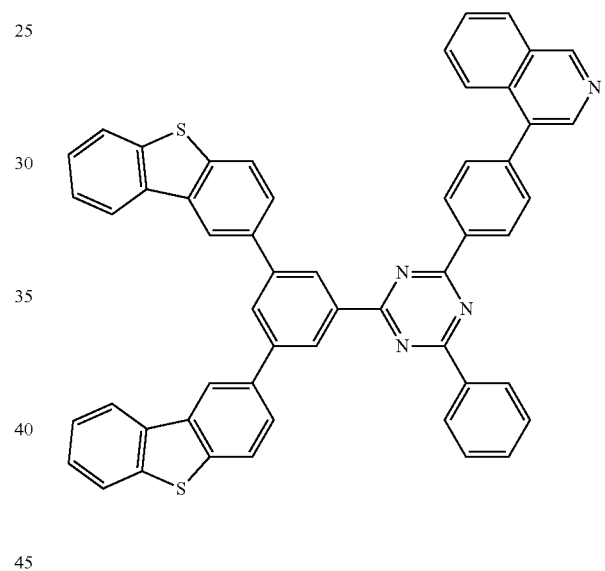
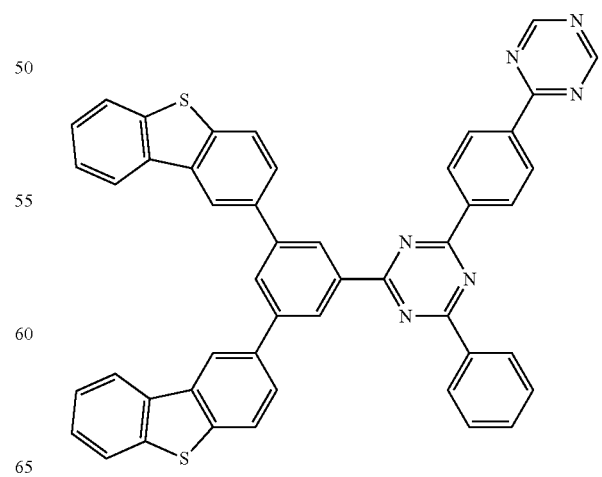

199
-continued
200
-continued
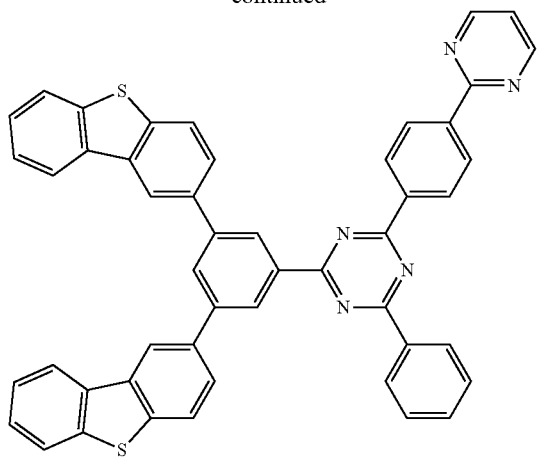
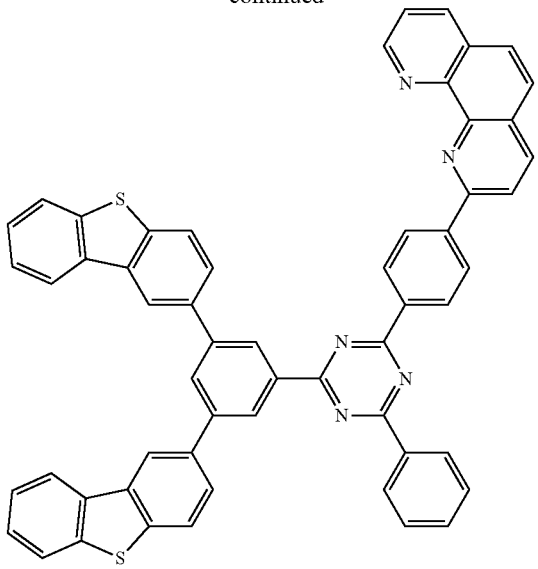
[Formula 101]
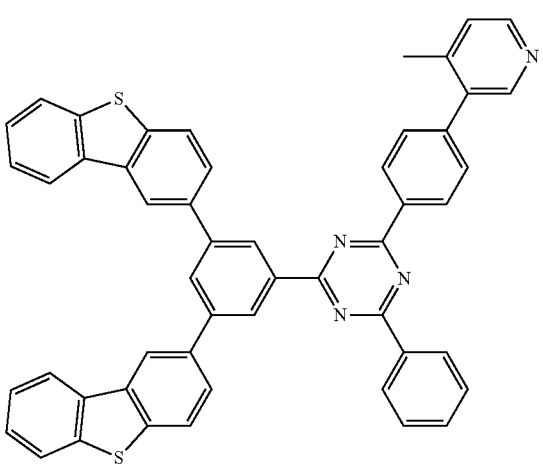
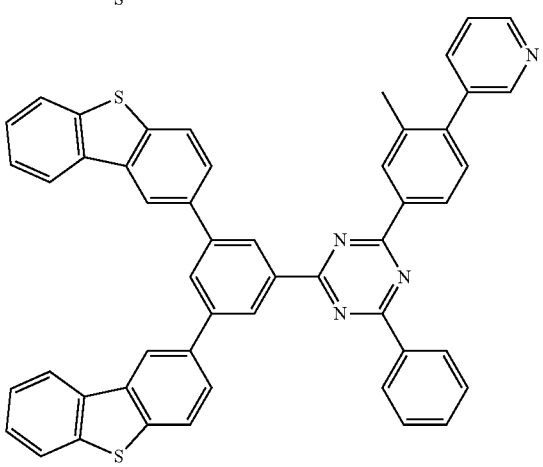
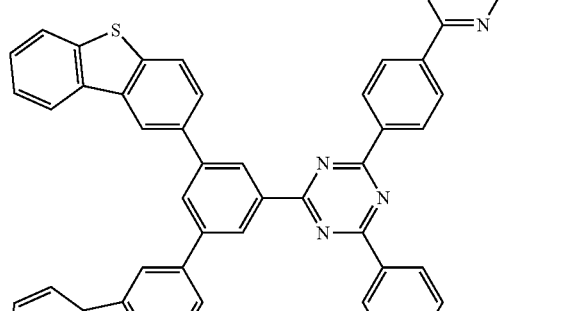

[Formula 102]
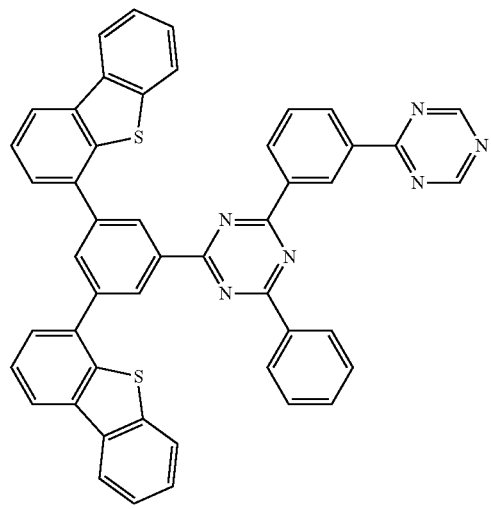
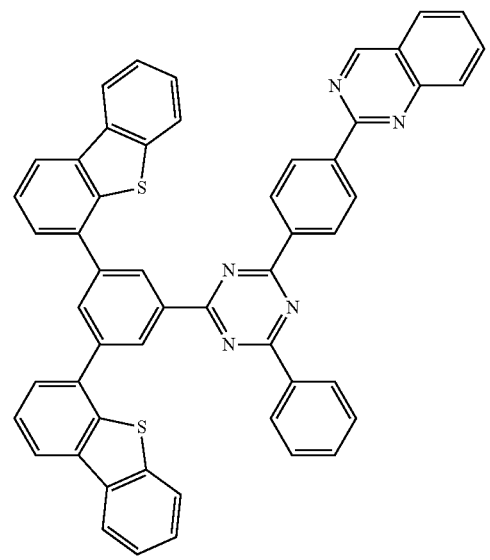
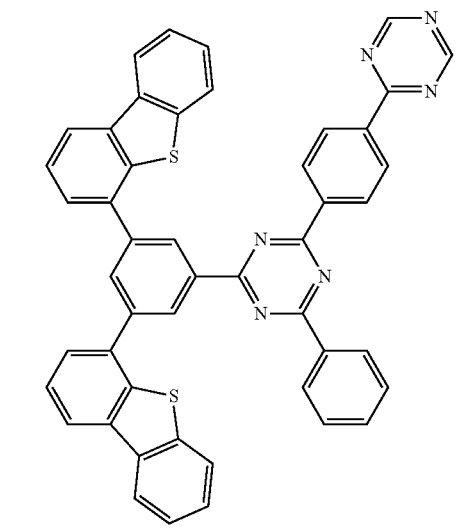
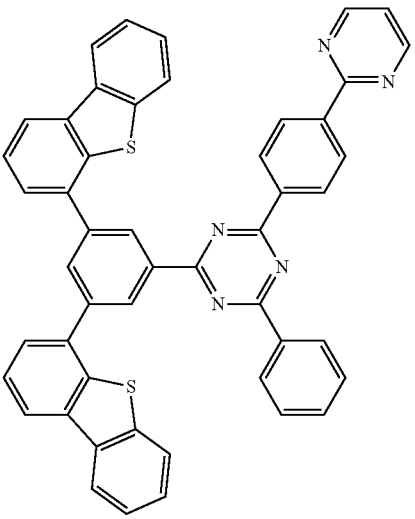
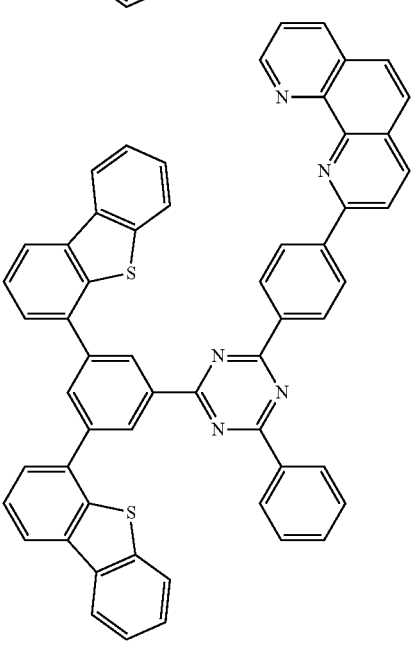
[Foemula 103]
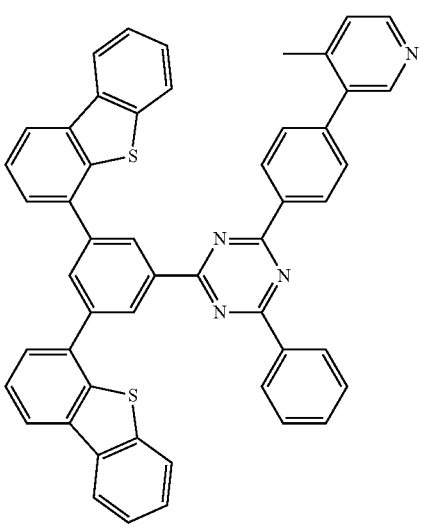

203
-continued
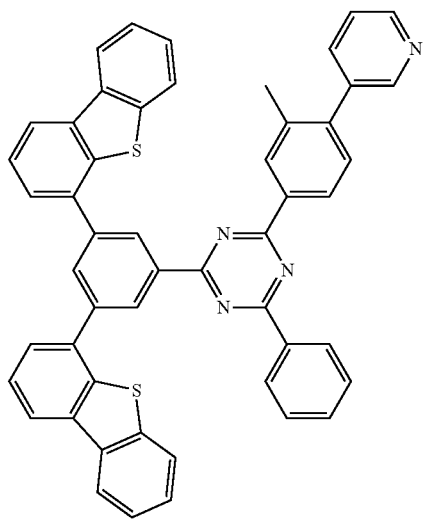
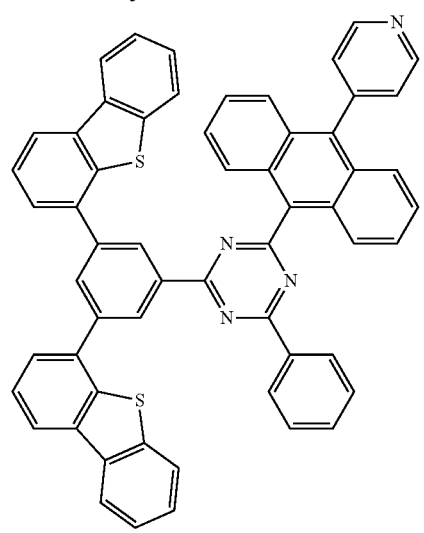
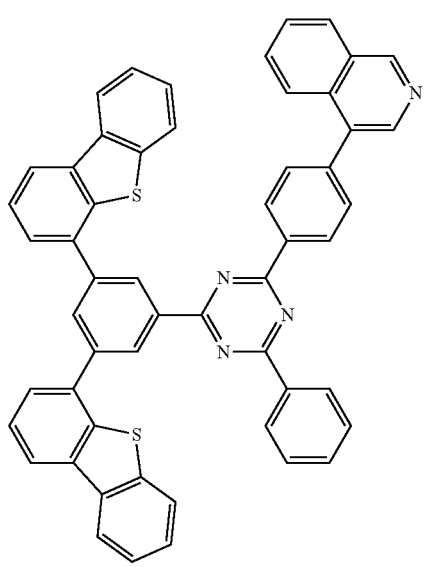
204
-continued
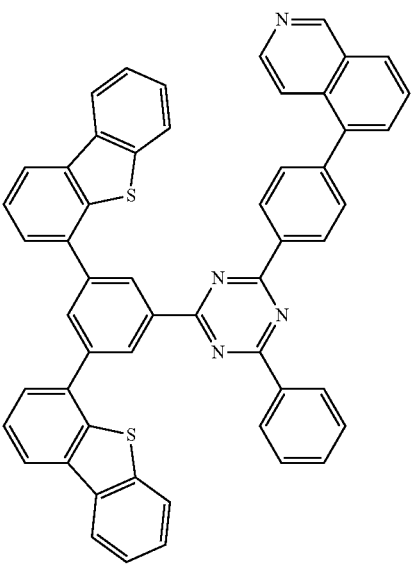
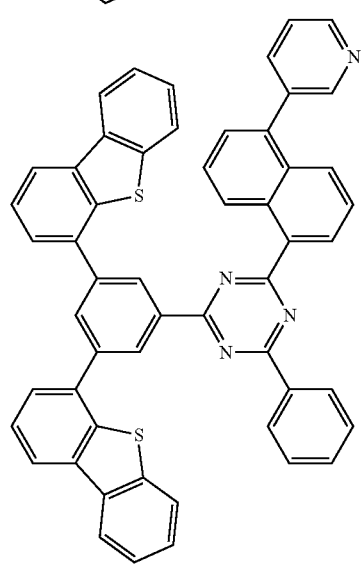
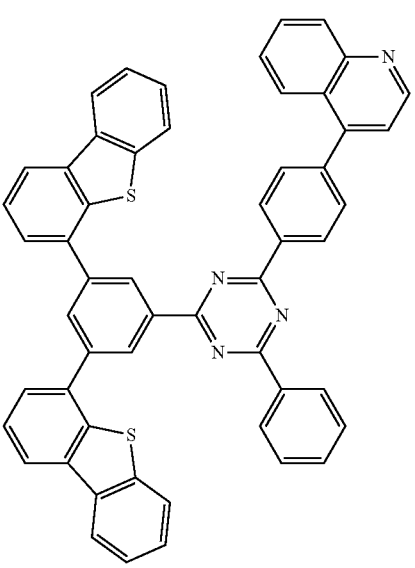

205
-continued
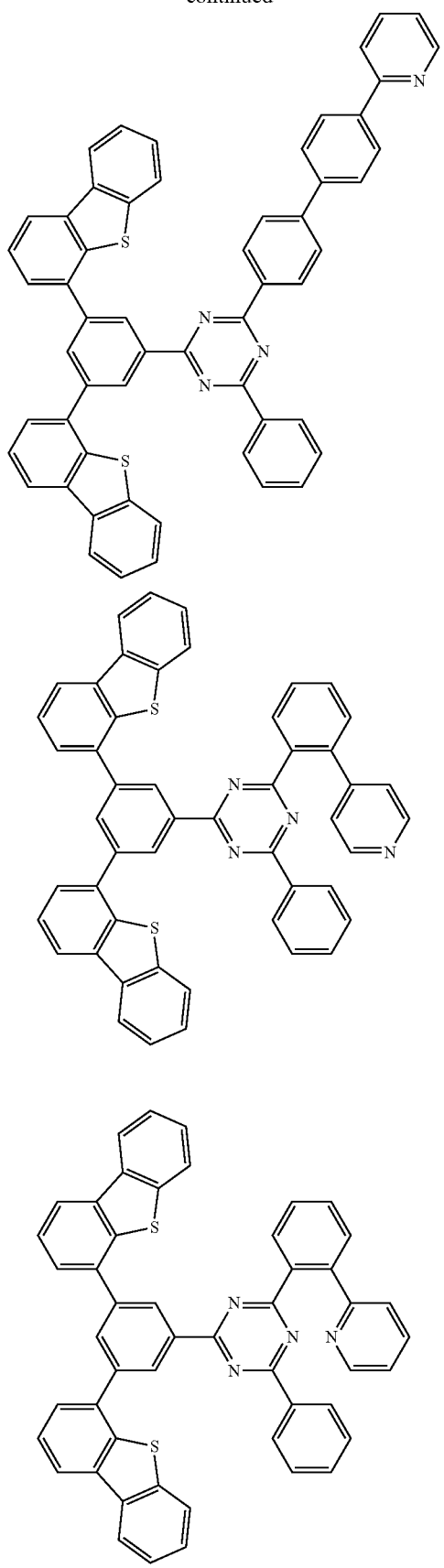
206
-continued
[Formula 104]
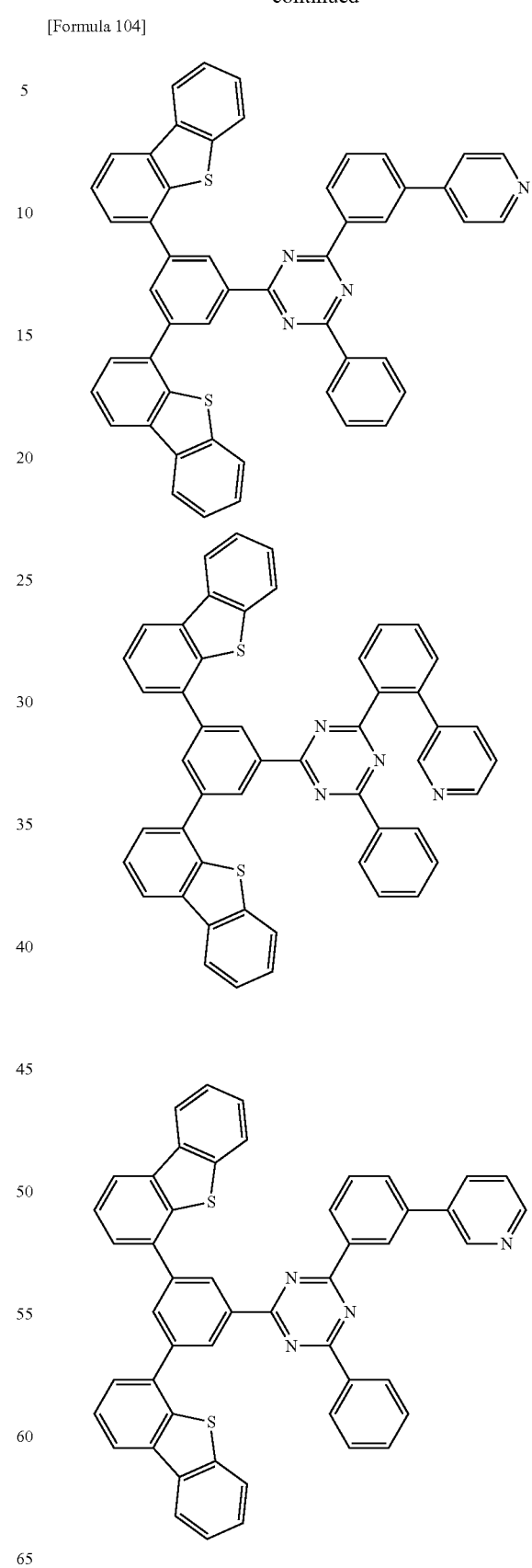

207
-continued
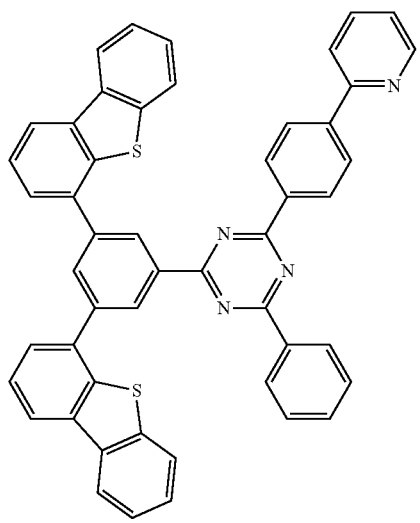
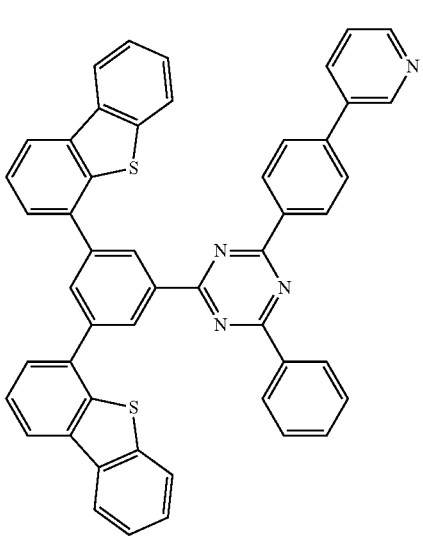
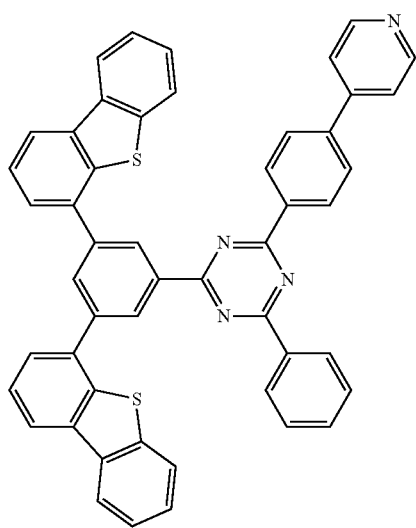
208
-continued
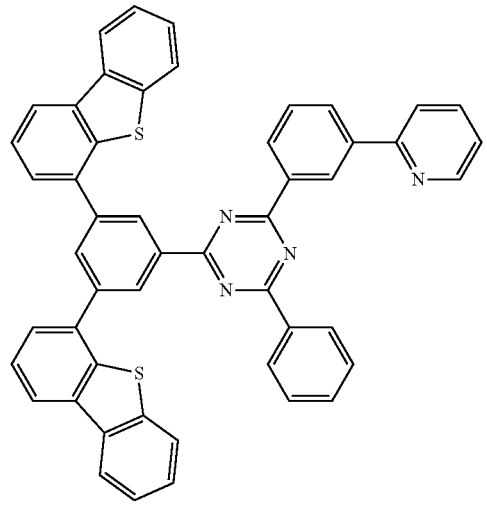
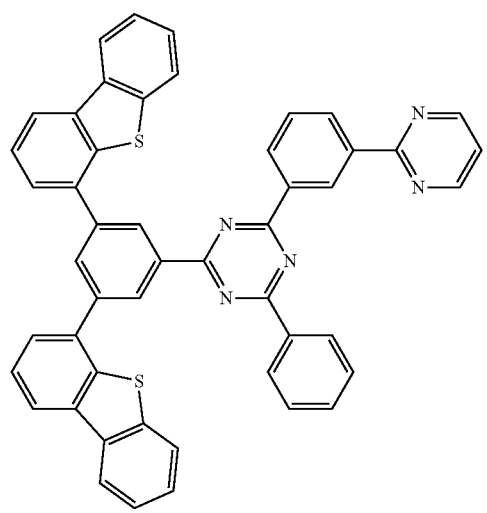
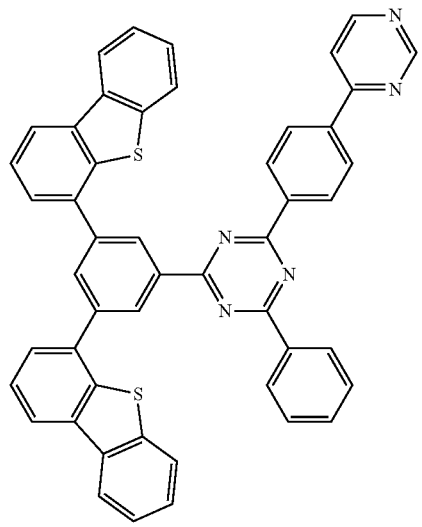

[Formula 105]
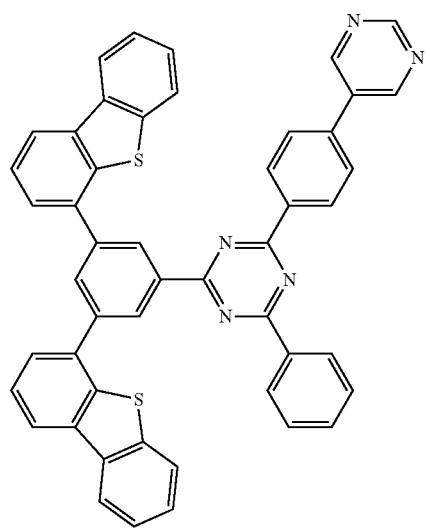
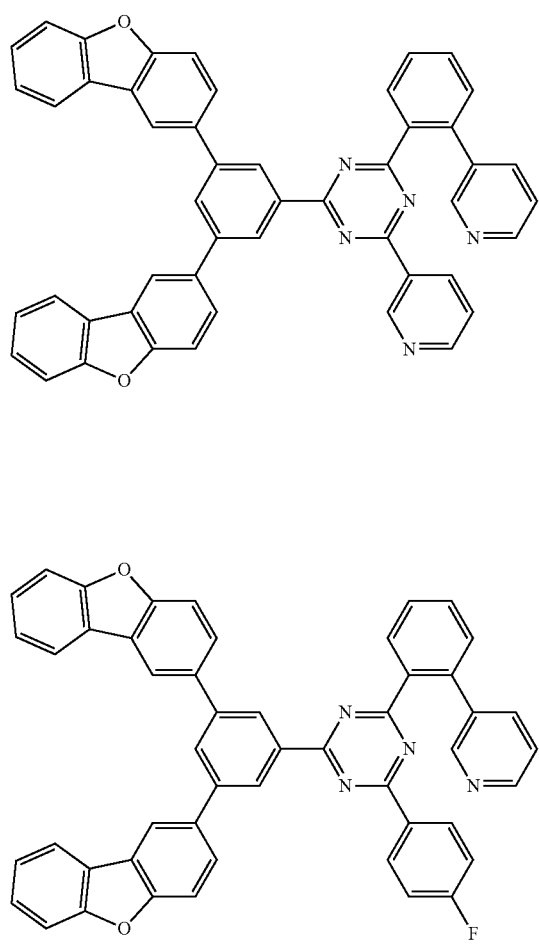
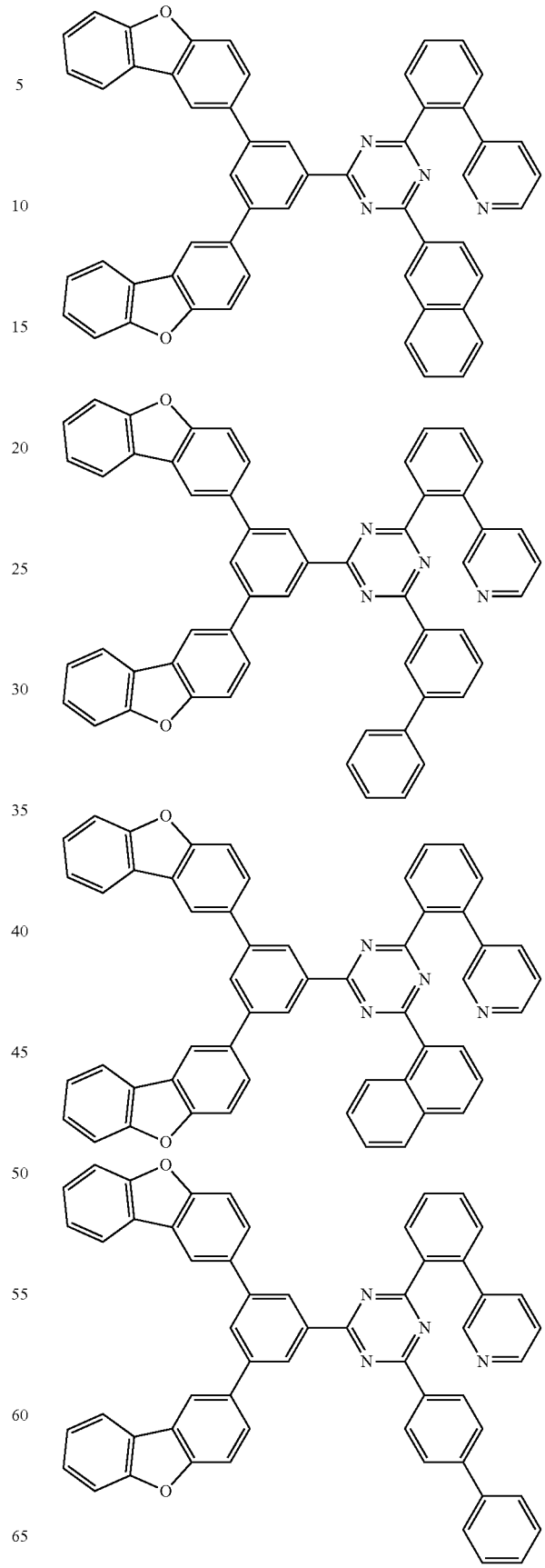

211
-continued
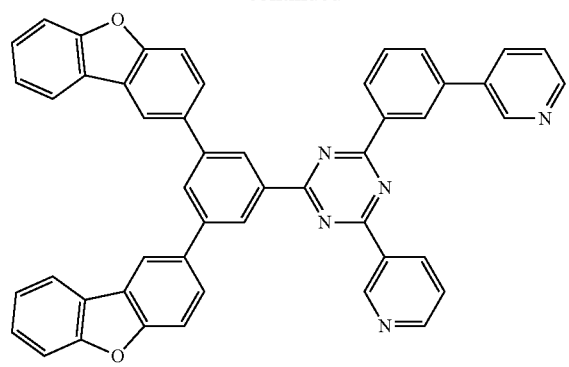
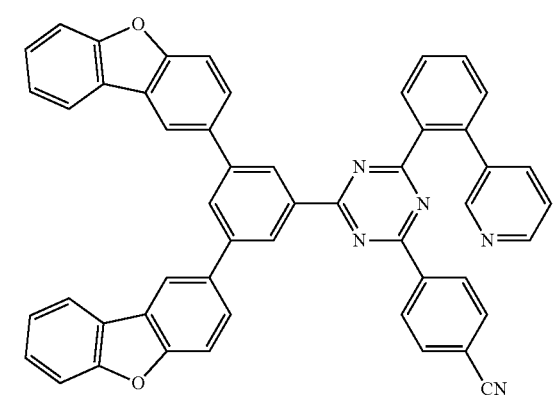
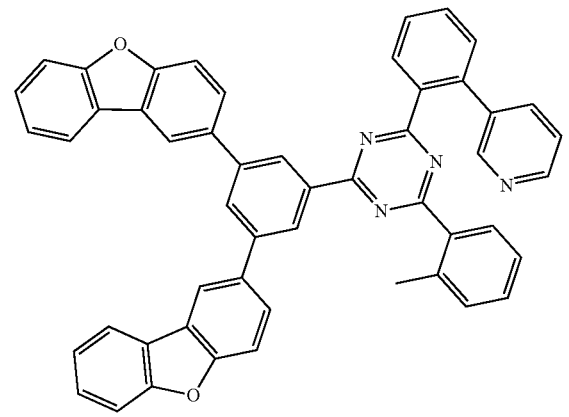
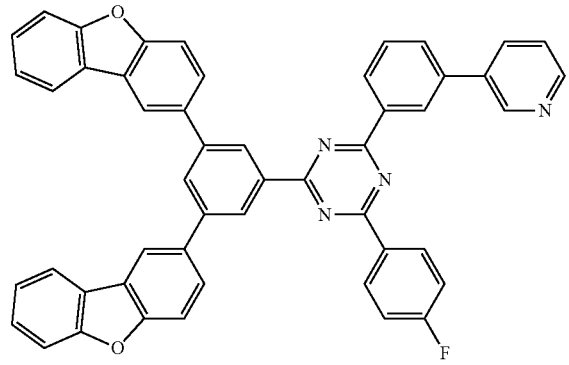
212
-continued
[Formula 106]
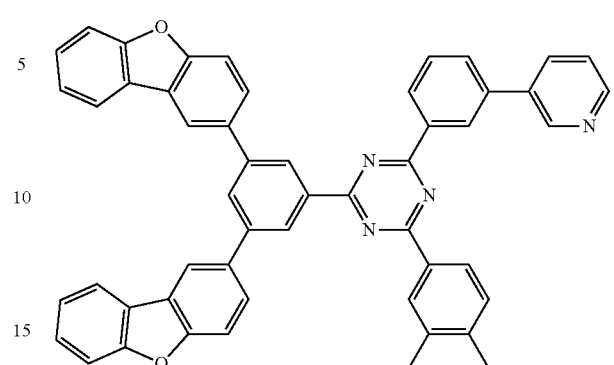
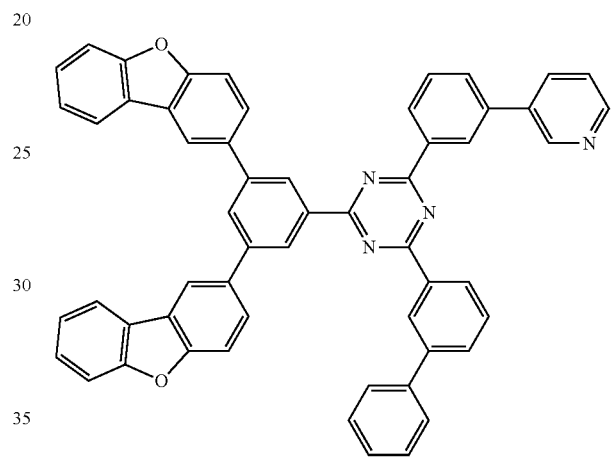
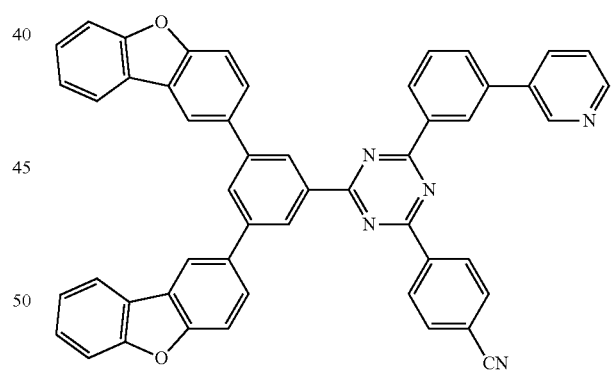
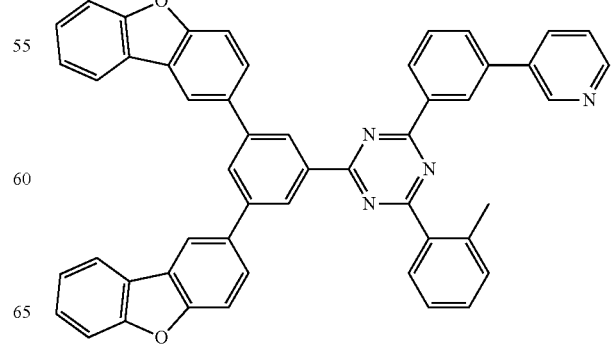

213
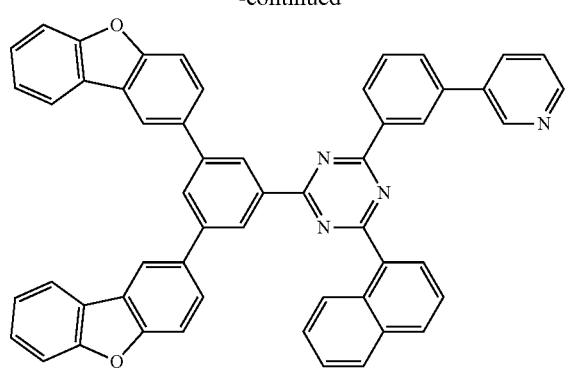
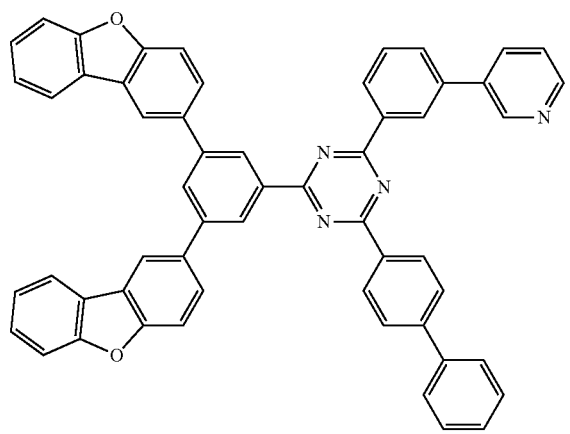
[Formula 107]
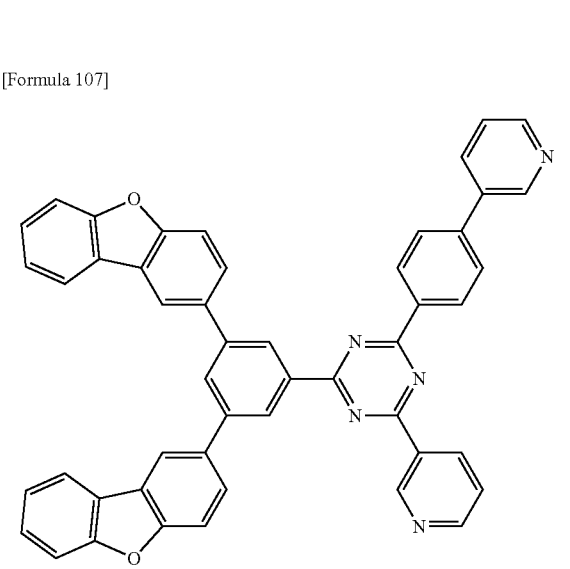
214
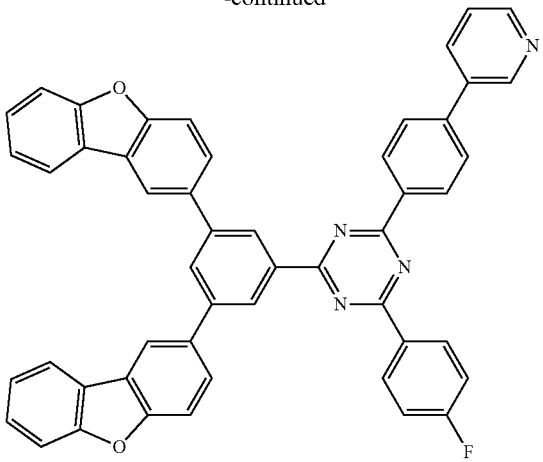
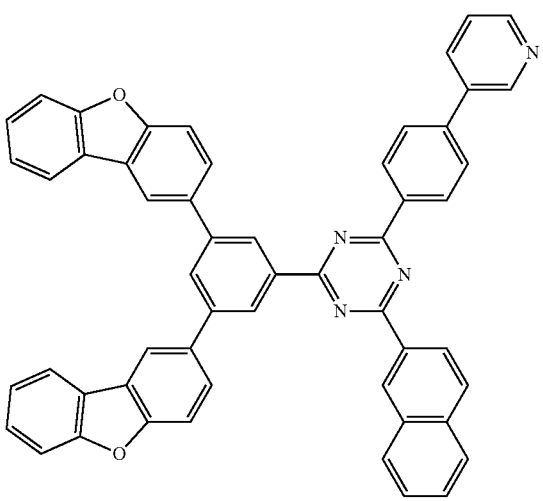
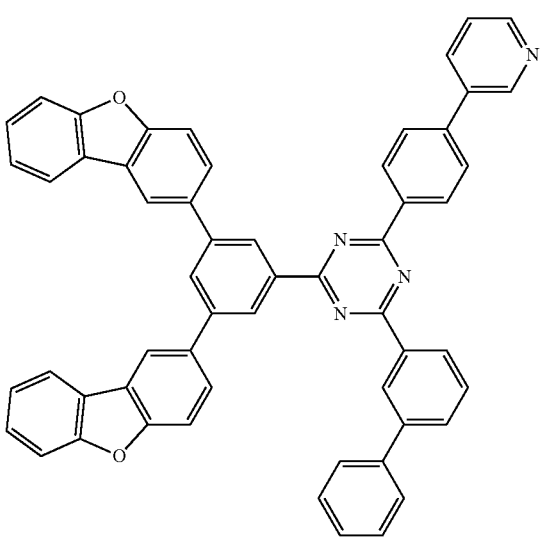

[Formula 108]
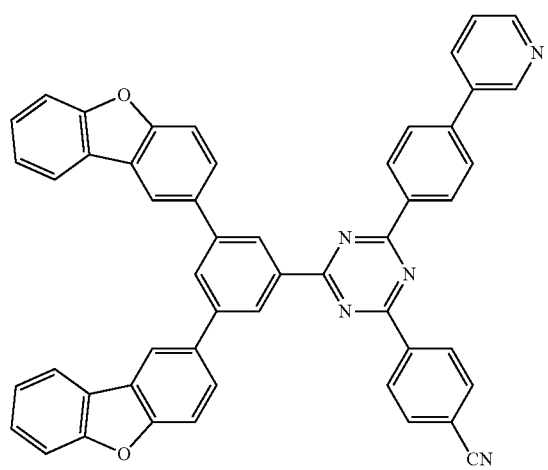
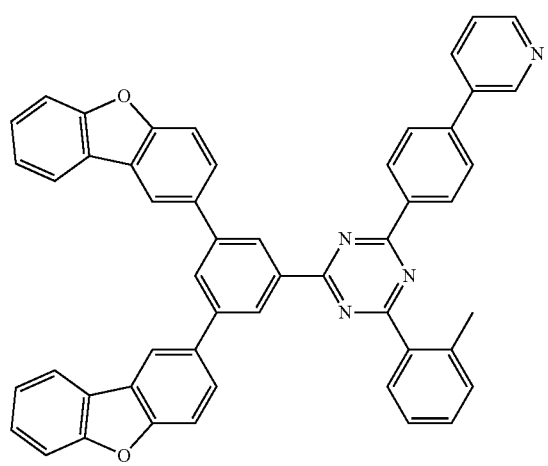
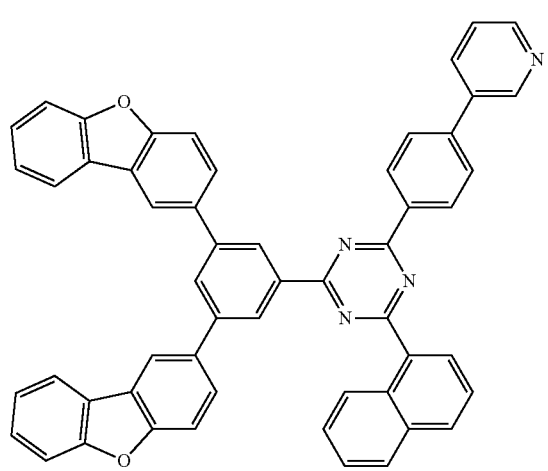
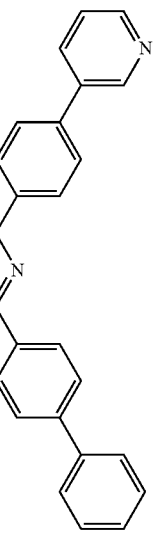
[Formula 109]
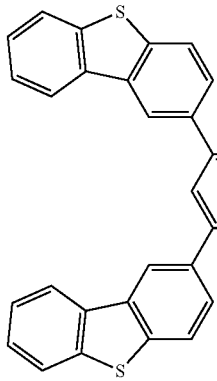
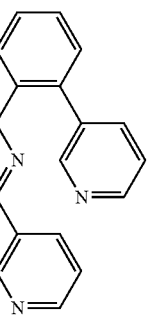
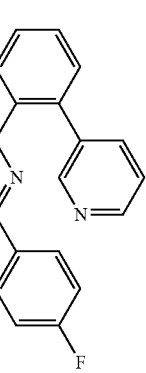

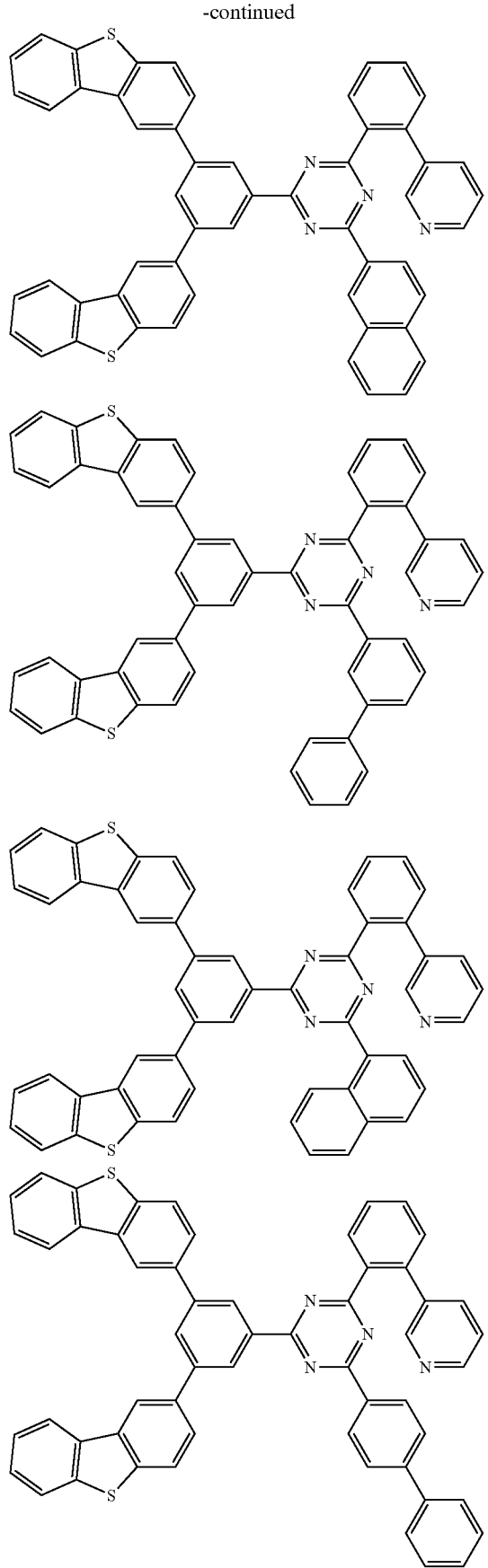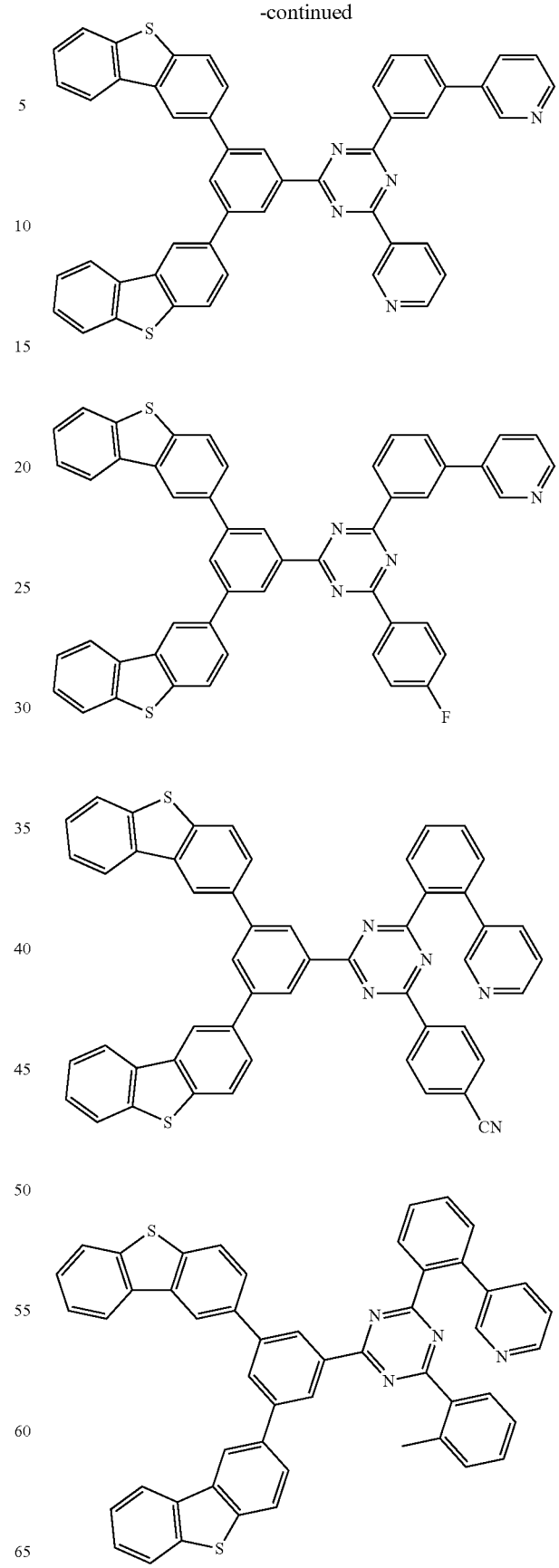

[Formula 110]
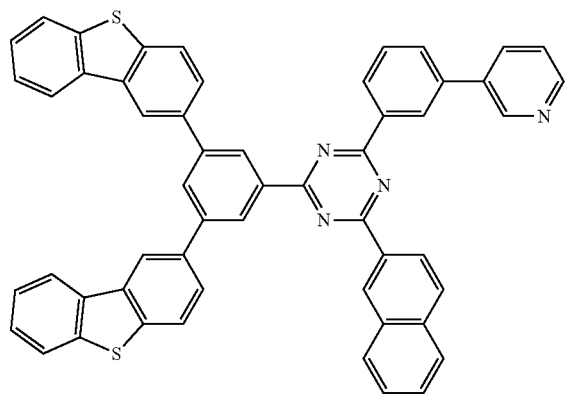
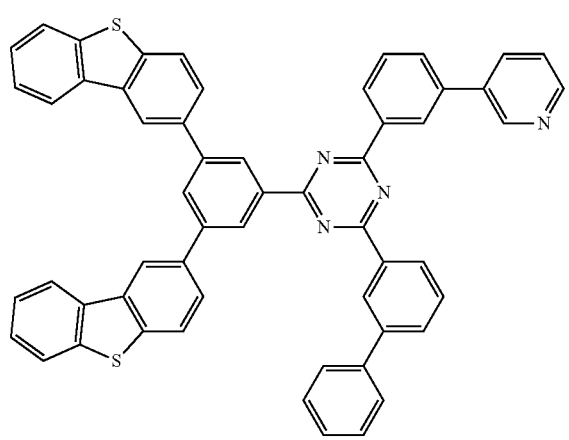
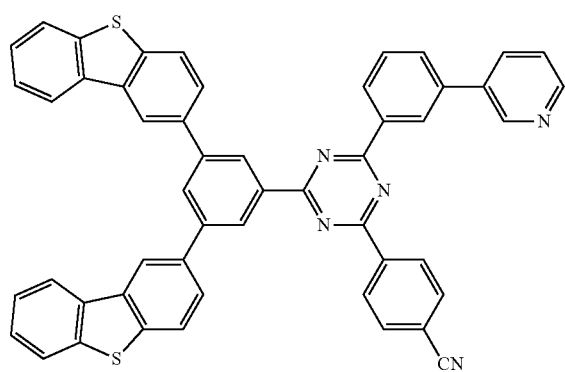
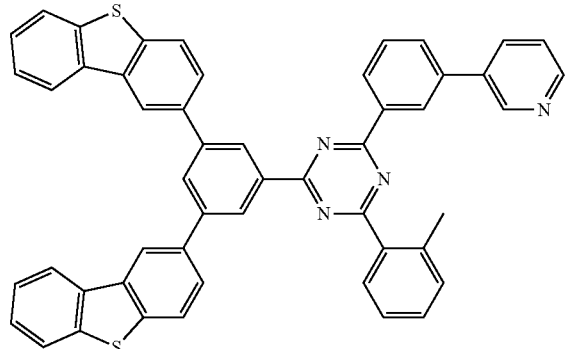
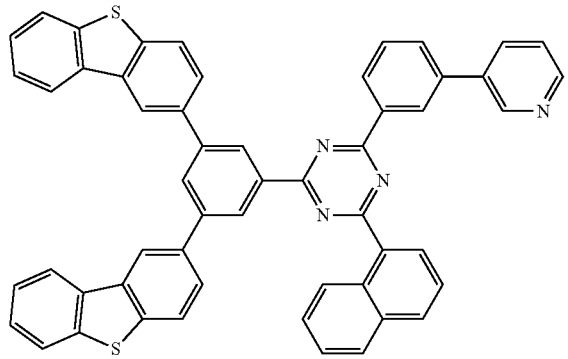
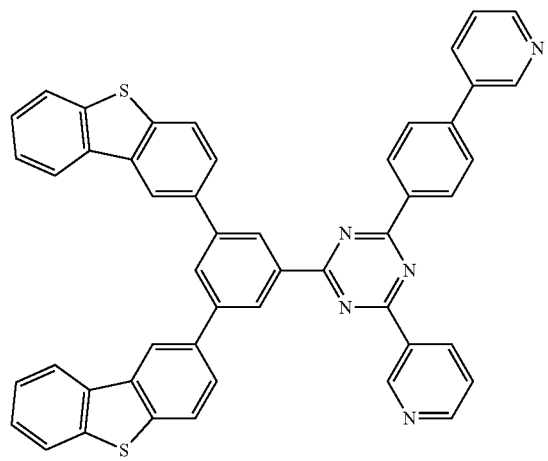
[Formula 111]

221
-continued
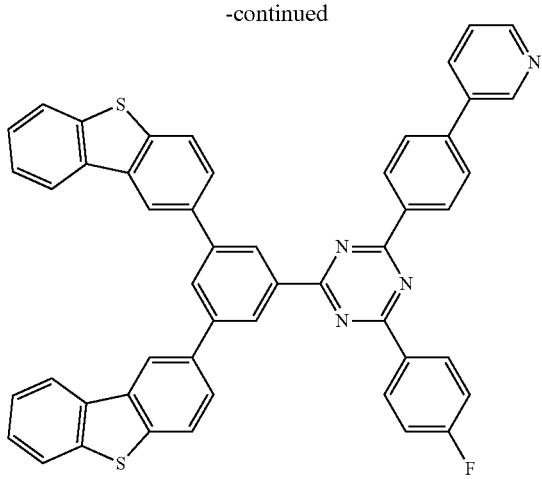
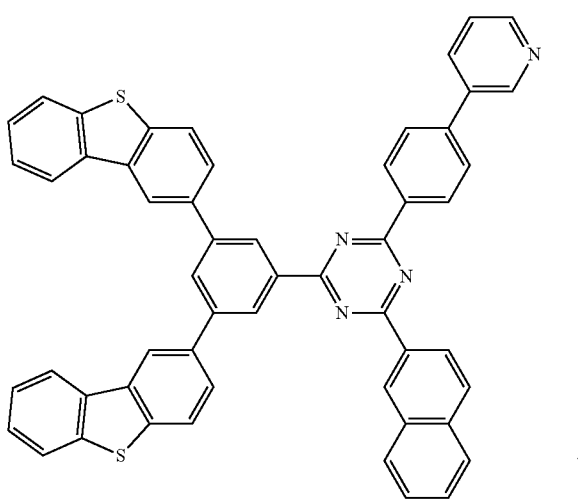
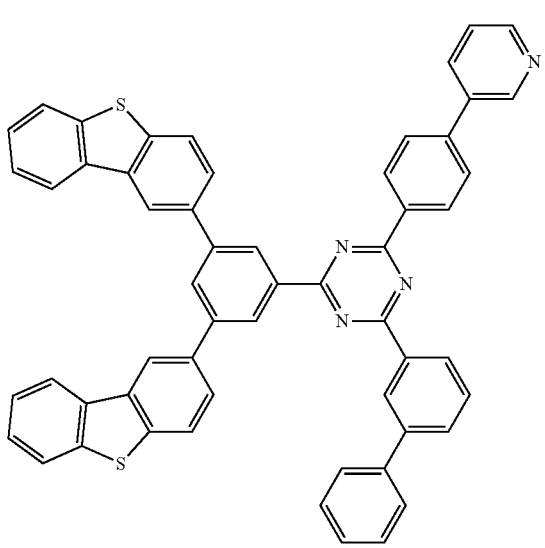
222
-continued
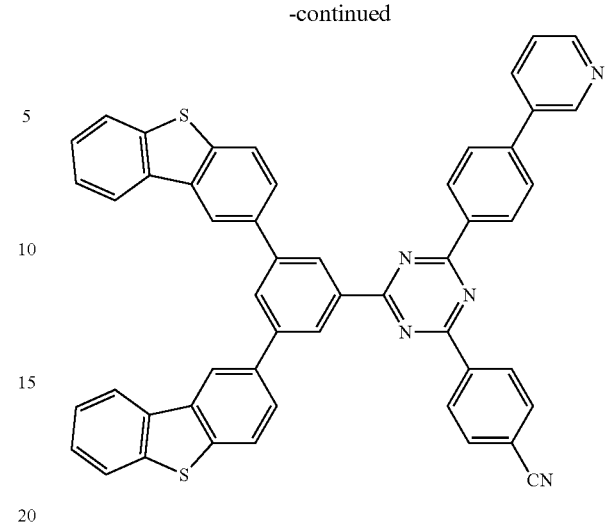
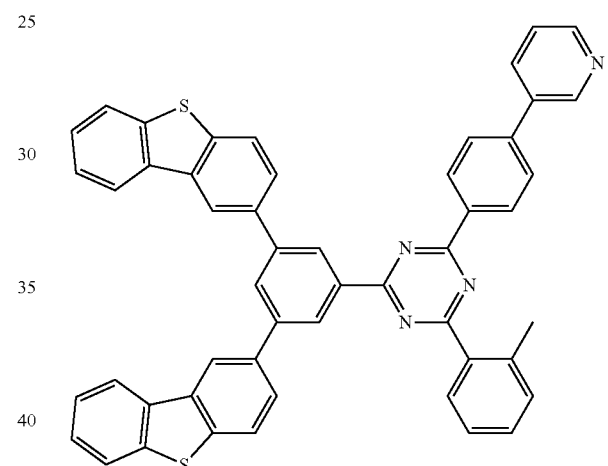
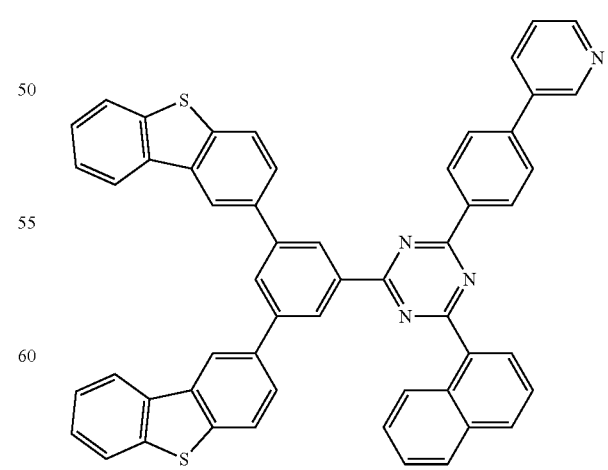

223
-continued
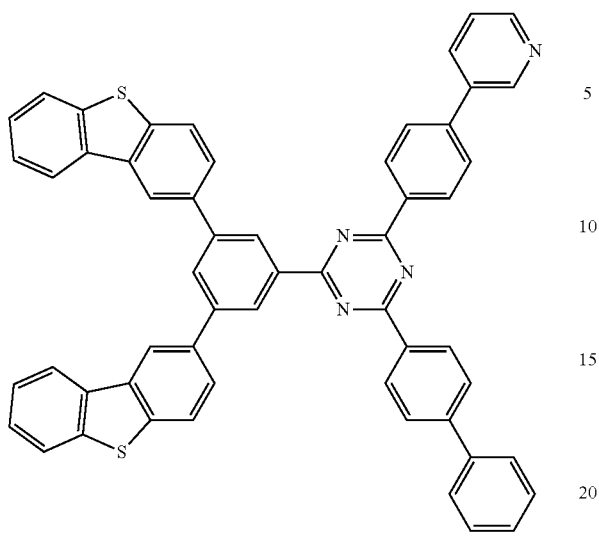
[Formula 112]
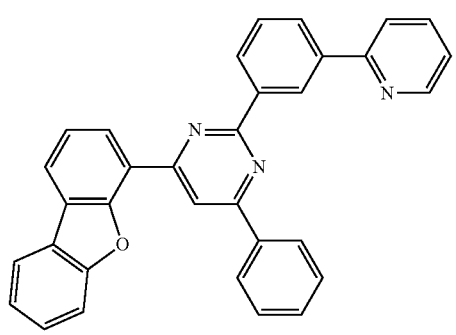
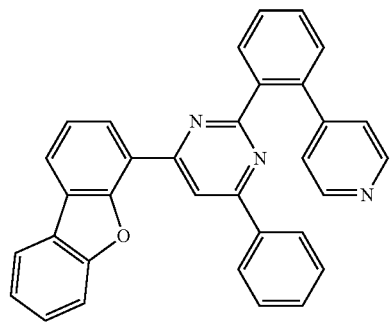
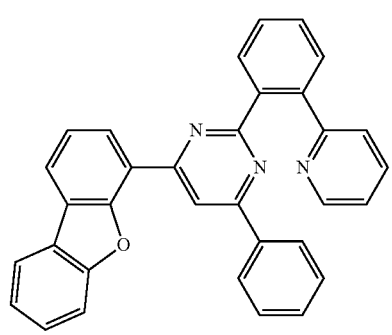
224
-continued
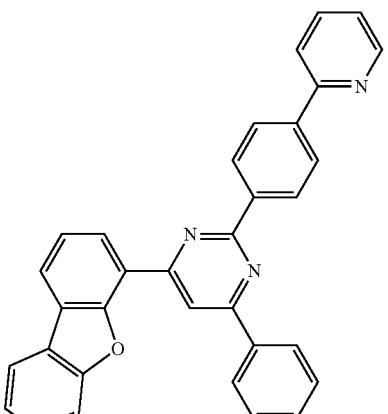
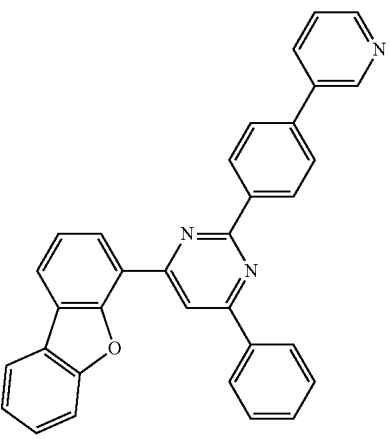
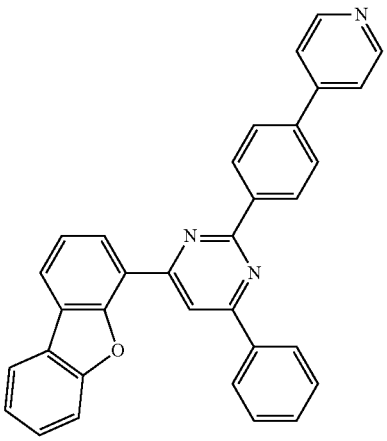
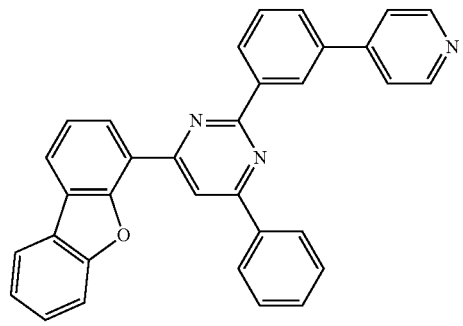

-continued
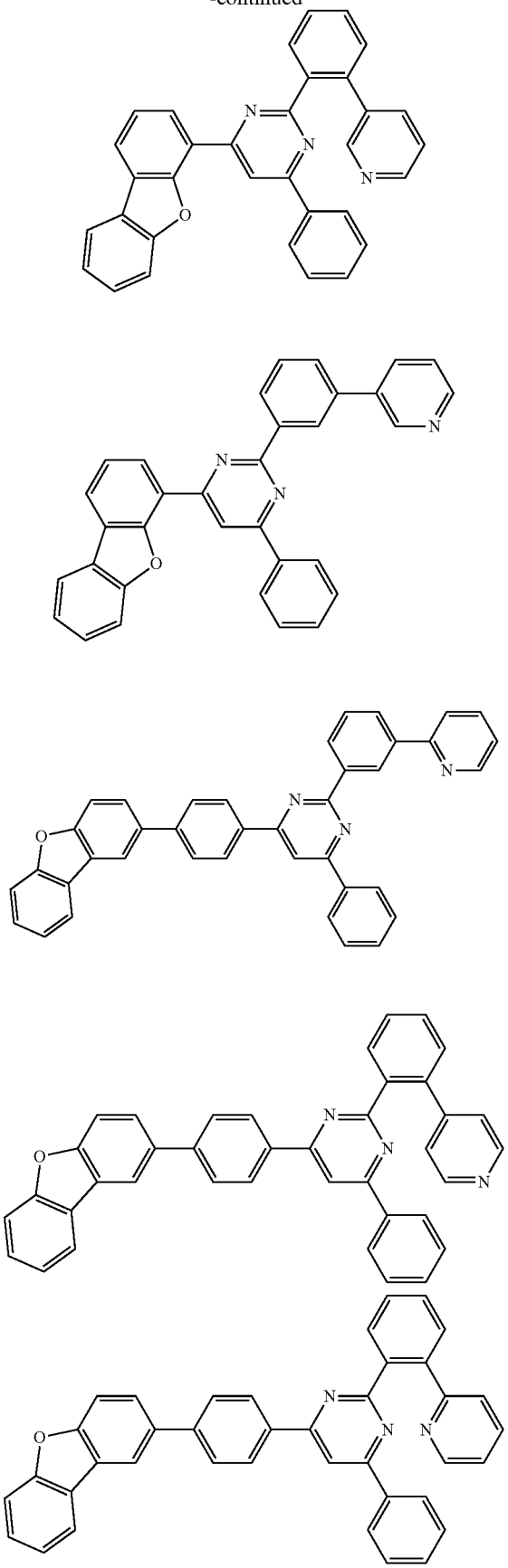
-continued
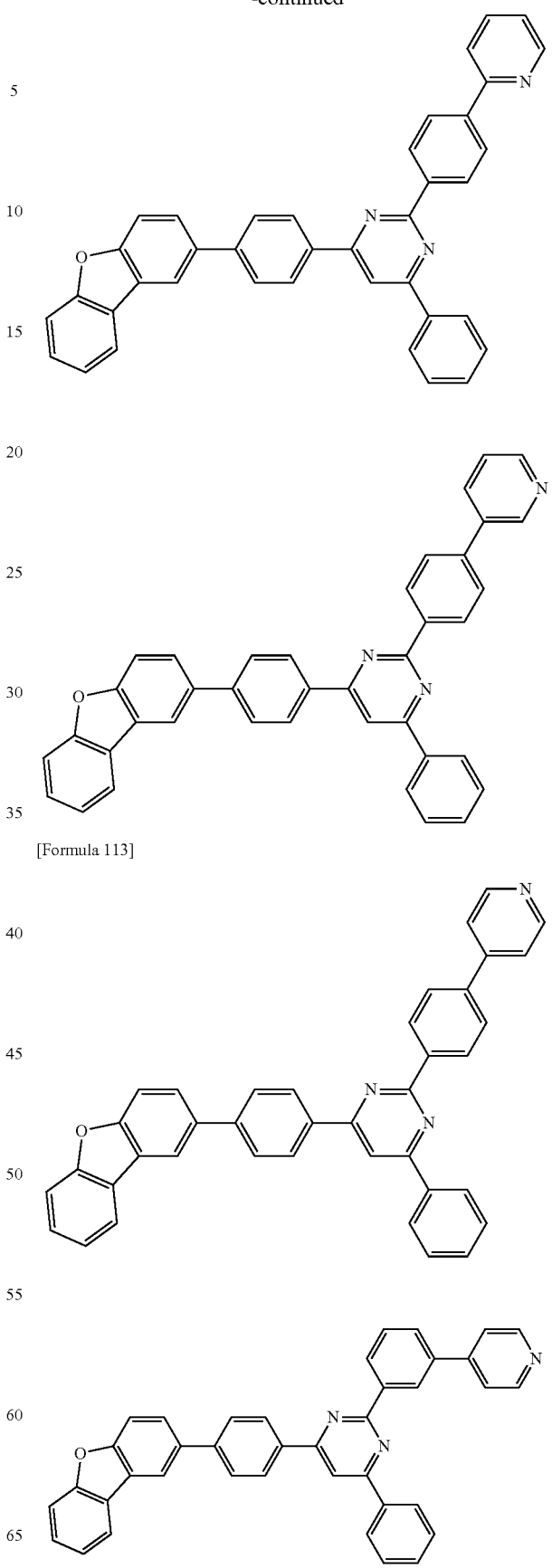
[Formula 113]

227
-continued
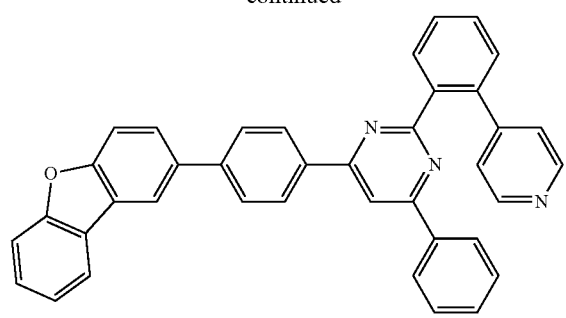
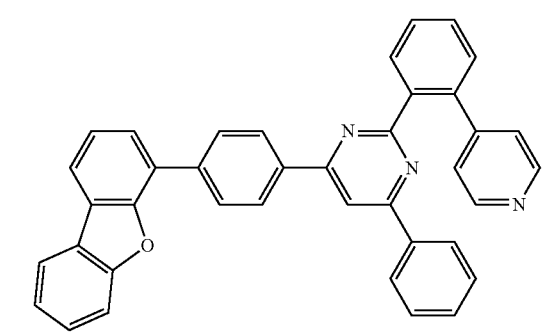
[Formula 114]
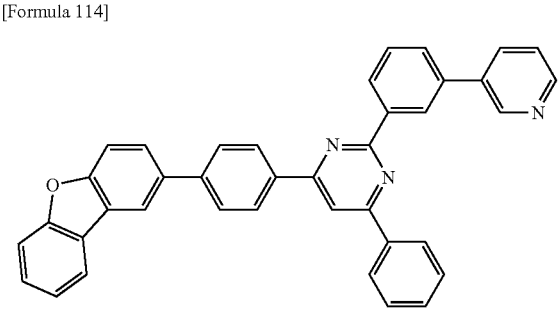
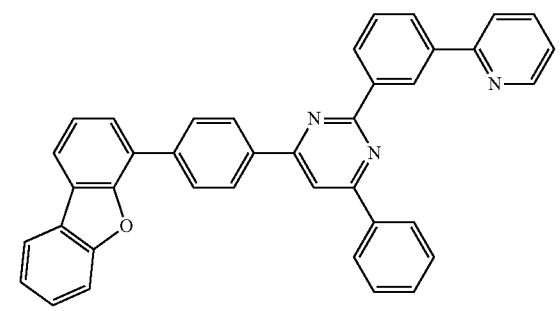
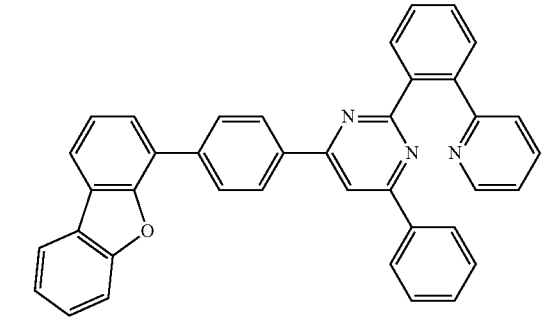
228
-continued
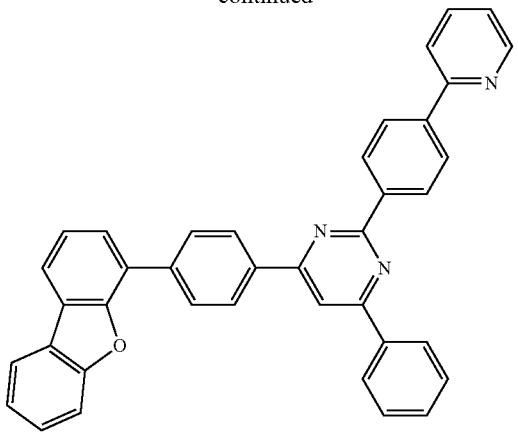
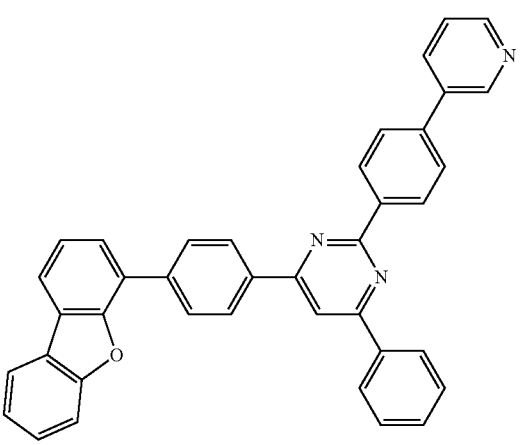
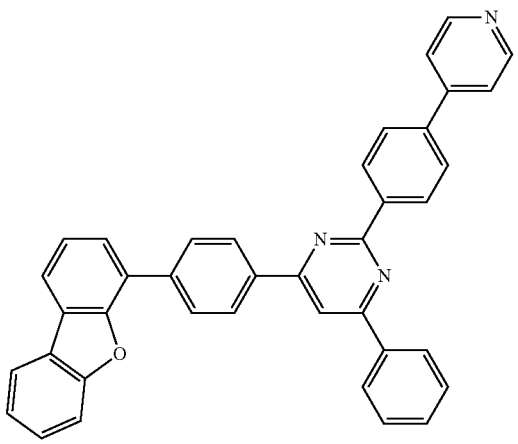
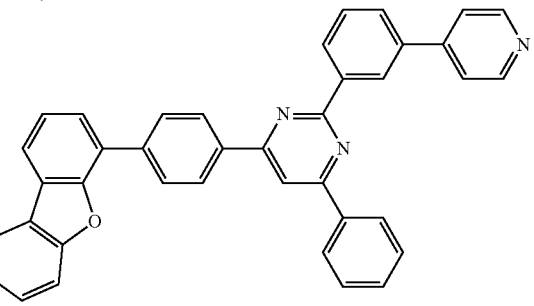

[Formula 115]
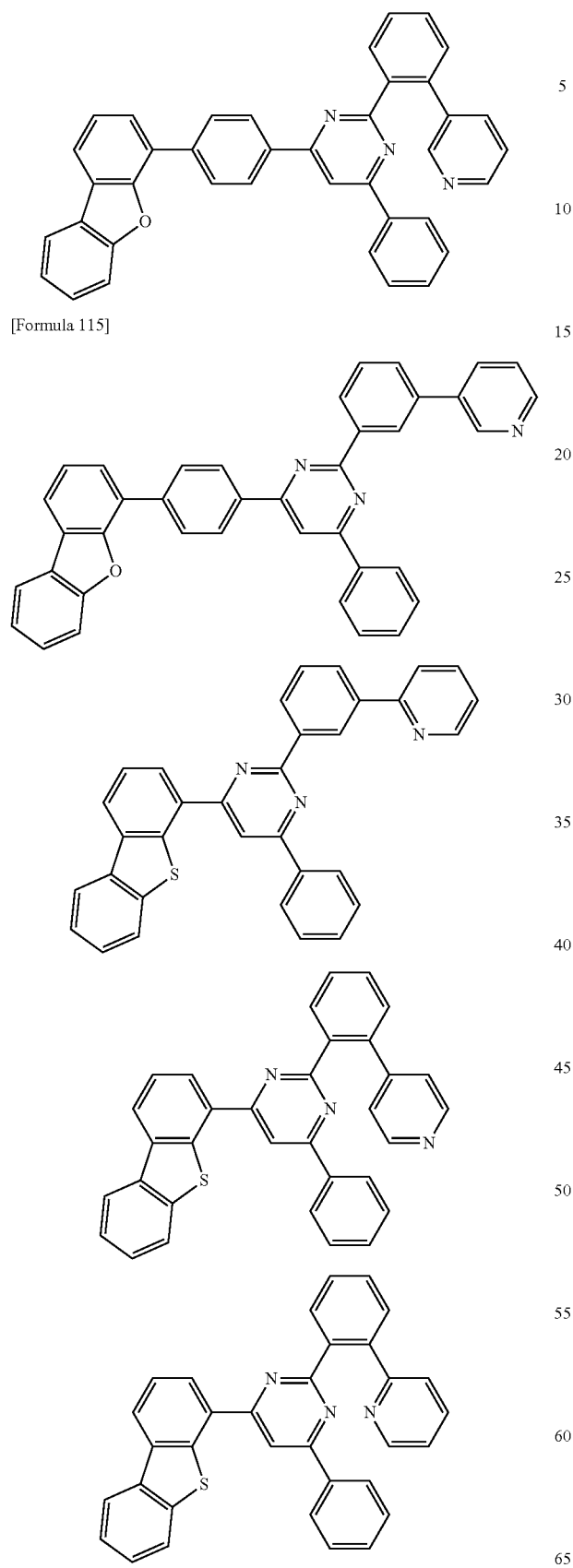
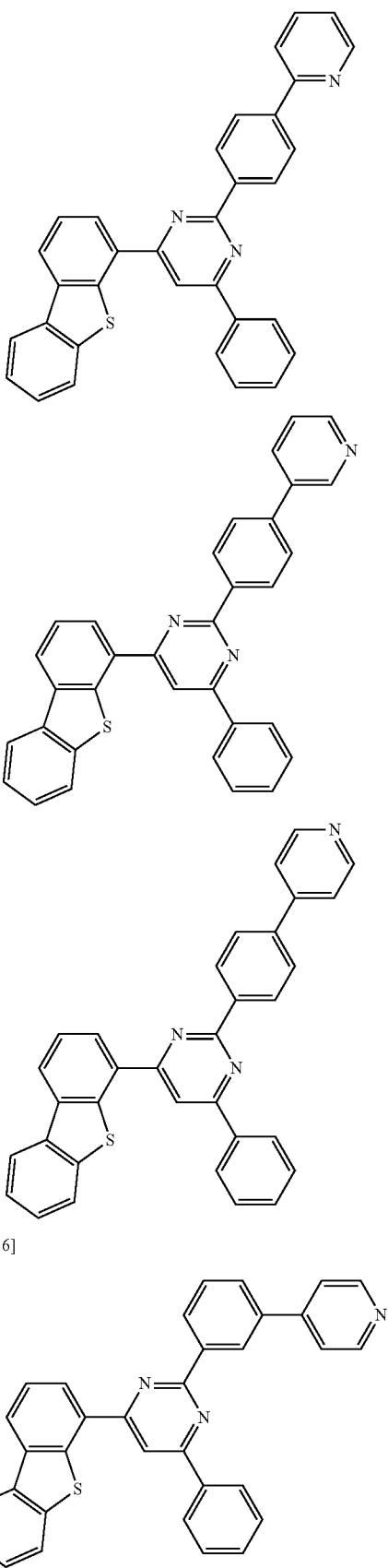
[Formula 116]

-continued
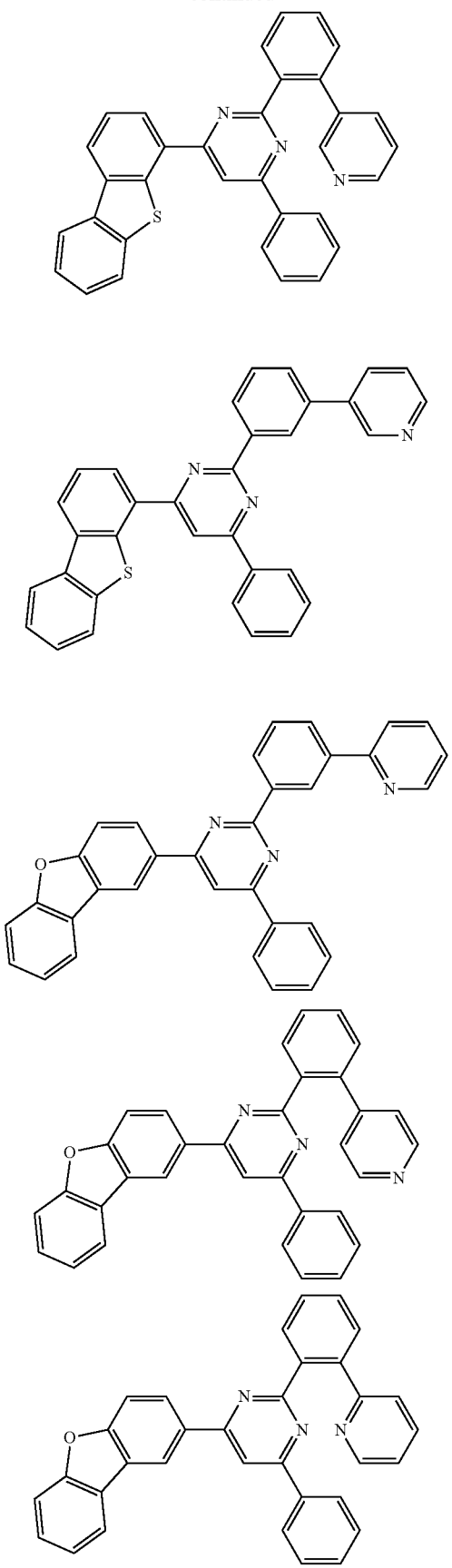
-continued
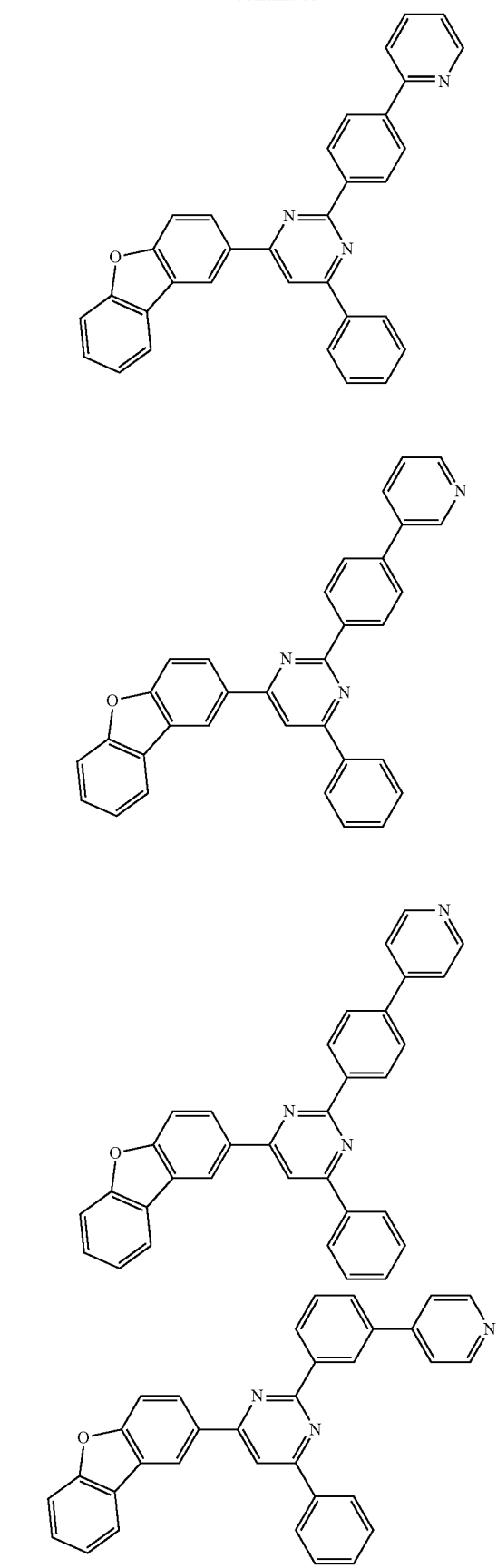

233
-continued
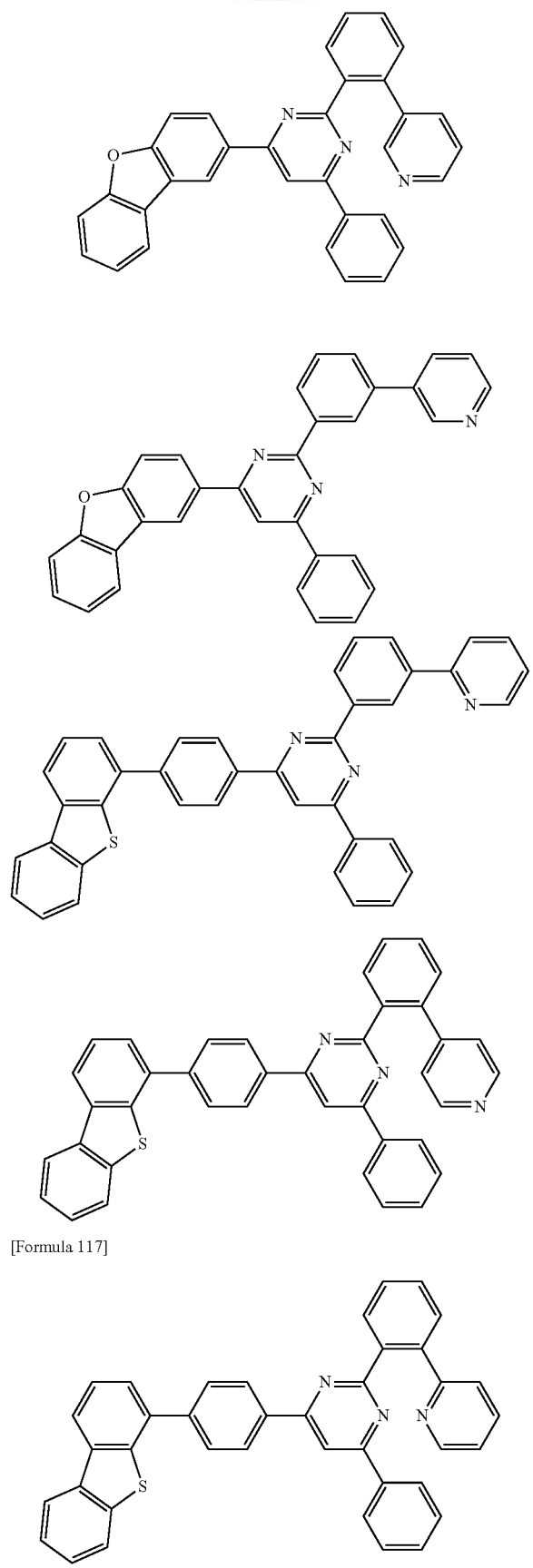
[Formula 117]
234
-continued
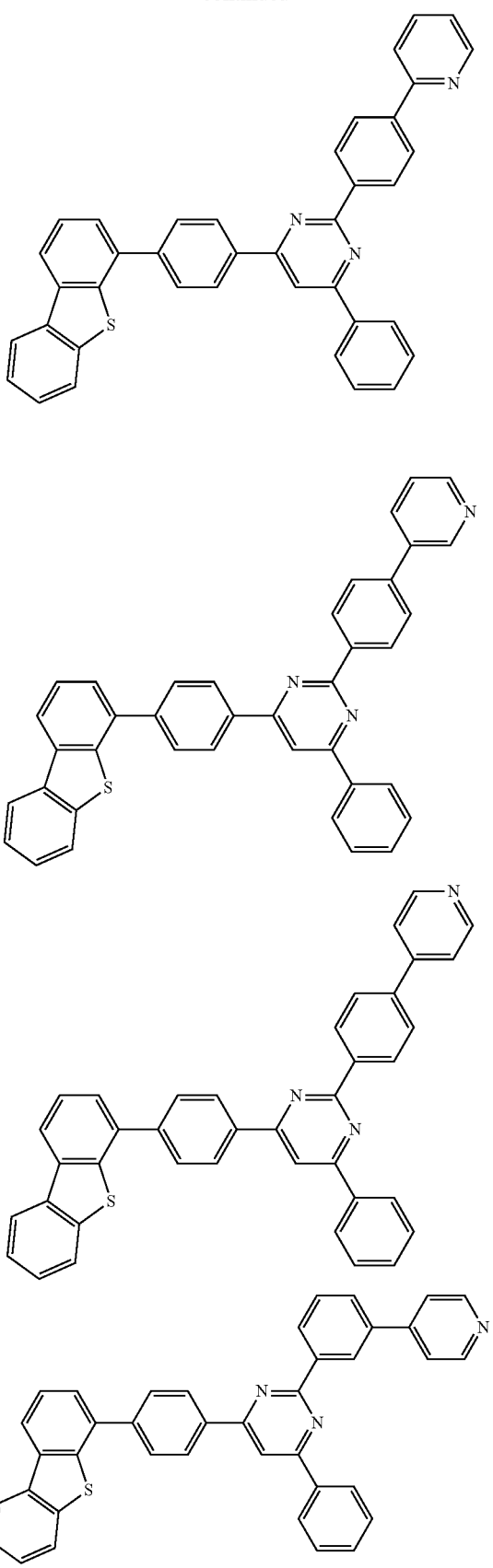

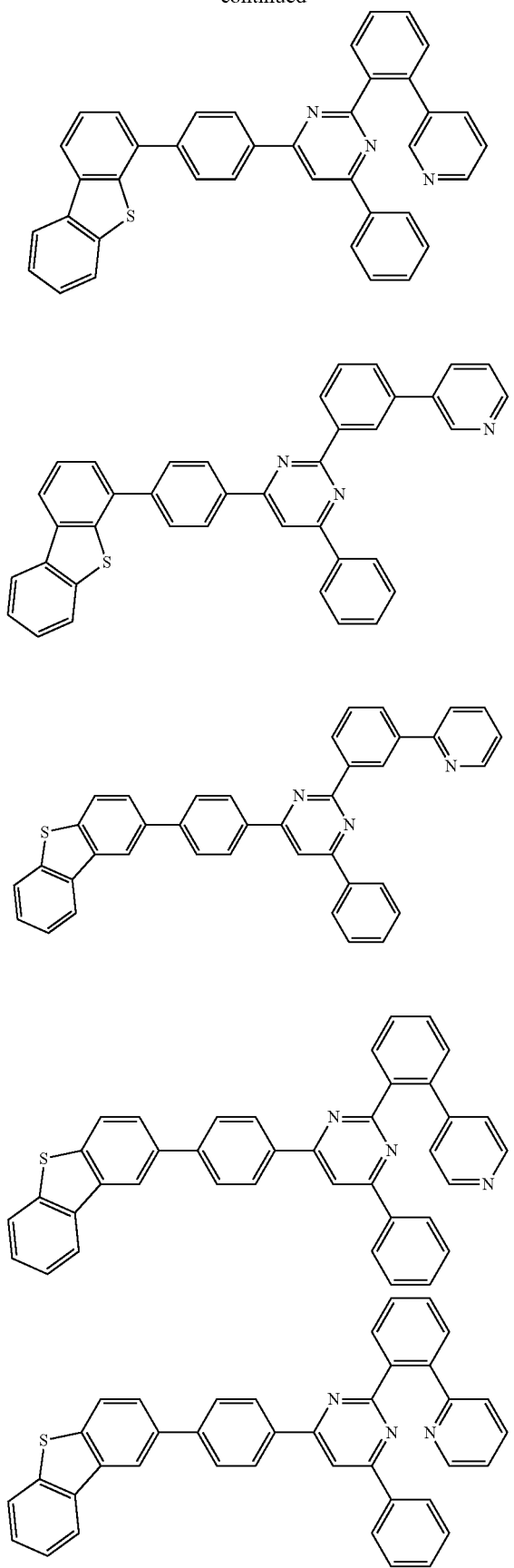
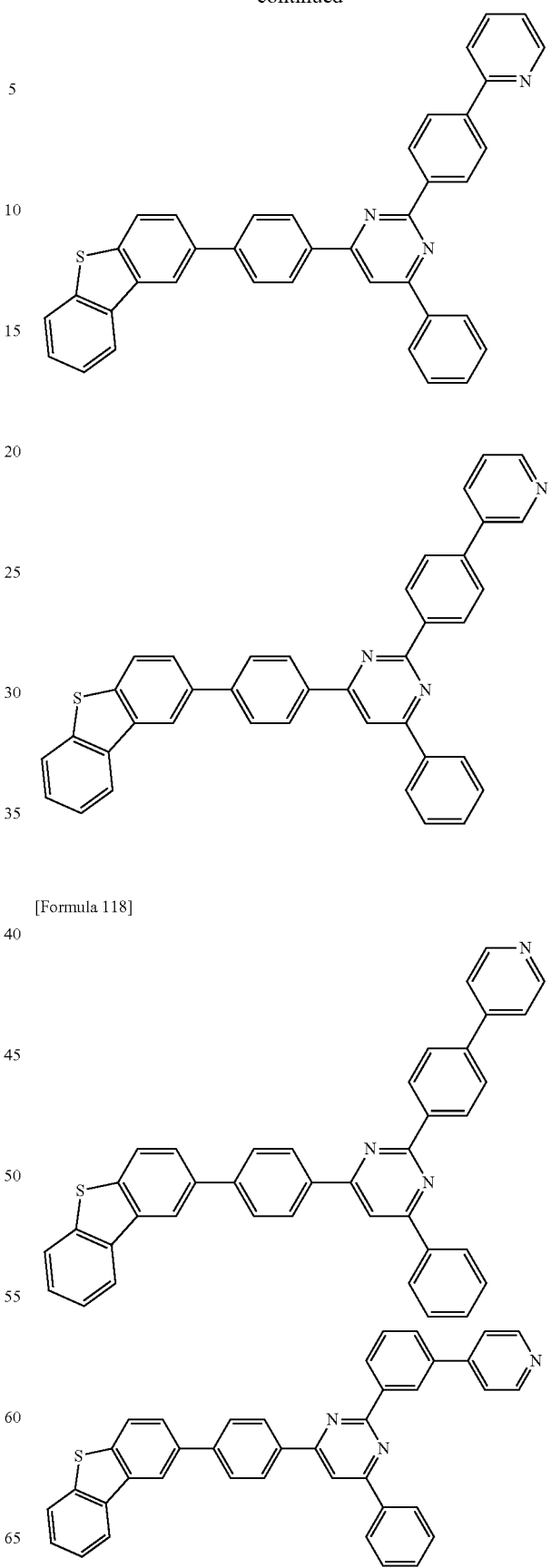
[Formula 118]

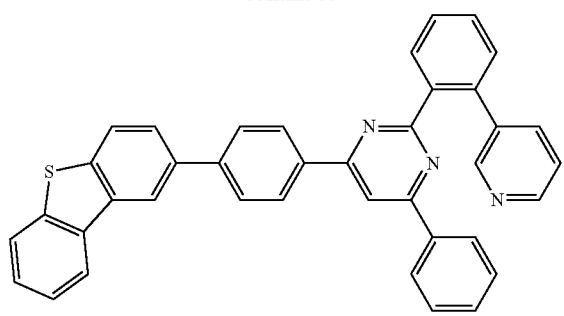
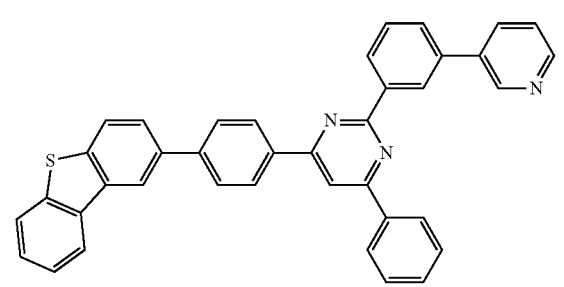
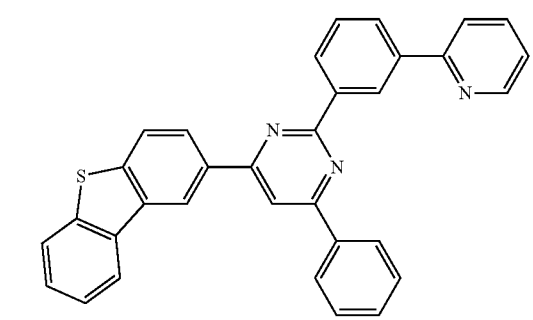
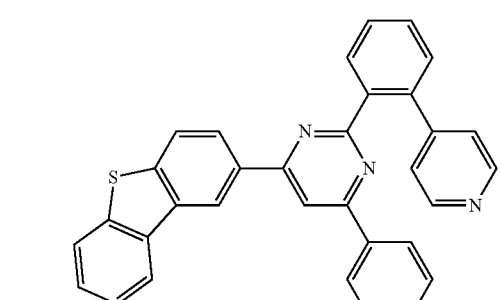
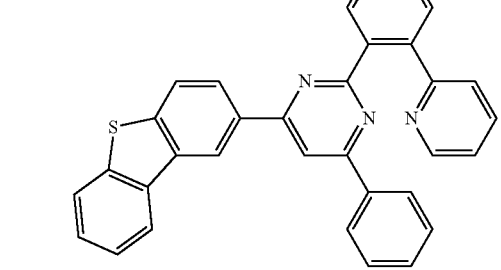
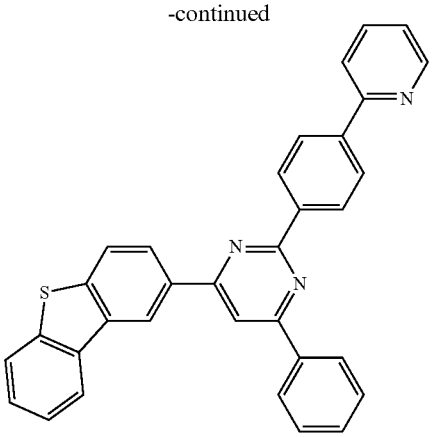
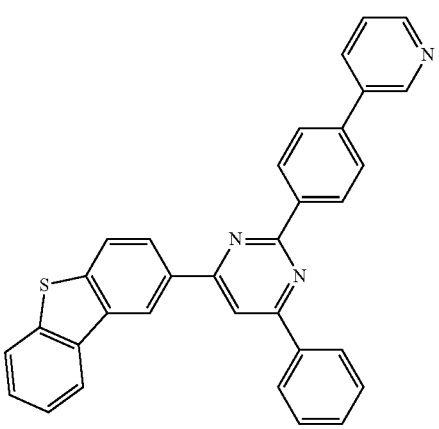
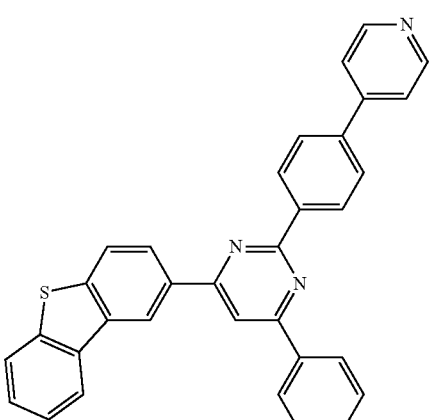
[Formula 119]
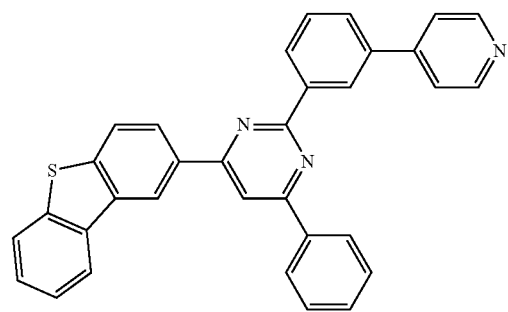

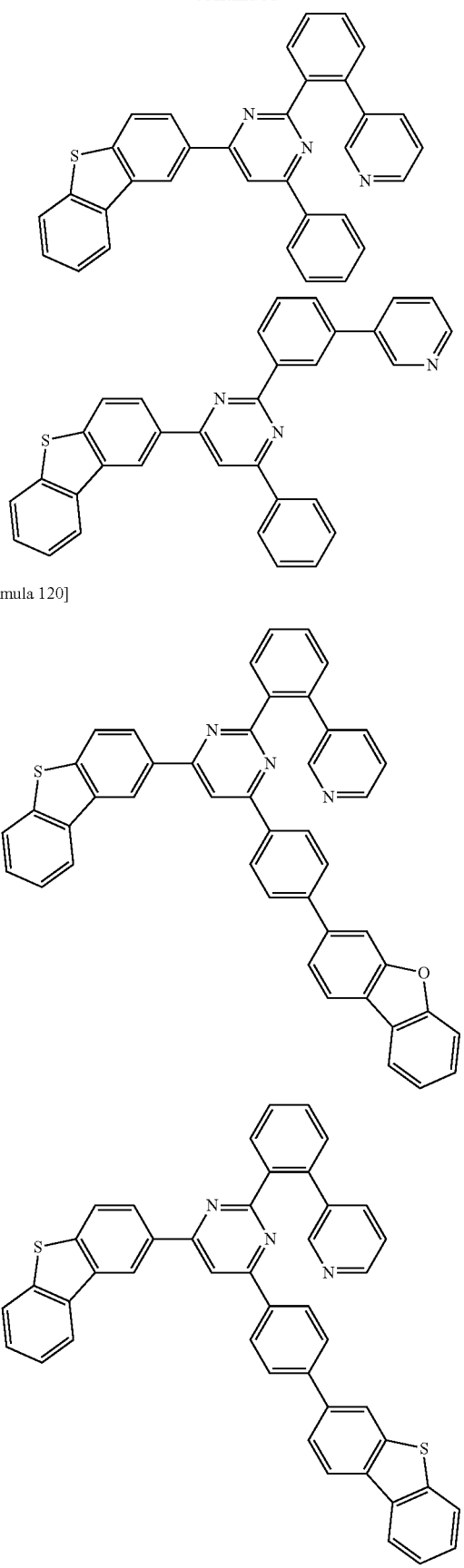

241
-continued
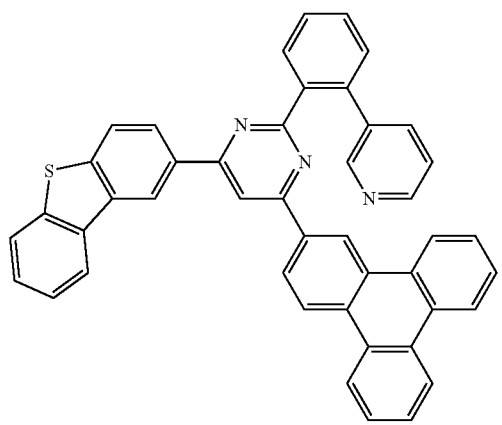
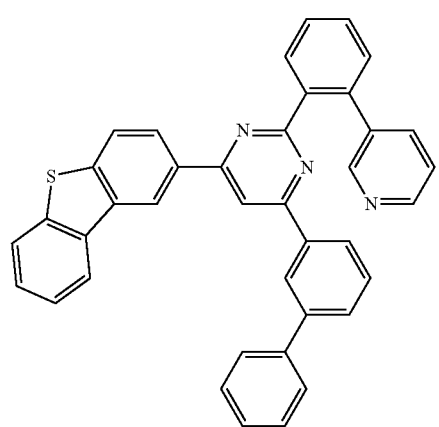
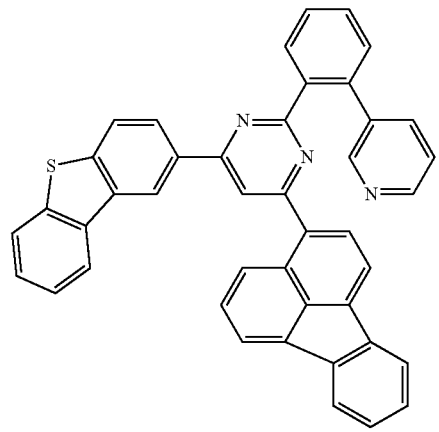
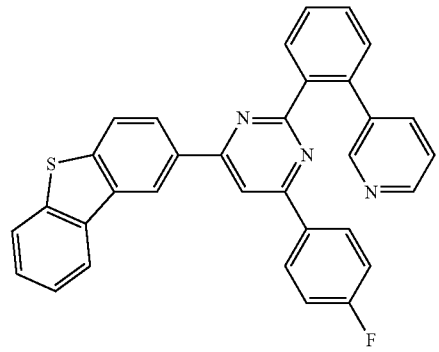
242
-continued
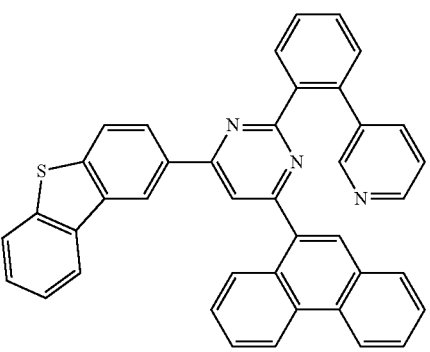
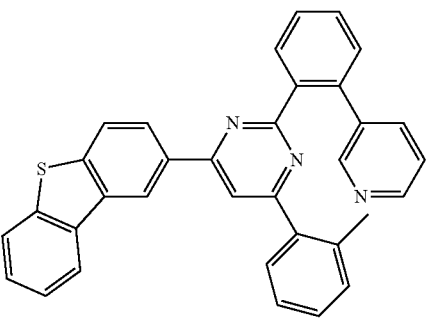
[Formula 121]
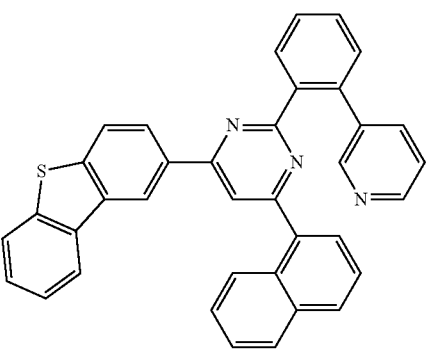

243
-continued
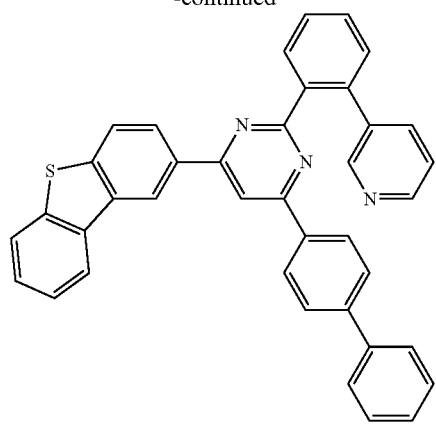
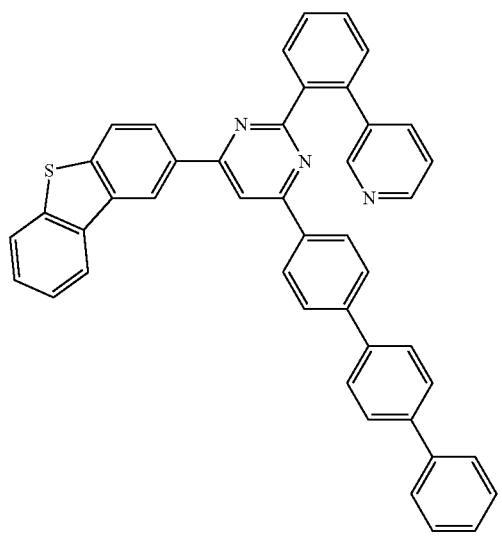
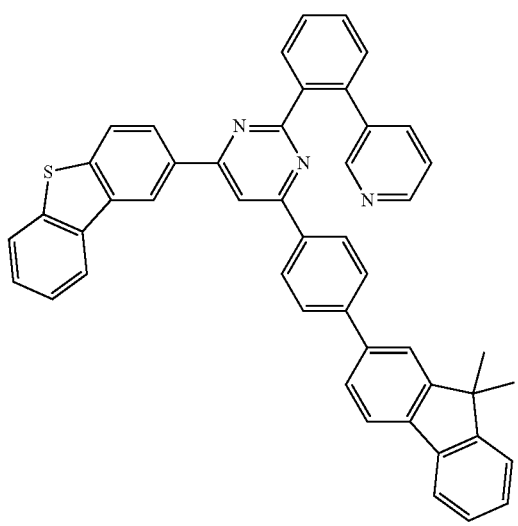
244
-continued
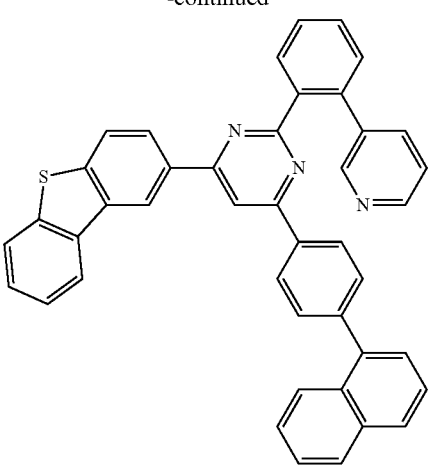
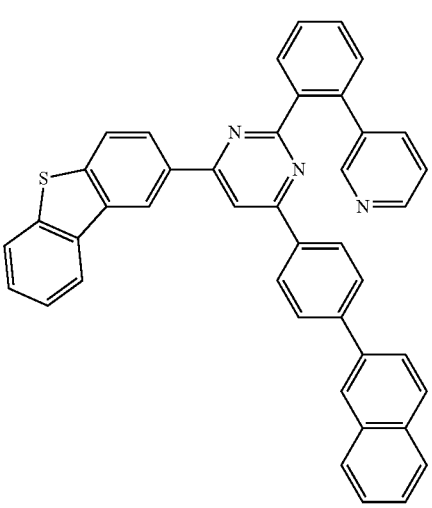
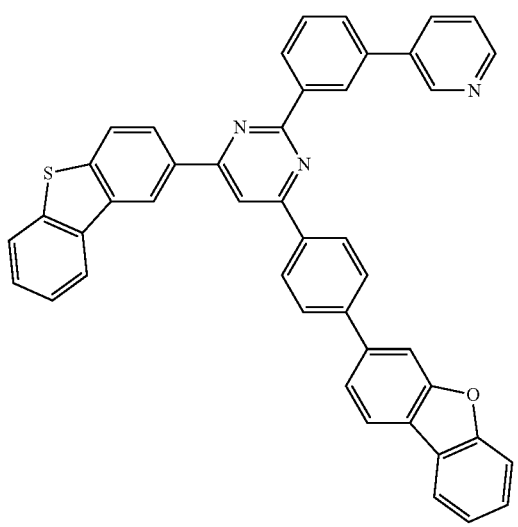

[Formula 122]
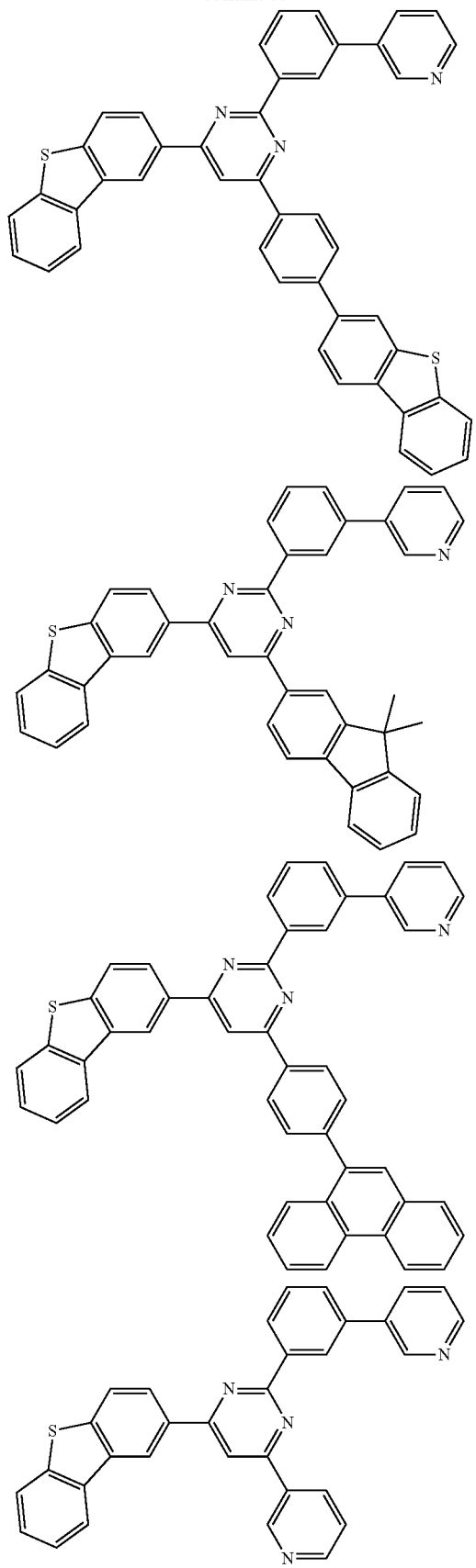
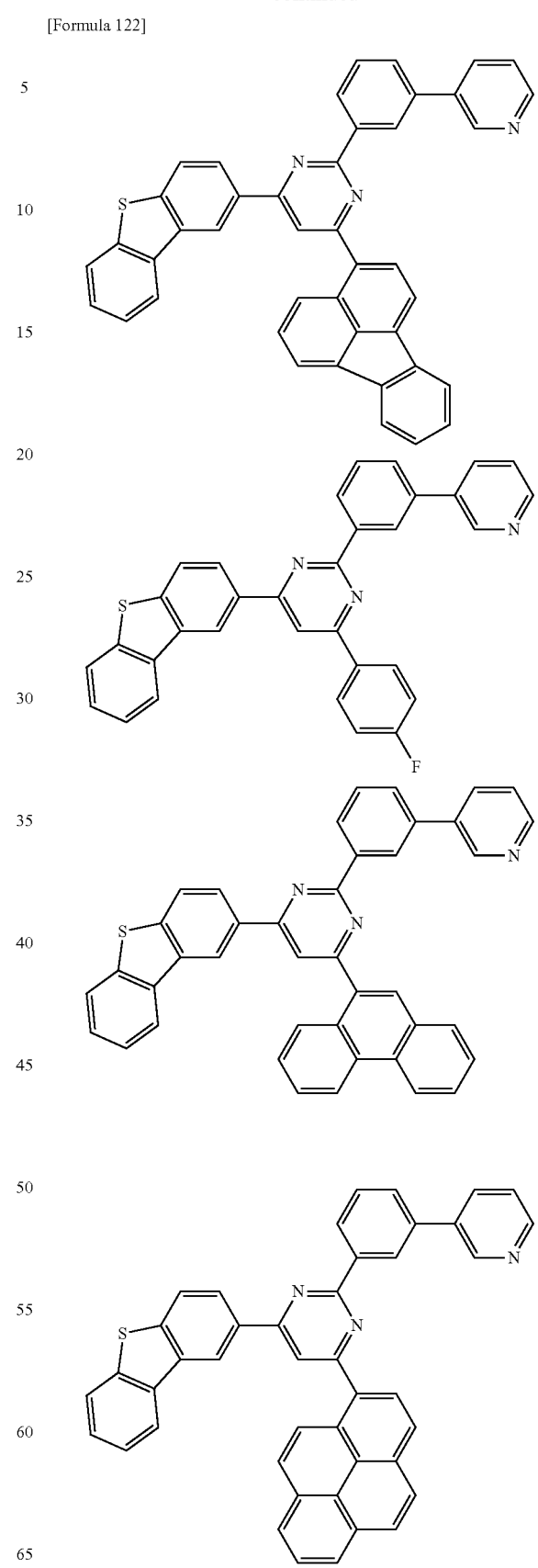

[Formula 123]
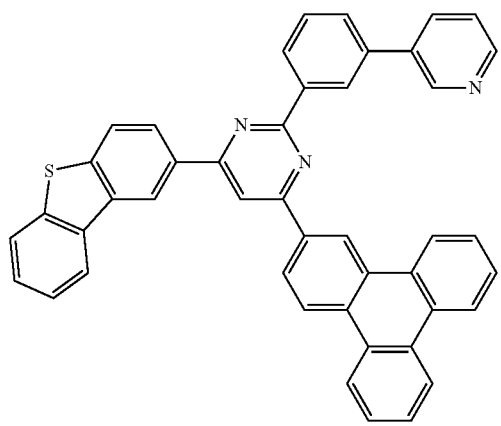
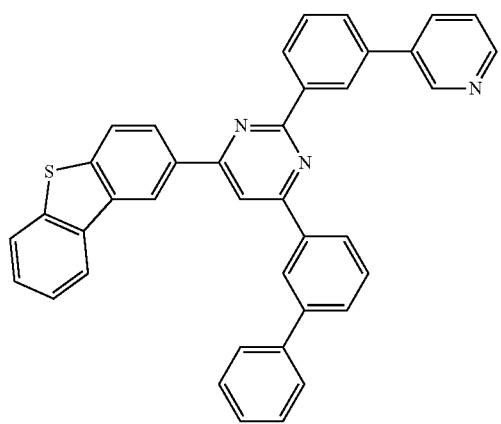
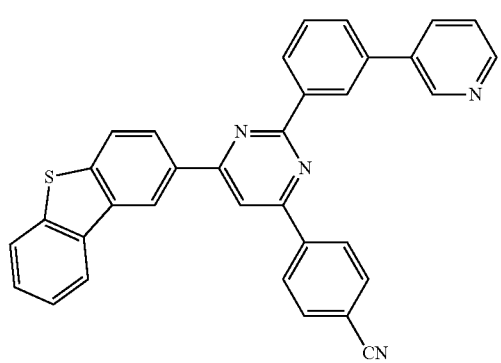
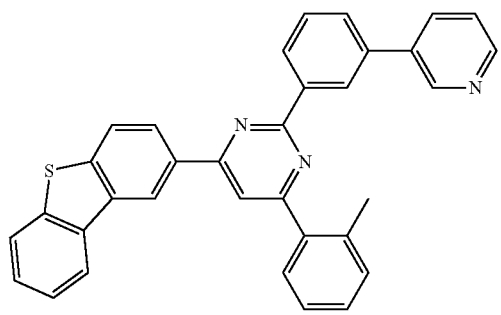
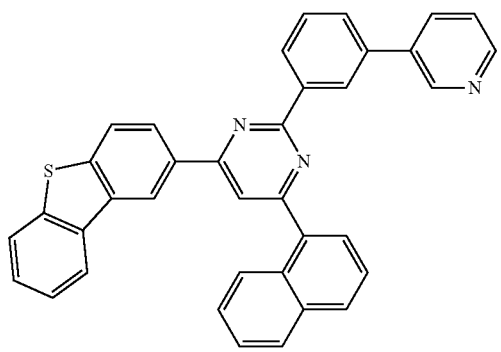
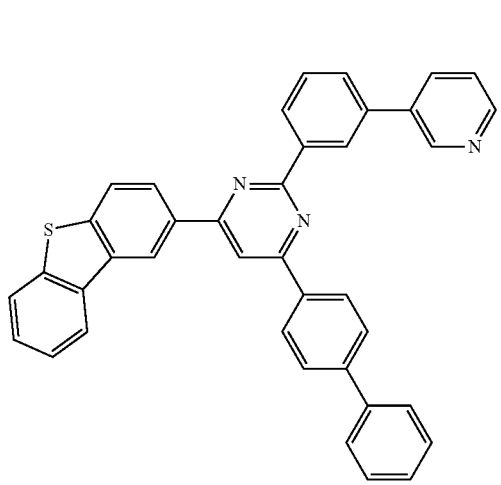
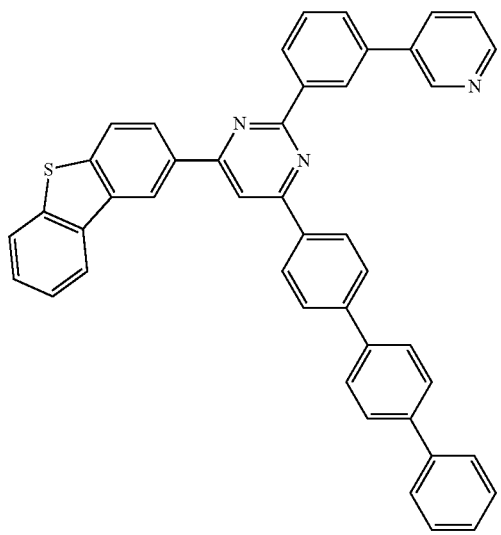

249
-continued
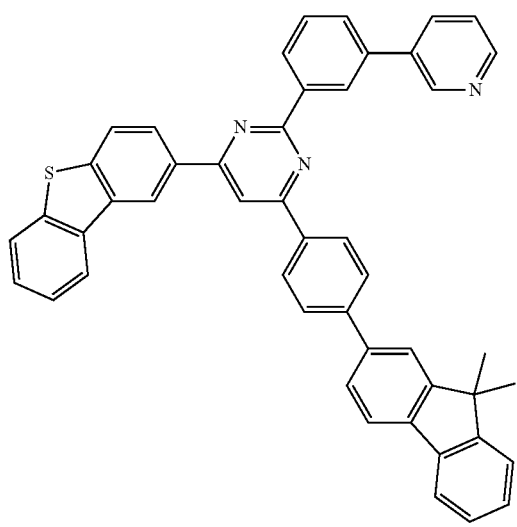
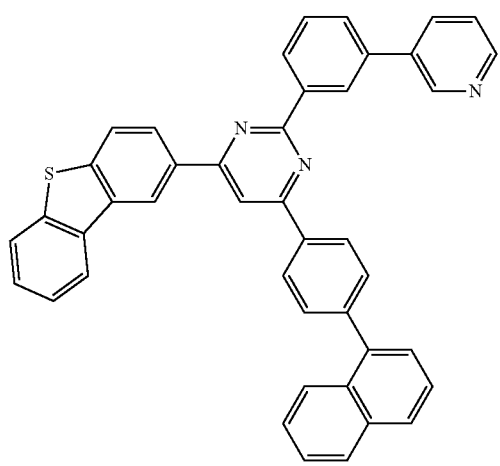
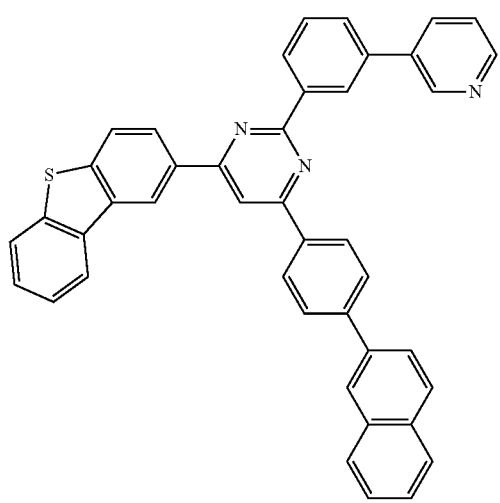
250
-continued
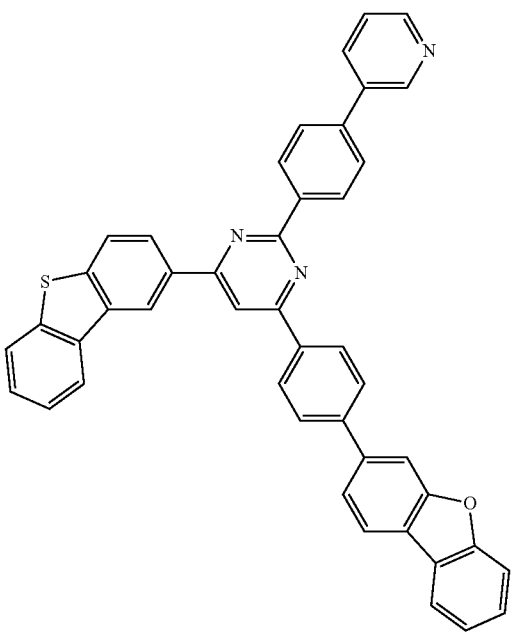
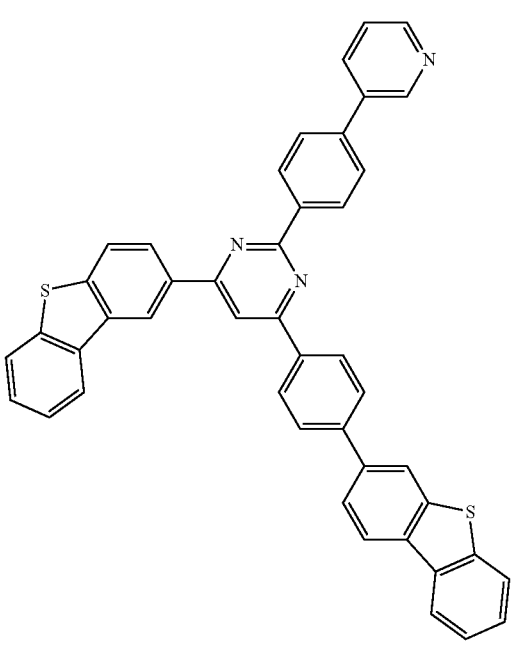

-continued
[Formula 124]
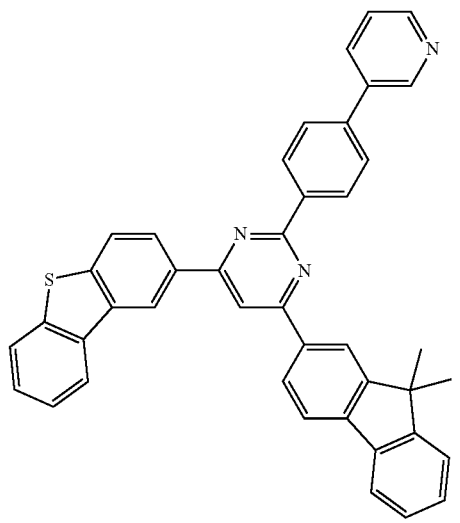
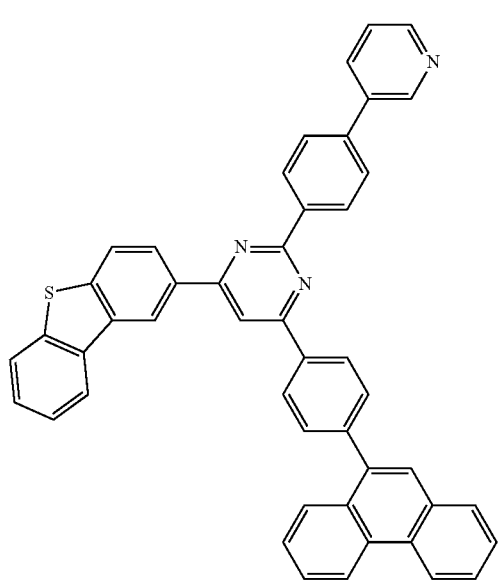
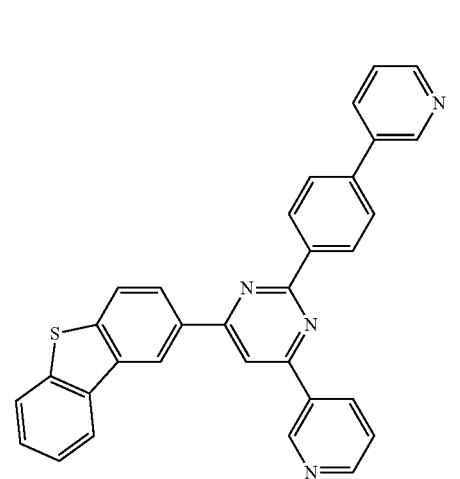 [SMILES: c1cncc(-c2ccc(-c3nc(-c4cccnc4)cc(-c4ccc5oc6ccccc6c5c4)n3)cc2)c1]
-continued
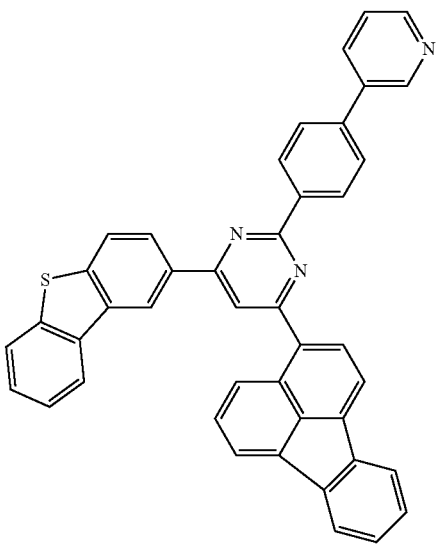
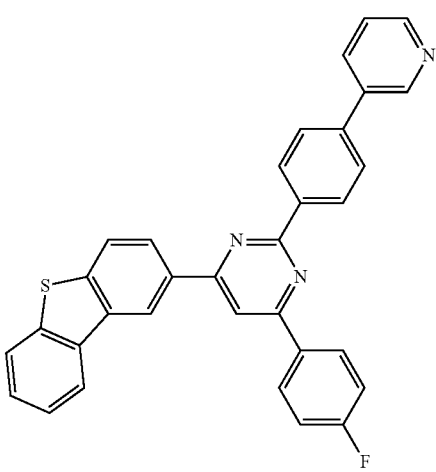
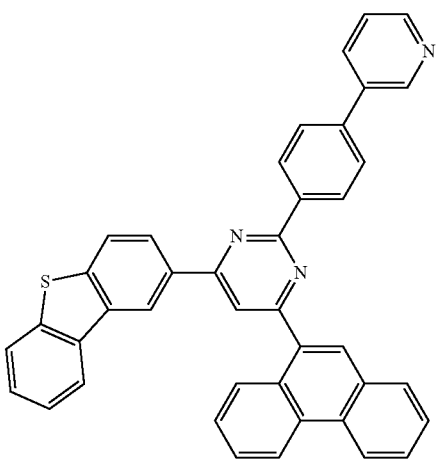

253
-continued
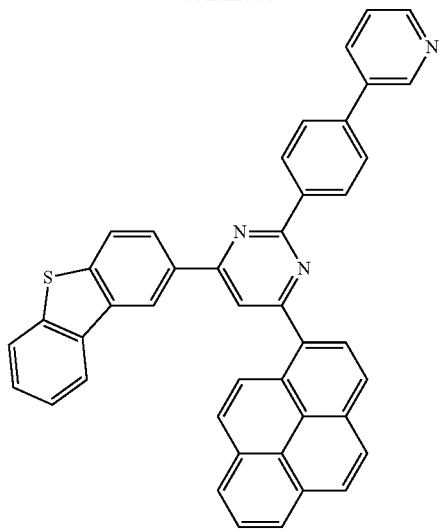
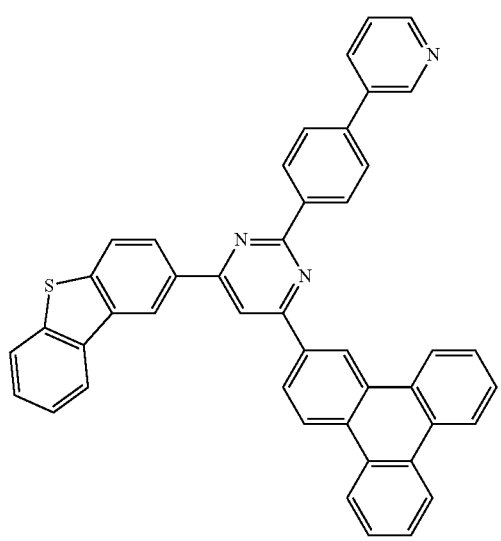
[Formula 125]
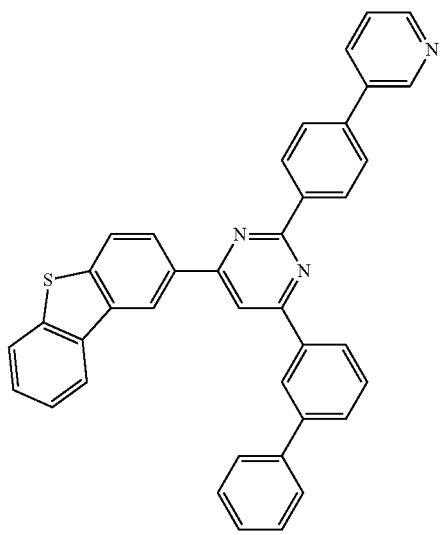
254
-continued
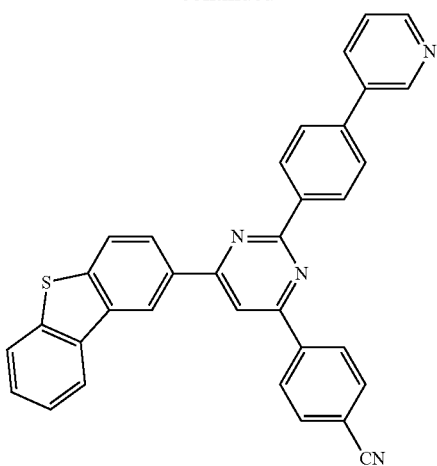
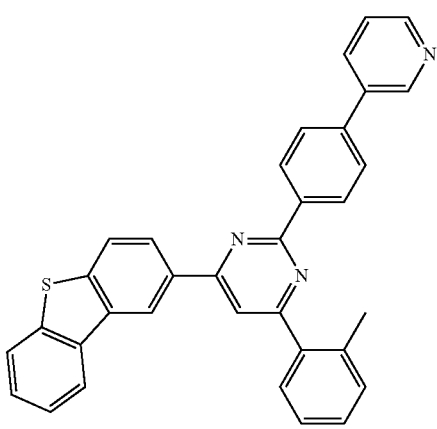
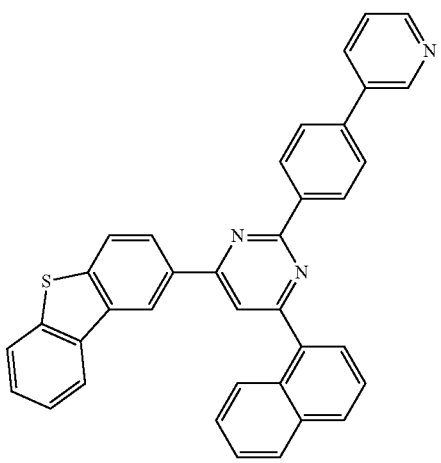

255
-continued
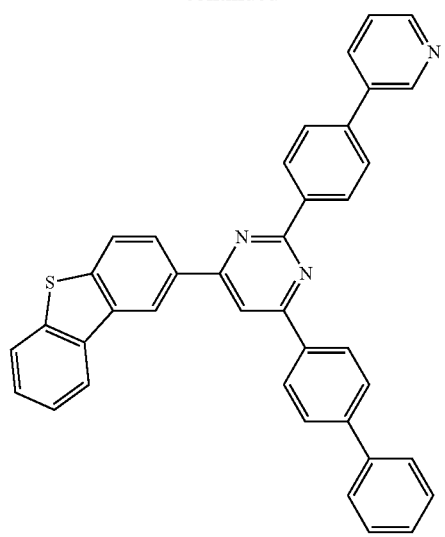
256
-continued
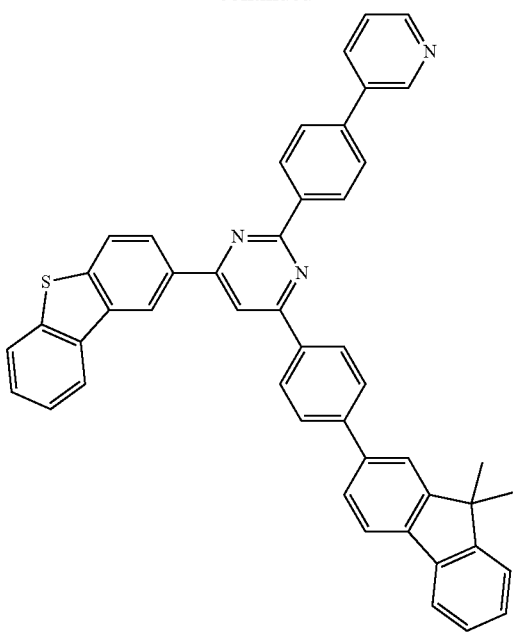
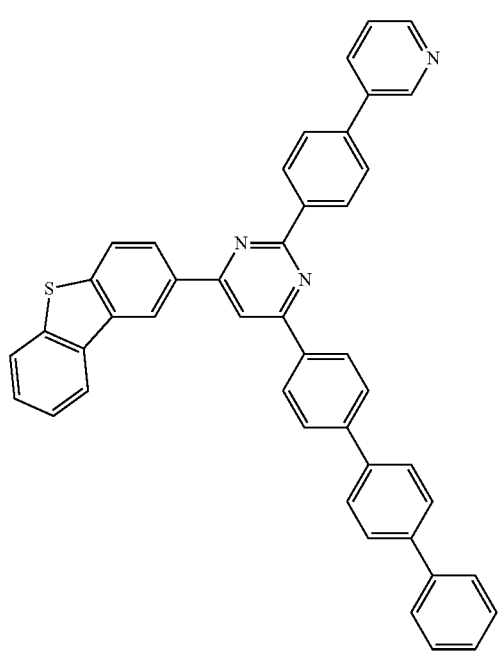
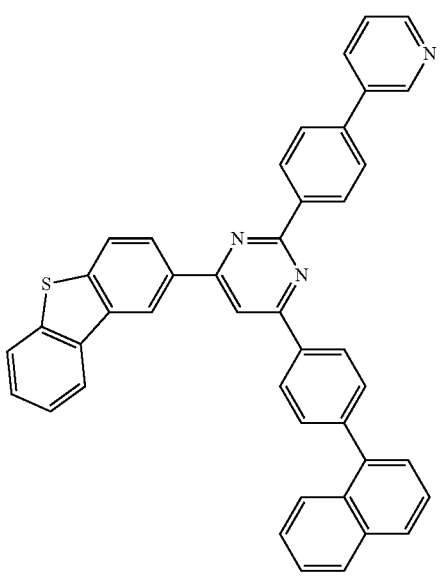

257
-continued
[Formula 126]
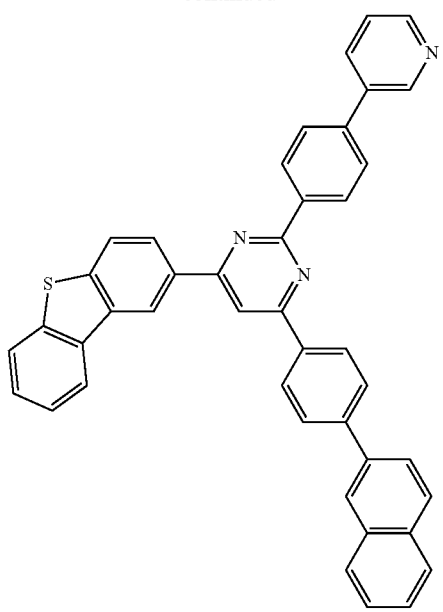
258
-continued
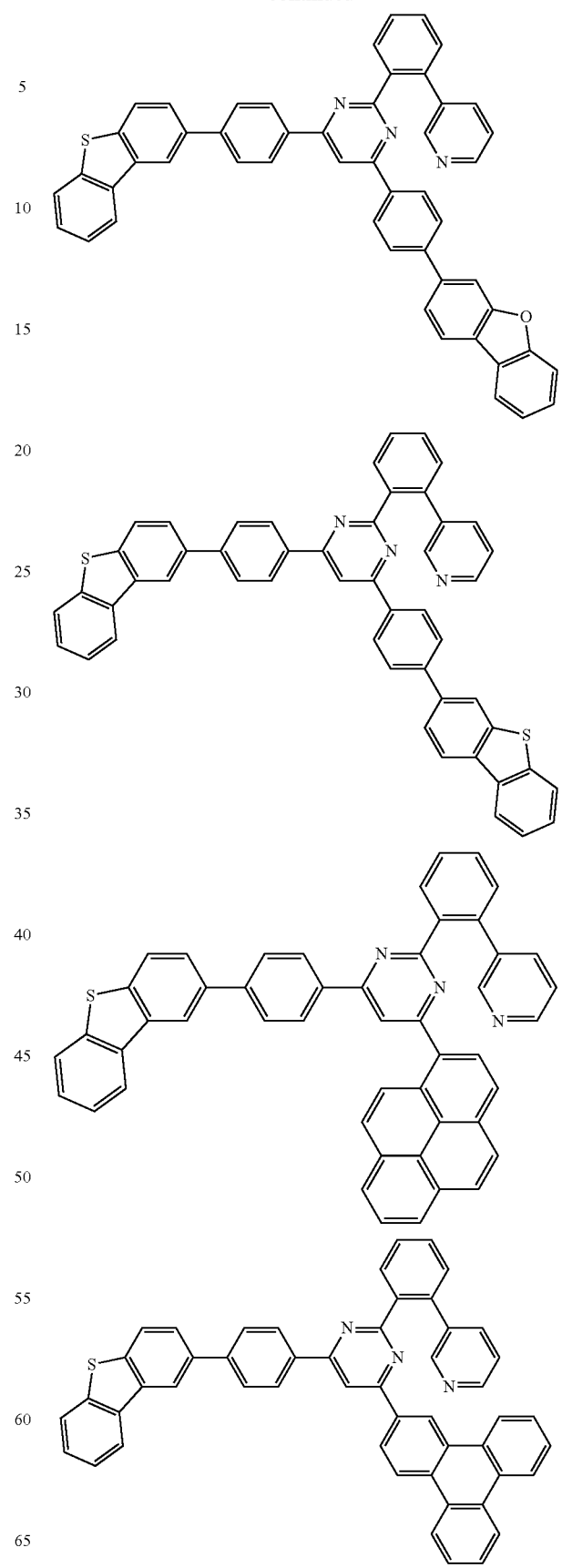

259
-continued
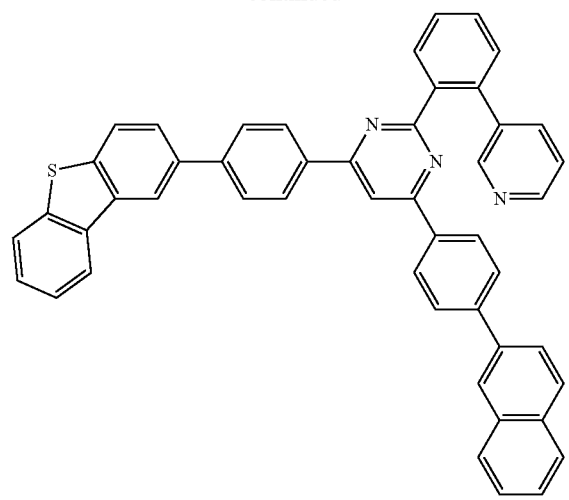
260
-continued
[Formula 127]
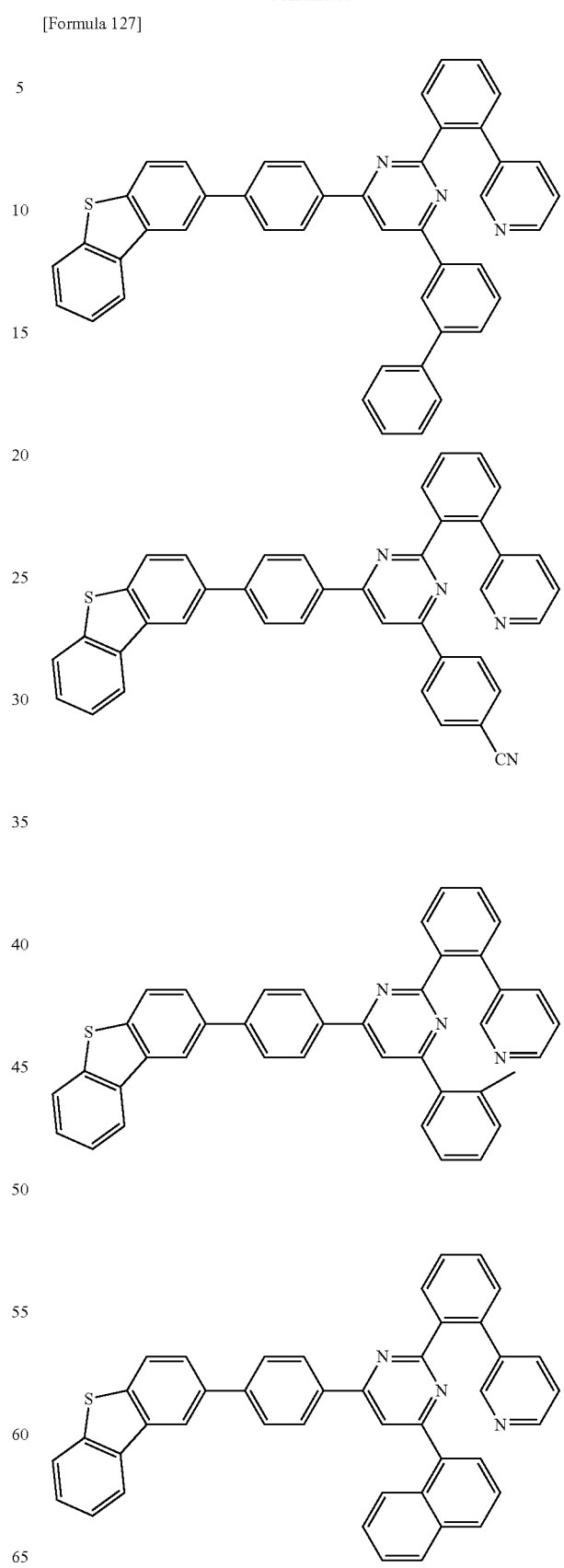

261
-continued
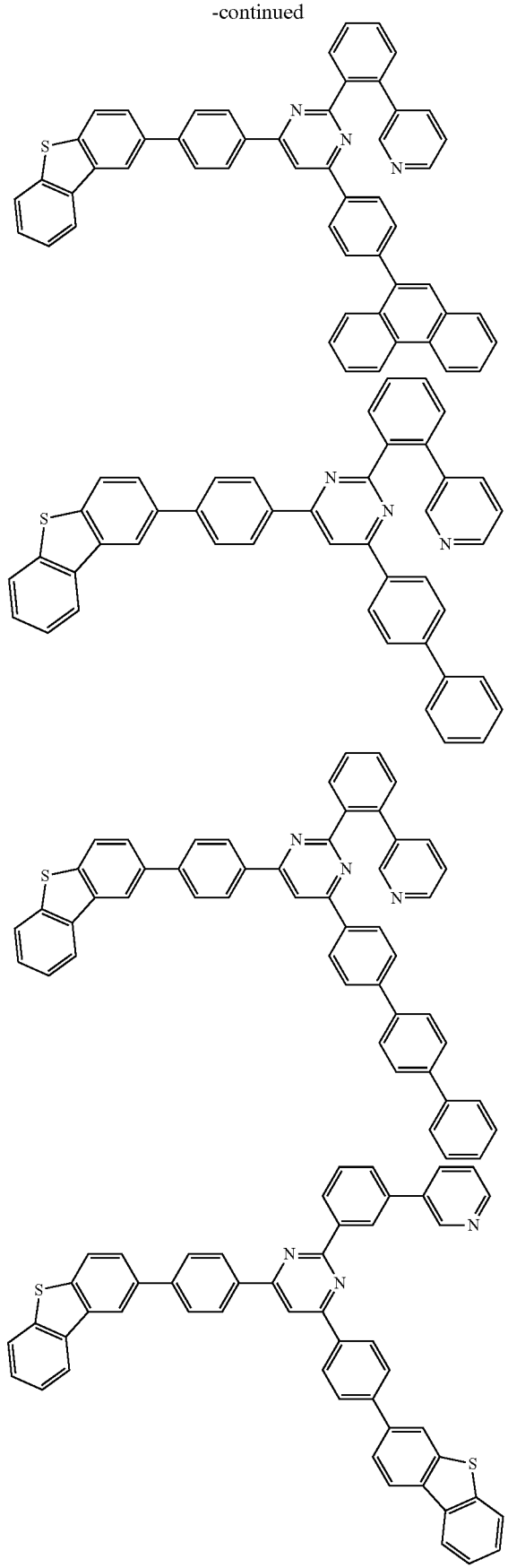
[Formula 128]
262
-continued
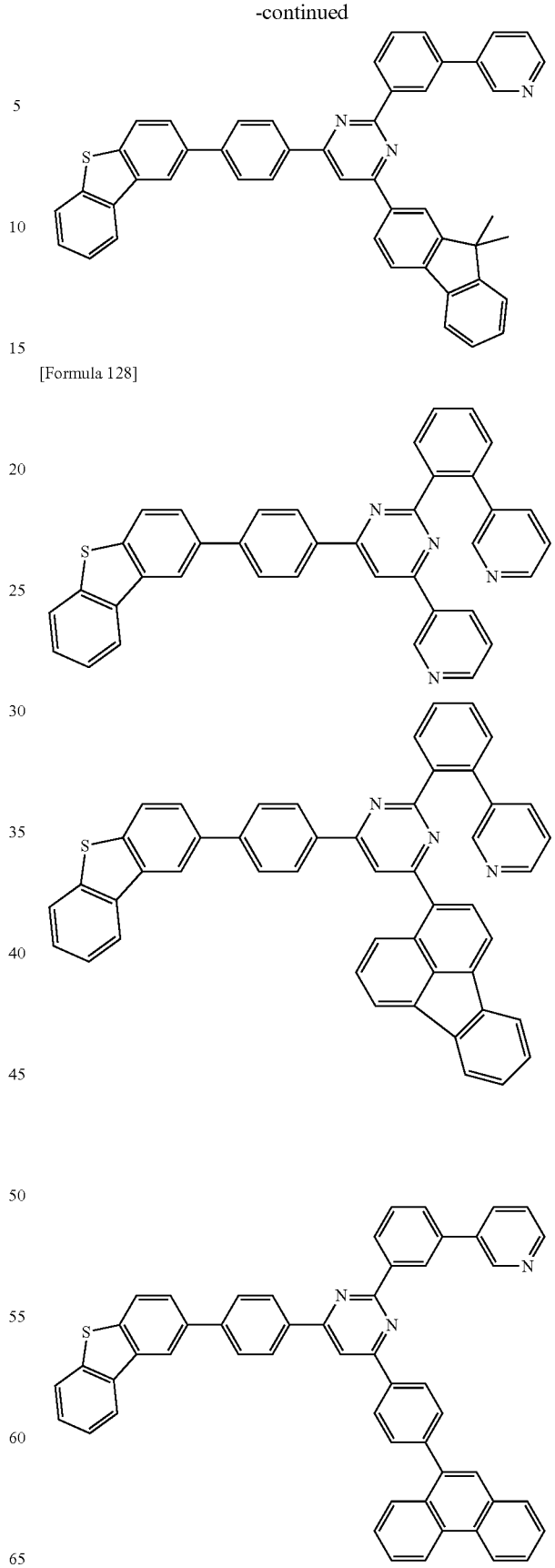

263
-continued
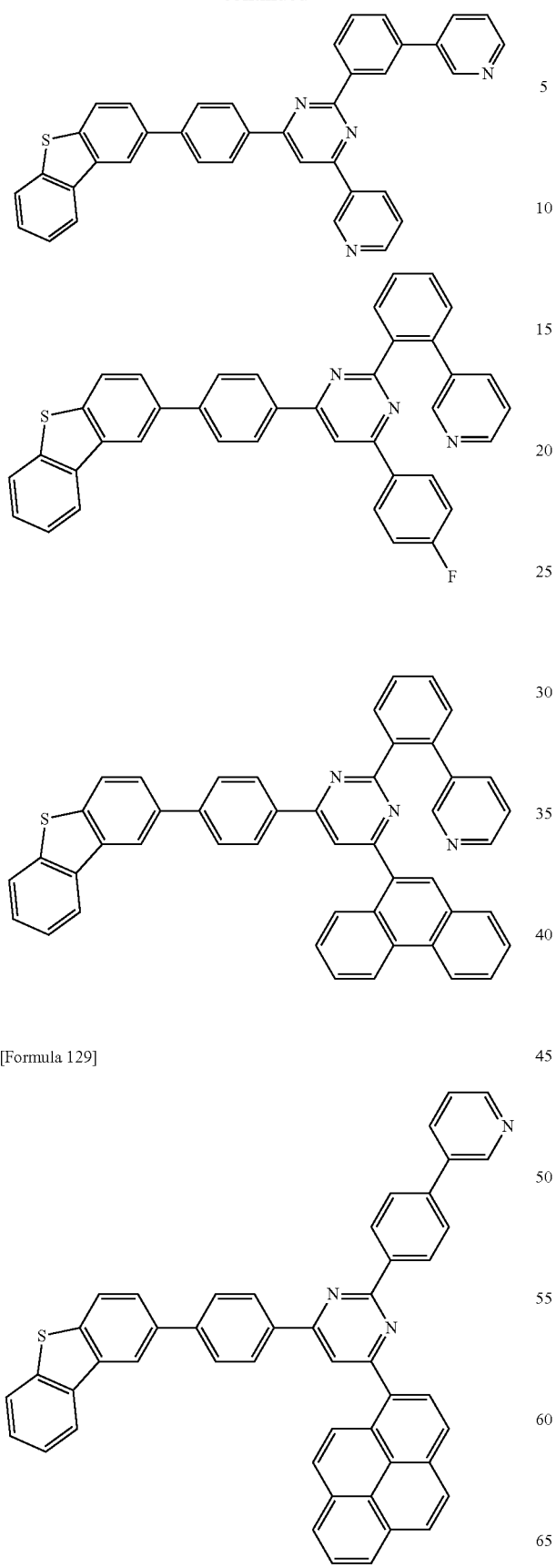
[Formula 129]
264
-continued
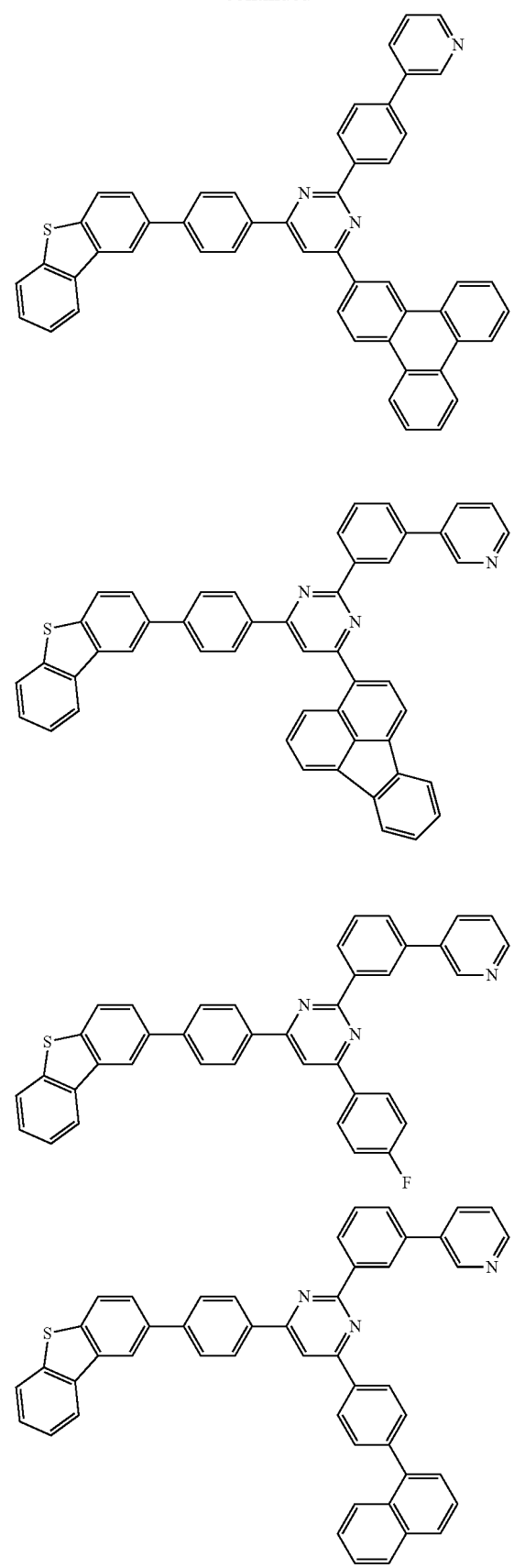

265
-continued
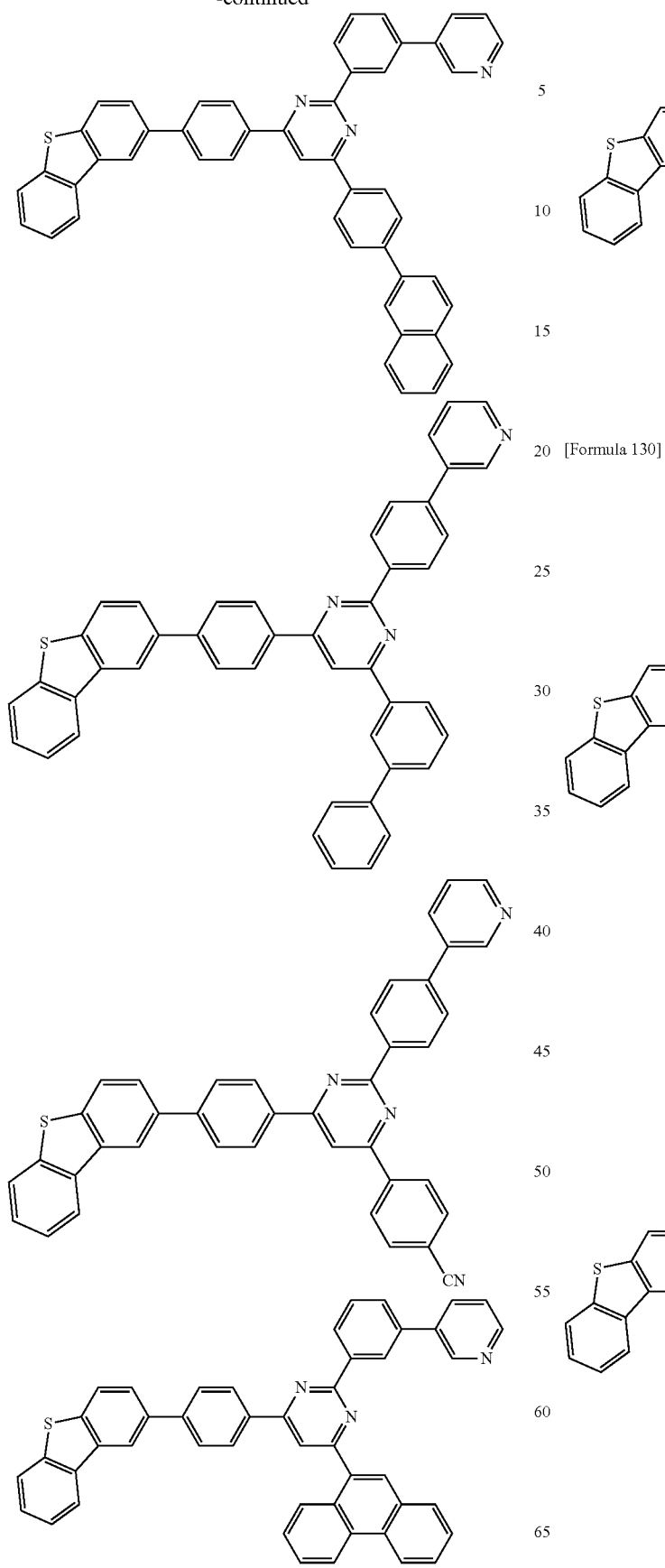
266
-continued
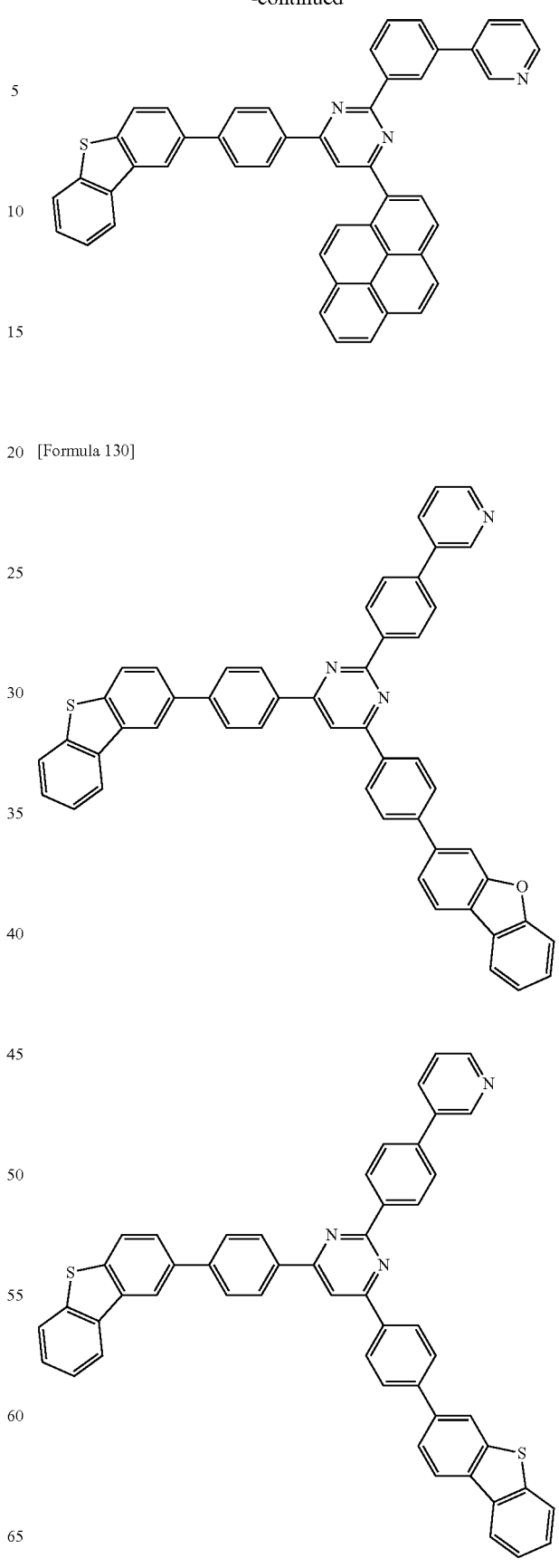
[Formula 130]

267
-continued
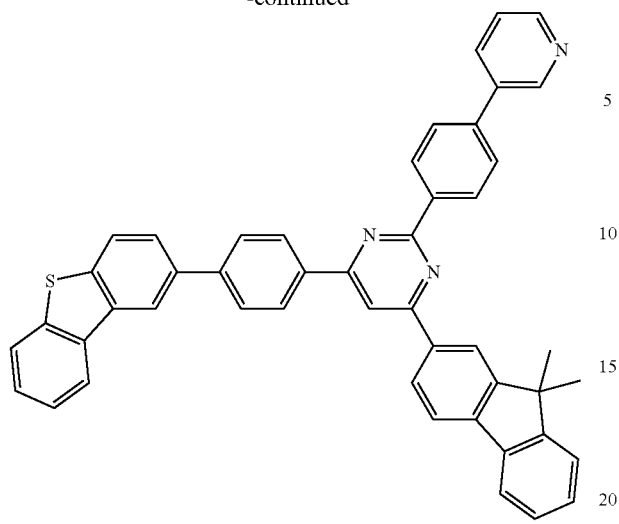
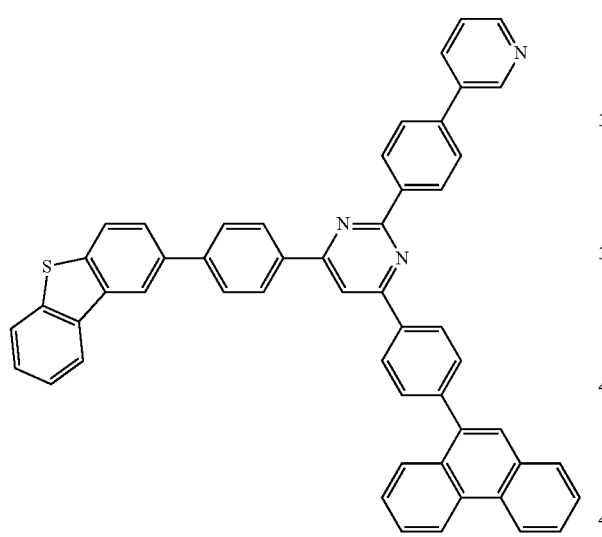
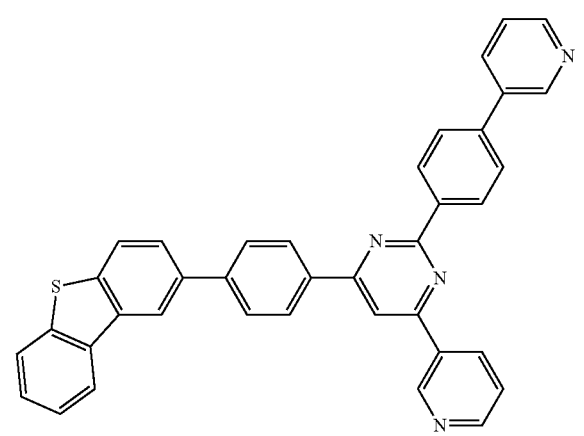
268
-continued
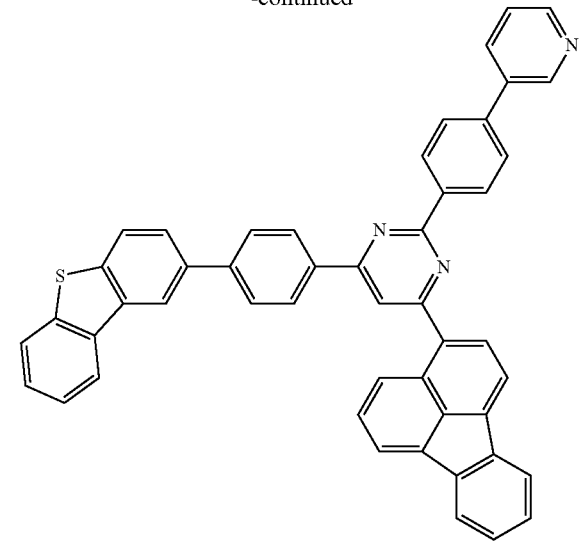
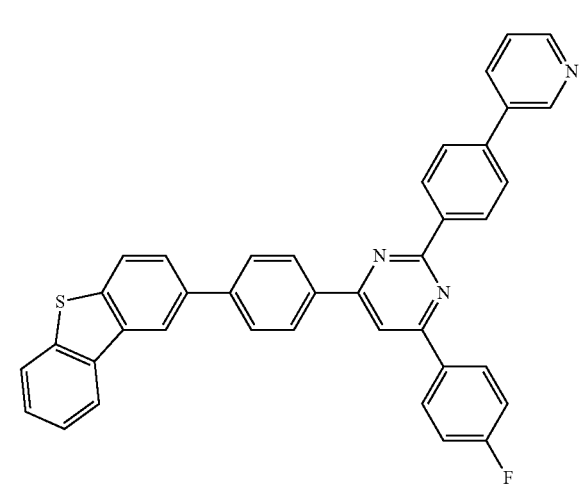
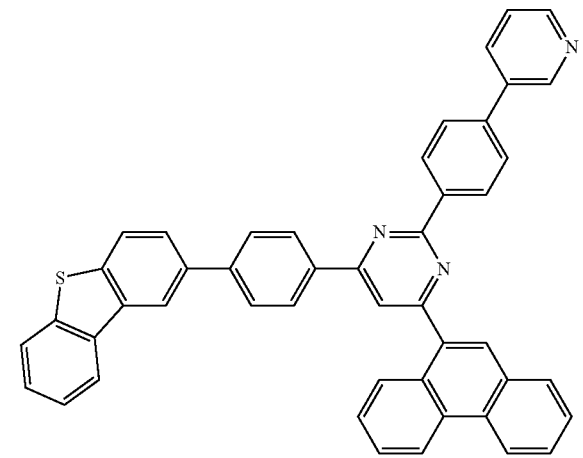

[Formula 131]
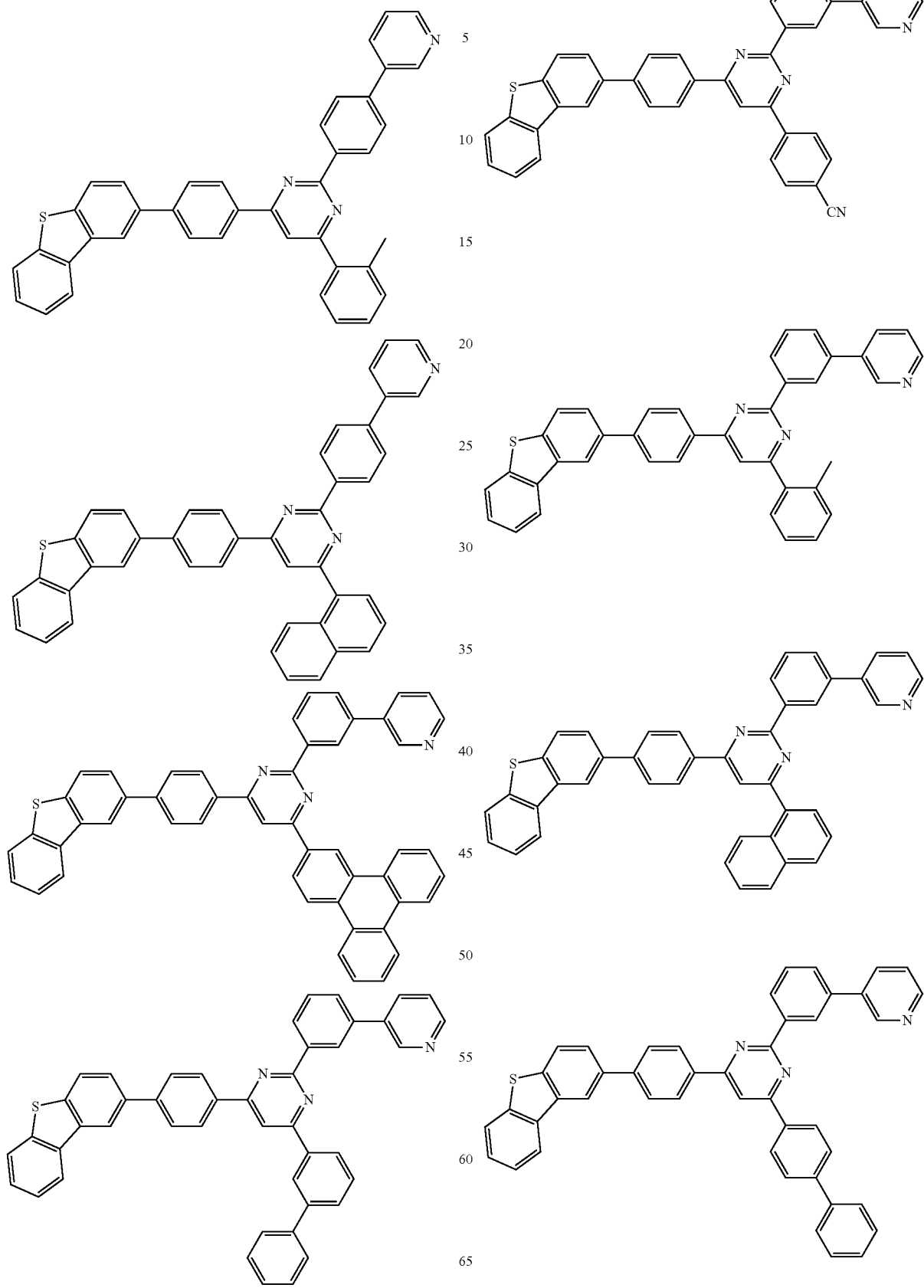

[Formula 132]
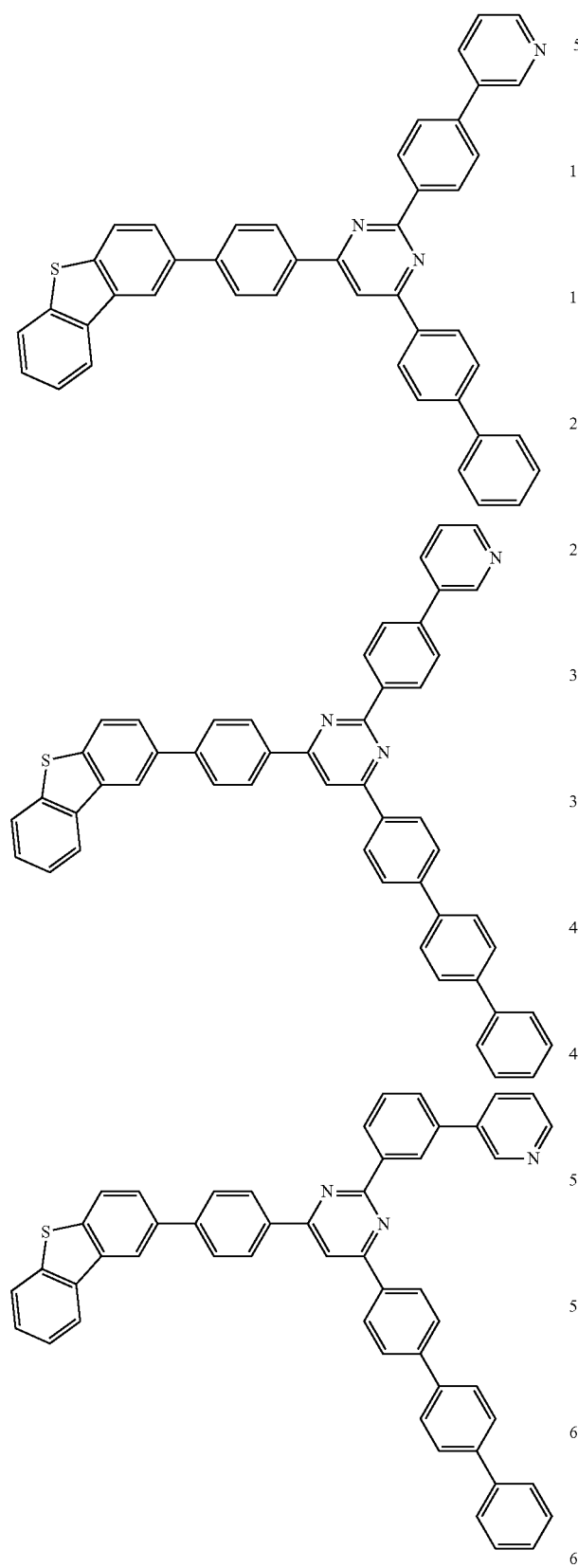
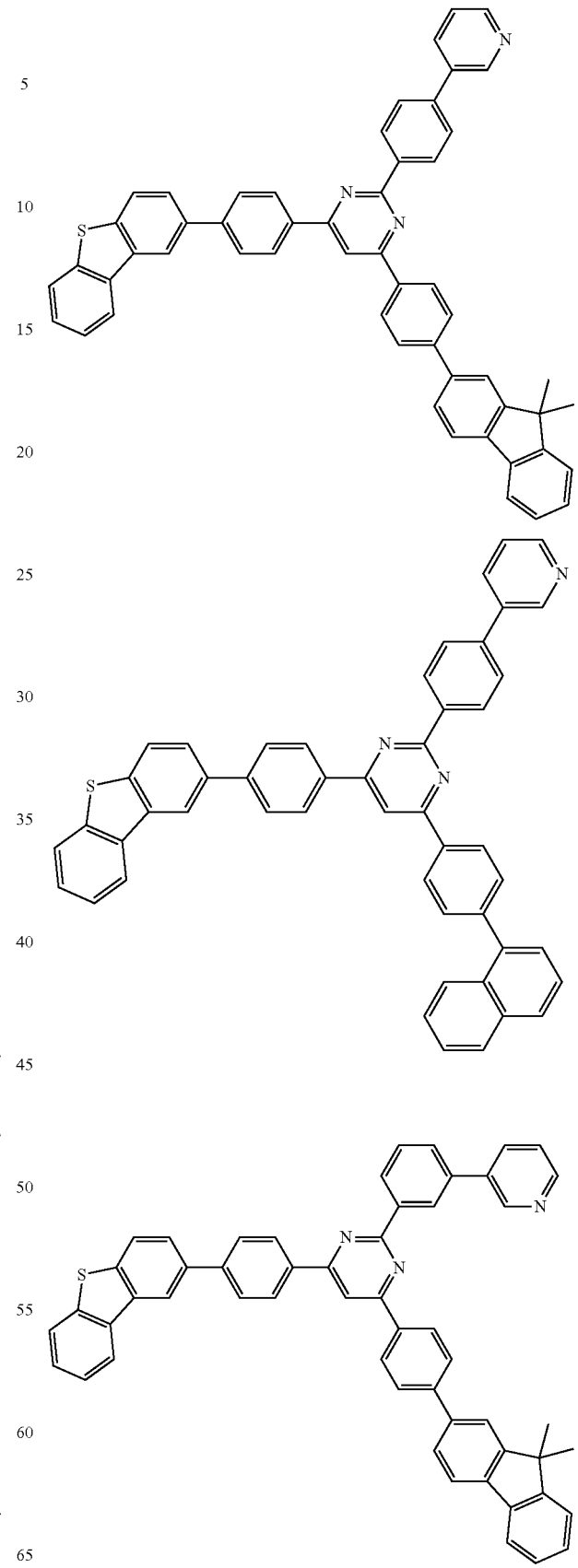

273
-continued
[Formula 133]
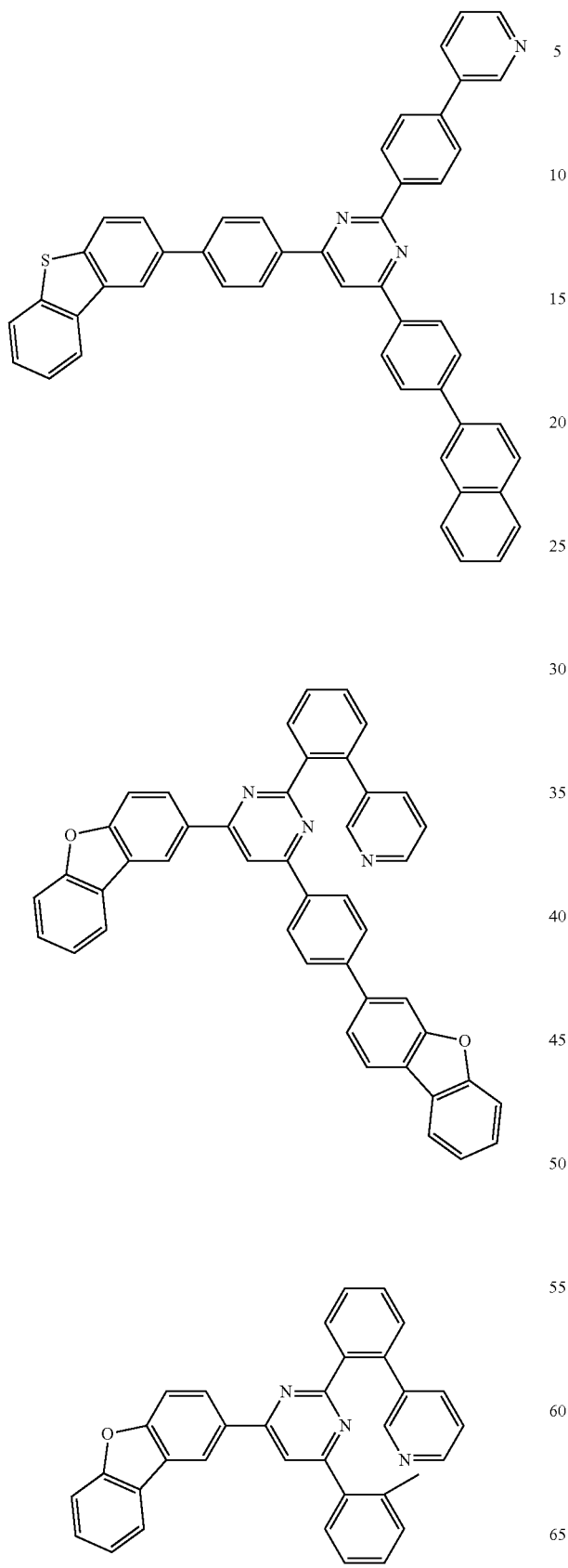
274
-continued
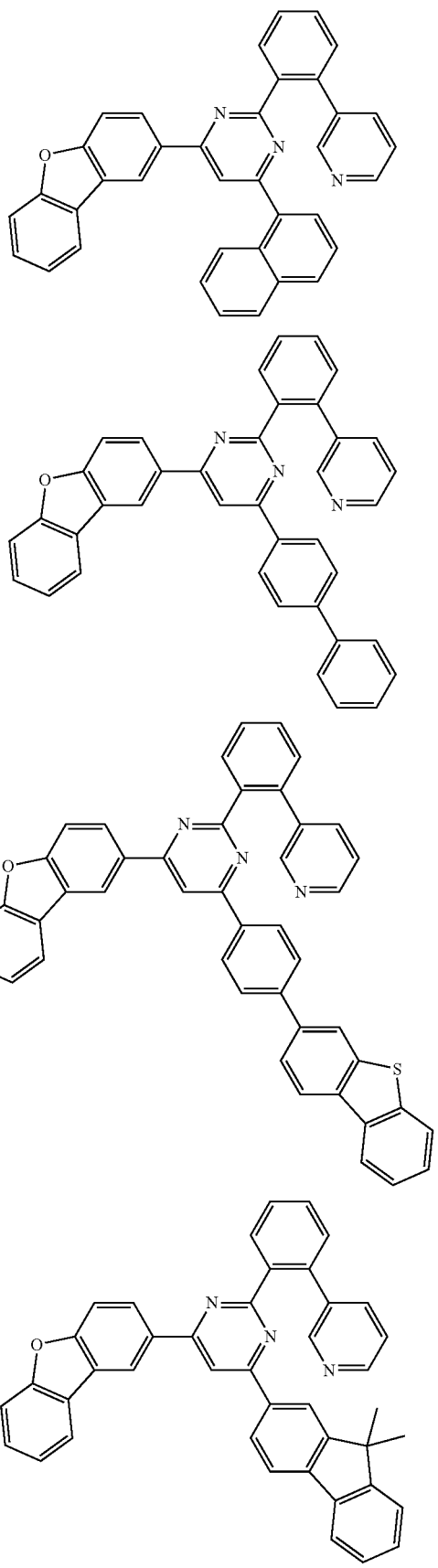

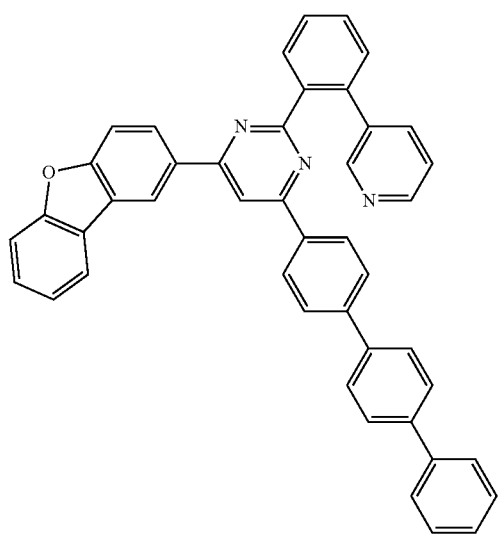
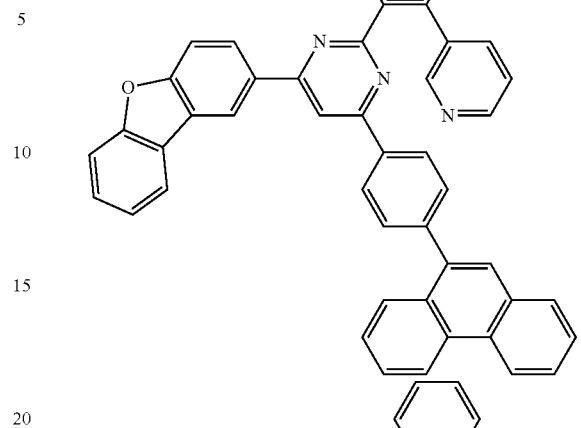
[Formula 134]
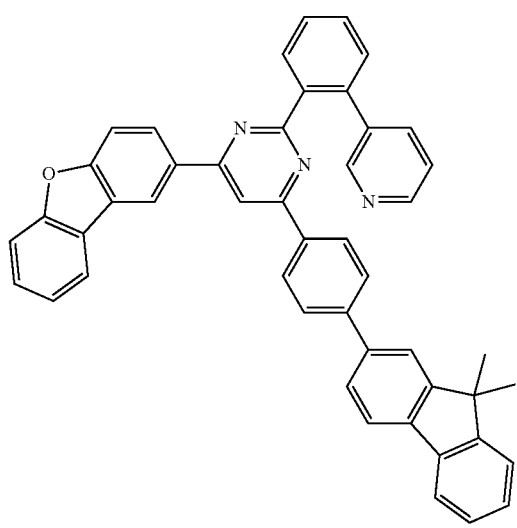
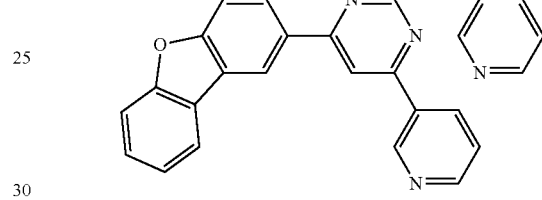
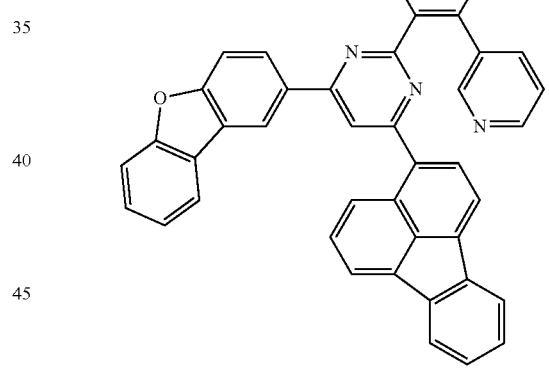
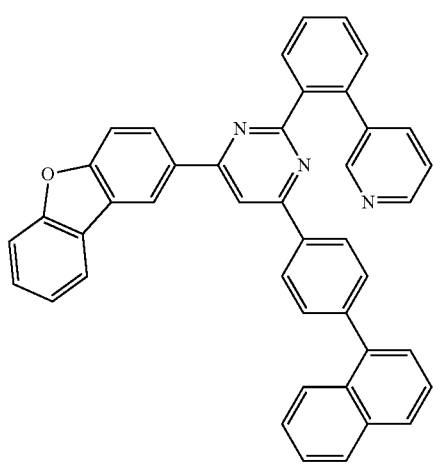
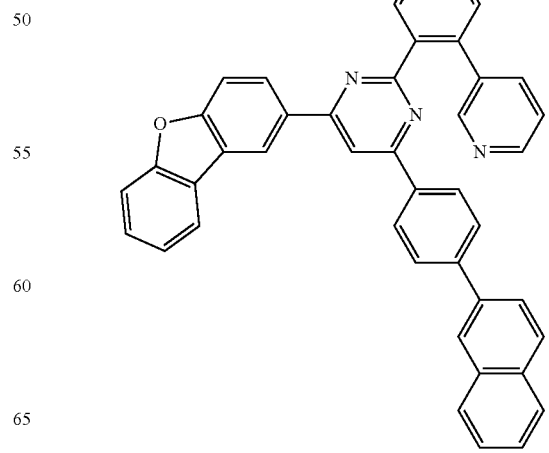

277
-continued
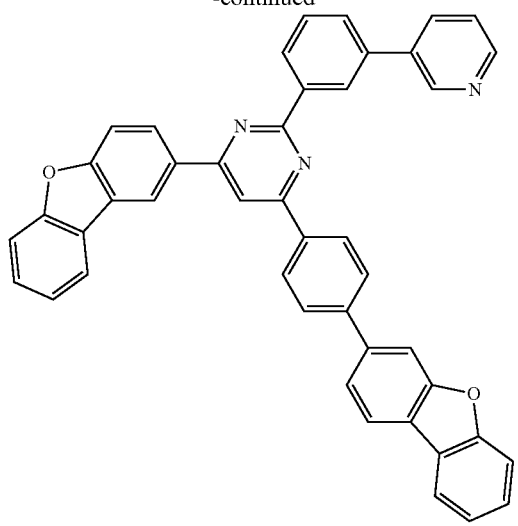
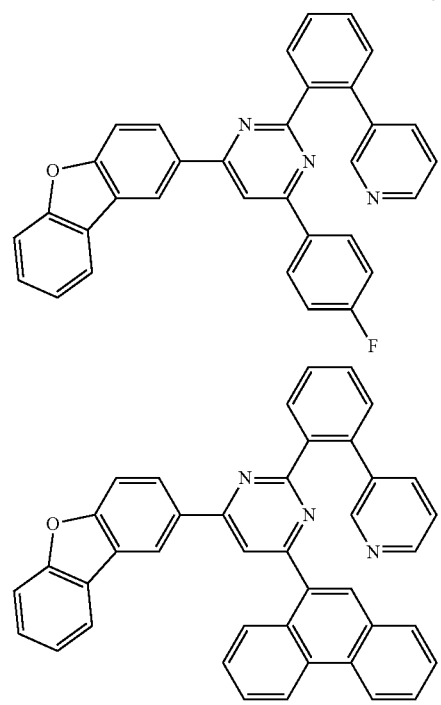
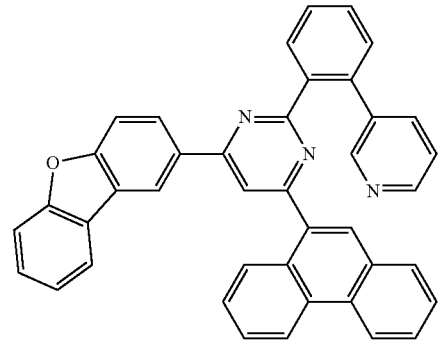
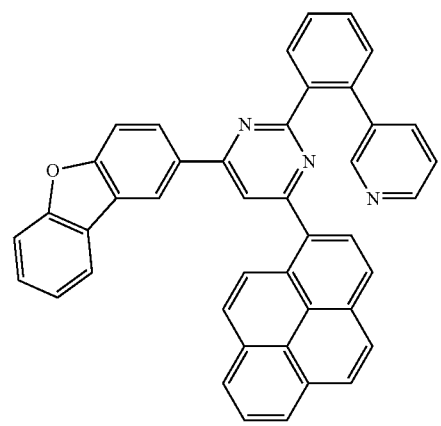
278
-continued
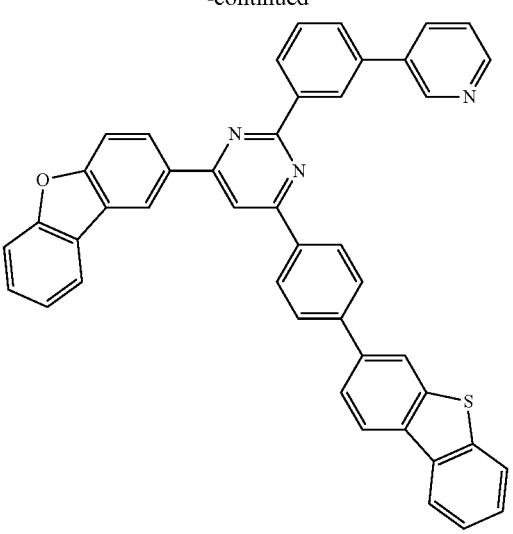
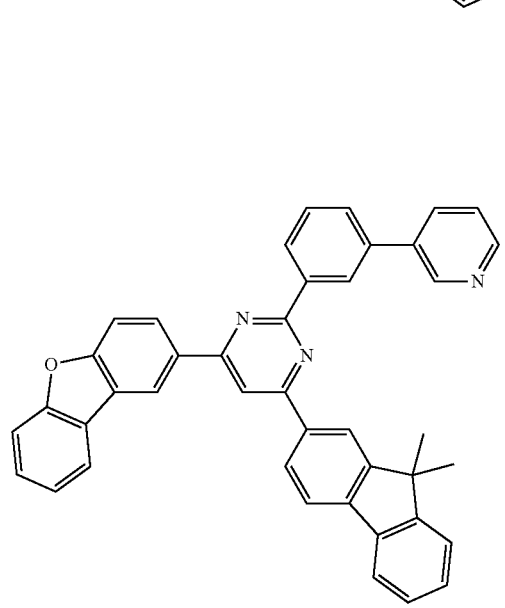
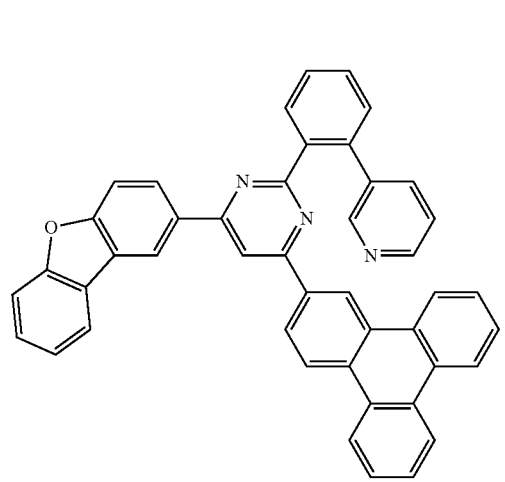

-continued
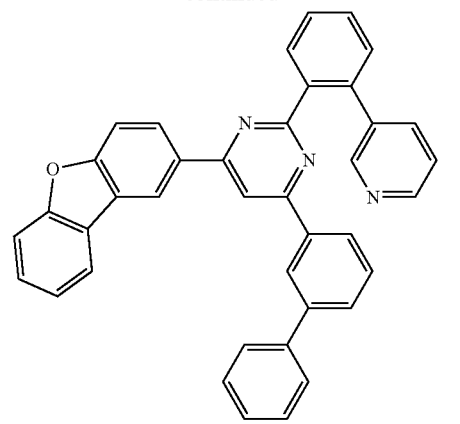
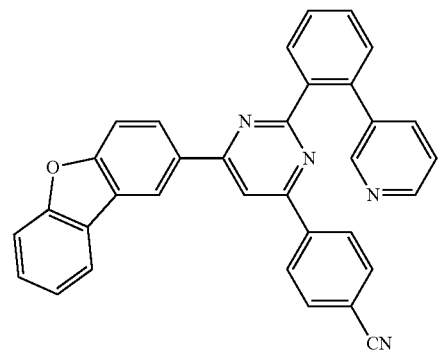
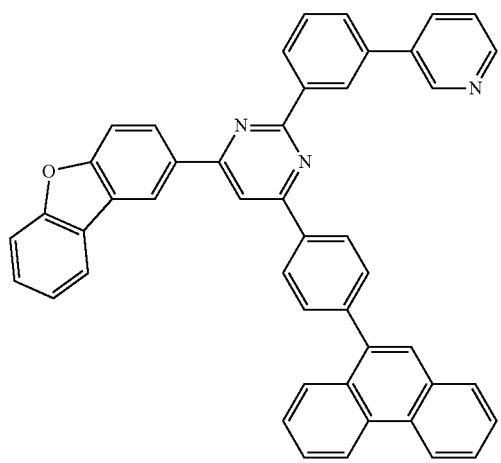
[Formula 135]
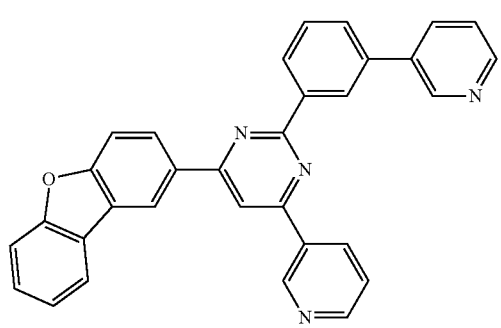
-continued
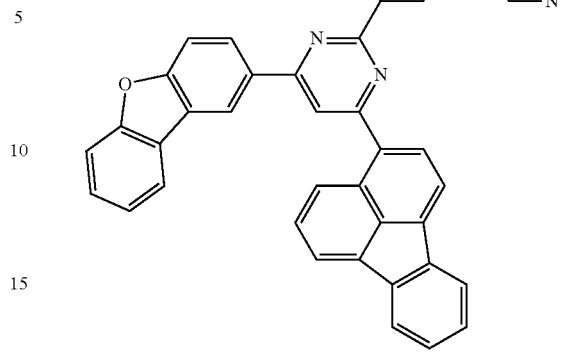
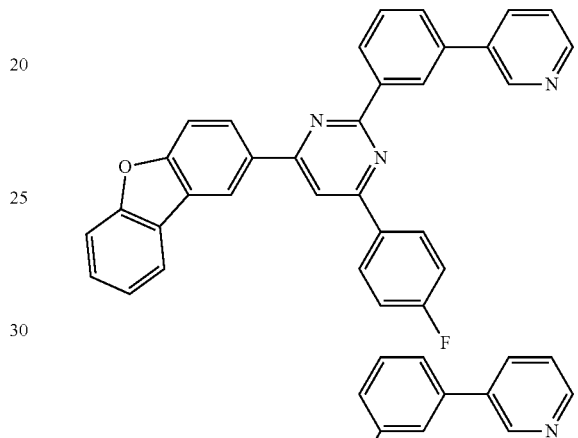
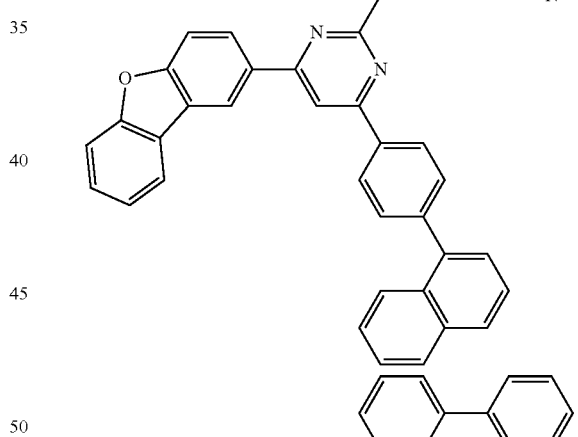
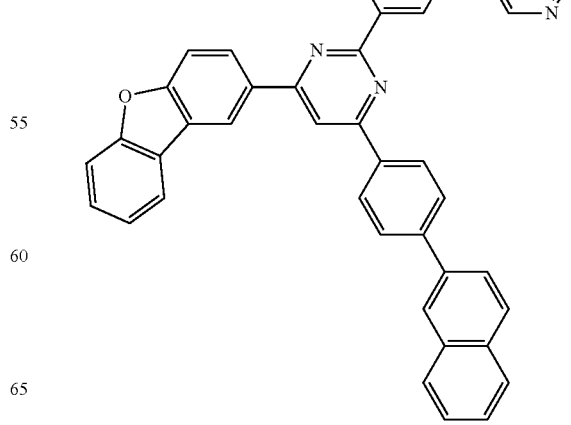

-continued
[Formula 136]
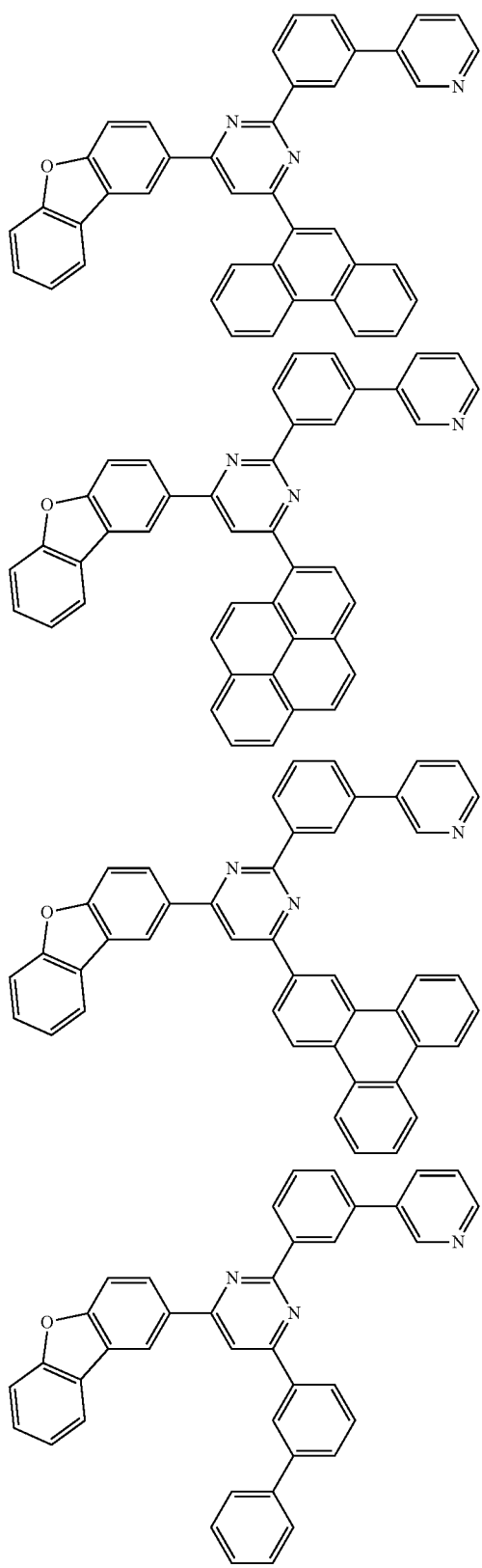
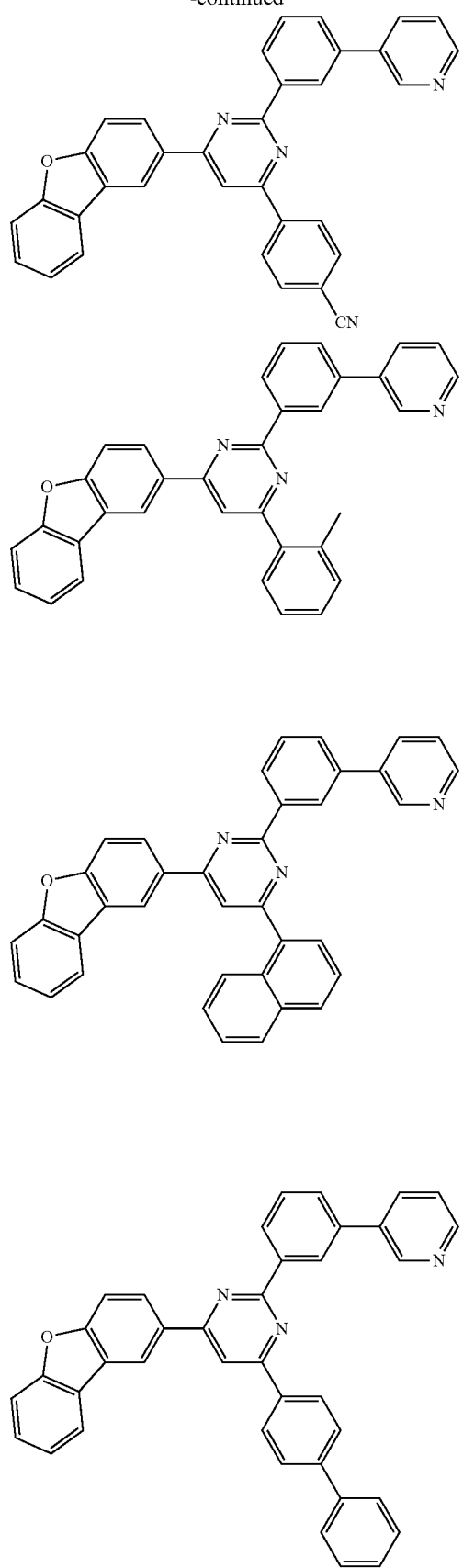

283
-continued
[Formula 137]
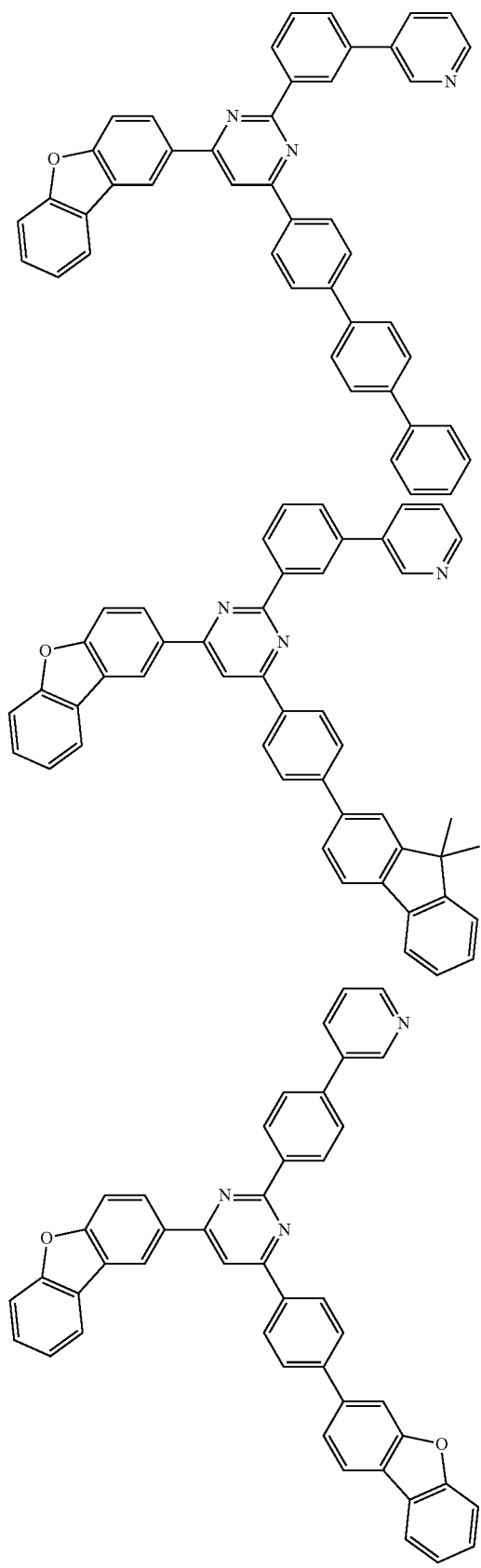
284
-continued
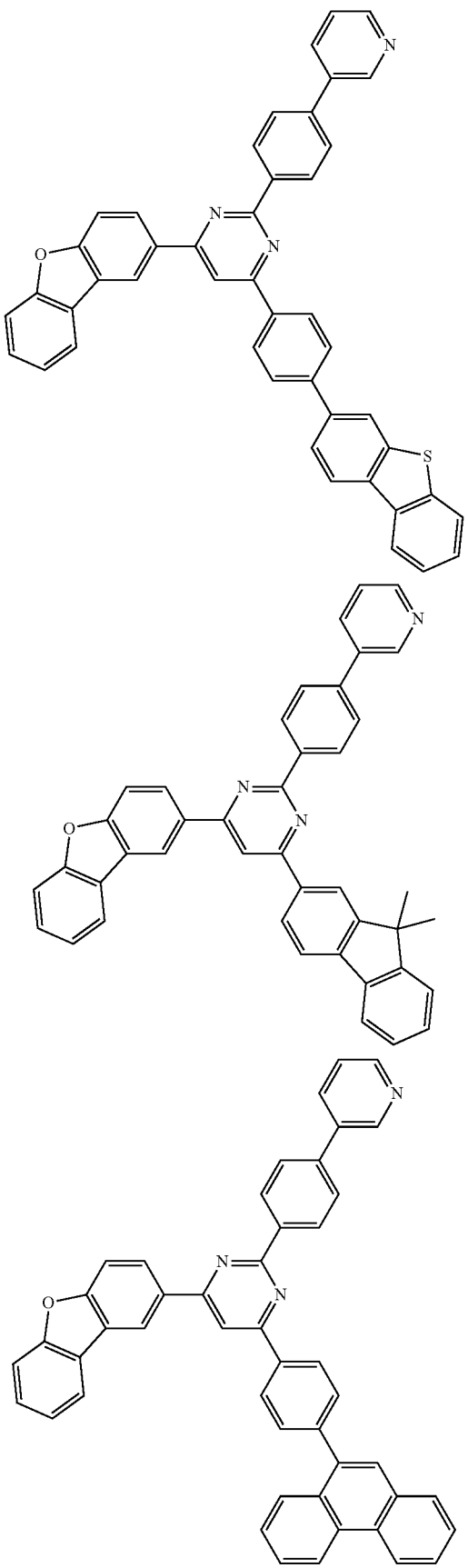

285
-continued
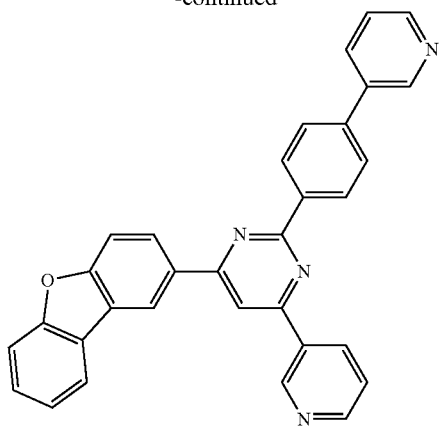
286
-continued
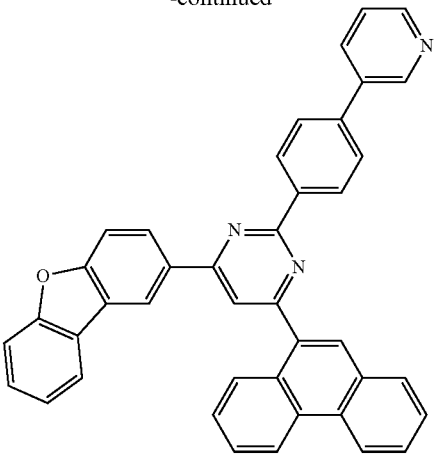
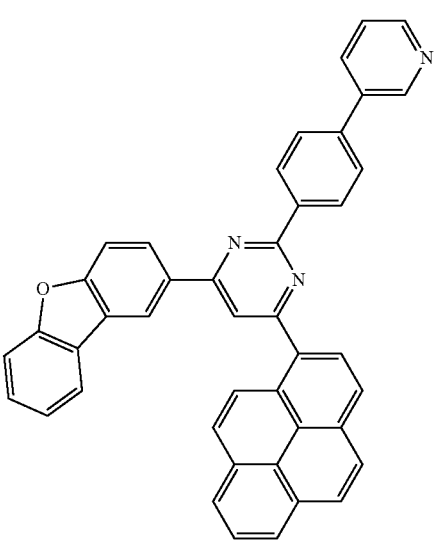
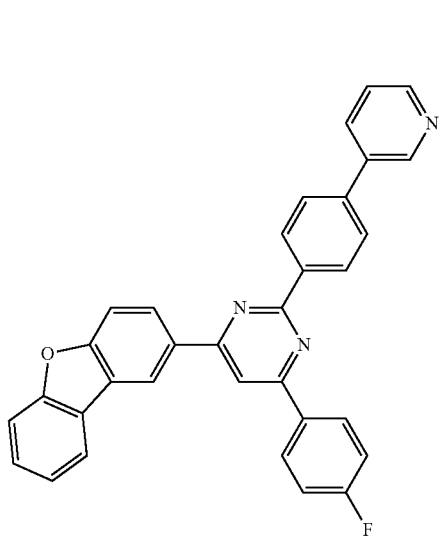

287
288
[Formula 138]
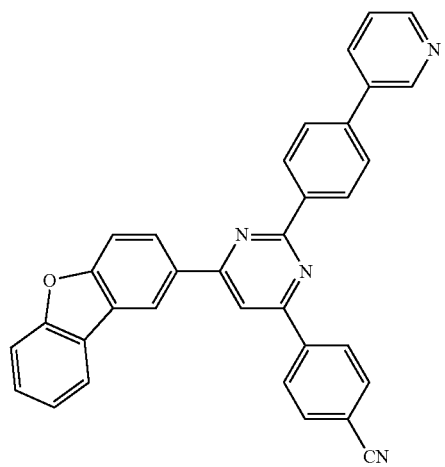
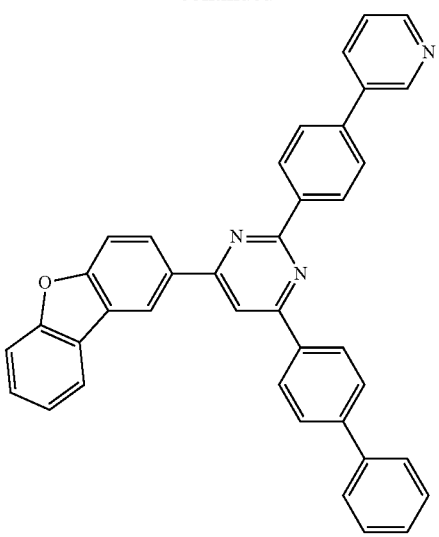
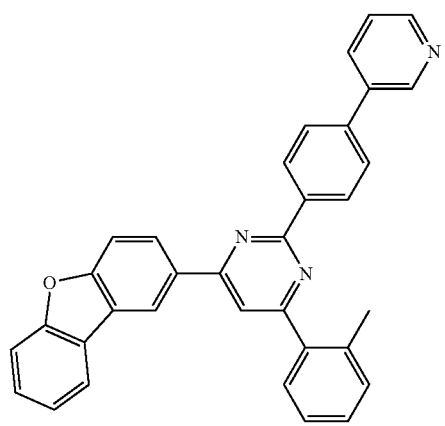
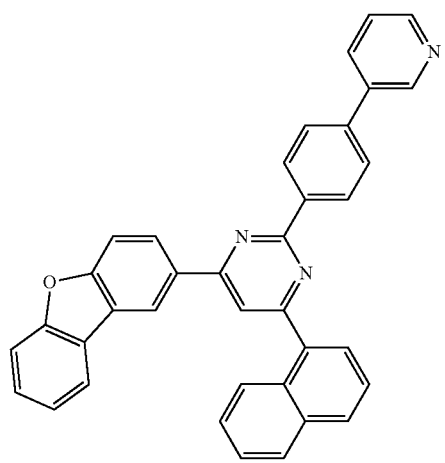
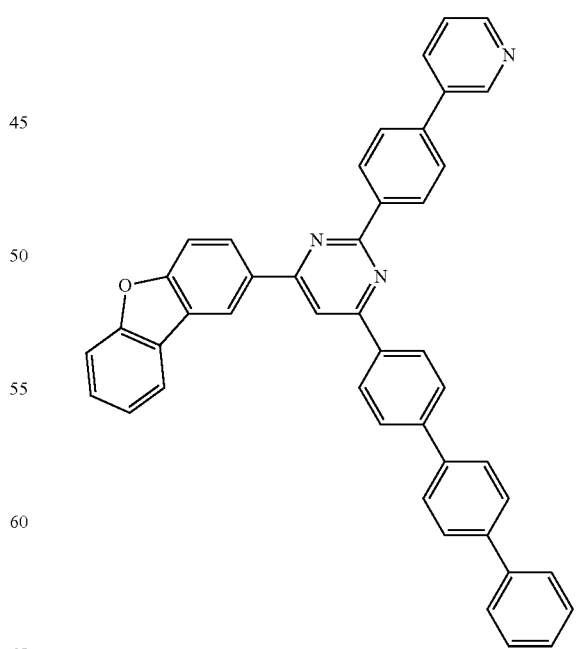

289
-continued
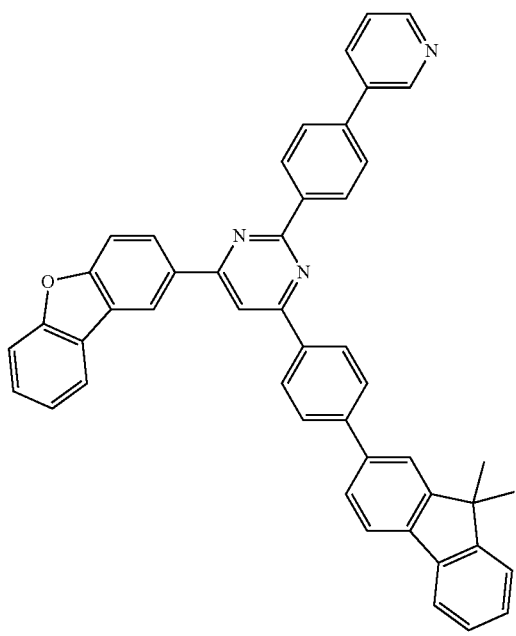
290
-continued
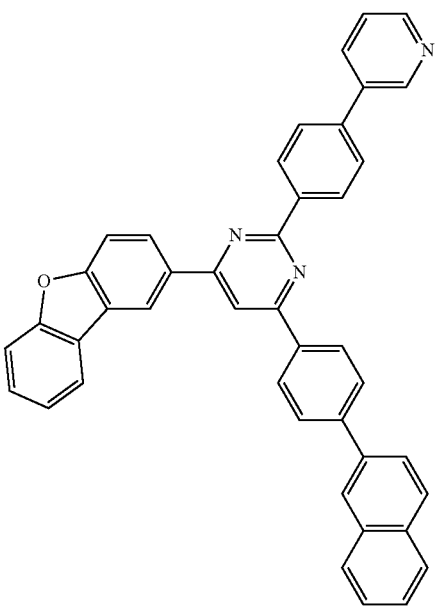
[Formula 139]
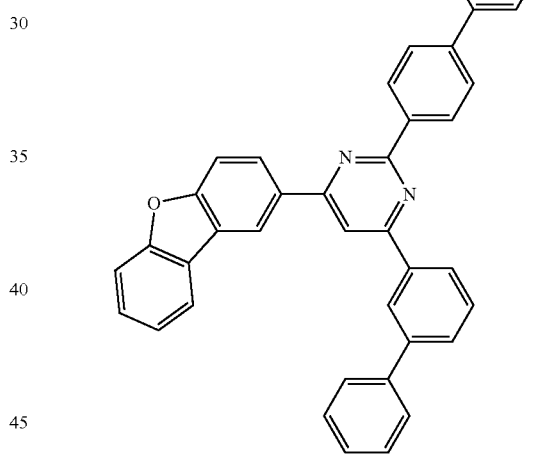
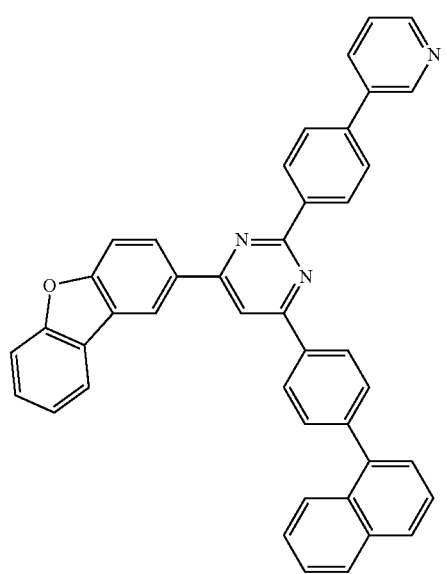
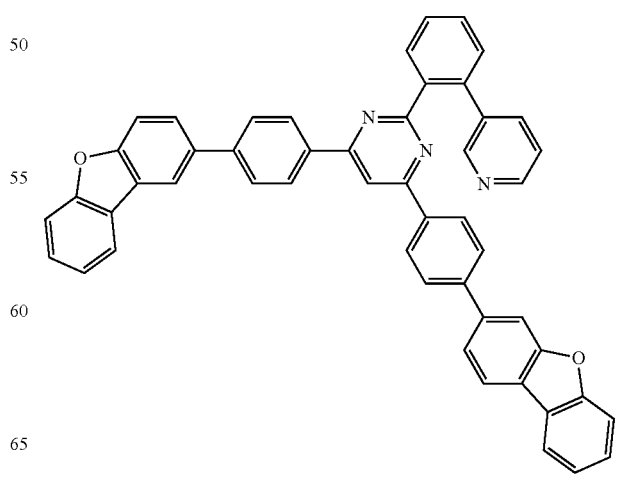

-continued
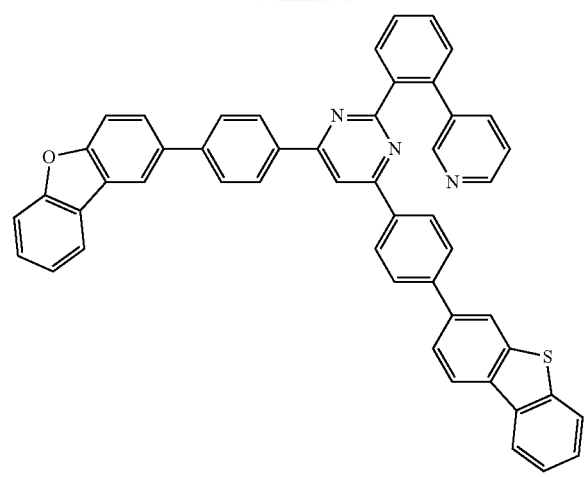
[Formula 140]
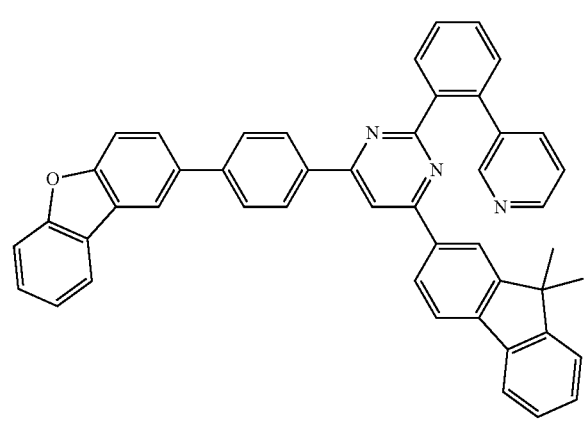
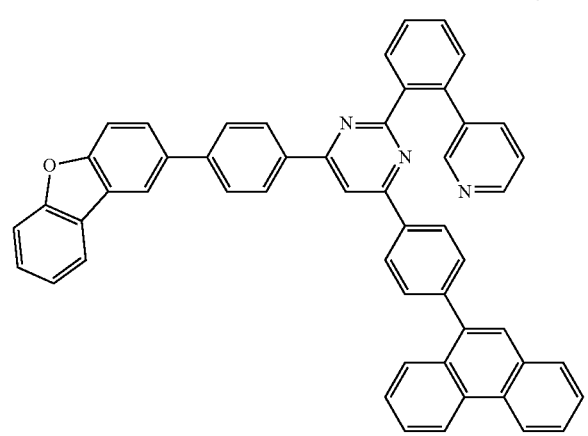
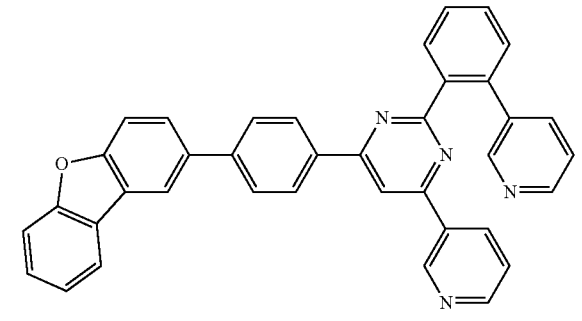
-continued
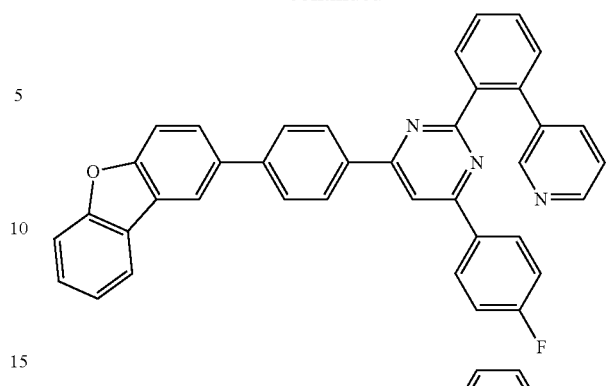
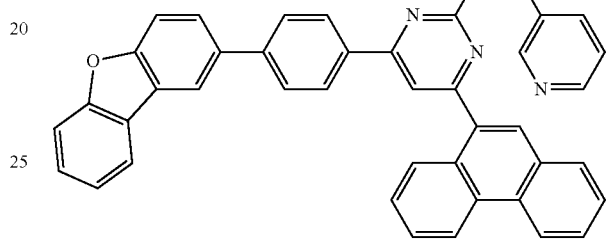
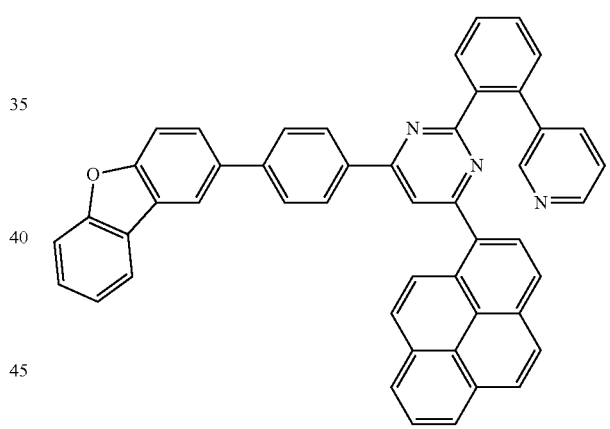
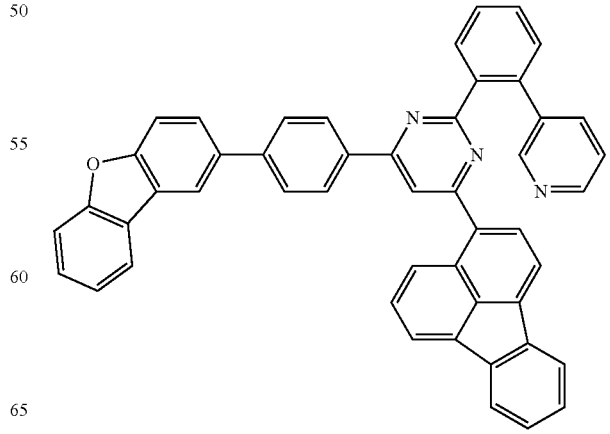

293
-continued
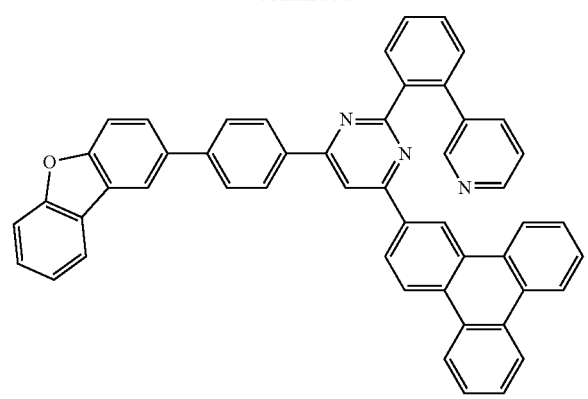
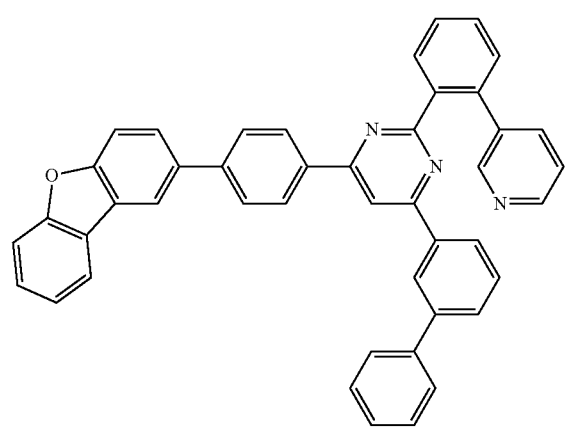
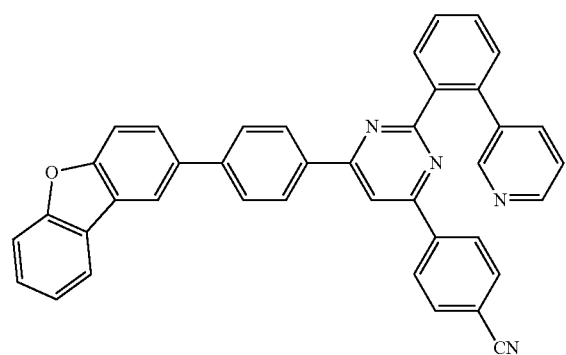
[Formula 141]
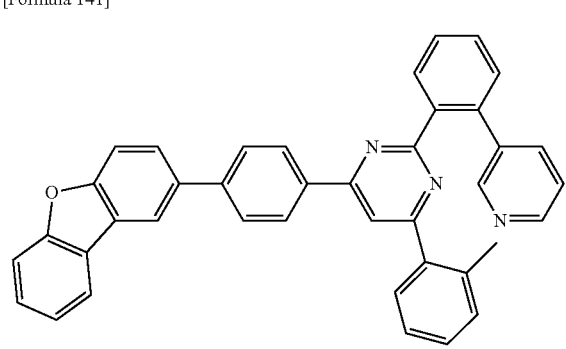
294
-continued
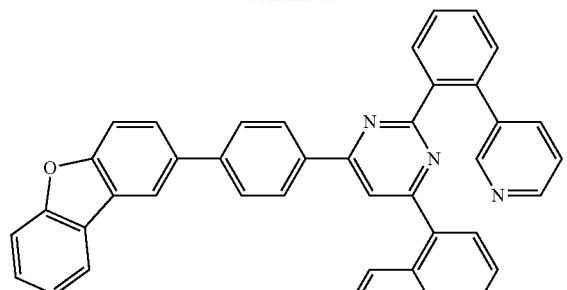
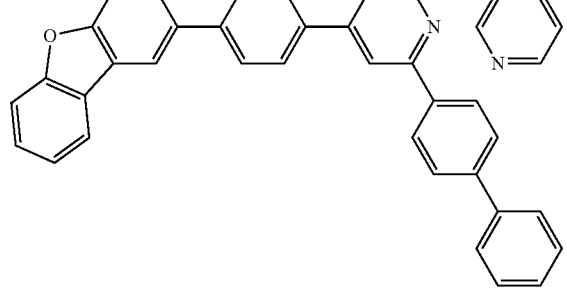
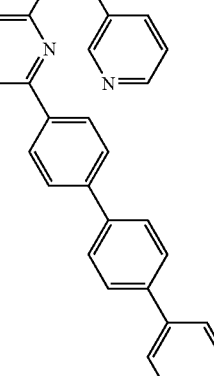
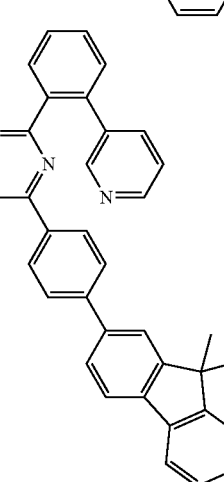

295
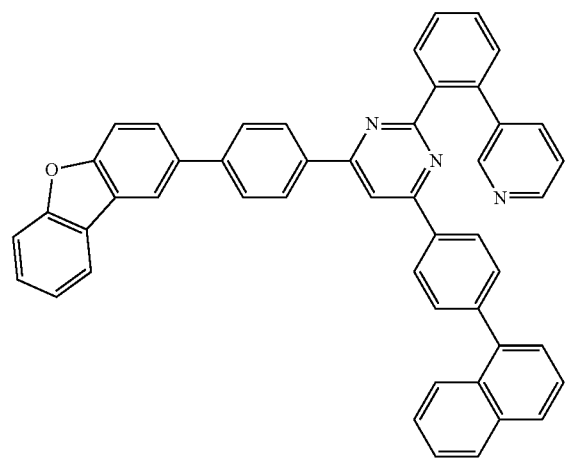
[Formula 142]
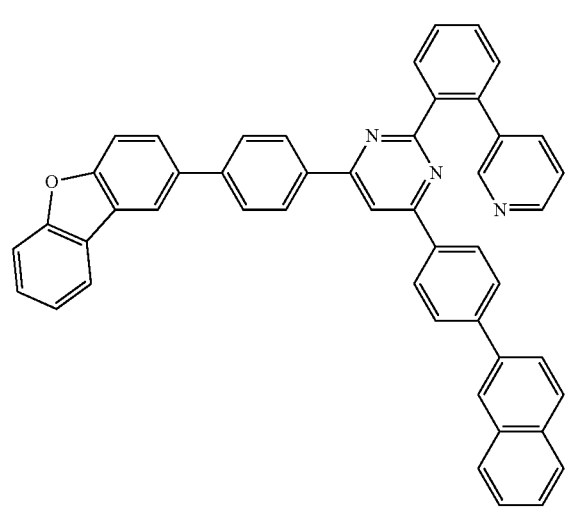
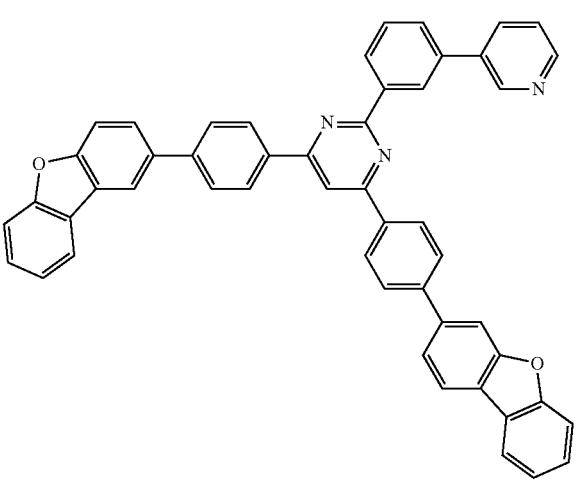
296
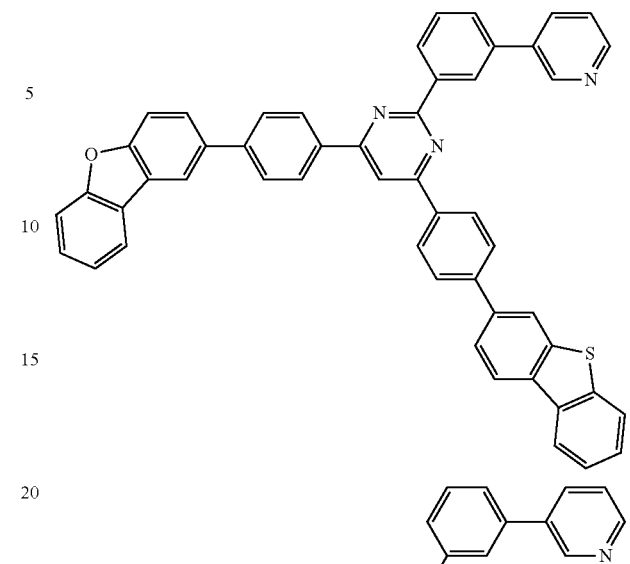
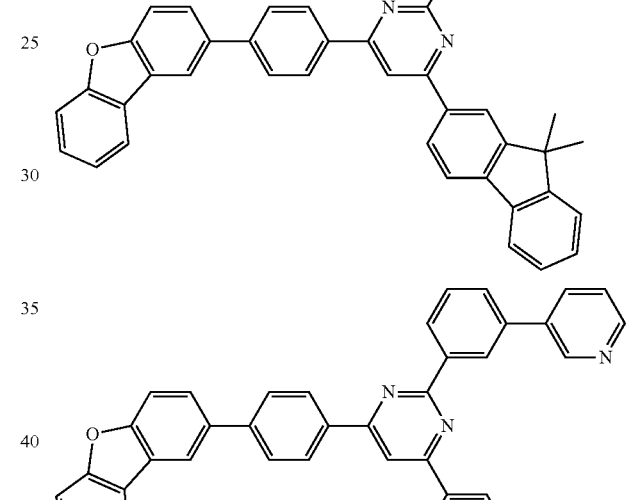
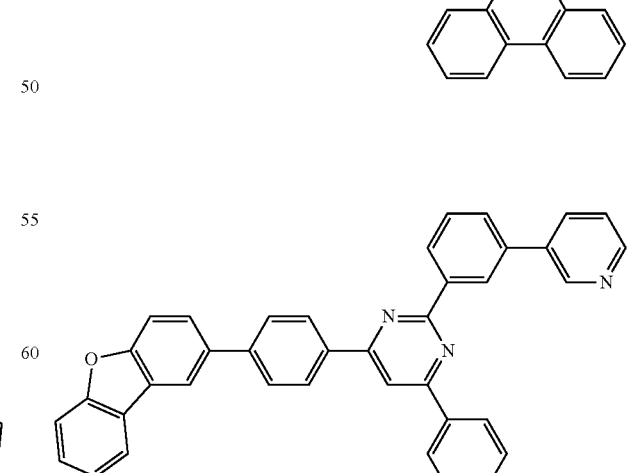

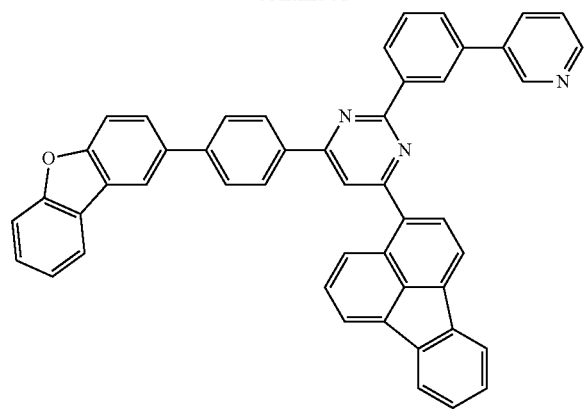
[Formula 143]
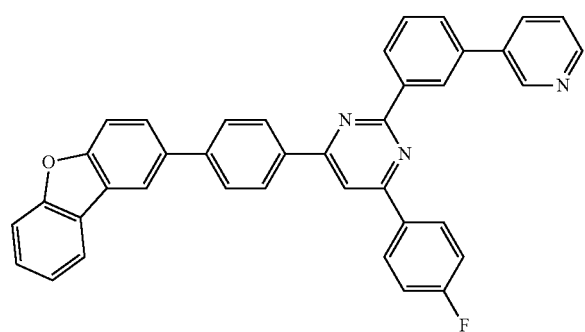
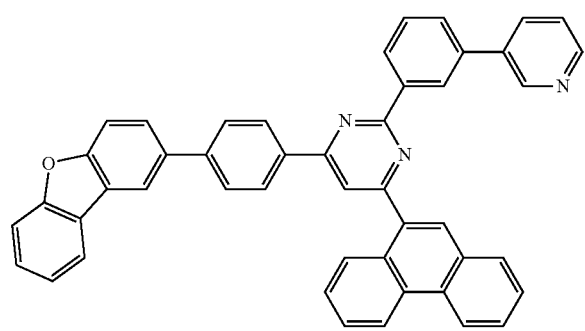
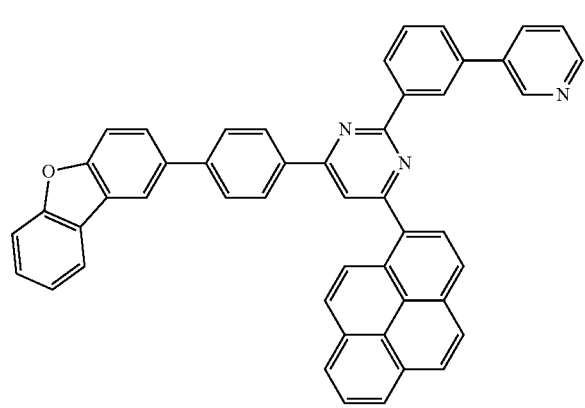
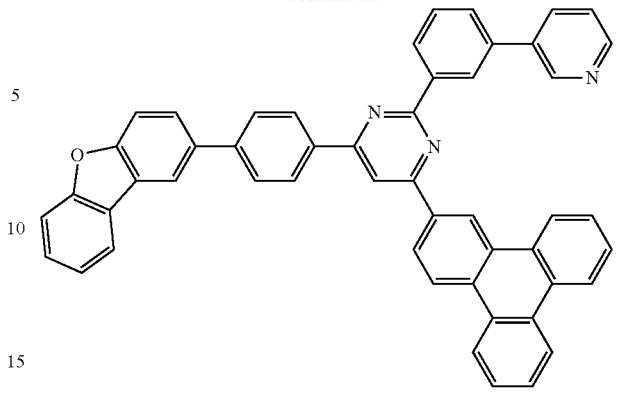
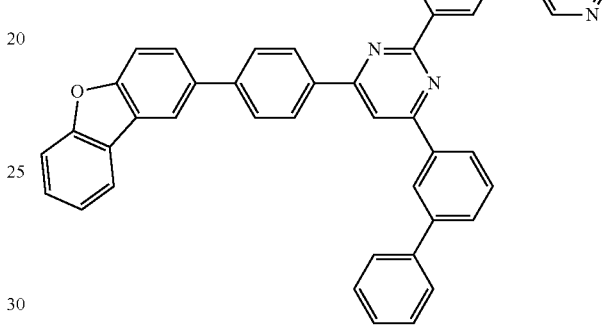
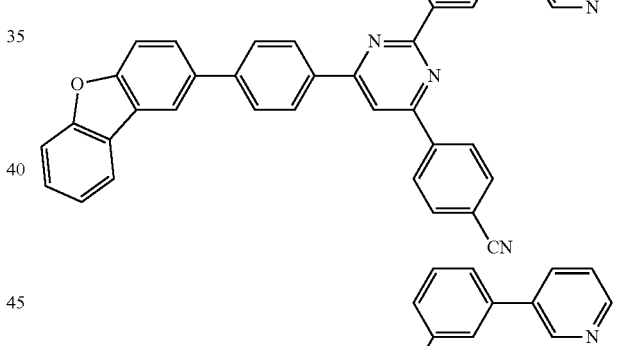
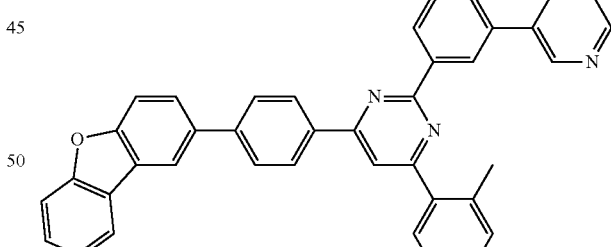
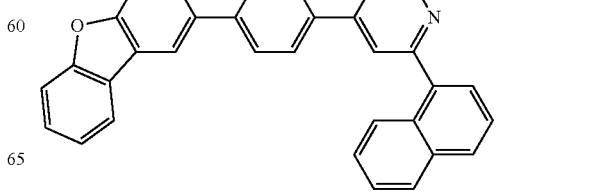

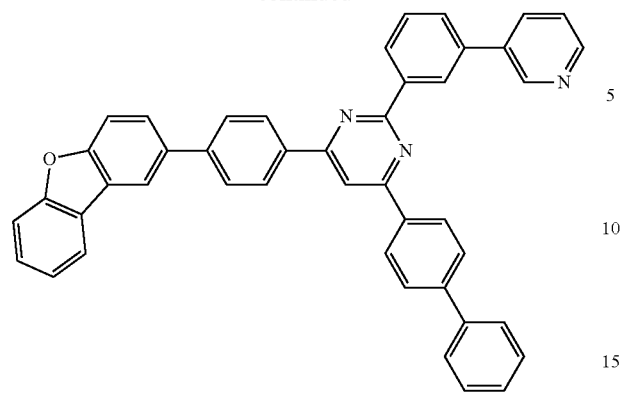
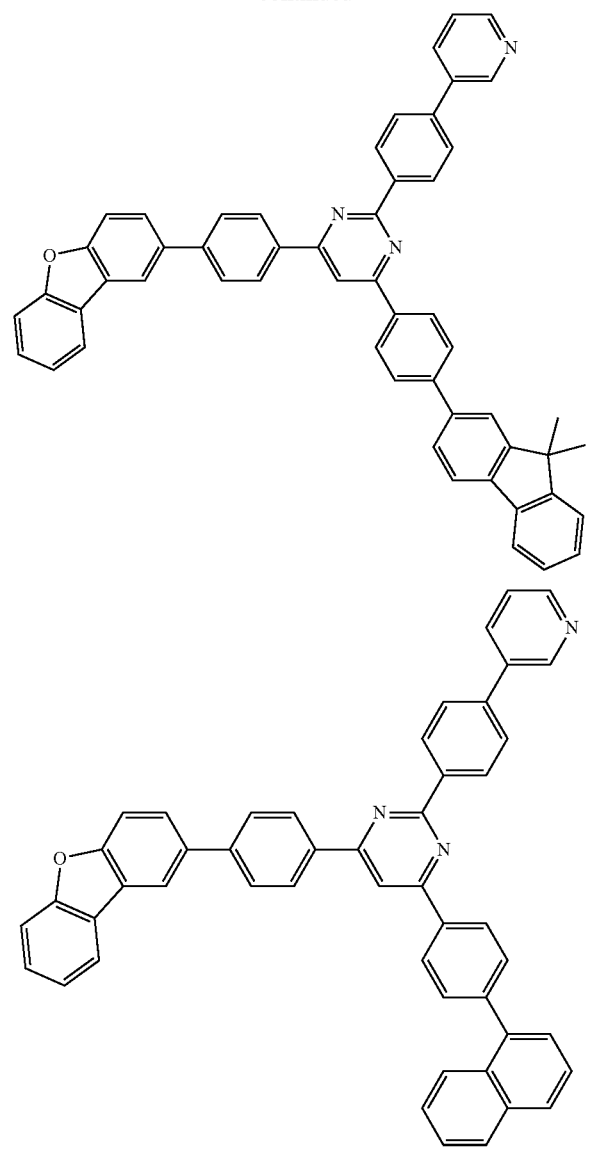
[Formula 144]
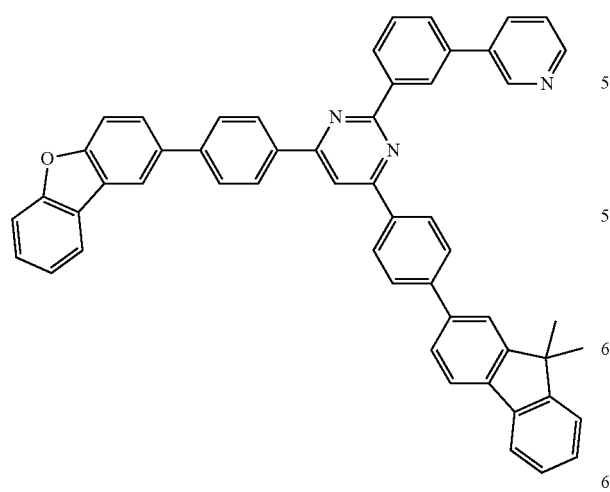
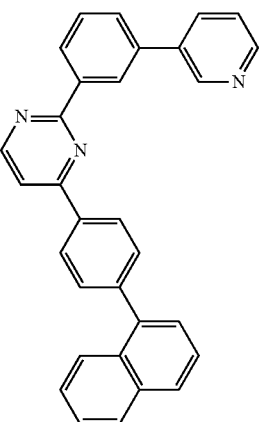

301
-continued
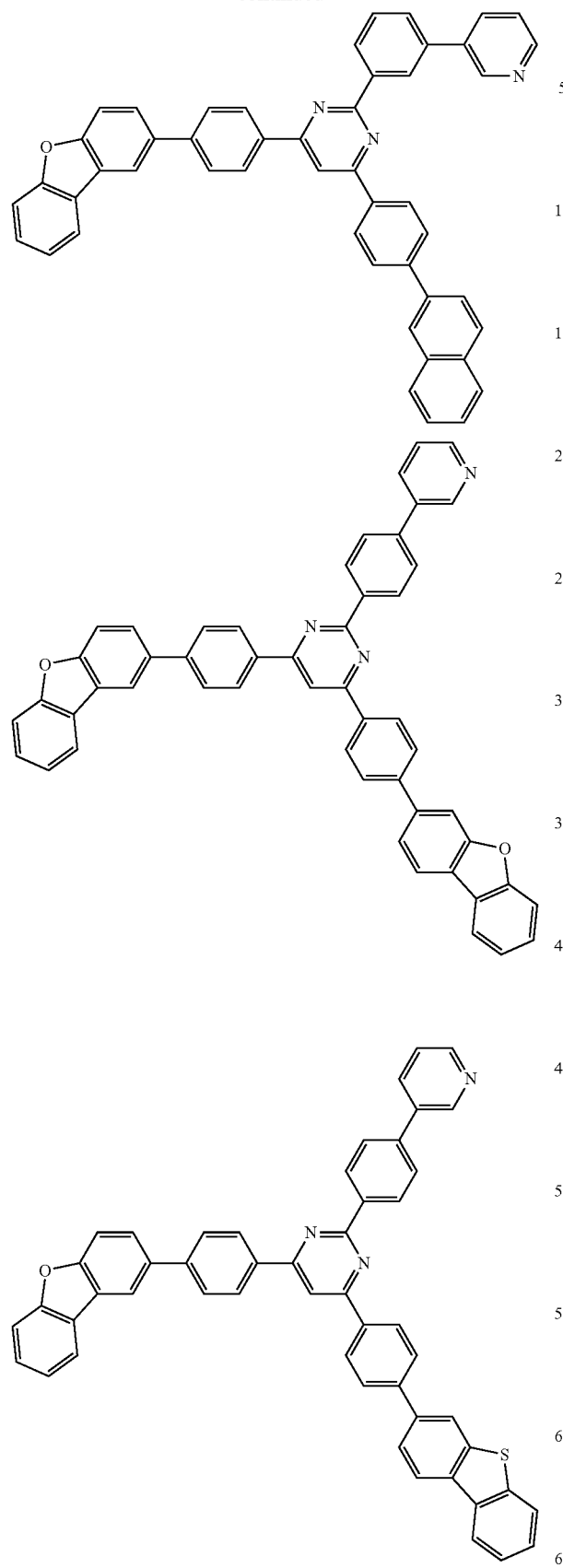
302
-continued
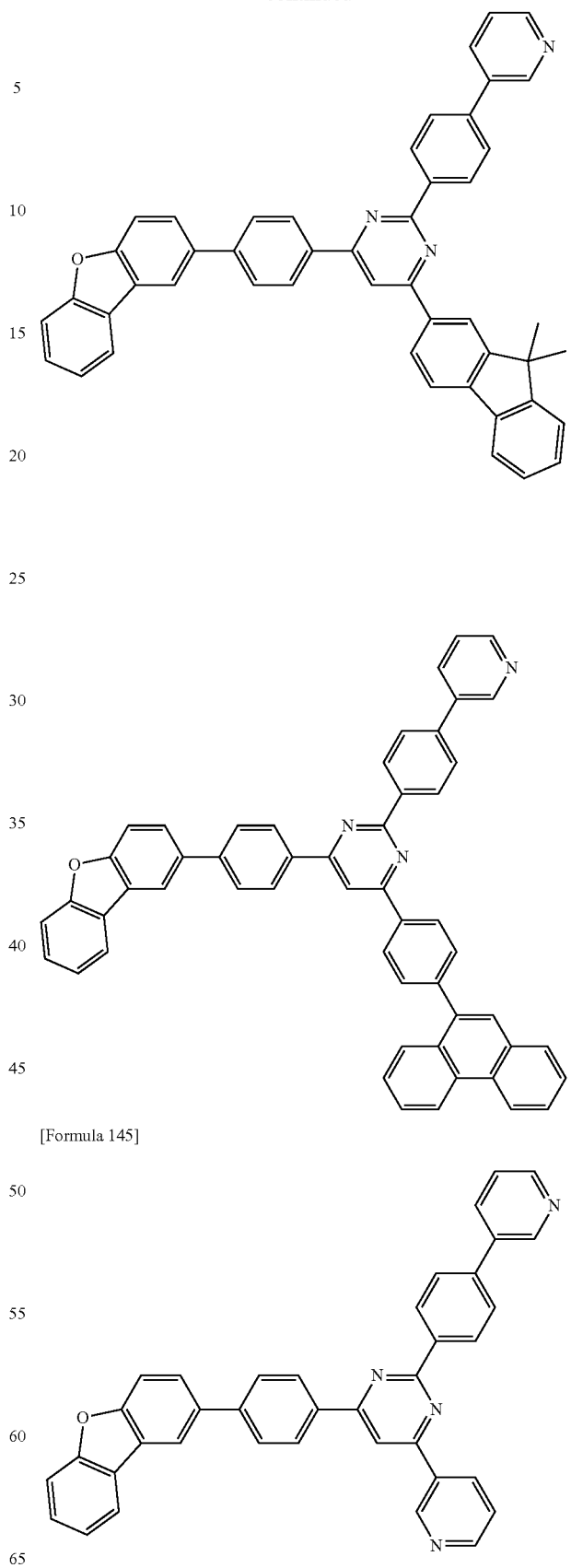
[Formula 145]

303
-continued
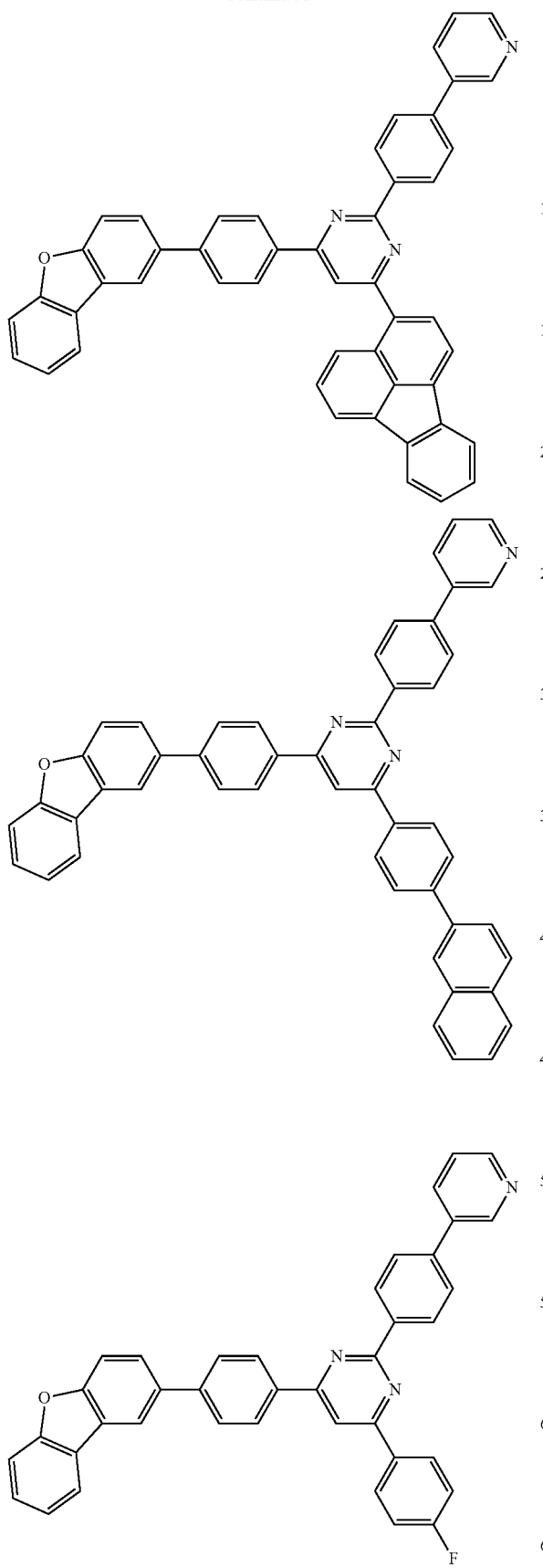
304
-continued
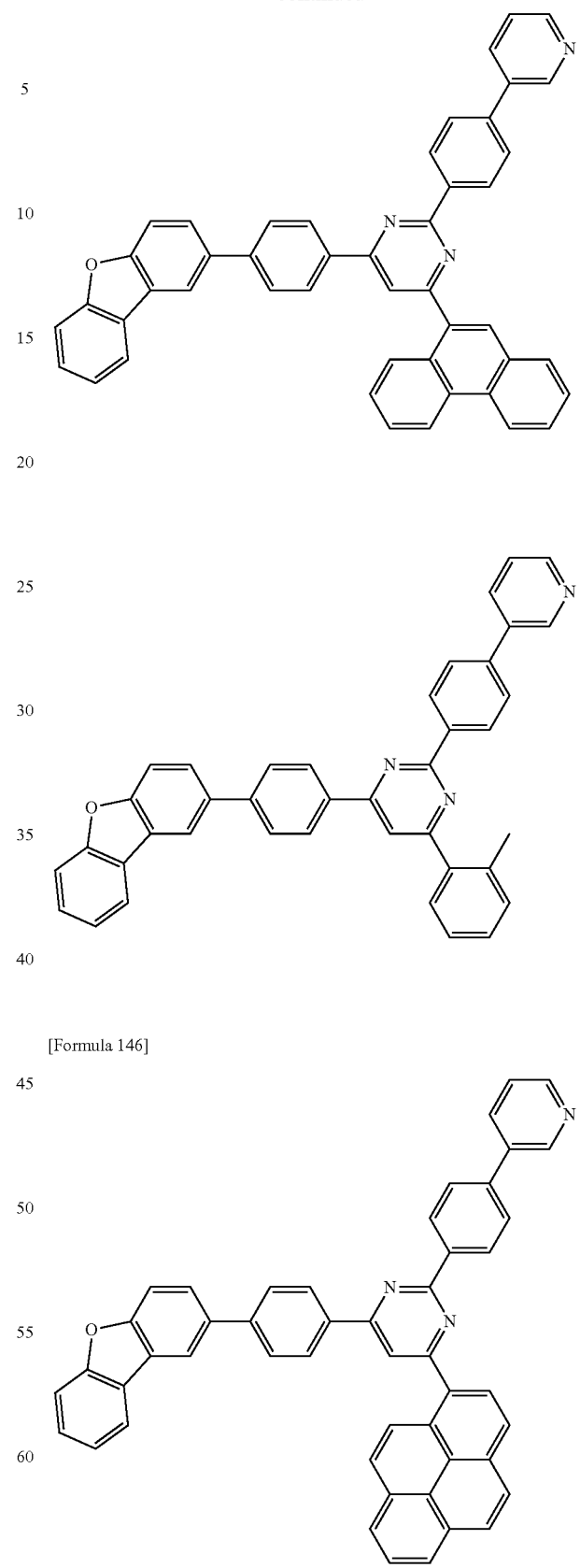
[Formula 146]

305
-continued
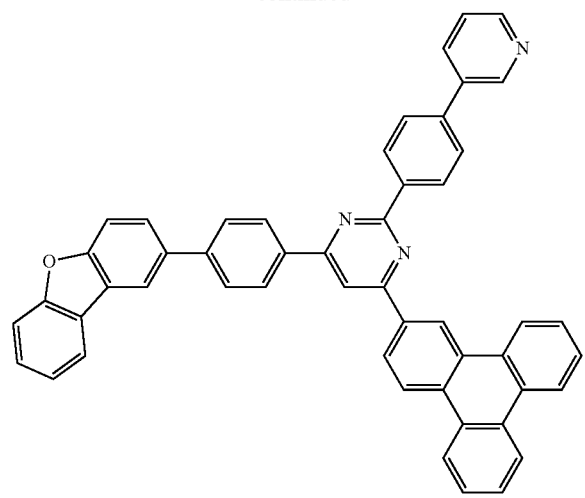
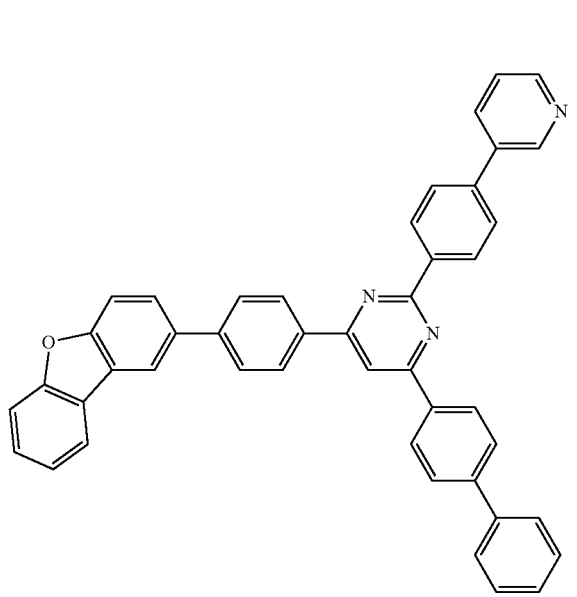
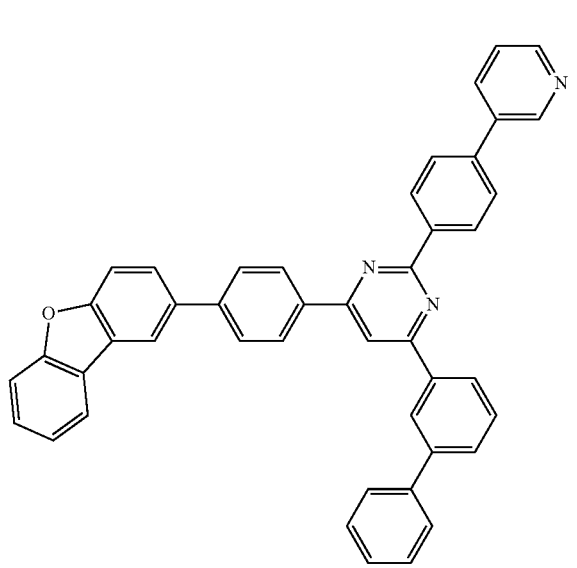
306
-continued
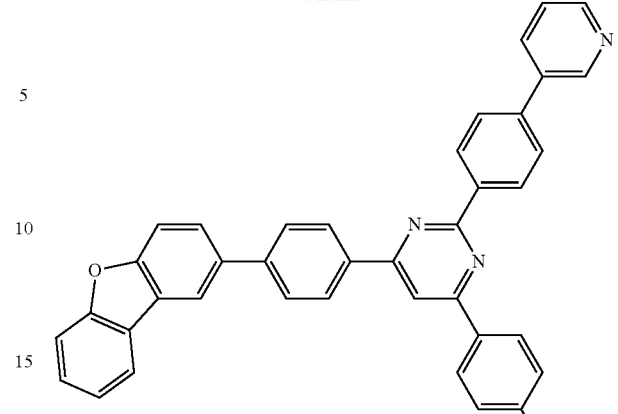
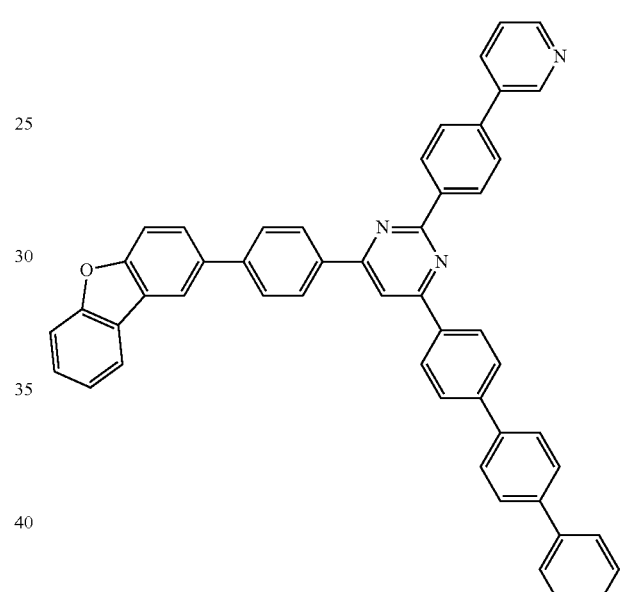
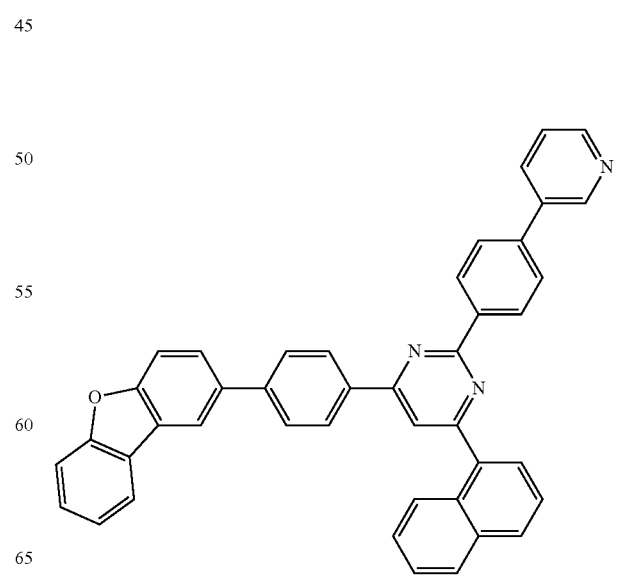

307
[Formula 147]
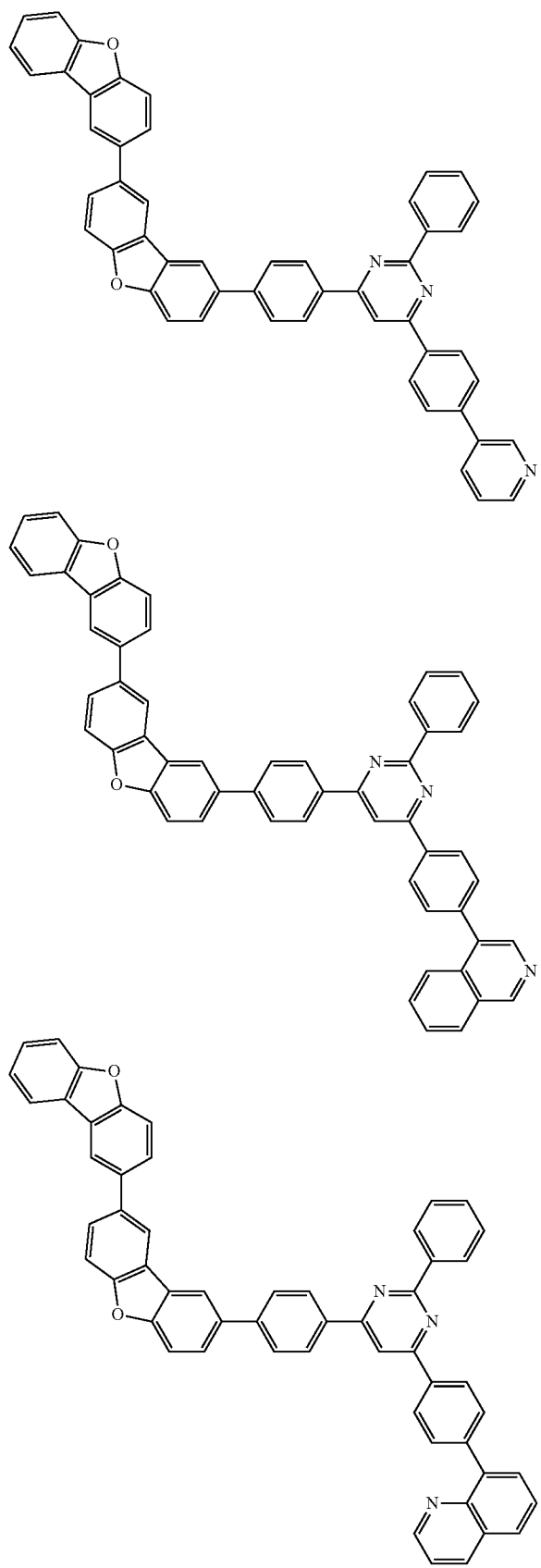
308
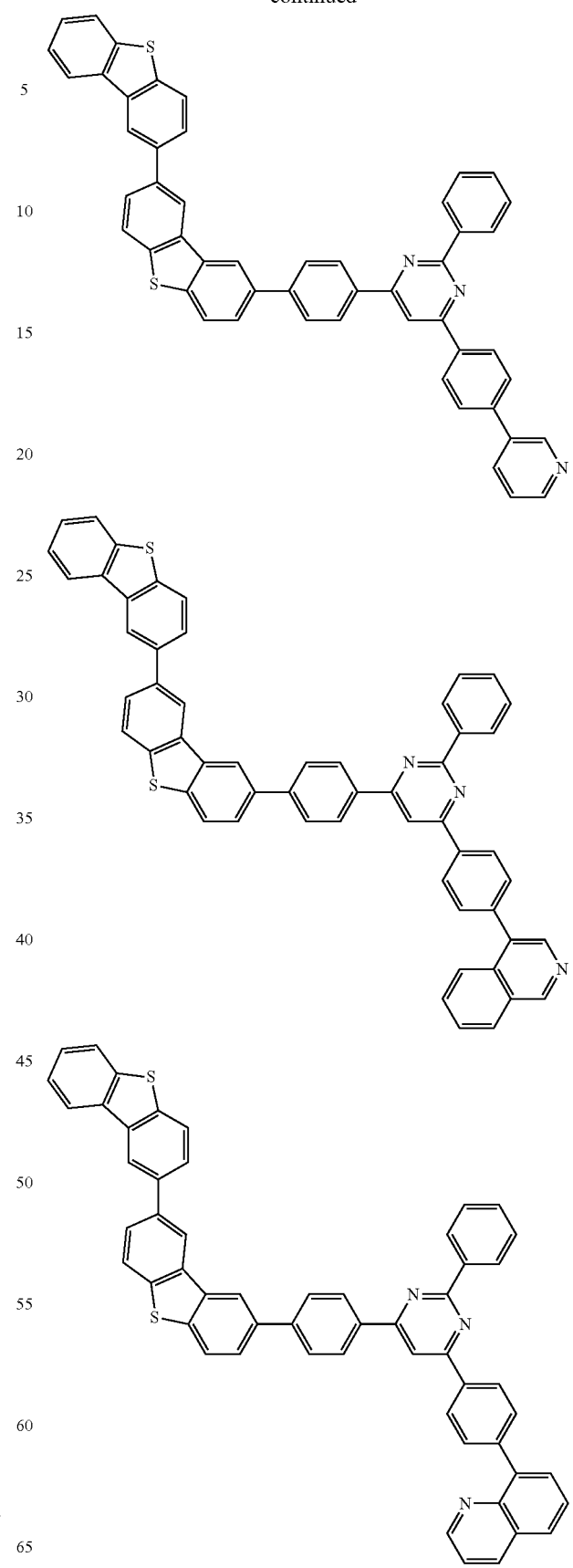

309
-continued
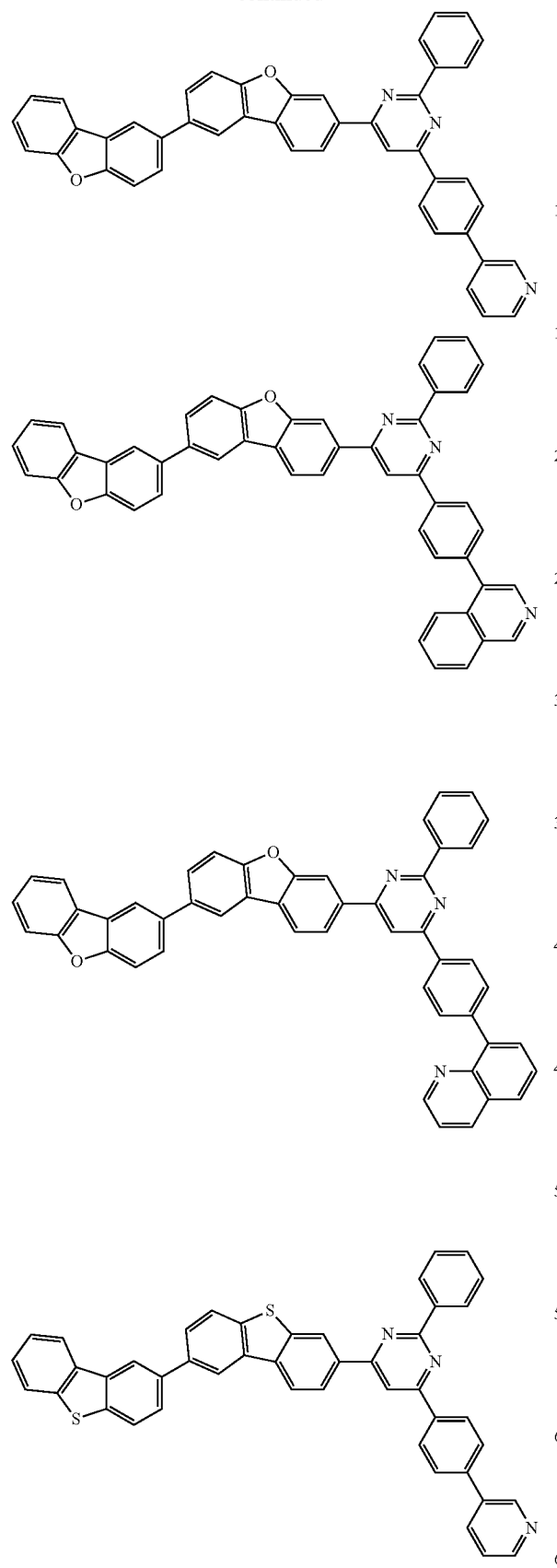
310
-continued
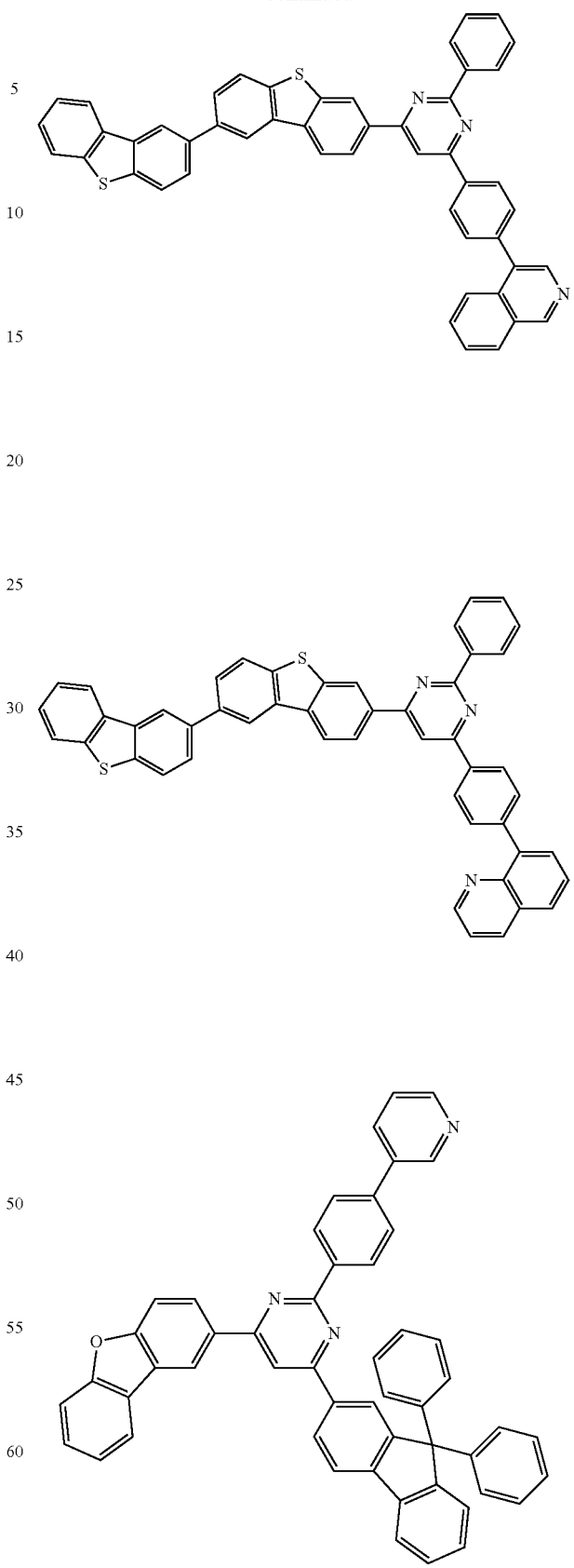

-continued

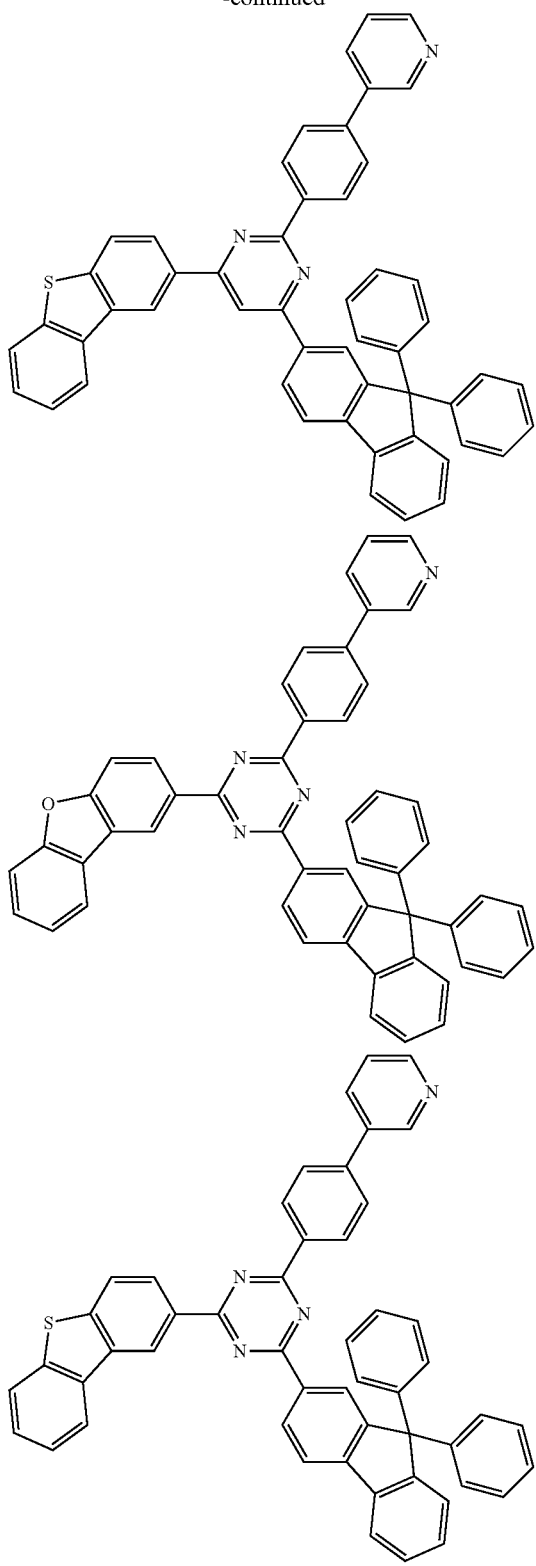

Organic-Electroluminescence-Device Material

The compounds of the exemplary embodiment are applicable as an organic-EL-device material. The compounds of the exemplary embodiment may be singly used as the organic-EL-device material or a mixture of the compound(s) of the exemplary embodiment and other material may be used as the organic-EL-device material.

Organic Electroluminescence Device

Arrangement(s) of Organic EL Device

Arrangement(s) of an organic EL device according to the exemplary embodiment will be described below.

The organic EL device includes an anode, a cathode and an organic layer. The organic layer includes one or more layers formed from an organic compound. The organic layer may further include an inorganic compound. At least one of the organic layers of the organic EL device of the exemplary embodiment includes the compound of the exemplary embodiment.

The FIGURE schematically shows an exemplary arrangement of the organic EL device according to the exemplary embodiment.

An organic EL device 1 includes a light-transmissive substrate 2, an anode 3, a cathode 4, and an organic layer 10 provided between the anode 3 and the cathode 4.

The organic layer 10 includes an emitting layer 7, a hole injecting layer 5 interposed between the anode 3 and the emitting layer 7, a hole transporting layer 6 interposed between the hole injecting layer 5 and the emitting layer 7, and an electron transporting zone 11 provided between the emitting layer 7 and the cathode 4.

The electron transporting zone 11 includes the above-described compound(s) of the exemplary embodiment. The electron transporting zone 11 includes the electron transporting layer 8 and the electron injecting layer 9. In the exemplary embodiment, the electron transporting layer 8 contains the compound(s) of the exemplary embodiment. It is preferable that the electron transporting layer 8 is in contact with the emitting layer 7.

It is preferable that the electron transporting zone 11 contains at least one of an electron-donating dopant and an organic metal complex. It is further preferable that the electron transporting layer 8 contains the compound(s) of the exemplary embodiment and at least one of the electron-donating dopant and the organic metal complex. The electron-donating dopant and the organic metal complex will be sometimes referred to as "electron-donating dopant and the like" hereinafter.

The electron-donating dopant and the like contained in the electron transporting zone 11 is preferably at least one compound selected from the group consisting of an alkali metal, an alkali metal compound, an alkali earth metal, an alkali earth metal compound, a rare-earth metal, a rare-earth metal compound, an organic metal complex including alkali metal, an organic metal complex including alkali earth metal and an organic metal complex including rare-earth metal.

The electron-donating dopant may be at least one compound selected from an alkali metal, an alkali metal compound, an alkali earth metal, an alkali earth metal compound, a rare-earth metal, and a rare-earth metal compound.

Examples of the alkali metal are lithium ($L_1$) (work function: 2.93 eV), sodium (Na) (work function: 2.36 eV), potassium (K) (work function: 2.28 eV), rubidium (Rb) (work function: 2.16 eV) and cesium (Cs) (work function: 1.95 eV). Among the above, an alkali metal having a work function of 2.9 eV or less is preferable. Among the alkali metals, at least one of K, Rb and Cs is preferable, Rb or Cs is more preferable and Cs is further more preferable.

Examples of the alkali earth metal are calcium (Ca) (work function: 2.9 eV), strontium (Sr) (work function: 2.0 to 2.5 eV), and barium (Ba) (work function: 2.52 eV). Among the above, an alkali earth metal having work function of 2.9 eV or less is preferable.

Examples of the rare earth metal include scandium (Sc), yttrium (Y), cerium (Ce), terbium (Tb) and ytterbium (Yb). Among the above, a rare-earth metal having work function of 2.9 eV or less is preferable.

Since the preferred metals among the alkali metal, alkali earth metal and rare-earth metal have higher reducibility than that of other metals, addition of a relatively small amount of the metals to an electron injecting zone can enhance luminance intensity and lifetime of the organic EL device.

Examples of the alkali metal compound include alkali oxide and alkali halide. Examples of the alkali oxide include lithium oxide ($Li_2O$), cesium oxide ($Cs_2O$) and potassium oxide ($K_2O$). Examples of alkali halide include lithium fluoride (LiF), sodium fluoride (NaF), cesium fluoride (CsF) or potassium fluoride (KF). At least one of lithium fluoride (LiF), lithium oxide ($Li_2O$) and sodium fluoride (NaF) is preferable as the alkali metal compound.

Examples of the alkali earth metal compound include barium oxide (BaO), strontium oxide (SrO) and calcium oxide (CaO). Other examples of the alkali earth metal compound are strontium barium oxide ($Ba_xSr_{1-x}O$) (0<x<1) obtained by mixing BaO and SrO and calcium barium oxide ($Ba_xCa_{1-x}O$) (0<x<1) obtained by mixing BaO and CaO. At least one of BaO, SrO and CaO is preferable as the alkali earth metal compound.

Examples of the rare-earth metal compound are ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$). At least one of $YbF_3$, $ScF_3$ and $TbF_3$ is preferable as the rare-earth metal compound.

The organic metal complex is not particularly limited, as long as at least one of alkali metal ion, alkali earth metal ion and rare-earth metal ion is contained therein as metal ion.

Ligand of the organic metal complex is not particularly limited. Examples of the ligand for the organic metal complexes are quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, beta-diketones, azomethines and a derivative thereof.

The electron-donating dopant and the organic metal complex contained in the electron transporting zone 11 are preferably at least one compound selected from the group consisting of lithium, a lithium compound, and an organic metal complex including lithium. It is more preferable that the electron transporting zone 11 contains 8-quinolinolato-lithium.

When the compound according to the exemplary embodiment, electron-donating dopant and the like are contained in the electron transporting layer 8, the mass ratio of the additive amount of each of the components (the compound according to the exemplary embodiment:electron-donating dopant, organic metal complex and the like) is preferably (100:1) to (1:100), more preferably (5:1) to (1:5) and further more preferably (2:1) to (1:2).

Film Thickness of Electron Transporting Layer

Though the film thickness of the electron transporting layer 8 is not particularly limited, the film thickness of the electron transporting layer 8 is usually typically preferably in a range from 0.1 nm to 1 μm.

The electron transporting zone 11 of the organic EL device 1 according to the exemplary embodiment may further include a second electron transporting layer in addition to the electron transporting layer 8. It is preferable that the electron transporting layer 8 is provided between the emitting layer 7 and the second electron transporting layer.

The second electron transporting layer is a layer containing a highly electron-transportable substance. For instance, at least one of 1) a metal complex such as an aluminum complex, beryllium complex and zinc complex, 2) a heteroaromatic compound such as an imidazole derivative, benzimidazole derivative, azine derivative, carbazole derivative, and phenanthroline derivative, and 3) a high-molecule compound are usable for the second electron transporting layer. Specifically, as a low-molecule organic compound, a metal complex such as Alq, tris(4-methyl-8-quinolinato)aluminum (abbreviation: $Almq_3$), bis(10-hydroxybenzo[h]quinolinato)beryllium (abbreviation: $BeBq_2$), BAlq, Znq, ZnPBO and ZnBTZ are usable, for instance. In addition to the metal complex, the hetero aromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzooxazole-2-yl)stilbene (abbreviation: BzOs) are usable, for instance. In the second electron transporting layer, a benzoimidazole compound is preferably usable. Moreover, a high-molecule compound is also usable for the second electron transporting layer. Examples of the high polymer compound include poly[(9,9-dihexylfluorene-2,7-diyl)-co-(pyridine-3,5-diyl)] (abbreviation: PF-Py) and poly[(9,9-dioctylfluorene-2,7-diyl)-co-(2,2'-bipyridine-6,6'-diyl)] (abbreviation: PF-BPy).

The above-described substances mostly have an electron mobility of $10^{-6}$ $cm^2/(V·s)$ or more. However, any substance having an electron transporting performance higher than a hole transporting performance may be used for the second electron transporting layer in addition to the above substances. Further, in addition to the electron transporting layer 8 (first electron transporting layer) and the second electron transporting layer, two or more layers containing the above substance may be additionally layered. In addition, the electron transporting layer 8 may further contain a compound usable for the second electron transporting layer.

Next, the other arrangement of the organic EL device 1 will be described.

Substrate

The substrate 2 is used as a support for the organic EL device 1. Examples of the substrate 2 include a glass substrate, quartz substrate, and plastic substrate. Moreover, a flexible substrate may be used. The flexible substrate means a bendable substrate. Examples of the flexible substrate include plastic substrates formed of polycarbonate, polyarylate, polyethersulfone, polypropylene, polyester, polyvinyl fluoride, polyvinyl chloride, polyimide, and polyethylene naphthalate. Moreover, an inorganic deposited film is also usable as the substrate.

Anode

Preferable examples of a material for the anode 3 formed on the substrate 2 include metal, an alloy, an electroconductive compound, and a mixture thereof, which have a large work function (specifically, 4.0 eV or more). Specific examples of the material include indium oxide-tin oxide (ITO: Indium Tin Oxide), indium oxide-tin oxide containing silicon or silicon oxide, indium oxide-zinc oxide, indium oxide containing tungsten oxide and zinc oxide, and graphene. In addition, the examples of the material further include gold (Au), platinum (Pt), nickel (Ni), tungsten (W), chrome (Cr), molybdenum (Mo), iron (Fe), cobalt (Co), copper (Cu), palladium (Pd), titanium (Ti), and a nitride of a metal material (e.g., titanium nitride).

The material is typically formed into a film by a sputtering method. For instance, the indium oxide-zinc oxide can be formed by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode 3 may be formed by a vacuum deposition method, a coating method, an inkjet method, a spin coating method or the like.

Among the organic layers formed on the anode 3, since the hole injecting layer 5 abutting on the anode 3 is formed of a composite material into which holes are easily injectable irrespective of the work function of the anode 3, a material usable as an electrode material (e.g., metal, an alloy, an electroconductive compound, a mixture thereof, and the elements belonging to the group 1 or 2 of the periodic table) is also usable for the anode 3.

The elements belonging to the group 1 or 2 of the periodic table, which are a material having a small work function, specifically, an alkali metal such as lithium (Li) and cesium (Cs), an alkaline earth metal such as magnesium (Mg), calcium (Ca) and strontium (Sr), an alloy containing the alkali metal and the alkaline earth metal (e.g., MgAg, AlLi), a rare earth metal such as europium (Eu) and ytterbium (Yb), and an alloy containing the rare earth metal are usable for the anode 3. It should be noted that the vacuum deposition method and the sputtering method are usable for forming the anode 3 using the alkali metal, alkaline earth metal and the alloy thereof. Further, when a silver paste is used for the anode 3, the coating method and the inkjet method are usable.

Hole Injecting Layer

The hole injecting layer 5 is a layer containing a substance exhibiting a high hole injectability. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Moreover, examples of the substance exhibiting a high hole injectability further include: an aromatic amine compound, which is a low molecular organic compound, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high polymer compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

Hole Transporting Layer

The hole transporting layer 6 is a layer containing a substance exhibiting a high hole transportability. An aromatic amine compound, carbazole derivative, anthracene derivative and the like are usable for the hole transporting layer 6. Specific examples of the substance usable for the hole transporting layer 6 include an aromatic amine compound such as 4,4'-bis[N-(1-naphthyl)-N-phenylamino]biphenyl (abbreviation: NPB) ❖ N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

For the hole transporting layer 6, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used, for instance. A high polymer compound such as poly(N-vinylcarbazole) (abbreviation: PVK) and poly(4-vinyltriphenylamine) (abbreviation: PVTPA) is also usable.

However, any substance having a hole transporting performance higher than an electron transporting performance may be used in addition to the above substances. A layer containing the highly hole-transporting substance may be provided in the form of a single layer or a laminate of two or more layers.

When two or more hole transporting layers are provided, one of the hole transporting layers containing a material having a larger energy gap is preferably provided closer to the emitting layer 7.

Emitting Layer

The emitting layer 7 is a layer containing a highly luminescent substance and various materials can be used for the emitting layer 7. For instance, a fluorescent compound that emits fluorescence and a phosphorescent compound that emits phosphorescence are usable as the highly luminescent substance. The fluorescent compound is a compound capable of emitting light from a singlet state. The phosphorescent compound is a compound capable of emitting light from a triplet state.

Examples of a blue fluorescent material usable in the emitting layer 7 include a pyrene derivative, styrylamine derivative, chrysene derivative, fluoranthene derivative, fluorene derivative, diamine derivative, and triarylamine derivative. Specific examples of the blue fluorescent material include N,N'-bis[4-(9H-carbazole-9-yl)phenyl]-N,N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA).

A green fluorescent material usable in the emitting layer 7 is exemplified by an aromatic amine derivative. Specific examples of the green fluorescent material include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthracene-2-amine (abbreviation: 2YGABPhA), and N,N,9-triphenylanthracene-9-amine (abbreviation: DPhAPhA).

Examples of a red fluorescent material usable in the emitting layer 7 include a tetracene derivative and a diamine derivative. Specific examples of the red fluorescent material include N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

A blue phosphorescent material usable for the emitting layer 7 is exemplified by a metal complex such as an iridium complex, osmium complex, and platinum complex. Specific examples of the blue phosphorescent material include bis[2-(4',6'-difluorophenyl)pyridinato-N,C2']iridium(III)tetrakis(1-pyrazolyl)borate (abbreviation: FIr6), bis[2-(4',6'-difluorophenyl)pyridinato-N,C2']iridium(III)picolinate (abbreviation: FIrpic), bis[2-(3',5'bistrifluoromethylphenyl)pyridinato-N,C2']iridium(III)picolinate (abbreviation: Ir(CF3ppy)2(pic)), and bis[2-(4',6'-difluorophenyl)pyridinato-N,C2']iridium(III)acetylacetonato (abbreviation: FIr(acac)).

A green phosphorescent material usable for the emitting layer 7 is exemplified by an iridium complex. Examples of the green phosphorescent material include tris(2-phenylpyridinatoN,C2')iridium(III) (abbreviation: Ir(ppy)$_3$), bis(2-phenylpyridinatoN,C2')iridium(III)acetylacetonato (abbreviation: Ir(ppy)$_2$(acac)), bis(1,2-diphenyl-1H-benzoimidazolato)iridium(III)acetylacetonato (abbreviation: Ir(pbi)$_2$(acac)), and bis(benzo[h]quinolinato)iridium(III)acetylacetonato (abbreviation: Ir(bzq)$_2$(acac)).

A red phosphorescent material usable for the emitting layer 7 is exemplified by a metal complex such as an iridium complex, platinum complex, terbium complex and europium complex. Specifically, the red phosphorescent material is exemplified by an organic metal complex such as bis[2-(2'-benzo[4,5-a]thienyl)pyridinato-N,C3']iridium(III)acetylacetonato (abbreviation: Ir(btp)$_2$(acac)), bis(1-phenylisoquinolinato-N,C2')iridium(III)acetylacetonato (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), and 2,3,7,8,12,13,17,18-octaethyl-21H,23H-porphyrinplatinum(II) (abbreviation: PtOEP).

Since a rare-earth metal complex such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)) produces emission from a rare earth metal ion (electron transition between different multiplicities), the rare earth metal complex is usable as the phosphorescent compound.

The emitting layer 7 may be provided by dispersing the above-described highly luminescent substance (guest material, or sometimes referred to as a dopant) in another substance (host material). As the substance for dispersing the highly luminescent substance, various substances are usable, among which a substance having a Lowest Unoccupied Molecular Orbital level (LUMO level) higher than that of the highly luminescent material and a Highest Occupied Molecular Orbital (HOMO level) lower than that of the highly luminescent substance is preferable.

Examples of the usable host material are 1) a metal complex such as an aluminum complex, beryllium complex and zinc complex, 2) a heterocyclic compound such as an oxadiazole derivative, benzimidazole derivative and phenanthroline derivative, 4) a fused aromatic compound such as a carbazole derivative, anthracene derivative, phenanthrene derivative, pyrene derivative and chrysene derivative, 3) an aromatic amine compound such as a triarylamine derivative and fused polycyclic aromatic amine derivative. Further, a plurality of types of the substances (host material) for dispersing the highly luminescent material (guest material) may be used.

Examples of the metal complex for the host material include tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ).

Examples of the heterocyclic compound for the host material include 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen) and bathocuproine (abbreviation: BCP).

Examples of the fused aromatic compound for the host material include 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), and 6,12-dimethoxy-5,11-diphenylchrysene.

Examples of the aromatic amine compound for the host material include N,N-diphenyl-9-[4-(10-phenyl-9-anthryl)phenyl]-9H-carbazole-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), NPB (or α-NPD), TPD, DFLDPBi, and BSPB.

Electron Injecting Layer

The electron injecting layer 9 is a layer containing a substance exhibiting a high electron injectability. For the electron injecting layer 9, an alkali metal, alkaline earth metal or a compound thereof are usable, examples of which include lithium (Li), cesium (Cs), calcium (Ca), lithium fluoride (LiF), cesium fluoride (CsF), calcium fluoride (CaF2), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode 4.

Alternatively, the electron injecting layer 9 may be provided by a composite material in a form of a mixture of the organic compound and an electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer 8 are usable. As the electron donor, any substance exhibiting electron donating performance to the organic compound is usable.

Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Cathode

It is preferable to use metal, an alloy, an electroconductive compound, and a mixture thereof, which have a small work function (specifically, 3.8 eV or less) for the cathode 4. Examples of such a material for the cathode include the elements belonging to the group 1 or 2 of the periodic table, specifically, an alkali metal such as lithium (Li) and cesium (Cs), an alkaline earth metal such as magnesium (Mg), calcium (Ca) and strontium (Sr), an alloy containing the alkali metal and the alkaline earth metal (e.g., MgAg, AlLi), a rare earth metal such as europium (Eu) and ytterbium (Yb), and an alloy containing the rare earth metal.

It should be noted that the vacuum deposition method and the sputtering method are usable for forming the cathode 4 using the alkali metal, alkaline earth metal and the alloy thereof. Further, when a silver paste is used for the cathode 4, the coating method and the inkjet method are usable.

By providing the electron injecting layer 9, various conductive materials such as Al, Ag, ITO, graphene, and indium oxide-tin oxide containing silicon or silicon oxide may be used for forming the cathode 4 regardless of the work function. The conductive materials can be formed into a film using the sputtering method, inkjet method, spin coating method and the like.

Layer Formation Method(s)

The method of forming the respective layers of the organic EL device 1 of the exemplary embodiment is not limited except for those specifically mentioned above, where known methods including dry film formation and wet film formation methods are applicable. Examples of the dry film formation method include vacuum deposition method, sputtering method, plasma process, and ion-plating method.

Examples of the wet film formation method include spin coating method, dipping method, flow coating method and inkjet method.

Film Thickness

The film thickness of each organic layer of the organic EL device 1 in the exemplary embodiment is subject to no limitation except for the thickness particularly described above. However, the thickness is typically preferably in a range of several nanometers to 1 μm because an excessively thin film is likely to entail defects such as pin holes while an excessively thick film requires high applied voltage and deteriorates efficiency.

In the exemplary embodiment, the ring carbon atoms refer to the number of carbon atoms among atoms forming a ring of a compound (e.g., a monocyclic compound, fused-ring compound, crosslinking compound, carbon ring compound, and heterocyclic compound) in which the atoms are bonded to each other to form the ring. When the ring is substituted by a substituent(s), carbon atom(s) contained in the substituent(s) is not counted in the ring carbon atoms. The same applies to "the ring carbon atoms" described below unless otherwise specified. For instance, a benzene ring has six ring carbon atoms, a naphthalene ring has ten ring carbon atoms, a pyridinyl group has five ring carbon atoms, and a furanyl group has four ring carbon atoms. When a benzene ring and/or a naphthalene ring is substituted by a substituent (e.g., an alkyl group), the number of carbon atoms of the alkyl group is not counted in the number of the ring carbon atoms. When a fluorene ring is substituted by a substituent (e.g., a fluorene ring) (i.e., a spirofluorene ring is included), the number of carbon atoms of the fluorene ring as the substituent is not counted in the number of the ring carbon atoms of the fluorene ring.

In the exemplary embodiment, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, ring assembly). An atom(s) not forming the ring (e.g., a hydrogen atom terminating a bond(s) of atoms forming the ring) and an atom(s) of a substituent used for substituting the ring are not counted in the ring atoms. The same applies to "the ring atoms" described below unless otherwise specified. For instance, a pyridine ring has six ring atoms, a quinazoline ring has ten ring atoms, and a furan ring has five ring atoms. A hydrogen atom(s) and/or an atom(s) of a substituent which are bonded to carbon atoms of a pyridine ring and/or quinazoline ring are not counted in the ring atoms. When a fluorene ring is substituted by a substituent (e.g., a fluorene ring) (i.e., a spirofluorene ring is included), the number of atoms of the fluorene ring as the substituent is not counted in the number of the ring atoms of the fluorene ring.

Next, each of the substituents represented by the above formulae will be described below.

Examples of the group (occasionally referred to as an aryl group) having 6 to 30 ring carbon atoms in the exemplary embodiment are a phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group preferably has 6 to 20 ring carbon atoms, more preferably 6 to 14 ring carbon atoms, further preferably 6 to 12 ring carbon atoms. Among the aryl group, a phenyl group, a biphenyl group, a naphthyl group, phenanthryl group, a terphenyl group and a fluorenyl group are particularly preferable. In a 1-fluorenyl group, 2-fluorenyl group, 3-fluorenyl group and 4-fluorenyl group, a carbon atom at a position 9 is preferably substituted by the substituted or unsubstituted alkyl group having 1 to 30 carbon atoms or an unsubstituted aryl group having 6 to 18 ring carbon atoms in a later-described exemplary embodiment.

The heterocyclic group (occasionally referred to as a hetero aryl group, hetero aromatic cyclic group, aromatic heterocyclic group) having 5 to 30 ring atoms in the exemplary embodiment preferably contains, as a hetero atom, at least one atom selected from the group consisting of nitrogen atom, sulfur atom, oxygen atom, silicon atom, selenium atom and germanium atom, more preferably at least one atom selected from the group consisting of nitrogen atom, sulfur atom and oxygen atom.

Examples of the heterocyclic group (occasionally referred to as a hetero aryl group, hetero aromatic cyclic group, aromatic heterocyclic group) having 5 to 30 ring atoms in the exemplary embodiment are a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. In 1-carbazolyl group, 2-carbazolyl group, 3-carbazolyl group and 4-carbazolyl group, a nitrogen atom at the ninth position is preferably substituted by a substituted or unsubstituted aryl group having 6 to 30 ring carbon atoms or a substituted or unsubstituted heterocyclic group having 5 to 30 ring atoms according to the exemplary embodiment.

In the exemplary embodiment, the heterocyclic group may be a group derived from partial structures represented by formulae (XY-1) to (XY-18) below.

[Formula 148]

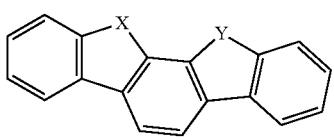

(XY-1)

-continued

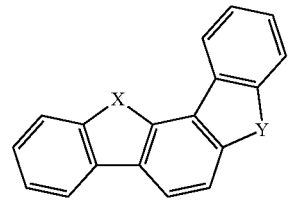

(XY-2)

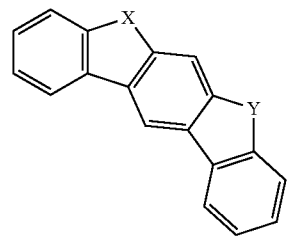

(XY-3)

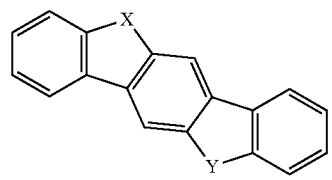

(XY-4)

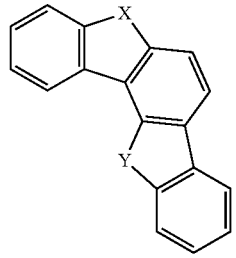

(XY-5)

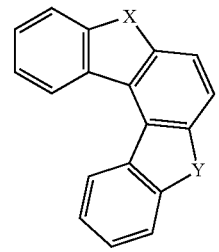

(XY-6)

[Formula 149]

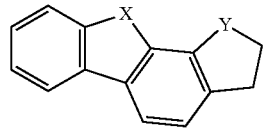

(XY-7)

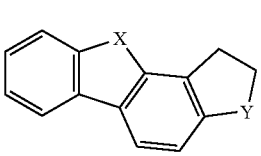

(XY-8)

(XY-9) 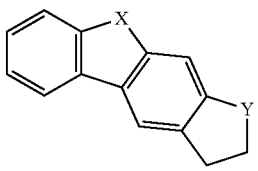

(XY-10) 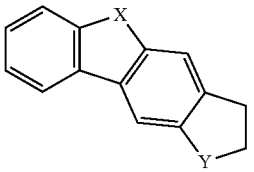

(XY-11) 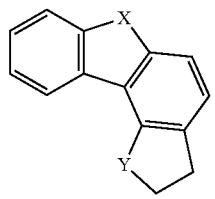

(XY-12) 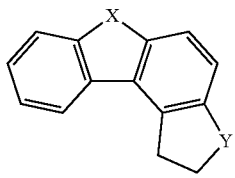

[Formula 150]

(XY-13) 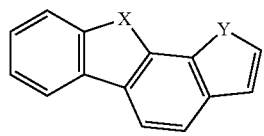

(XY-14) 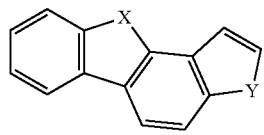

(XY-15) 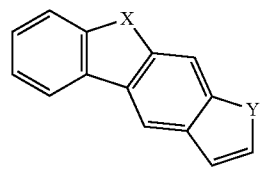

(XY-16) 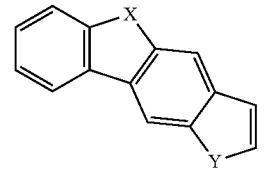

(XY-17) 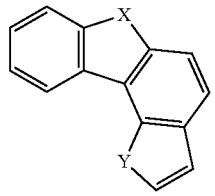

(XY-18) 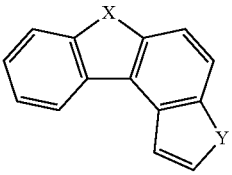

In the formulae (XY-1) to (XY-18), X and Y are each independently a hetero atom, preferably an oxygen atom, sulfur atom, selenium atom, silicon atom, or germanium atom. Each of the partial structures represented by the respective formulae (XY-1) to (XY-18) has a bond at any position to provide a heterocyclic group. The heterocyclic group may be substituted.

In the exemplary embodiment, for instance, a substituted or unsubstituted carbazolyl group may include a group in which a ring is further fused to a carbazole ring represented by a formula below. Such a group may have a substituent. Moreover, the position of the bond may be changed as needed

[Formula 151]

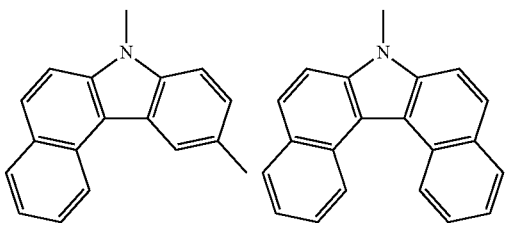

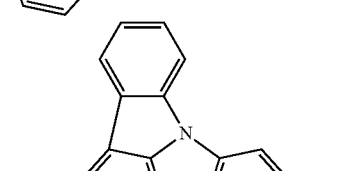

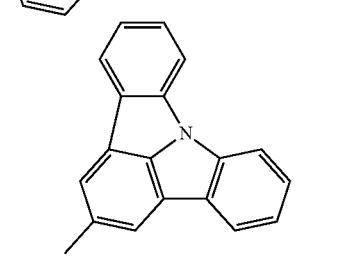

The alkyl group having 1 to 30 carbon atoms in the exemplary embodiment may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, amyl group, isoamyl group, 1-methylpentyl group, 2-methylpentyl group, 1-pentylhexyl group, 1-butylpentyl group, 1-heptyloctyl group and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are particularly preferable.

Examples of the cycloalkyl group having 3 to 30 carbon atoms in the exemplary embodiment are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are particularly preferable.

A halogenated alkyl group provided by substituting the alkyl group with a halogen atom is exemplified by a halogenated alkyl group provided by substituting the alkyl group having 1 to 30 carbon atoms with one or more halogen groups. Specific examples of the above halogenated alkyl group are a fluoromethyl group, difluoromethyl group, trifluoromethyl group, fluoroethyl group, trifluoromethylmethyl group, trifluoroethyl group and pentafluoroethyl group.

The alkenyl group having 2 to 30 carbon atoms in the exemplary embodiment may be linear, branched or cyclic. Examples of the alkenyl group are a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group and cyclohexadienyl group.

The alkynyl group having 2 to 30 carbon atoms in the exemplary embodiment may be linear, branched or cyclic. Examples of the alkynyl group having 2 to 30 carbon atoms are an ethynyl group, a propynyl group and a 2-phenylethynyl group.

Examples of the substituted silyl group in the exemplary embodiment are an alkylsilyl group having 3 to 30 carbon atoms and arylsilyl group having 6 to 30 ring carbon atoms.

The alkylsilyl group having 3 to 30 carbon atoms in the exemplary embodiment is exemplified by a trialkylsilyl group having the above examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyldimethylsilyl group, propyldimethylsilyl group, and triisopropylsilyl group. Three alkyl groups in the trialkylsilyl group may be the same or different.

Examples of the arylsilyl group having 6 to 30 ring carbon atoms in the exemplary embodiment are a dialkylarylsilyl group, alkyldiarylsilyl group and triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms.

The triarylsilyl group is exemplified by a triarylsilyl group including three of the aryl group listed as the examples of the aryl group having 6 to 30 ring carbon atoms. The triarylsilyl group preferably has 18 to 30 carbon atoms.

The alkoxy group having 1 to 30 carbon atoms in the exemplary embodiment is represented by $-OZ_1$. $Z_1$ is exemplified by the above alkyl group having 1 to 30 carbon atoms. Examples of the alkoxy group are a methoxy group, ethoxy group, propoxy group, butoxy group, pentyloxy group and hexyloxy group. The alkoxy group preferably has 1 to 20 carbon atoms.

A halogenated alkoxy group provided by substituting the alkoxy group with a halogen atom is exemplified by a halogenated alkoxy group provided by substituting the alkoxy group having 1 to 30 carbon atoms with one or more fluorine groups.

The aryloxy group having 6 to 30 ring carbon atoms in the exemplary embodiment is represented by $-OZ_2$. $Z_2$ is exemplified by the above aryl group having 6 to 30 ring carbon atoms. The aryloxy group preferably has 6 to 20 ring carbon atoms. The aryloxy group is exemplified by a phenoxy group.

The alkylthio group having 1 to 30 carbon atoms is represented by $-SR_V$. $R_V$ is exemplified by the alkyl group having 1 to 30 carbon atoms. The alkylthio group preferably has 1 to 20 carbon atoms.

The arylthio group having 6 to 30 ring carbon atoms is represented by $-SR_W$. $R_W$ is exemplified by the above aryl group having 6 to 30 ring carbon atoms. The arylthio group preferably has 6 to 20 ring carbon atoms.

Examples of the halogen atom are a fluorine atom, a chlorine atom, a bromine atom and an iodine atom, among which a fluorine atom is preferable.

An aldehyde group, a carbonyl group, an ester group, a carbamoyl group and an amino group may be substituted by an aliphatic hydrocarbon, an alicyclic hydrocarbon, an aromatic hydrocarbon or a hetero ring, where the aliphatic hydrocarbon, the alicyclic hydrocarbon, the aromatic hydrocarbon, and the hetero ring may further include a substituent.

A siloxanyl group is a silicon compound group with an ether bond, examples of which include a trimethylsiloxanyl group.

Herein, "carbon atoms forming a ring (ring carbon atoms)" mean carbon atoms forming a saturated ring, unsaturated ring, or aromatic ring. "Ring atoms" mean carbon atoms and hetero atoms forming a hetero ring including a saturated ring, an unsaturated ring and an aromatic ring.

Further, in the exemplary embodiment, a hydrogen atom includes isotopes having different numbers of neutrons, specifically, protium, deuterium and tritium.

Examples of the substituent meant by "substituted or unsubstituted" include aralkyl group, alkylamino group, arylamino group, hydroxyl group, nitro group and carboxy group in addition to the above-described aryl group, heterocyclic group, alkyl group (linear or branched alkyl group, cycloalkyl group and haloalkyl group), alkenyl group, alkynyl group, alkylsilyl group, arylsilyl group, alkoxy group, aryloxy group, alkylthio group, arylthio group, halogen atom and cyano group.

Among the above substituents, an aryl group, a heterocyclic group, an alkyl group, a halogen atom, an alkylsilyl group, an arylsilyl group and a cyano group are preferable. More preferable substituents are one listed as the preferable substituents described for each substituent.

The above substituents may further be substituted by an aralkyl group, alkylamino group, arylamino group, hydroxyl group, nitro group and carboxy group in addition to the above-described aryl group, heterocyclic group, alkyl group, alkenyl group, alkynyl group, alkylsilyl group, arylsilyl group, alkoxy group, aryloxy group, alkylthio group, arylthio group, halogen atom and cyano group. In addition, adjacent two or more of the substituents may be bonded to each other to form a ring.

The aralkyl group preferably has 6 to 30 ring carbon atoms and is represented by —$Z_3$—$Z_4$. $Z_3$ is exemplified by an alkylene group corresponding to the above alkyl group having 1 to 30 carbon atoms. $Z_4$ is exemplified by the above aryl group having 6 to 30 ring carbon atoms. The aralkyl group is preferably an aralkyl group having 7 to 30 carbon atoms, in which an aryl portion has 6 to 30 carbon atoms, preferably 6 to 20 carbon atoms, more preferably 6 to 12 carbon atoms, and an alkyl portion has 1 to 30 carbon atoms, preferably 1 to 20 carbon atoms, more preferably 1 to 10 carbon atoms, further preferably 1 to 6 carbon atoms. Examples of the aralkyl group include a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

The alkylamino group having 2 to 30 carbon atoms is represented by —$NHR_V$ or —$N(R_V)_2$. $R_V$ is exemplified by the alkyl group having 1 to 30 carbon atoms.

The acylamino group having 6 to 60 ring carbon atoms is represented by —$NHR_W$ or —$N(R_W)_2$. $R_W$ is exemplified by the above aryl group having 6 to 30 ring carbon atoms.

"Unsubstituted" in "substituted or unsubstituted" means that a group is not substituted by the above-described substituents but bonded with a hydrogen atom.

In the exemplary embodiment, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Here, "YY" is larger than "XX." Each of "XX" and "YY" represents an integer of 1 or more.

In the exemplary embodiment, "XX to YY atoms" in the description of "substituted or unsubstituted ZZ group having XX to YY atoms" represent atoms of an unsubstituted ZZ group and does not include atoms of a substituent(s) of the substituted ZZ group. Here, "YY" is larger than "XX." Each of "XX" and "YY" represents an integer of 1 or more.

In the exemplary embodiment, when the substituents are bonded to each other to form a ring structure, the ring structure is in a form of a saturated ring, an unsaturated ring, an aromatic hydrocarbon ring or a hetero ring. Moreover, in the exemplary embodiment, examples of the aromatic hydrocarbon ring and the hetero ring include a cyclic structure from which the above monovalent group is derived.

In the exemplary embodiment, examples of the aromatic hydrocarbon group and the heterocyclic group in the linking group include a divalent or multivalent group obtained by eliminating one or more atoms from the above monovalent groups. Further, the "linear or branched hydrocarbon group having a carbon-carbon double bond and 2 to 30 carbon atoms" in the linking group is exemplified by a divalent or multivalent group obtained by eliminating one or more atoms from the above alkenyl groups, and the "linear or branched hydrocarbon group having a carbon-carbon triple bond and 2 to 30 carbon atoms" in the linking group is exemplified by a divalent or multivalent group obtained by eliminating one or more atoms from the above alkynyl groups.

Since the compound of the exemplary embodiment has the above-described arrangement, it is believed that the electron mobility is appropriately restrained. In the organic EL device 1 containing the compound of the exemplary embodiment in the electron transporting layer 8, it is believed that the position at which electrons and holes are recombined to emit light is remote from the hole transporting layer 6. It is believed that, as a result, the degradation of the compound contained in the hole transporting layer 6 is restrained to prolong the lifetime of the organic EL device 1. Further, according to the compound of the exemplary embodiment, since the electron mobility is restrained at an appropriate level, the organic EL device 1 can emit light while the drive voltage is kept at an appropriate level.

Electronic Device

The organic EL device 1 according to the exemplary embodiment of the invention is usable for an electronic device such as a display device and a light-emitting device. Examples of the display device include a display component such as an organic EL panel module, TV, mobile phone, tablet and personal computer. Examples of the light-emitting device include an illuminator and a vehicle light.

Modification of Embodiment(s)

It should be noted that the invention is not limited to the above exemplary embodiments but may include any modification and improvement as long as such modification and improvement are compatible with the invention.

The arrangement of the organic EL device is not limited to the arrangement described in the exemplary embodiment.

For instance, a blocking layer may be provided adjacent to the emitting layer closer to the anode and/or closer to the cathode. The blocking layer preferably abuts on the emitting layer and blocks at least one of holes, electrons and excitons.

For instance, when the blocking layer is provided abutting on the side of the emitting layer closer to the cathode, the blocking layer transports the electrons and blocks the holes from reaching a layer (e.g., the electron transporting layer) closer to the cathode beyond the blocking layer. When the organic EL device includes the electron transporting layer, the organic EL device preferably includes the blocking layer between the emitting layer and the electron transporting layer.

When the blocking layer is provided abutting on the side of the emitting layer closer to the anode, the blocking layer transports the holes and blocks the electrons from reaching a layer (e.g., the hole transporting layer) closer to the anode beyond the blocking layer. When the organic EL device includes the hole transporting layer, the organic EL device preferably includes the blocking layer between the emitting layer and the hole transporting layer.

Moreover, the blocking layer may abut on the emitting layer so that excited energy does not leak out from the emitting layer toward neighboring layer(s). Accordingly, the blocking layer blocks excitons generated in the emitting layer from transferring to a layer(s) (e.g., the electron transporting layer and the hole transporting layer) closer to the electrode(s) beyond the blocking layer.

The emitting layer and the blocking layer preferably abut on each other.

In addition, the specific structure and shapes for practicing the invention may be altered to other structures and shapes as long as such other structures and shapes are compatible with the invention.

The compound according to the exemplary embodiment may be contained in the electron injecting layer 9 or may be contained in both of the electron transporting layer 8 and the electron injecting layer 9. The compound according to the exemplary embodiment may be contained in the other organic layer(s).

EXAMPLES

Examples of the invention will be described below. It should be understood that, however, the scope of the invention is not limited by the Examples.

Synthesis Example 1

A synthesis scheme of a compound (1) is shown below.

[Formula 152]

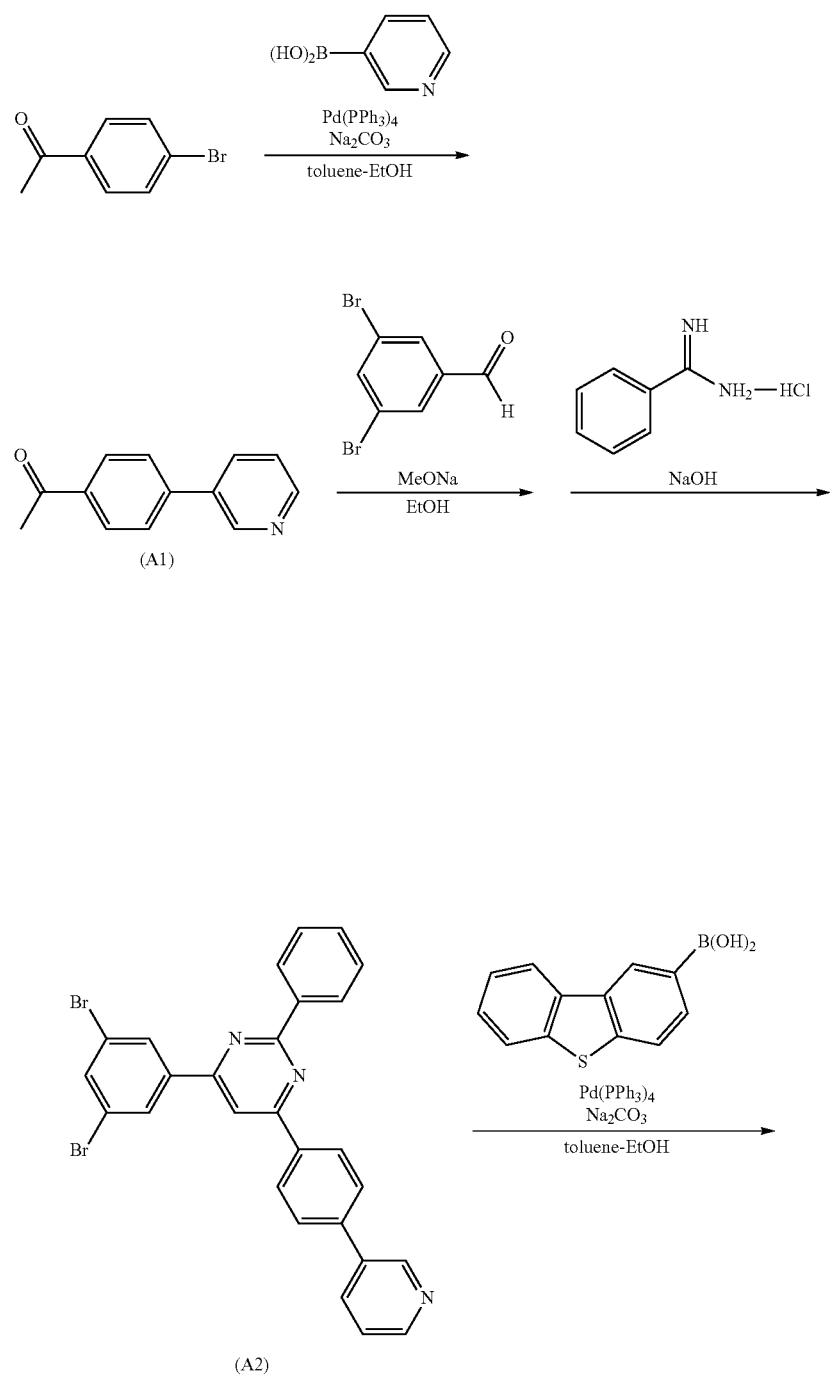

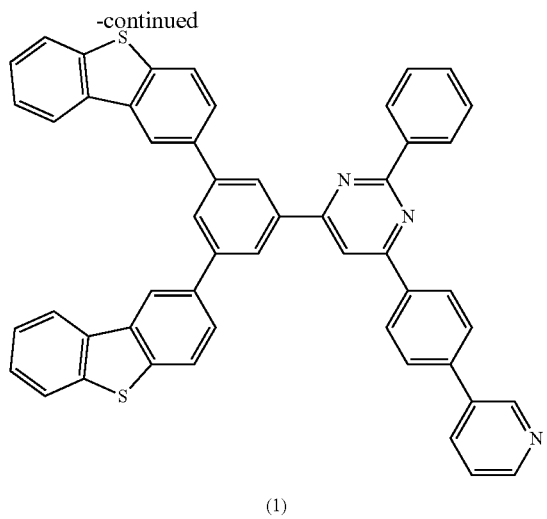

(1)

(1-1) Synthesis of Intermediate (A1)

Under an argon gas atmosphere, toluene (2250 mL) and ethanol (750 mL) were added to a mixture of 4-bromoacetophenone (183 g, 0.919 mol), 3-pyridine boronic acid (124 g, 1.01 mol), tetrakis(triphenylphosphine)palladium(0) (21.3 g, 0.0184 mol) and 2M aqueous solution of sodium carbonate (1.38 L, 2.76 mol), and the mixture solution was stirred at 75 degrees C. for 12 hours. After the reaction, the mixture solution was cooled to a room temperature, added with 3 L of water and separated. Subsequently, an organic layer was condensed under reduced pressure. The mixture was dissolved in toluene at a reflux temperature and was passed through a short column chromatography of silica gel. The obtained solution was condensed under reduced pressure and added with heptane, where crystals were precipitated, so that an intermediate (A1) (182 g, 0.923 mol) was obtained. An yield of the intermediate (A1) was 100%.

(1-2) Synthesis of Intermediate (A2)

Under an argon gas atmosphere, methanol solution (28%, 50 mL) of sodium methoxide was dropped to a mixture of 3,5-dibromobenzaldehyde (180 g, 0.682 mol), the intermediate (A1) (135 g, 0.682 mol) and ethanol (4 L), and the mixture solution was stirred at room temperature for 3 hours. After stirring, benzamidine hydrochloride (107 g, 0.682 mol) and sodium hydroxide (33 g, 0.818 mol) were added to the mixture solution and the mixture solution was stirred at 75 degrees C. for 18 hours. After the reaction, the mixture solution was cooled to a room temperature, and the precipitate was filtrated and washed using methanol. After washing, the precipitate was heated and dissolved in toluene and was filtrated. After cooling the filtrate, precipitate was separated by filtration to obtain an intermediate (A2) (140 g, 0.258 mol). An yield of the intermediate (A2) was 37%.

(1-3) Synthesis of Compound (1) Under an argon gas atmosphere, toluene (750 mL) and ethanol (250 mL) were added to a mixture of the intermediate (A2) (52.0 g, 95.7 mmol), dibenzothiophene-2-boronic acid (48.0 g, 211 mmol), tetrakis(triphenylphosphine)palladium(0) (4.40 g, 3.83 mmol) and 2M aqueous solution of sodium carbonate (30.4 g, 287 mmol) and the mixture solution was stirred at 85 degrees C. for 17 hours. After the reaction, the mixture solution was cooled to a room temperature, and precipitated crystals were separated by filtration. After the filtration, the precipitated crystals were purified using xylene and chlorobenzene in a recrystallization method to obtain a compound (1) (47.5 g, 62.7 mmol). An yield of the compound (1) was 66%. As a result of mass spectroscopy, it was found that m/e=749 and the compound was identified to be the above compound (1) (Exact mass: 749.20).

Synthesis Example 2

A synthesis scheme of a compound (2) is shown below.

[Formula 153]

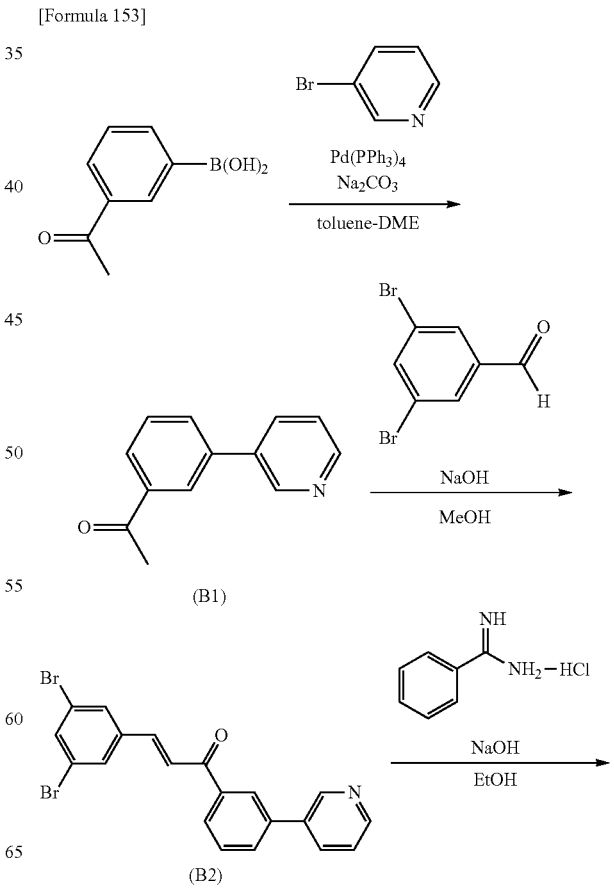

-continued

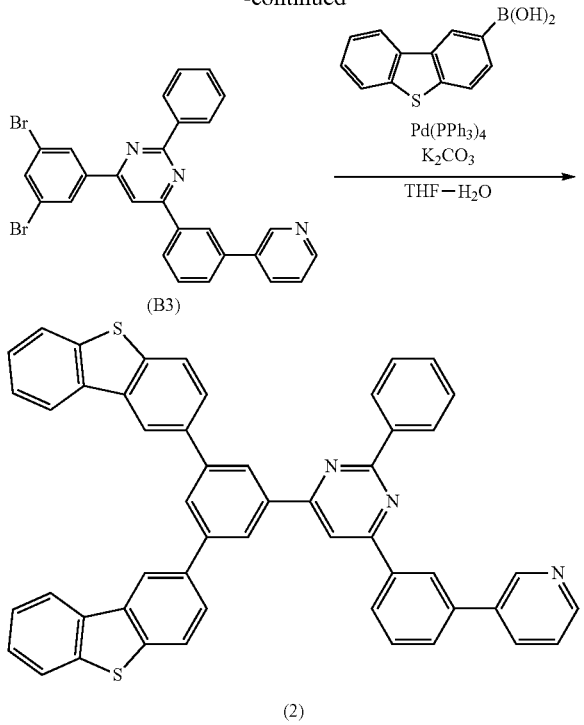

(B3)

(2)

(2-1) Synthesis of Intermediate (B1)

Under an argon gas atmosphere, toluene (158 mL) and 1,2-dimethoxyethane (158 mL) were added to a mixture of 3-bromopyridine (10.0 g, 63.3 mmol), 3-acetylphenyl boronic acid (12.5 g, 75.9 mol), tetrakis(triphenylphosphine) palladium(0) (2.20 g, 1.90 mmol) and 2M aqueous solution of sodium carbonate (26.8 g, 253 mmol), and the mixture solution was stirred at a reflux temperature for 10 hours. After the reaction, the mixture solution was cooled to a room temperature. After cooling, the mixture was filtrated. After the filtration, the filtrated substance was subjected to extraction using acetic ether. After the extraction, the extracted substance was washed using saturated saline. After washing, the solution obtained after drying using sodium sulfate was condensed under a reduced pressure. After the condensation under the reduced pressure, the condensed substance was purified by a silica-gel column chromatography, thereby obtaining an intermediate (B1) (10.8 g, 54.8 mmol). An yield of the intermediate (B1) was 87%.

(2-2) Synthesis of Intermediate (B2)

Under an argon gas atmosphere, sodium hydride (900 mg, 22.7 mmol) was added to a mixture of 3,5-dibromobenzaldehyde (6.00 g, 22.7 mmol), the intermediate (B1) (4.50 g, 22.7 mmol) and methanol (57 mL), and the mixture solution was stirred at room temperature for 3 hours. After the reaction, the reactant was separated by filtration and washed with methanol to obtain an intermediate (B2) (6.36 g, 14.4 mmol). An yield of the intermediate (B2) was 63%.

(2-3) Synthesis of Intermediate (B3)

Under an argon gas atmosphere, sodium hydride (50 mg, 1.36 mmol) was added to a mixture of the intermediate (B2) (500 mg, 1.13 mmol), benzamidine hydrochloride (180 mg, 1.13 mol) and ethanol (6 mL), and the mixture solution was stirred while being heated and refluxed for 8 hours. After the reaction, the mixture solution was cooled to a room temperature and the precipitate was separated by filtration and washed with water and methanol to obtain an intermediate (B3) (260 mg, 0.479 mmol). An yield of the intermediate (B3) was 42%.

(2-4) Synthesis of Compound (2)

Under an argon gas atmosphere, tetrahydrofuran (35 mL) was added to the intermediate (B3) (3.80 g, 6.99 mmol), dibenzothiophene-2-boronic acid (4.00 g, 17.5 mmol), tetrakis(triphenylphosphine)palladium(0) (480 mg, 0.419 mmol) and 2M aqueous solution of sodium carbonate (3.90 g, 28.0 mmol), and the mixture solution was heated and refluxed while being stirred for 8 hours. After the reaction, the mixture solution was cooled to a room temperature, and precipitated crystals were separated by filtration and washed using water and methanol. After being washed, the precipitated crystals were dissolved in heated toluene, passed through a short column chromatography and was condensed under a reduced pressure. Then, the solution was purified through recrystallization in toluene and methanol washing to obtain a compound (2) (3.78 g, 5.04 mmol). An yield of the compound (2) was 72%. As a result of mass spectroscopy, it was found that m/e=749 and the compound was identified to be the above compound (2) (Exact mass: 749.20).

Synthesis Example 3

A synthesis scheme of a compound (3) is shown below.

[Formula 154]

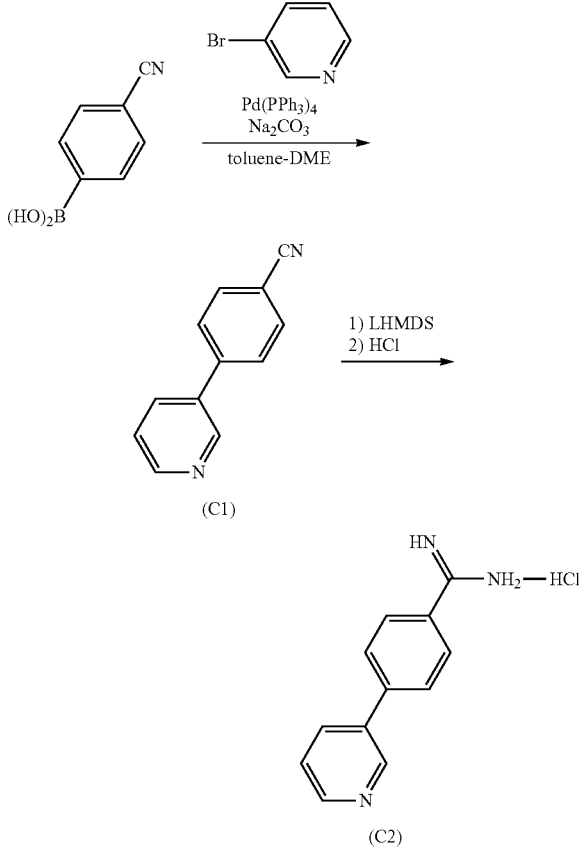

[Formula 155]

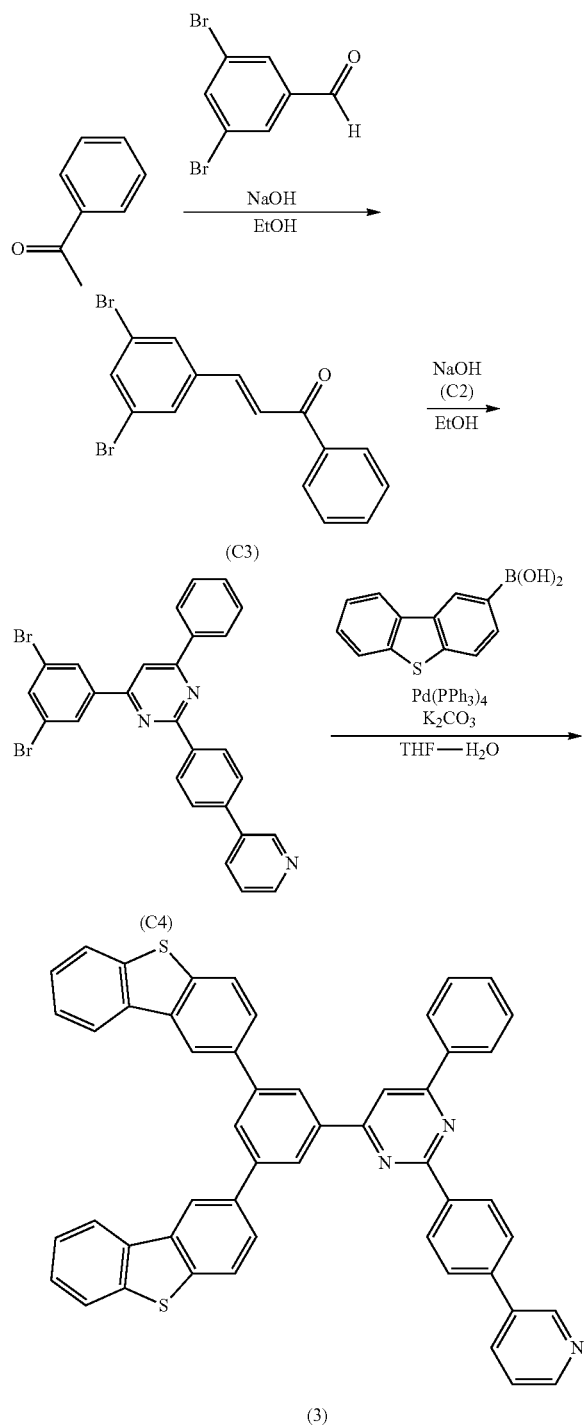

(3-1) Synthesis of Intermediate (C1)

Under an argon gas atmosphere, toluene (158 mL) and 1,2-dimethoxyethane (158 mL) were added to a mixture of 3-bromopyridine (10.0 g, 63.3 mmol), 4-cyanophenyl boronic acid (11.2 g, 75.9 mmol), tetrakis(triphenylphosphine)palladium(0) (2.20 g, 1.90 mmol) and 2M aqueous solution of sodium carbonate (26.8 g, 253 mmol), and the mixture solution was stirred at a reflux temperature for 8 hours. After the reaction, the mixture solution was cooled to a room temperature. After cooling, the mixture was filtrated. After the filtration, the filtrated substance was subjected to extraction using acetic ether. After the extraction, the extracted substance was washed using saturated saline. After washing, the solution obtained after drying using sodium sulfate was condensed under a reduced pressure. After the condensation under the reduced pressure, the condensed substance was purified by a silica-gel column chromatography, thereby obtaining an intermediate (C1) (9.59 g, 53.2 mmol). An yield of the intermediate (C1) was 84%.

(3-2) Synthesis of Intermediate (C2)

Under an argon gas atmosphere, tetrahydrofuran (92.5 mL) was added to the intermediate (C1) (3.00 g, 16.7 mmol) and the mixture solution was cooled to −5 degrees C. After cooling, 26% tetrahydrofuran solution (1.3 mol/L, 51 mL, 66.6 mmol) of lithium bis(trimethylsilyl)amide was dropped while being cooled in an ice bath. After the dropping process, the temperature of the solution was raised to an ambient temperature. After raising the temperature, the solution was again cooled to −5 degrees C. While cooling in an ice bath, cyclopentylmethylether solution of hydrochloric acid (4 mol/L, 55.5 mL, 222 mmol) was dropped in the solution and the solution was stirred at 0 degrees C. for two hours. After the reaction, precipitated crystal was separated by filtration and washed with hexane and diethylether to obtain a crude product of an intermediate (C2) (7.94 g). It should be noted that lithium bis(trimethylsilyl)amide is sometimes abbreviated as LHMDS herein.

(3-3) Synthesis of Intermediate (C3)

Under an argon gas atmosphere, sodium hydride (0.990 g, 24.6 mmol) was added to a mixture of acetophenone (2.28 g, 19.0 mmol), 3,5-dibromobenzaldehyde (5.00 g, 19.0 mmol), ethanol (50 mL) and water (10 mL), and the mixture solution was stirred at room temperature for 6 hours. After the reaction, the mixture was separated by filtration and washed with water to obtain an intermediate (C3) (5.96 g, 16.3 mmol). An yield of the intermediate (C3) was 86%.

(3-4) Synthesis of Intermediate (C4)

Under an argon gas atmosphere, sodium hydride (540 mg, 13.5 mmol) was added to a mixture of the intermediate (C3) (500 mg, 1.37 mmol), the intermediate (C2) (670 mg, 2.47 mol) and ethanol (14 mL), and the mixture solution was stirred while being heated and refluxed for 14 hours. After the reaction, the mixture solution was cooled to a room temperature, and the precipitate was separated by filtration and washed with water and ethanol to obtain an intermediate (C4) (320 mg, 0.589 mmol). An yield of the intermediate (C4) was 43%.

(3-5) Synthesis of Compound (3)

Under an argon gas atmosphere, tetrahydrofuran (46 mL) was added to a mixture of the intermediate (C4) (5.00 g, 9.20 mmol), dibenzothiophene-2-boronic acid (5.20 g, 23.0 mmol), tetrakis(triphenylphosphine)palladium(0) (640 mg, 0.552 mmol) and 2M aqueous solution of sodium carbonate (5.10 g, 36.8 mmol) and the solution was heated and refluxed while being stirred for 7 hours. After the reaction, the mixture solution was cooled to a room temperature, and the precipitated solid was separated by filtration and washed using water and methanol. After being washed, the precipitated solid was dissolved in heated toluene, passed through a short column chromatography and was condensed under a reduced pressure. After the condensation under a reduced pressure, the solid was purified through recrystallization in toluene and methanol washing to obtain a compound (3) (4.22 g, 5.62 mmol). An yield of the compound (3) was 61%.

As a result of mass spectroscopy, it was found that m/e=749 and the compound was identified to be the above compound (3) (Exact mass: 749.20).

Synthesis Example 4

A synthesis scheme of a compound (4) is shown below.

[Formula 156]

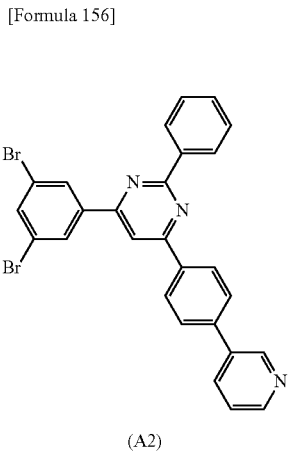
(A2)

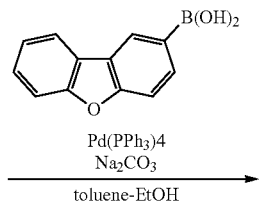

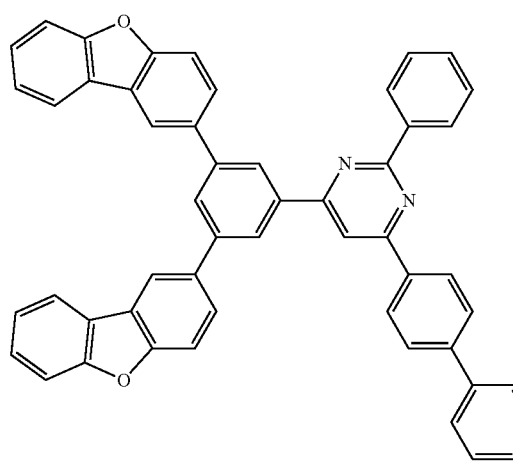
(4)

(4-1) Synthesis of Compound (4)

Under an argon gas atmosphere, toluene (750 mL) and ethanol (250 mL) were added to a mixture of the intermediate (A2) (52.0 g, 95.7 mmol), dibenzofuran-2-boronic acid (44.7 g, 211 mmol), tetrakis(triphenylphosphine)palladium (0) (4.40 g, 3.83 mmol) and 2M aqueous solution of sodium carbonate (30.4 g, 287 mmol) and the solution was stirred at 85 degrees C. for 15 hours. After the reaction, the mixture solution was cooled to a room temperature, and precipitated crystals were separated by filtration. After the filtration, the precipitated crystals were purified using xylene and chlorobenzene in a recrystallization method to obtain a compound (4) (42.4 g, 59.0 mmol). An yield of the compound (4) was 66%. As a result of mass spectroscopy, it was found that m/e=717 and the compound was identified to be the above compound (4) (Exact mass: 717.24).

Synthesis Example 5

A synthesis scheme of a compound (5) is shown below.

[Formula 157]

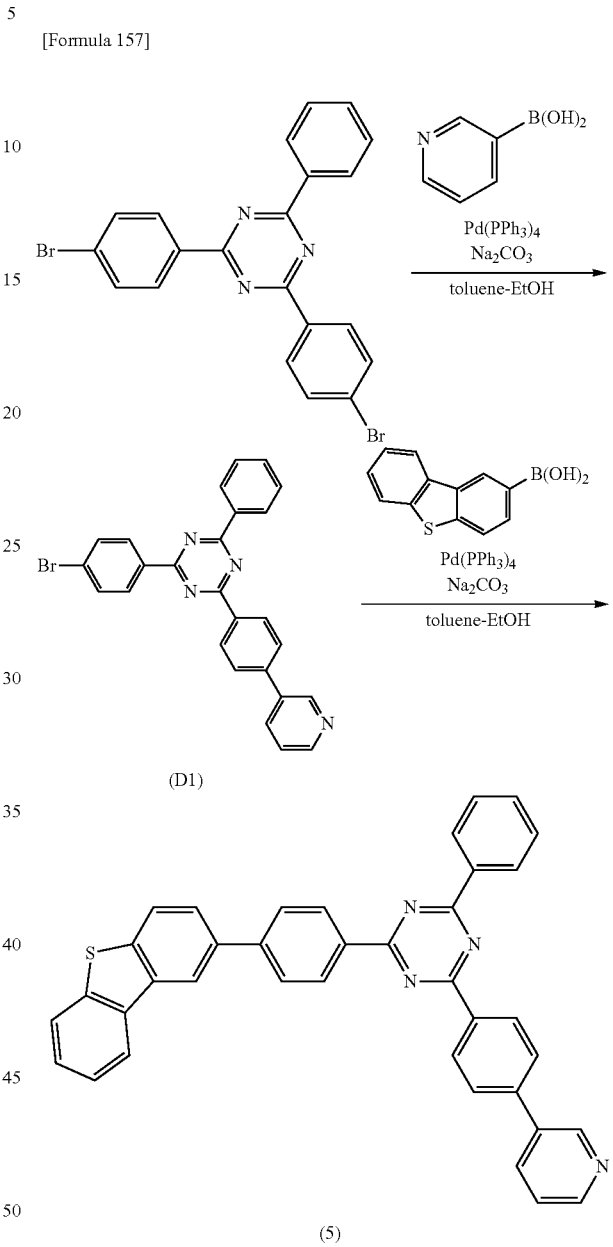

(5-1) Synthesis of Intermediate (D1)

Under an argon gas atmosphere, toluene (1500 mL) and ethanol (500 mL) were added to a mixture of 2,4-bis(4-bromophenyl)-6-phenyl-1,3,5-triazine (128 g, 275 mmol), 3-pyridyl boronic acid (33.8 g, 275 mmol), tetrakis(triphenylphosphine)palladium(0) (6.36 g, 5.50 mmol) and 2M aqueous solution of sodium carbonate (43.8 g, 413 mmol), and the mixture solution was stirred at 85 degrees C. for 8 hours. After the reaction, the mixture solution was cooled to a room temperature, and precipitated crystals were separated by filtration. After the filtration, the precipitated crystals were purified by silica-gel column chromatography, thereby obtaining an intermediate (D1) (51.2 g, 110 mmol). An yield of the intermediate (D1) was 40%.

(5-2) Synthesis of Compound (5)

Under an argon gas atmosphere, toluene (750 mL) and ethanol (250 mL) were added to a mixture of the intermediate (D1) (50.0 g, 107 mmol), dibenzothiophene-2-boronic acid (26.9 g, 118 mmol), tetrakis(triphenylphosphine)palladium(0) (1.46 g, 1.27 mmol) and 2M aqueous solution of sodium carbonate (17.1 g, 161 mmol) and the mixture solution was stirred at 85 degrees C. for 15 hours. After the reaction, the mixture solution was cooled to a room temperature, and precipitated crystals were separated by filtration. After the filtration, the precipitated crystals were purified using xylene and chlorobenzene in a recrystallization method to obtain a compound (5) (42.6 g, 74.9 mmol). An yield of the compound (5) was 70%. As a result of mass spectroscopy, it was found that m/e=568 and the compound was identified to be the above compound (5) (Exact mass: 568.17).

Synthesis Example 6

A synthesis scheme of a compound (6) is shown below.

[Formula 158]

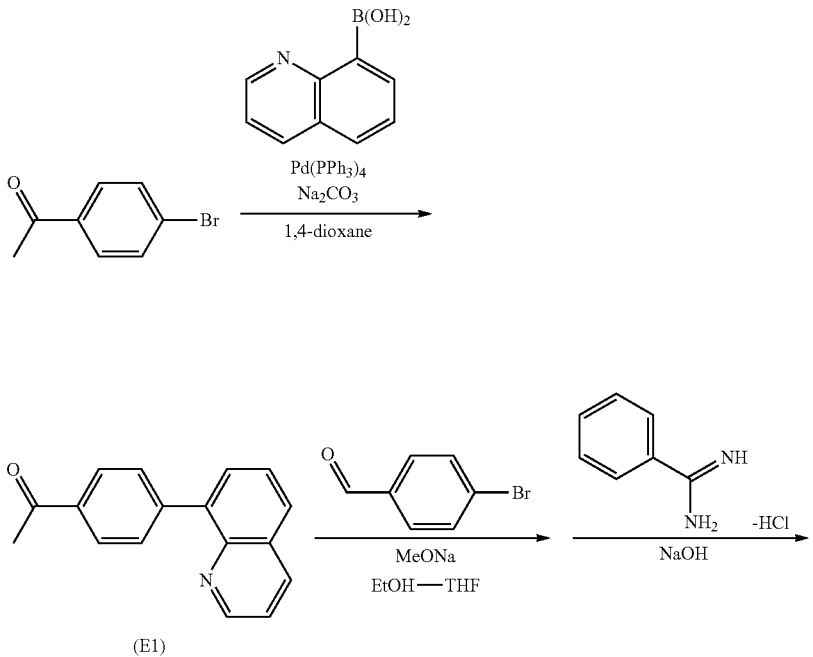

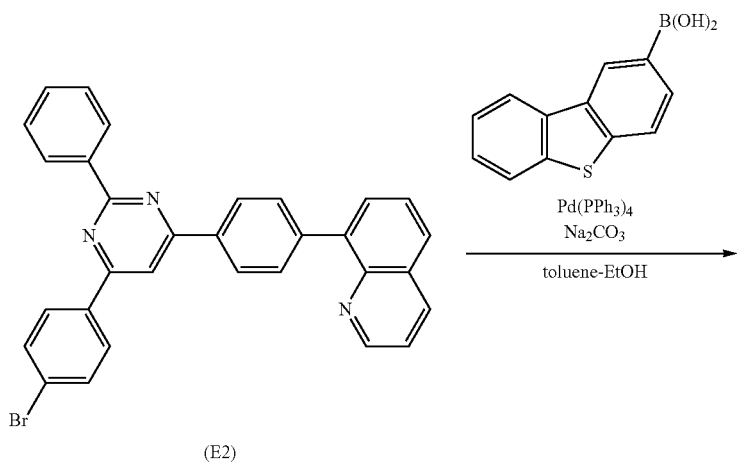

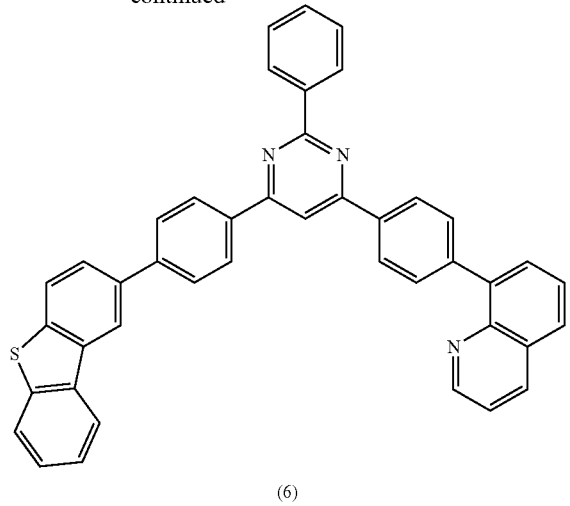

(6)

(6-1) Synthesis of Intermediate (E1)

Under an argon gas atmosphere, dioxane (520 mL) was added to a mixture of 4-bromoacetophenone (27.9 g, 140 mmol), quinoline-8-boronic acid (24.2 g, 140 mmol), tetrakis(triphenylphosphine)palladium(0) (3.20 g, 2.80 mmol), and 2M aqueous solution of sodium carbonate (140 mL, 280 mol), and the mixture solution was stirred at 85 degrees C. for 58 hours. After the reaction, the mixture solution was cooled to a room temperature, added with toluene (300 mL) and water (300 mL) and separated. Subsequently, an organic layer was condensed under reduced pressure. The mixture was dissolved in toluene and was passed through a short column chromatography of silica gel. The obtained solution was condensed under reduced pressure, where crystals were precipitated, thereby obtaining an intermediate (E1) (27.4 g, 109 mmol). An yield of the intermediate (E1) was 78%.

(6-2) Synthesis of Intermediate (E2)

Under an argon gas atmosphere, methanol solution (28%, 9 mL) of sodium methoxide was dropped to a mixture of 4-bromobenzaldehyde (20.5 g, 111 mmol), the intermediate (E1) (27.4 g, 111 mmol), ethanol (410 mL) and tetrahydrofuran (270 mL), and the mixture solution was stirred at room temperature all night. After stirring, benzamidine hydrochloride (17.4 g, 111 mmol) and sodium hydroxide (5.30 g, 130 mmol) were added to the mixture solution and the mixture solution was stirred at 70 degrees C. for 23 hours. After the reaction, the mixture solution was cooled to a room temperature, water (280 mL) was added and precipitated substances were separated by filtration and washed using methanol. After being washed, the mixture was dissolved in heated toluene and was passed through a short column chromatography of silica gel. The obtained solution was condensed under reduced pressure, where crystals were precipitated, thereby obtaining an intermediate (E2) (15.4 g, 30.0 mmol). An yield of the intermediate (E2) was 27%.

(6-3) Synthesis of Compound (6)

Under an argon gas atmosphere, toluene (180 mL) and ethanol (60 mL) were added to a mixture of the intermediate (E2) (15.4 g, 25.0 mmol), dibenzothiophene-2-boronic acid (6.27 g, 27.5 mmol), tetrakis(triphenylphosphine)palladium (0) (0.578 g, 0.500 mmol) and 2M aqueous solution of sodium carbonate (3.98 g, 37.5 mmol), and the solution was stirred at 85 degrees C. for 17 hours. After the reaction, the mixture solution was cooled to a room temperature, and precipitated crystals were separated by filtration. After the filtration, the precipitated crystals were purified using xylene and chlorobenzene in a recrystallization method to obtain a compound (6) (10.8 g, 17.5 mmol). An yield of the compound (6) was 70%. As a result of mass spectroscopy, it was found that m/e=617 and the compound was identified to be the above compound (6) (Exact mass: 617.19).

Synthesis Example 7

A synthesis scheme of a compound (7) is shown below.

[Formula 159]

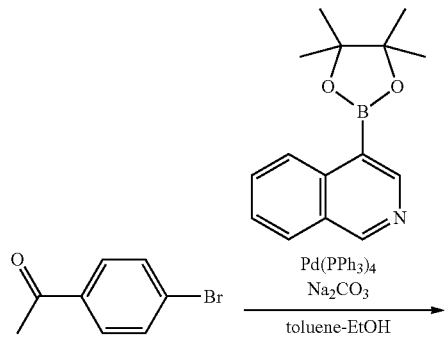

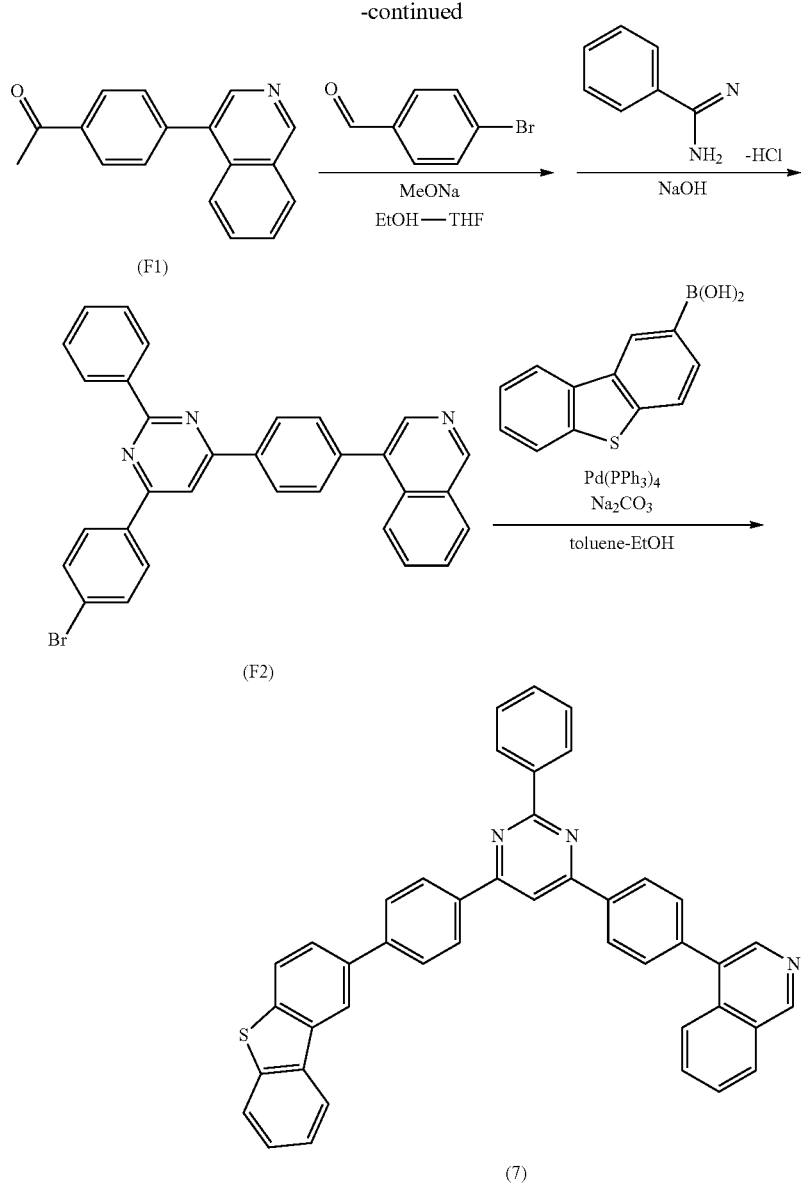

(7-1) Synthesis of Intermediate (F1)

Under an argon gas atmosphere, toluene (416 mL) and ethanol (154 mL) were added to a mixture of 4-bromoacetophenone (25.0 g, 126 mmol), 4-(4,4,5,5-tetramethyl-1,3,2-dioxaborolane-2-yl)isoquinoline (32.0 g, 126 mmol), tetrakis(triphenylphosphine)palladium(0) (2.90 g, 2.51 mmol) and 2M aqueous solution of sodium carbonate (126 mL, 251 mol), and the mixture solution was stirred at 75 degrees C. for 39 hours. After the reaction, the mixture solution was cooled to a room temperature, added with toluene (200 mL) and water (200 mL) and separated. Subsequently, an organic layer was condensed under reduced pressure. The mixture was dissolved in toluene and was passed through a short column chromatography of silica gel. The obtained solution was condensed under reduced pressure, where crystals were precipitated, thereby obtaining an intermediate (F1) (23.7 g, 95.8 mmol). An yield of the intermediate (F1) was 76%.

(7-2) Synthesis of Intermediate (F2)

Under an argon gas atmosphere, methanol solution (28%, 7.2 mL) of sodium methoxide was dropped to a mixture of 4-bromobenzaldehyde (17.2 g, 93.0 mmol), the intermediate (F1) (23.0 g, 93.0 mmol), ethanol (400 mL) and tetrahydrofuran (200 mL), and the mixture solution was stirred at room temperature for 2 hours. After stirring, benzamidine hydrochloride (14.6 g, 3.0 mmol) and sodium hydroxide (4.46 g, 112 mmol) were added to the mixture solution and the mixture solution was stirred at 72 degrees C. for 17 hours. After the reaction, the mixture solution was cooled to a room temperature, water (400 mL) was added and precipitated substances were separated by filtration and washed using water and methanol. After being washed, the mixture was dissolved in heated toluene and was passed through a short column chromatography of silica gel. The obtained solution was condensed under reduced pressure, where crystals were precipitated, thereby obtaining an intermediate (F2) (19.0 g, 37.2 mmol). An yield of the intermediate (F2) was 40%.

(7-3) Synthesis of Compound (7)

Under an argon gas atmosphere, toluene (230 mL) and ethanol (80 mL) were added to a mixture of the intermediate (F2) (17.0 g, 33.0 mmol), dibenzothiophene-2-boronic acid (8.28 g, 36.3 mmol), tetrakis(triphenylphosphine)palladium (0) (0.763 g, 0.660 mmol) and 2M aqueous solution of sodium carbonate (5.25 g, 49.5 mmol), and the mixture solution was stirred at 85 degrees C. for 20 hours. After the reaction, the mixture solution was cooled to a room temperature, and precipitated crystals were separated by filtration. After the filtration, the precipitated crystals were purified using xylene and chlorobenzene in a recrystallization method to obtain a compound (7) (14.3 g, 23.1 mmol). An yield of the compound (7) was 70%. As a result of mass spectroscopy, it was found that m/e=617 and the compound was identified to be the above compound (7) (Exact mass: 617.19).

Other compounds of the exemplary embodiment can be synthesized according to known substitution reactions and materials in accordance with a target compound in a manner similar to the above reactions.

(8-1) Evaluation of Compounds

Electron mobility $\mu_e$ of each of the compounds was evaluated using impedance spectroscopy. Single carrier devices having the following layer structure were prepared.

Al (80)/measurement target compound (200)/compound E-2 (10)/LiF (1)/Al (80)

Numerals in parentheses represent a film thickness (unit: nm).

The used measurement target compounds were the compound (1), the compound (3) and the following compound E-1.

In order to measure the electron mobility, DC voltage with 100 mV of alternating voltage is applied to each of the single carrier devices to measure a complex modulus. With a proviso that a frequency at which the imaginary part of the complex modulus is the maximum is represented by $f_{max}$ (Hz), a response time T (sec.) was calculated as $T=1/2/\pi/f_{max}$, and electric-field-intensity dependency of the electron mobility was determined using the calculated value. Values when the electric field intensity was 0.25 MV/cm are shown in Table 1.

TABLE 1

|  | $\mu_e$ (cm$^2$/V · s)) |
|---|---|
| Compound 1 | $6.3 \times 10^{-5}$ |
| Compound 3 | $6.6 \times 10^{-6}$ |
| Compound E-1 | $1.0 \times 10^{-4}$ |

Manufacture of Organic EL Device

Compounds used for manufacturing an organic EL device will be shown below.

[Formula 160]

E-1

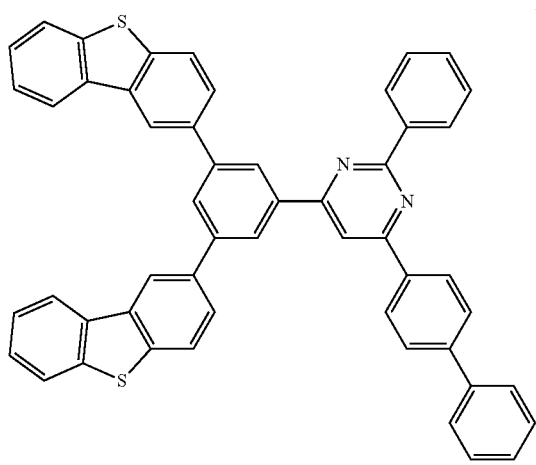

[Formula 161]

HI-1

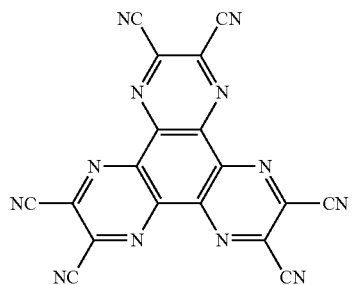

HT-1

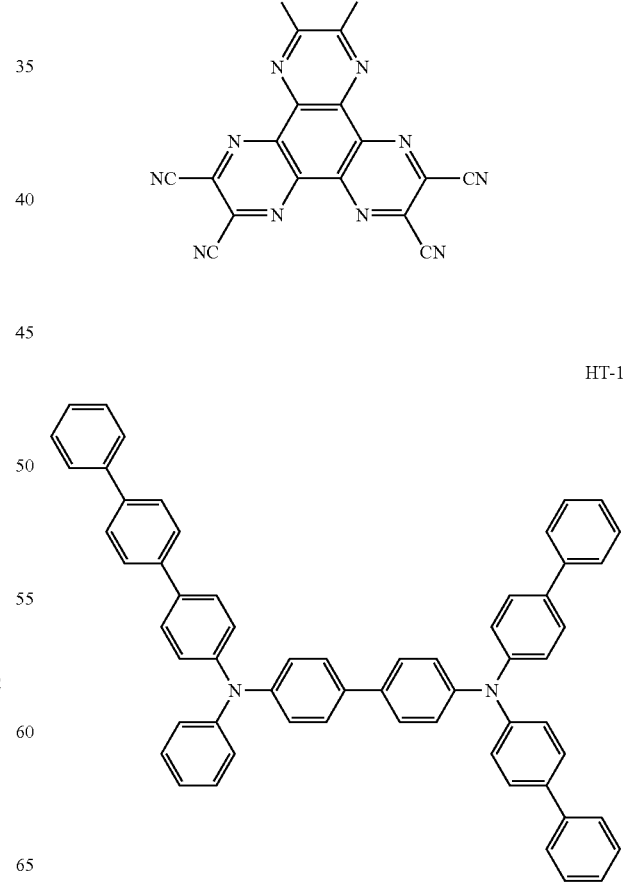

E-2

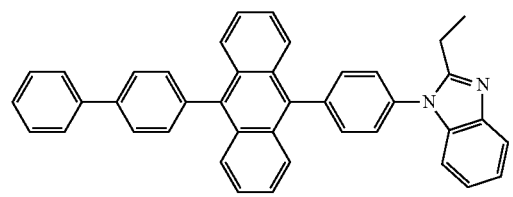

-continued

HT-2

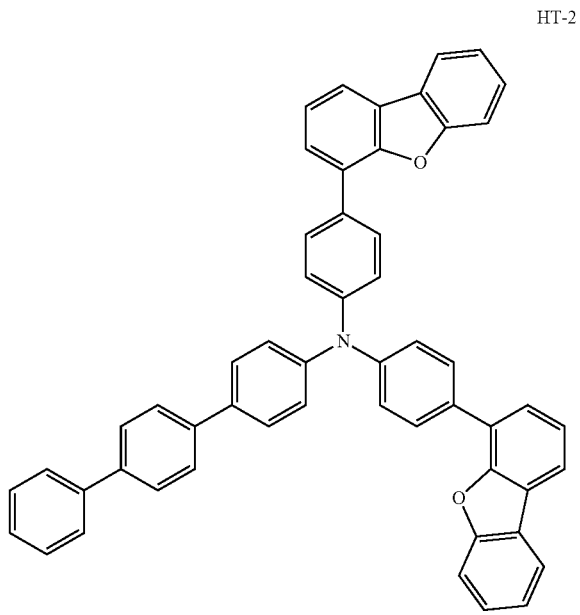

[Formula 162]

BH-1

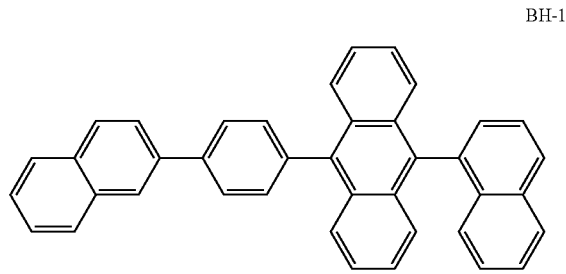

BD-1

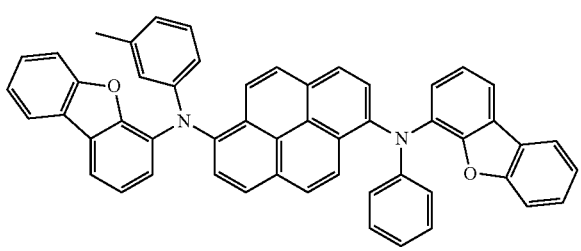

[Formula 163]

E-3

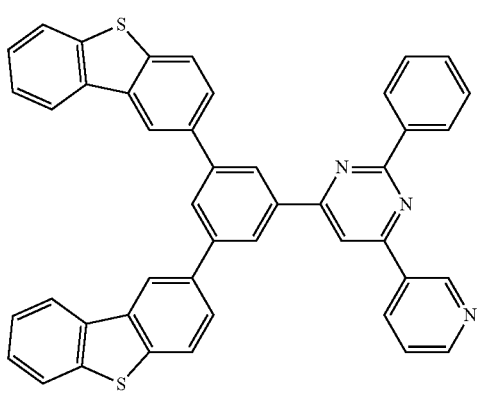

Example 1

A glass substrate (size: 25 mm×75 mm×1.1-mm thick, manufactured by Geomatec Co., Ltd.) having an ITO transparent electrode (anode) was subjected to ultrasonic-cleaning in isopropyl alcohol for five minutes, and then UV/ozone-cleaning for 30 minutes. After the glass substrate having the transparent electrode line was cleaned, the glass substrate was mounted on a substrate holder of a vacuum evaporation apparatus. Initially, a compound HI-1 was deposited on a surface of the glass substrate where the transparent electrode line was provided in a manner to cover the transparent electrode, thereby forming a 5-nm thick HI-1 film as a hole injecting layer.

Next, the compound HT-1 as a first hole transporting material was deposited on the hole injecting layer to form an 80-nm thick HT-1 film as a first hole transporting layer.

Next, the compound HT-2 was deposited on the first hole transporting layer to form a 10-nm thick HT-2 film as a second hole transporting layer.

The compound BH-1 and the compound BD-1 (mass ratio of BH-1 to BD-1 was 24:1) were co-deposited on the HT-2 film to form a 25-nm thick emitting layer.

Subsequently to the formation of the emitting layer, the compound (1) and 8-quinolinolatolithium (Liq) (mass ratio of the compound (1) to 8-quinolinolatolithium was 50:50) were co-deposited on the emitting layer to form a 25-nm thick electron transporting layer.

Liq was deposited on the electron transporting layer to form a 1-nm thick electron injecting layer.

A metal Al was deposited on the electron injecting layer to form an 80-nm thick metal cathode.

Thus, the organic EL device of Example 1 was prepared.

A device arrangement of the organic EL device in Example 1 is schematically shown as follows.

ITO (130)/HI-1 (5)/HT-1 (80)/HT-2 (10)/BH-1:BD-1 (25, 4%)/compound (1):Liq (25, 50%)/Liq (1)/Al (80)

Numerals in parentheses represent a film thickness (unit: nm). The numerals represented by percentage in parentheses indicate a concentration (mass %) of BD-1 in the emitting layer or a concentration (mass %) of Liq in the electron transporting layer.

Example 2

An organic EL device of Example 2 was prepared in the same manner as the organic EL device of Example 1 except that the compound (3) was used in place of the compound (1) in Example 1.

Comparative Example 1

An organic EL device of Comparative Example 1 was prepared in the same manner as the organic EL device of Example 1 except that the compound E-1 was used in place of the compound (1) in Example 1.

The organic EL devices prepared in the above-described Examples and Comparative Examples were measured according to the methods described below to evaluate the performance thereof. The results are shown in Table 2.

(1) Drive Voltage

Voltage was applied between the anode (ITO transparent electrode) and metal cathode (metal Al) such that a current density was 10 mA/cm$^2$, where the voltage (unit: V) was measured.

(2) External Quantum Efficiency

Voltage was applied on each of the organic EL devices such that a current density was 10 mA/cm$^2$, where spectral radiance spectra were measured by a spectroradiometer (CS-1000 manufactured by Konica Minolta, Inc.). The external quantum efficiency EQE (at 10 mA/cm$^2$, unit: %) was calculated from the obtained spectral-radiance spectra, assuming that Lambertian radiation was carried out.

Using the maximum luminance efficiency and luminance efficiency ratio at 10 mA/cm$^2$, the maximum external quantum efficiency (EQE max.) based on the external quantum efficiency (at 10 mA/cm$^2$) was calculated.

(3) Lifetime

A continuous direct-current energization test was performed with an initial current density being set at 50 mA/cm$^2$, and a lifetime (LT90) until the initial luminance at the start of the test decreased to 90% of the initial luminance was measured.

TABLE 2

|  | Voltage (V) (at 10 mA/cm$^2$) | EQE max. (%) | LT90 (hr) |
|---|---|---|---|
| Example 1 | 4.2 | 10 | 321 |
| Example 2 | 4.1 | 10 | 282 |
| Comparative Example 1 | 4.2 | 10 | 220 |

As shown in Table 2, it is understood that the organic EL devices according to Example 1 using the compound (1) and Example 2 using the compound (3) of the exemplary embodiment achieve a long lifetime while keeping the drive voltage at an appropriate level as compared to Comparative Example 1. As shown in Table 1, the compounds (1) and (3) have lower electron mobility than the compound E-1 used in Comparative Example 1. Accordingly, it is supposed that the amount of electrons flowing from the electron transporting layer to the emitting layer is decreased to reduce the electrons leaking from the emitting layer to the hole transporting layer, thereby mitigating the degradation of the hole transporting material and prolonging the lifetime.

Example 3

An organic EL device of Example 3 was prepared in the same manner as the organic EL device of Example 1 except that the compound (4) was used in place of the compound (1) in Example 1.

Example 4

An organic EL device of Example 4 was prepared in the same manner as the organic EL device of Example 1 except that the compound (5) was used in place of the compound (1) in Example 1.

Example 5

An organic EL device of Example 5 was prepared in the same manner as the organic EL device of Example 1 except that the compound (6) was used in place of the compound (1) in Example 1.

Example 6

An organic EL device of Example 6 was prepared in the same manner as the organic EL device of Example 1 except that the compound (7) was used in place of the compound (1) in Example 1.

Comparative Example 2

An organic EL device of Comparative Example 2 was prepared in the same manner as the organic EL device of Example 1 except that the compound E-3 was used in place of the compound (1) in Example 1.

The organic EL devices prepared in Examples 3 to 6 and Comparative Example 2 were measured according to the above-described methods to evaluate the performance thereof. The results are shown in Table 3.

TABLE 3

|  | Voltage (V) (at 10 mA/cm$^2$) | EQE max. (%) | LT90 (hr) |
|---|---|---|---|
| Example 3 | 4.2 | 10 | 305 |
| Example 4 | 4.1 | 10 | 314 |
| Example 5 | 4.1 | 10 | 276 |
| Example 6 | 4.2 | 10 | 320 |
| Comparative Example 2 | 4.0 | 10 | 222 |

As shown in Table 3, it is understood that the organic EL devices according to Examples 3 to 6 using the compounds (4), (5), (6) and (7) of the exemplary embodiment achieve a long lifetime while keeping the drive voltage at an appropriate level as compared to Comparative Examples 1 and 2.

Though the exemplary embodiment(s) and/or Examples of the invention have been described above in detail, it would be easily understood by those skilled in the art that the above exemplary embodiment(s) and/or Examples can be modified in various manners without substantively departing from the new teachings and effects of the invention. Thus, the various modifications are also included in the scope of the invention.

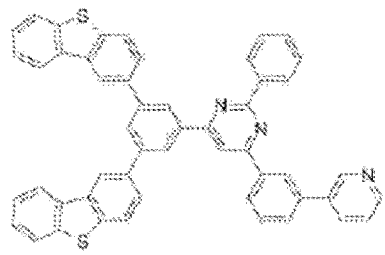

The invention claimed is:

1. A compound represented by a formula (100) below,

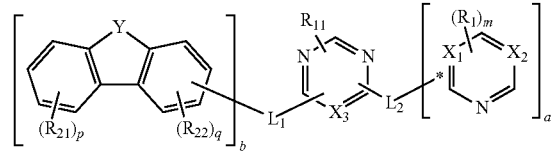

(100)

where:
- $X_3$ is a nitrogen atom, or a carbon atom ($CR_2$) bonded with $R_2$;
- $R_2$ is a hydrogen atom;
- $R_{11}$ is a substituted or unsubstituted aryl group having 6 to 30 ring carbon atoms;
- Y is an oxygen atom, a sulfur atom, or a silicon atom ($SiR_{31}R_{32}$) bonded with $R_{31}$ and $R_{32}$;
- $R_{21}$ and $R_{22}$ are each independently selected from the group consisting of a hydrogen atom, a substituted or unsubstituted alkyl group having 1 to 30 carbon atoms, and a substituted or unsubstituted aryl group having 6 to 30 ring carbon atoms;
- a first moiety represented by a formula (10c) below in the compound represented by the formula (100) is selected from a moiety represented by any one of formulae (10c-1) to (10c-27) below, -continued

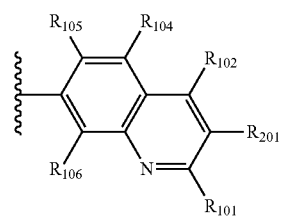
(10c-14)
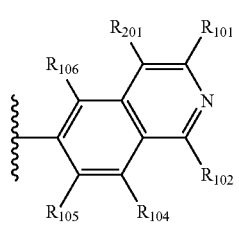
(10c-20)
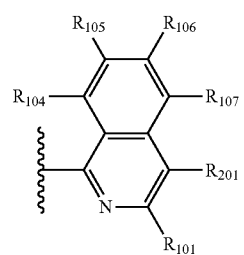
(10c-15)
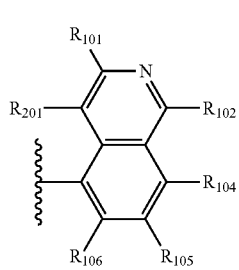
(10c-21)
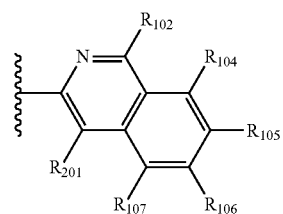
(10c-16)
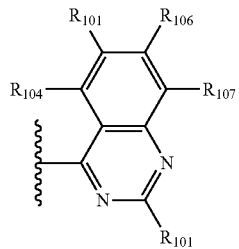
(10c-22)
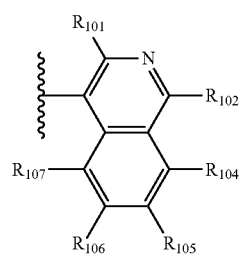
(10c-17)
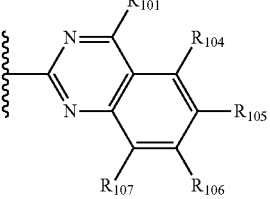
(10c-23)
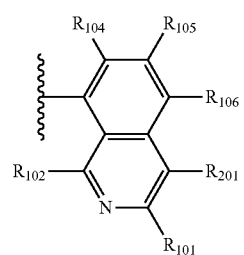
(10c-18)
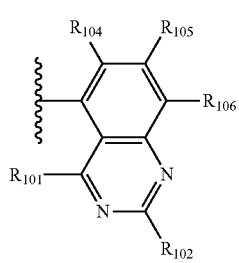
(10c-24)
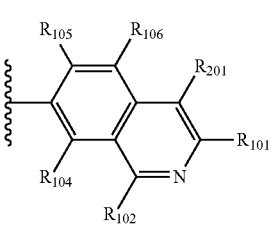
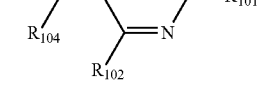
(10c-19)
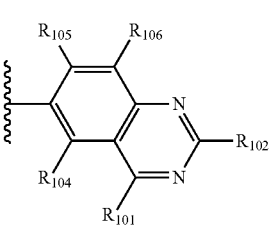
(10c-25)

-continued (10c-26)

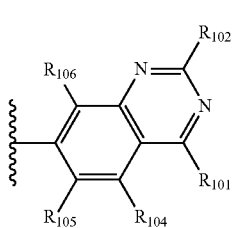

(10c-27)

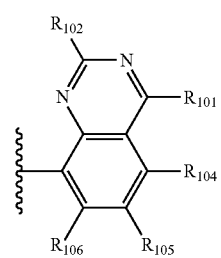

$R_{101}$ to $R_{107}$, $R_{201}$ and $R_{202}$ are each independently selected from the group consisting of: a hydrogen atom and a substituted or unsubstituted alkyl group having 1 to 30 carbon atoms;

$R_{31}$ and $R_{32}$ are each independently selected from the group consisting of: a hydrogen atom; an unsubstituted alkyl group having 1 to 30 carbon atoms; and an unsubstituted aryl group having 6 to 30 ring carbon atoms;

$L_1$ is a single bond or a linking group selected from the group consisting of: a substituted or unsubstituted aromatic hydrocarbon group having 6 to 30 ring carbon atoms;

$L_2$ is a linking group selected from the group consisting of: a substituted or unsubstituted aromatic hydrocarbon groups having 6 to 30 ring carbon atoms;

p is an integer ranging from 0 to 4, a plurality of $R_{21}$ being the same or different when p is an integer in a range from 2 to 4;

the plurality of $R_{21}$ are optionally bonded to each other to form a ring structure;

q is an integer ranging from 0 to 3, a plurality of $R_{22}$ being the same or different when q is 2 or 3;

the plurality of $R_{22}$ are optionally bonded to each other to form a ring structure;

a is an integer ranging from 1 to 5, a plurality of first moieties represented by formula (10c) in parentheses parenthesized by a being the same or different when the plurality of first moieties are bonded to $L_2$; and b is an integer ranging from 1 to 5, a plurality of second moieties being the same or different when the plurality of second moieties in parentheses parenthesized by b are bonded to $L_1$.

2. The compound according to claim 1, wherein the compound is represented by a formula (10) below, (10)

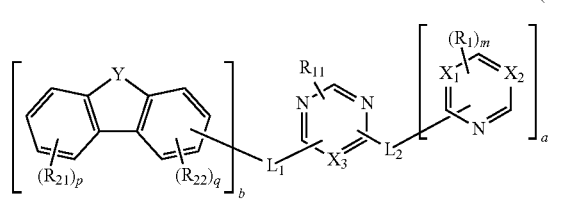

wherein $X_3$, Y, $R_2$, $R_{11}$, $R_{21}$, $R_{22}$, $R_{31}$, $R_{32}$, $L_1$, $L_2$, p, q, a and b respectively are the same as $X_3$, Y, $R_2$, $R_{11}$, $R_{21}$, $R_{22}$, $R_{31}$, $R_{32}$, $L_1$, $L_2$, p, q, a and b in the formula (100), and the first moiety represented by the formula (10c) in the compound represented by the formula (10) is selected from the group consisting of moieties represented by any one of the formulae (10c-1) to (10c-27).

3. The compound according to claim 1, wherein the compound is represented by a formula (11) below, (11)

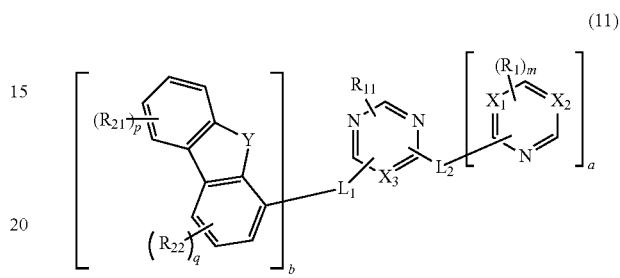

wherein $X_3$, Y, $R_2$, $R_{11}$, $R_{21}$, $R_{22}$, $R_{31}$, $R_{32}$, $L_1$, $L_2$, p, q, a and b respectively are the same as $X_3$, Y, $R_2$, $R_{11}$, $R_{21}$, $R_{22}$, $R_{31}$, $R_{32}$, $L_1$, $L_2$, p, q, a and b in the formula (100), and the first moiety represented by the formula (10c) in the compound represented by the formula (11) is selected from the group consisting of moieties represented by any one of the formulae (10c-1) to (10c-27).

4. The compound according to claim 1, wherein a and b are each independently 1 or 2.

5. The compound according to claim 1, wherein a and b are 1.

6. The compound according to claim 1, wherein a is 1 and b is 2.

7. The compound according to claim 1, wherein $L_2$ is selected from the group consisting of substituted or unsubstituted aromatic hydrocarbon groups having 6 to 18 ring carbon atoms.

8. The compound according to claim 1, wherein $L_2$ is selected from the group consisting of a substituted or unsubstituted phenylene group, a substituted or unsubstituted naphthylene group and a substituted or unsubstituted biphenyldiyl group.

9. The compound according to claim 1, wherein $L_2$ is a substituted or unsubstituted phenylene group.

10. The compound according to claim 1, wherein $R_{31}$ and $R_{32}$ are each independently selected from the group consisting of a hydrogen atom and an unsubstituted alkyl group having 1 to 30 carbon atoms.

11. The compound according to claim 1, wherein $R_{11}$ is a substituted or unsubstituted aryl group having 6 to 18 ring carbon atoms.

12. The compound according to claim 1, wherein $R_{11}$ is a group selected from the group consisting of a substituted or unsubstituted phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group and perylenyl group.

13. The compound according to claim 1, wherein $R_{11}$ is substituted or unsubstituted phenyl group.

14. The compound according to claim 1, wherein the first moiety represented by formula (10c) is selected from the moieties represented by any one of the formulae (10c-1), (10c-2), (10c-3), and (10c-8) to (10c-21).

15. The compound according to claim 1, wherein $X_3$ is a carbon atom ($CR_2$) bonded with $R_2$.

16. The compound according to claim 1, wherein $X_3$ is a nitrogen atom.

17. The compound according to claim 1, wherein Y is an oxygen atom or a sulfur atom.

18. The compound according to claim 1, wherein $L_1$ is a substituted or unsubstituted aromatic hydrocarbon group having 6 to 30 ring carbon atoms.

19. The compound according to claim 1, wherein $L_1$ is selected from the group consisting of a substituted or unsubstituted phenylene group, a substituted or unsubstituted naphthylene group and a substituted or unsubstituted biphenyldiyl group.

20. The compound according to claim 1, wherein
Y is an oxygen atom or a sulfur atom,
$L_1$ and $L_2$ are each independently selected from the group consisting of a substituted or unsubstituted phenylene group, a substituted or unsubstituted naphthylene group, and a substituted or unsubstituted biphenyldiyl group, and
$R_{11}$ is selected from the group consisting of a phenyl group, a biphenyl group, a terphenyl group, a naphthyl group, an anthryl group, a phenanthryl group, a fluorenyl group, a pyrenyl group, a chrysenyl group, a fluoranthenyl group, a benzo[a]anthryl group, a benzo[c]phenanthryl group, a triphenylenyl group, a benzo[k]fluoranthenyl group, a benzo[g]chrysenyl group, a benzo[b]triphenylenyl group, a picenyl group, and a perylenyl group.

21. An organic-electroluminescence-device material comprising the compound according to claim 1.

22. An organic electroluminescence device comprising:
an anode;
a cathode; and
one or more organic layers comprising an emitting layer, wherein
at least one of the organic layers comprises the compound according to claim 1.

23. An organic electroluminescence device comprising:
an anode;
a cathode; and
an organic layer comprising an emitting layer and an electron transporting zone, wherein
the emitting layer is provided between the anode and the cathode,
the electron transporting zone is provided between the emitting layer and the cathode, and
the electron transporting zone comprises the compound according to claim 1.

24. The organic electroluminescence device according to claim 23, wherein the electron transporting zone further comprises at least one of an electron-donating dopant and an organic metal complex.

25. The organic electroluminescence device according to claim 24, wherein the electron-donating dopant and the organic metal complex are at least one compound selected from the group consisting of an alkali metal, an alkali metal compound, an alkali earth metal, an alkali earth metal compound, a rare-earth metal, a rare-earth metal compound, an organic metal complex comprising alkali metal, an organic metal complex comprising alkaline earth metal and an organic metal complex comprising rare-earth metal.

26. The organic electroluminescence device according to claim 24, wherein the electron-donating dopant and the organic metal complex are at least one compound selected from the group consisting of lithium, a lithium compound and an organic metal complex comprising lithium.

27. The organic electroluminescence device according to claim 23, wherein the electron transporting zone further comprises 8-quinolinolatolithium.

28. An electronic device comprising the organic electroluminescence device according to claim 22.

29. The compound according to claim 1, wherein
a and b are each independently 1 or 2,
$L_2$ is selected from the group consisting of substituted or unsubstituted aromatic hydrocarbon groups having 6 to 18 ring carbon atoms,
$R_{31}$ and $R_{32}$ are each independently selected from the group consisting of a hydrogen atom, an unsubstituted alkyl group having 1 to 30 carbon atoms, and an unsubstituted aryl group having 6 to 30 ring carbon atoms, and
$L_1$ is a substituted or unsubstituted aromatic hydrocarbon group having 6 to 30 ring carbon atoms.

30. The compound according to claim 1, wherein when Ru has a sub stituent, the sub stituent is selected from the group consisting of aryl group, alkyl group, alkenyl group, alkynyl group, alkylsilyl group, arylsilyl group, alkoxy group, aryloxy group, alkylthio group, arylthio group, halogen atom, cyano group, aralkyl group, alkylamino group, arylamino group, hydroxyl group, nitro group and carboxy group.

31. The compound according to claim 1, wherein b is 2.

32. The compound according to claim 1, wherein
$L_1$ is a substituted or unsubstituted aromatic hydrocarbon group having 6 to 30 ring carbon atoms,
$L_2$ is a substituted or unsubstituted phenylene group, and
$R_{11}$ is a substituted or unsubstituted phenyl group.

33. The compound according to claim 1, wherein
$L_1$ is selected from the group consisting of a substituted or unsubstituted phenylene group, a substituted or unsubstituted naphthylene group and a substituted or unsubstituted biphenyldiyl group,
$L_2$ is a substituted or unsubstituted phenylene group, and
$R_{11}$ is a substituted or unsubstituted phenyl group.

34. The compound according to claim 1, wherein $R_{101}$ to $R_{107}$, $R_{201}$ and $R_{202}$ are each independently a hydrogen atom or an unsubstituted alkyl group having 1 to 30 carbon atoms.

35. The compound according to claim 1, wherein $R_{101}$ to $R_{107}$, $R_{201}$ and $R_{202}$ are hydrogen atoms.

36. The compound according to claim 1, wherein
the substituent meant by "substituted or unsubstituted" is selected from the group consisting of an unsubstituted aryl group and unsubstituted alkyl group.

37. The compound according to claim 1, wherein
the substituent meant by "substituted or unsubstituted" is selected from the group consisting of an unsubstituted phenyl group and unsubstituted methyl group.

38. The compound according to claim 1, wherein
$L_1$ is selected from the group consisting of a substituted or unsubstituted phenylene group, a substituted or unsubstituted naphthylene group, and a substituted or unsubstituted biphneyldiyl group,
$L_2$ is a substituted or unsubstituted phenylene group,
$R_{11}$ is a substituted or unsubstituted phenyl group,
the substituent meant by "substituted or unsubstituted" is selected from the group consisting of an unsubstituted aryl group and unsubstituted alkyl group,
$R_{101}$ to $R_{107}$, and $R_{201}$ and $R_{202}$ are each a hydrogen atom,
Y is an oxygen atom or a sulfur atom, and
a and b are each independently 1 or 2.

39. The compound according to claim 1, wherein the first moiety represented by the formula (10c) is selected from the group consisting of the moieties represented by the formulae (10c-1) to (10c-9), (10c-15) to (10c-17), and (10c-22) to (10c-23).
40. The compound according to claim 1, wherein the compound is selected from the group consisting of compounds (1) to (7) below,
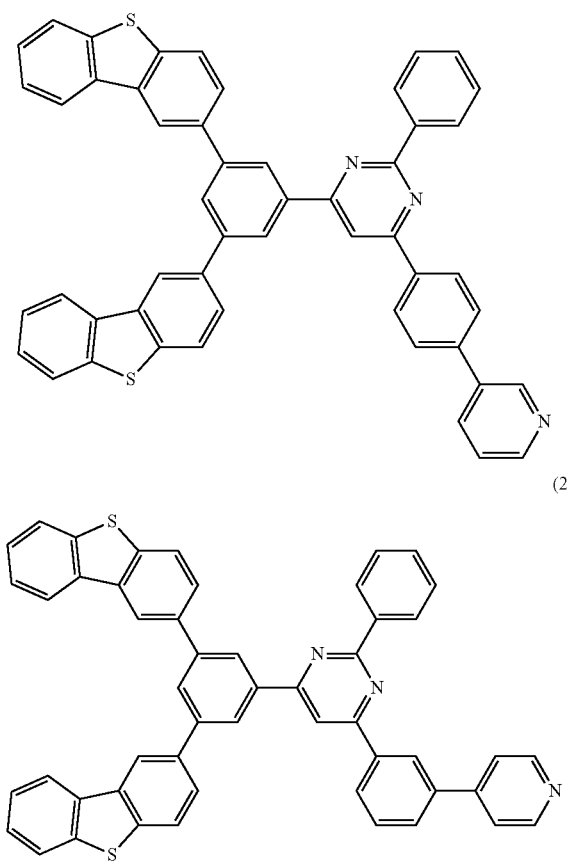
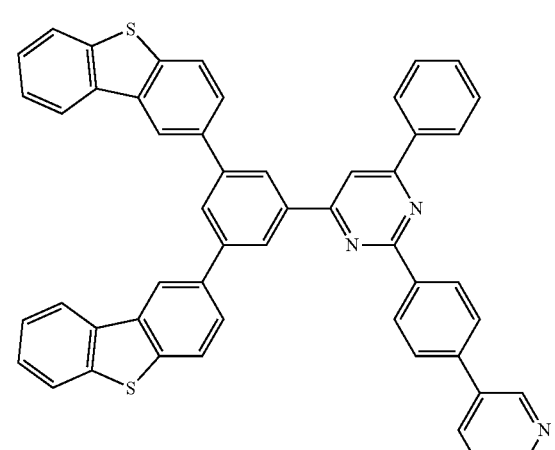
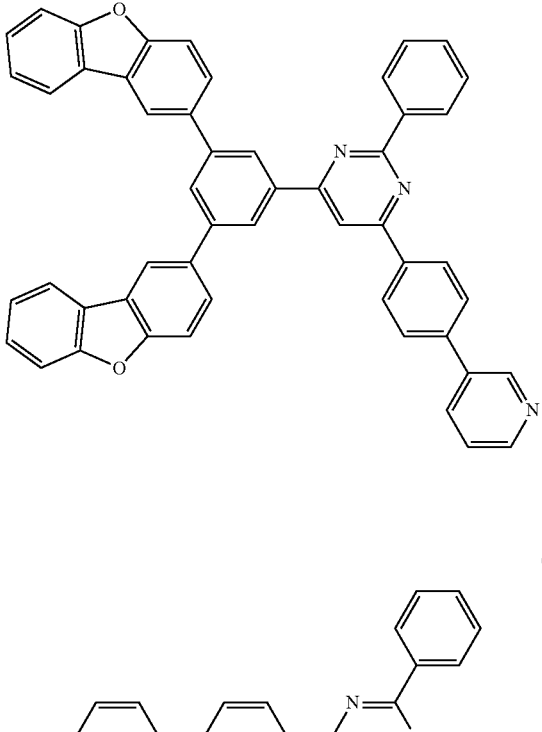
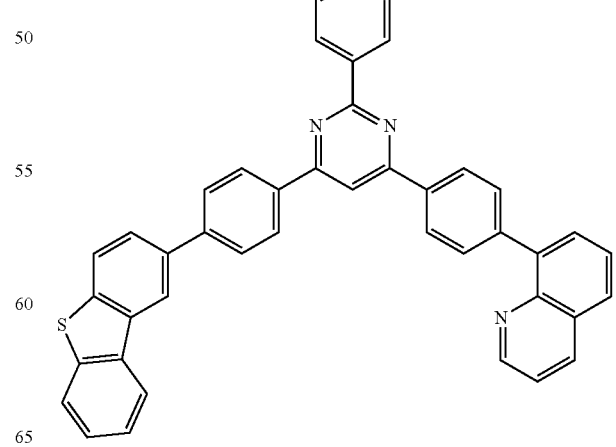

(7)
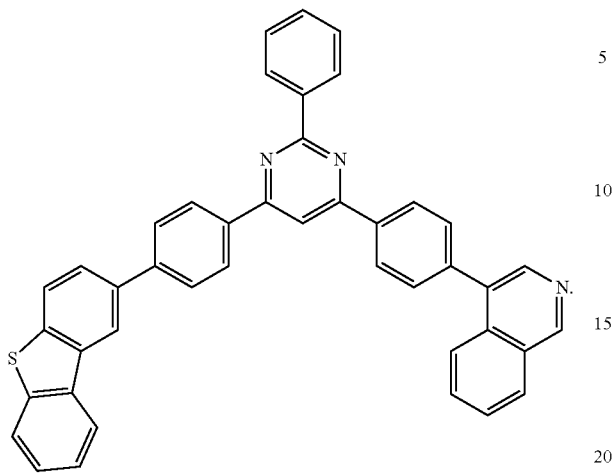

UNITED STATES PATENT AND TRADEMARK OFFICE
CERTIFICATE OF CORRECTION

PATENT NO. : 10,784,446 B2
APPLICATION NO. : 15/329442
DATED : September 22, 2020
INVENTOR(S) : Tomoharu Hayama et al.

Page 1 of 3

It is certified that error appears in the above-identified patent and that said Letters Patent is hereby corrected as shown below:

In the Claims

Please replace Formula (10c-10) Claim 1, Column 352, Lines 21-30, with:

(10c-10)

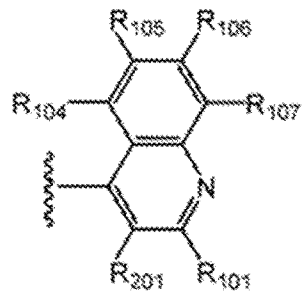

Please replace Formula (10c-11) Claim 1, Column 352, Lines 31-40, with:

(10c-11)

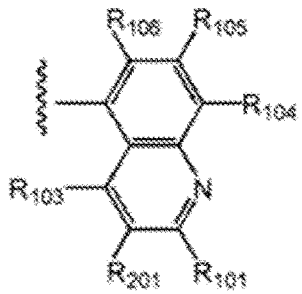

Signed and Sealed this
Third Day of August, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,784,446 B2

Please replace Formula (10c-14) Claim 1, Column 353, Lines 1-10, with:

(10c-14)

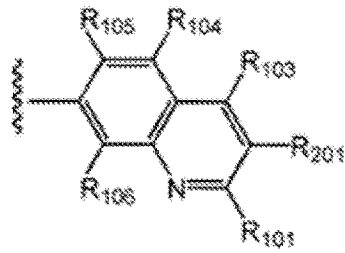

Please replace Formula (10c-22) Claim 1, Column 354, Lines 22-32, with:

(10c-22)

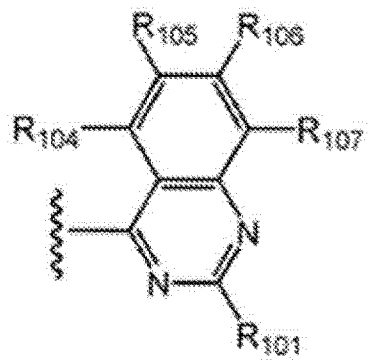

Please replace Formula (10) Claim 2, Column 355, Lines 57-66, with:

(10)

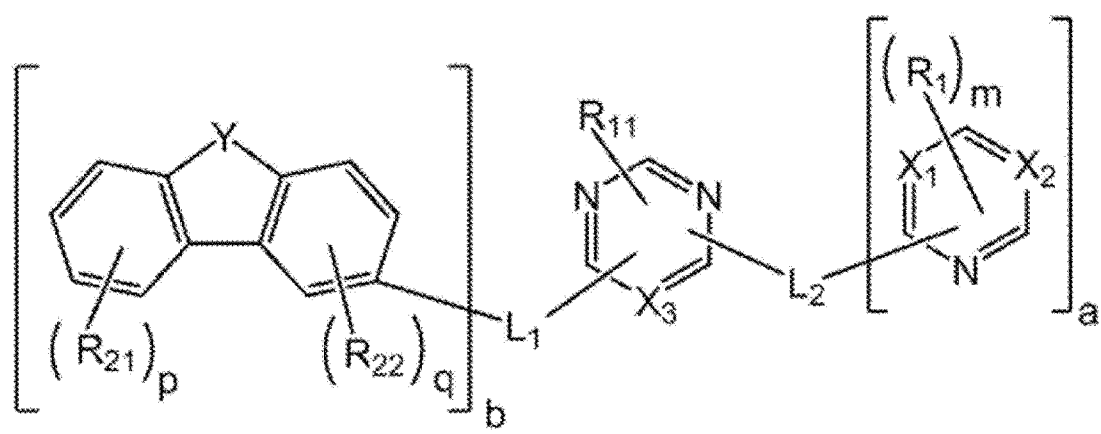

Claim 30, Column 358, Line 22:
Please delete:
"Ru has a sub stitutent, the subs stituent is selected from the"
Please replace with:
$R_{11}$ has a substituent, the substituent is selected from the

CERTIFICATE OF CORRECTION (continued)
U.S. Pat. No. 10,784,446 B2

Please replace Formula (2) Claim 40, Column 359, Lines 31-45, with:

(2)